United States Patent
Roth et al.

(10) Patent No.: US 8,835,472 B2
(45) Date of Patent: Sep. 16, 2014

(54) COMPOUNDS, PHARMACEUTICAL COMPOSITIONS AND USES THEREOF

(75) Inventors: Gerald Juergen Roth, Biberach an der Riss (DE); Martin Fleck, Warthausen (DE); Niklas Heine, Eberhardzell (DE); Joerg Kley, Biberach an der Riss (DE); Thorsten Lehmann-Lintz, Ochsenhausen (DE); Heike Neubauer, Eberhardzell (DE); Bernd Nosse, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 205 days.

(21) Appl. No.: 13/211,472

(22) Filed: Aug. 17, 2011

(65) Prior Publication Data

US 2012/0214785 A1 Aug. 23, 2012

(30) Foreign Application Priority Data

Sep. 2, 2010 (EP) .................................. 10175100

(51) Int. Cl.
*C07D 231/14* (2006.01)
*C07D 277/32* (2006.01)
(Continued)

(52) U.S. Cl.
CPC ............. *C07C 233/18* (2013.01); *C07C 317/44* (2013.01); *C07D 207/12* (2013.01); *C07D 305/08* (2013.01); *C07D 239/26* (2013.01); *C07D 213/79* (2013.01); *C07D 2101/08* (2013.01); *C07C 323/41* (2013.01); *C07C 255/46* (2013.01); *C07D 239/28* (2013.01); *C07D 307/24* (2013.01); *C07D 215/12* (2013.01); *C07D 413/12* (2013.01); *C07D 237/08* (2013.01); *C07D 417/12* (2013.01); *C07C 271/16* (2013.01); *C07D 211/76* (2013.01); *C07C 311/10* (2013.01); *C07D 217/06* (2013.01); *C07D 277/24* (2013.01); *C07D 249/10* (2013.01); *C07C 237/42* (2013.01); *C07D 239/38* (2013.01); *C07C 233/20* (2013.01); *C07D 213/75* (2013.01); *C07D 307/14* (2013.01); *C07D 319/08* (2013.01); *C07C 275/24* (2013.01); *C07C 295/192* (2013.01); *C07C 233/05* (2013.01); *C07D 233/64* (2013.01); *C07D 207/10* (2013.01); *C07D 403/04* (2013.01); *C07C 255/19* (2013.01); *C07D 213/65* (2013.01); *C07C 237/22* (2013.01); *C07D 321/10* (2013.01); *C07C 233/60* (2013.01); *C07D 405/12* (2013.01); *C07D 213/40* (2013.01); *C07C 233/47* (2013.01); *C07D 253/07* (2013.01); *C07D 2101/04* (2013.01); *C07D 209/44* (2013.01); *C07D 239/42* (2013.01); *C07D 261/18* (2013.01); *C07C 255/60* (2013.01); *C07D 205/08* (2013.01); *C07D 213/30* (2013.01); *C07D 211/16* (2013.01); *C07D 295/088* (2013.01); *C07C 233/36* (2013.01); *C07C 233/13* (2013.01); *C07D 213/82* (2013.01); *C07D 309/12* (2013.01); *C07D 231/14* (2013.01); *C07C 235/08* (2013.01); *C07B 2200/07* (2013.01); *C07D 271/08* (2013.01); *C07C 233/31* (2013.01); *C07D 401/12* (2013.01); *C07D 213/64* (2013.01); *C07D 261/08* (2013.01); *C07C 2101/02* (2013.01); *C07D 213/74* (2013.01); *C07D 213/643* (2013.01); *C07D 263/32* (2013.01); *C07C 311/04* (2013.01); *C07D 233/90* (2013.01); *C07D 231/12* (2013.01); *C07D 239/52* (2013.01); *C07D 277/28* (2013.01); *C07C 235/40* (2013.01); *C07D 261/14* (2013.01); *C07D 205/04* (2013.01); *C07D 263/34* (2013.01); *C07C 2102/08* (2013.01); *C07D 277/56* (2013.01); *C07C 275/40* (2013.01); *C07C 233/58* (2013.01); *C07D 307/79* (2013.01); *C07D 307/68* (2013.01); *C07D 209/08* (2013.01); *C07D 237/14* (2013.01); *C07D 263/58* (2013.01); *C07C 311/14* (2013.01); *C07D 305/06* (2013.01); *C07D 317/62* (2013.01); *C07D 239/34* (2013.01); *C07C 237/08* (2013.01); *C07D 207/325* (2013.01); *C07D 401/04* (2013.01)
USPC ........... 514/365; 514/406; 514/624; 514/629; 548/200; 548/374.1; 564/190; 564/215

(58) Field of Classification Search
CPC .. C07D 231/14; C07D 277/32; A61K 31/415; A61K 31/426
USPC ............... 548/200, 374.1; 514/365, 406, 624, 514/629; 564/190, 215
See application file for complete search history.

(56) References Cited

U.S. PATENT DOCUMENTS

2006/0063926 A1 3/2006 Ma et al.
2012/0010247 A1 1/2012 Kamata et al.

FOREIGN PATENT DOCUMENTS

WO 2005094822 A1 10/2005
WO 2006103449 A2 10/2006
(Continued)

OTHER PUBLICATIONS 2- and 4-(.alpha.,.alpha.,.beta.,.-Tetrafluorophenethyl)benzylamines, Merck and Co., Inc., Jan. 18, 2012, XP002667443 Database CA [Online] Chemical Abstracts Service, Columbus, Ohio. US.
(Continued)

*Primary Examiner* — Deepak Rao
(74) *Attorney, Agent, or Firm* — Michael P. Morris; Alan R. Stempel

(57) ABSTRACT

The invention relates to new compounds of the formula I

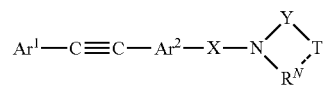

to their use as medicaments, to methods for their therapeutic use and to pharmaceutical compositions containing them.

8 Claims, No Drawings

(51) Int. Cl.

| | | |
|---|---|---|
| A61K 31/415 | (2006.01) | |
| C07C 317/44 | (2006.01) | |
| C07D 207/12 | (2006.01) | |
| C07D 305/08 | (2006.01) | |
| C07D 239/26 | (2006.01) | |
| C07D 213/79 | (2006.01) | |
| C07C 323/41 | (2006.01) | |
| C07C 255/46 | (2006.01) | |
| C07D 239/28 | (2006.01) | |
| C07D 307/24 | (2006.01) | |
| C07D 215/12 | (2006.01) | |
| C07D 413/12 | (2006.01) | |
| C07D 237/08 | (2006.01) | |
| C07D 417/12 | (2006.01) | |
| C07C 271/16 | (2006.01) | |
| C07D 211/76 | (2006.01) | |
| C07C 311/10 | (2006.01) | |
| C07D 217/06 | (2006.01) | |
| C07D 277/24 | (2006.01) | |
| C07D 249/10 | (2006.01) | |
| C07C 237/42 | (2006.01) | |
| C07D 239/38 | (2006.01) | |
| C07C 233/20 | (2006.01) | |
| C07D 213/75 | (2006.01) | |
| C07D 307/14 | (2006.01) | |
| C07D 319/08 | (2006.01) | |
| C07C 275/24 | (2006.01) | |
| C07D 295/192 | (2006.01) | |
| C07C 233/05 | (2006.01) | |
| C07C 233/64 | (2006.01) | |
| C07D 207/10 | (2006.01) | |
| C07D 403/04 | (2006.01) | |
| C07C 255/19 | (2006.01) | |
| C07D 213/65 | (2006.01) | |
| C07C 237/22 | (2006.01) | |
| C07C 233/18 | (2006.01) | |
| C07D 321/10 | (2006.01) | |
| C07C 233/60 | (2006.01) | |
| C07D 405/12 | (2006.01) | |
| C07D 213/40 | (2006.01) | |
| C07C 233/47 | (2006.01) | |
| C07D 253/07 | (2006.01) | |
| C07D 209/44 | (2006.01) | |
| C07D 239/42 | (2006.01) | |
| C07D 261/18 | (2006.01) | |
| C07C 255/60 | (2006.01) | |
| C07D 205/08 | (2006.01) | |
| C07D 213/30 | (2006.01) | |
| C07D 211/16 | (2006.01) | |
| C07D 295/088 | (2006.01) | |
| C07C 233/36 | (2006.01) | |
| C07C 233/13 | (2006.01) | |
| C07D 213/82 | (2006.01) | |
| C07D 309/12 | (2006.01) | |
| C07C 235/08 | (2006.01) | |
| C07D 271/08 | (2006.01) | |
| C07C 233/31 | (2006.01) | |
| C07D 401/12 | (2006.01) | |
| C07D 213/64 | (2006.01) | |
| C07D 261/08 | (2006.01) | |
| C07D 213/74 | (2006.01) | |
| C07D 213/643 | (2006.01) | |
| C07D 263/32 | (2006.01) | |
| C07C 311/04 | (2006.01) | |
| C07D 233/90 | (2006.01) | |
| C07D 231/12 | (2006.01) | |
| C07D 239/52 | (2006.01) | |
| C07D 277/28 | (2006.01) | |
| C07C 235/40 | (2006.01) | |
| C07D 261/14 | (2006.01) | |
| C07D 205/04 | (2006.01) | |
| C07D 263/34 | (2006.01) | |
| C07D 277/56 | (2006.01) | |
| C07C 275/40 | (2006.01) | |
| C07C 233/58 | (2006.01) | |
| C07D 307/79 | (2006.01) | |
| C07D 307/68 | (2006.01) | |
| C07D 209/08 | (2006.01) | |
| C07D 237/14 | (2006.01) | |
| C07D 263/58 | (2006.01) | |
| C07C 311/14 | (2006.01) | |
| C07D 305/06 | (2006.01) | |
| C07D 317/62 | (2006.01) | |
| C07D 239/34 | (2006.01) | |
| C07C 237/08 | (2006.01) | |
| C07D 207/325 | (2006.01) | |
| C07D 401/04 | (2006.01) | |

(56) References Cited

FOREIGN PATENT DOCUMENTS

| WO | WO 2007/141009 | * 12/2007 |
|---|---|---|
| WO | 2009094123 A1 | 7/2009 |
| WO | 2010050445 A1 | 5/2010 |
| WO | 2011002910 A1 | 1/2011 |
| WO | 2011051201 A1 | 5/2011 |

OTHER PUBLICATIONS

Agejas-Chicharro et al., Preparation of pyridines as mGlu5 receptor antagonists, Eli Lilly and Company, USA, Oct. 13, 2005, XP002667442 Database CA [Online] Chemical Abstracts Service, Columbus, Ohio, US.

Caiazzo et al., Synergy between chemo- and bio-catalysts in multistep transformations, Organic & Biomolecular Chemistry, 7(14), 2926-2932 CODEN: OBCRAK; ISSN: 1477-0520, 2009. Database CA [Online] Chemical Abstracts Service, Columbus, Ohio, US.

Enomoto et al., Gold(I)-catalyzed hydroamination as a general approach toward the synthesis of substituted hydroisoquinolines: remarkable acceleration by ethanol, SYNLETT , (1 1 ), 1647-1650 CODEN: SYNLES: ISSN: 0936-5214, 2008. Database CA [Online], Chemical Abstracts Service, Columbus, Ohio, US.

Enomoto et al., Gold(I)-Catalyzed Tandem Reactions Initiated by Hydroamination of Alkynyl Carbamates: Application to the Synthesis of Nitidine, Journal of Organic Chemistry, 74(23), 9158-9164 CODEN: JOCEAH; ISSN: 0022-3263, 2009 Database CA [Online] Chemical Abstracts Service, Columbus, Ohio, US.

Furukawa et al., Preparation of nitrogen-containing heteroaryl derivatives and fungicides for agricultural and horticultural use, Nippon Soda Go., Ltd., Japan, Dec. 2, 2010. Database CA [Online] Chemical Abstracts Service, Columbus, Ohio, US.

Garcia et al, Chemoenzymic coupling reactions, SYNTHONBV, Sep. 14, 2006, XP002667439 Database CA [Online] Chemical Abstracts Service, Columbus, Ohio, US.

International Search report, Form PCT/ISA1210, and Written Opinion, Form PCT/ISA/237, for cooresponding application PCT/EP2011/065080, date of mailing Feb. 6, 2012.

Kimura et al: Thermal cyclization of nonconjugated aryl-yne-carbodiimide furnishing a dibenzonaphthyridine derivative, Chemical & Pharmaceutical Bulletin ,57(4), 393-396 CODEN: CPBTAL;ISSN: 0009-2363, 2009. Database CA [Online] Chemical Abstracts Service, Columbus, Ohio, US.

(56) References Cited

OTHER PUBLICATIONS

Moser et al., Preparation of antibacterial agents, Achaogen, Inc., USA, Dec. 18, 2008, XP002667437 Database CA [Online] Chemical Abstracts Service, Columbus, Ohio, US.

Mujahidin et al., Enantioselective synthesis of (+)-(S)-laudanosine and (−)-(S)-xylopinine, European Journal of Organic Chemistry, (13), 2689-2693 CODEN: EJOCFK; ISSN: 1434-193X, 2005. Database CA [Online] Chemical Abstracts Service, Columbus, Ohio, US.

Nakamoto et al., Preparation of heterocyclic compounds as novel antimalaria agents, Eisai Co., Ltd., Feb. 16, 2006, XP002667440 Database CA [Online] Chemical Abstracts Service, Columbus, Ohio, US.

Nakamura et al., Preparation of fungicidal acid amide derivatives, Ishihara Sangyo Kaisha, Ltd., Japan, Feb. 16, 2006, XP002667441 Database CA [Online] Chemical Abstracts Service, Columbus, Ohio, US.

Scott et al., Amine derivatives and their preparation, pharmaceutical compositions and use in the treatment of ophthalmic diseases, Acucela, Inc., USA, May 7, 2009, XP002667435 Database CA [Online] Chemical Abstracts Service, Columbus, Ohio, US.

Stierli et al., Preparation of 4-amidopyrazoles for control and prevention of plant infestation by phytopathogenic microorganisms, Syngenta Participations A.-G., Switz., Feb. 26, 2009, XP002667436 Database CA [Online] Chemical Abstracts Service, Columbus, Ohio, US.

Stierli et al., Preparation of N-(1-alkyl-2-phenylethyl)azolecarboxamides as agrochemical fungicides, Syngenta Participations AG, Switz.; Syngenta Limited, Dec. 13, 2007, XP002667438 Database CA [Online] Chemical Abstracts Service, Columbus, Ohio, US.

* cited by examiner

COMPOUNDS, PHARMACEUTICAL COMPOSITIONS AND USES THEREOF

FIELD OF THE INVENTION

This invention relates to new compounds, in particular ethyne derivatives, to processes for preparing such compounds, to their use as inhibitors of acetyl-CoA carboxylases, to methods for their therapeutic use, in particular in diseases and conditions mediated by the inhibition of acetyl-CoA carboxylase enzyme(s), and to pharmaceutical compositions comprising them.

BACKGROUND OF THE INVENTION

Obesity is a major public health issue not only for the EU, USA, Japan but also for the world in general. It is associated with a number of serious diseases including diabetes, dyslipidemia, hypertension, cardiovascular and cerebrovascular diseases.

Although the underlying mechanisms are not yet fully understood, the impairement of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G I Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (D Saggerson, Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62(2):237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, nonalcoholic steatohepatitis (NASH) and the metabolic syndrome (L. Tong, H J Harwood Jr., Journal of Cellular Biochemistry 99:1476-1488, 2006; J W Corbett, J H Jr. Harwood, Recent Pat Cardiovasc Drug Discov. 2007 November; 2(3):162-80). Furthermore recent data show that cellular toxicity mediated by lipids (lipotoxicity) is implicated in the susceptibility to diabetes associated nephropathy (for review see M Murea, B I Freedmann, J S Parks, P A Antinozzi, S C Elbein, L M Ma; Clin J Am Soc Nephrol. 2010; 5:2373-9). A large-scale genome-wide association study in japanese patients identified single nucleotide polymorphism in the ACC2 gene (ACACB) associated with diabetic nephropathy risk which was replicated in nine independent cohorts. In the kidney, dysregulation of fatty acid metabolism leading to increased fatty acid levels is believed to lead to glomerular and tubular dysfunction (M Murea, B I Freedmann, J S Parks, P A Antinozzi, S C Elbein, L M Ma; Clin J Am Soc Nephrol. 2010; 5:2373-9). Therefore inhibitors targeting ACC as key molecule involved in lipid oxidation have the potential to be beneficial for favorably affecting diabetic nephropathy.

Additionally, insulin resistance, deregulated lipid metabolism, lipotoxicity and increased intramuscular lipids have also been described to play a role in type 1 diabetes (I E Schauer, J K Snell-Bergeon, B C Bergman, D M Maahs, A Kretowski, R H Eckel, M Rewers Diabetes 2011; 60:306-14; P Ebeling, B Essén-Gustaysson, J A Tuominen and V A Koivisto Diabetologia 41: 111-115; K J Nadeau, J G Regensteiner, T A Bauer, M S Brown, J L Dorosz, A Hull, P Zeitler, B Draznin, J E B. Reusch J Clin Endocrinol Metab, 2010, 95:513-521). Therefore ACC inhibitors are also considered as interesting drugs for the treatment of type 1 diabetes.

In addition ACC inhibitors also have the potential to intervene in the progression of diseases that result from the rapid growth of malignant cells or invading organisms that are dependent on endogenous lipid synthesis to sustain their rapid proliferation. De novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao Front Biosci 2010; 2:515-26)

Furthermore in central nervous system disorders including but not limited to Alzheimer's disease, Parkinson disease and epilepsy, impairements in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (S T Henderson Neurotherapeutics, 2008, 5:470-480; L C Costantini, L J Barr, J L Vogel, S T Henderson BMC Neurosci. 2008, 9 Suppl 2:S16; K W Barañano, A L Hartman. Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, AD, hypoxia, ischemia, amyotrophic lateral sclerosis and glioma (L C Costantini, L J Barr, J L Vogel, S T Henderson BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson BMC Neurosci. 2008, 9 Suppl 2:S16; K W Barañano, A L Hartman. Curr Treat Options Neurol. 2008; 10:410-9).

Furthermore, the potential of ACC inhibitors as antifungal agents and as antibacterial agents is well documented (L. Tong, H J Harwood Jr. Journal of Cellular Biochemistry 99:1476-1488, 2006). In addition, ACC inhibitors can be used to combat viral infections. It was discovered recently that viruses rely on the metabolic network of their cellular hosts to provide energy and building blocks for viral replication (Munger J, B D Bennett, A Parikh, X J Feng, J McArdle, H A Rabitz, T Shenk, J D Rabinowitz. *Nat. Biotechnol.* 2008; 26:1179-86). A flux measurement approach to quantify changes in metabolic activity induced by human cytomegalovirus (HCMV) elucidated that infection with HCMV markedly changed fluxes through much of the central carbon metabolism, including glycolysis, tricarboxylic acid cycle and fatty acid biosynthesis. Pharmacological inhibition of fatty acid biosynthesis suppressed the replication of two divergent enveloped viruses (HCMV and influenza A) indicating that fatty acid synthesis is essential for the replication. These examples show that acetyl-CoA fluxes and de novo fatty acid biosynthesis are critical to viral survival and propagation as the newly synthesized fatty acids and phospholipids are important for formation of viral envelopes. Changing the metabolic flux influences the absolute quantity of phospholipid available, the chemical composition and physical properties of the envelope negatively affect viral growth and replication. Hence, ACC inhibitors acting on key enzymes in the fatty acid metabolism, have the potential to be antiviral drugs.

AIM OF THE PRESENT INVENTION

The aim of the present invention is to provide new compounds, in particular new ethyne derivatives, which are active with regard to acetyl-CoA carboxylase enzyme(s).

Another aim of the present invention is to provide new compounds, in particular new ethyne derivatives, which are active with regard to ACC2.

A further aim of the present invention is to provide new compounds, in particular new ethyne derivatives, which have an inhibitory effect on the enzyme acetyl-CoA carboxylase enzyme(s) in vitro and/or in vivo and possess suitable pharmacological and pharmacokinetic properties to use them as medicaments.

A further aim of the present invention is to provide new compounds, in particular new ethyne derivatives, which have an inhibitory effect on the enzyme ACC2 in vitro and/or in vivo and possess suitable pharmacological and pharmacokinetic properties to use them as medicaments.

A further aim of the present invention is to provide effective ACC inhibitors, in particular for the treatment of metabolic disorders, for example of obesity and/or diabetes.

A further aim of the present invention is to provide methods for treating a disease or condition mediated by the inhibition of acetyl-CoA carboxylase enzyme(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular ethyne derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

Within the scope of the present invention it has now surprisingly been found that the new compounds of general formula (I) as described hereinafter exhibit an inhibiting activity with regard to enzyme(s) of acetyl-CoA carboxylases.

According to another aspect of the present invention it has been found that the new compounds of general formula (I) as described hereinafter exhibit an inhibiting activity with regard to ACC2.

Therefore, in a first aspect the present invention provides a compound of general formula (I)

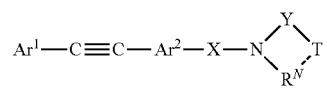

wherein
Ar¹ is selected from the group Ar¹-G1 consisting of aryl and heteroaryl all of which may be optionally substituted with one or more substituents $R^A$, wherein two substituents $R^A$ linked to adjacent C-atoms of Ar¹ may be connected with each other and together form a $C_{3-5}$-alkylene bridging group in which 1, 2 or 3-$CH_2$-groups may be replaced by O, C(=O), S, S(=O), S(=O)$_2$, NH or N($C_{1-4}$-alkyl)-, wherein the alkylene bridge may optionally be substituted by one or two $C_{1-3}$-alkyl groups; and $R^A$ is selected from the group $R^A$-G1 consisting of H, F, Cl, Br, I, CN, OH, —NO$_2$, $C_{1-6}$-alkyl, $C_{2-6}$-alkenyl, $C_{2-6}$-alkynyl, $C_{3-10}$-carbocyclyl, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{1-6}$-alkyl-S(=O)—, $C_{1-6}$-alkyl-S(=O)$_2$—, $C_{3-10}$-carbocyclyl-S—, $C_{3-10}$-carbocyclyl-$C_{1-3}$-alkyl-S—, $C_{1-4}$-alkyl-C(=O)—, $C_{3-10}$-carbocyclyl-C(=O)—, $R^{N1}R^{N2}N$—, $R^{N1}R^{N2}N$—$C_{2-3}$-alkyl-O—, $R^{N1}R^{N2}N$—C(=O)—, $R^{N1}R^{N2}N$—S(=O)$_2$—, $C_{1-6}$-alkyl-C(=O)—NR$^{N1}$—, $C_{1-6}$-alkyl-S(=O)$_2$—NR$^{N1}$—, $C_{1-6}$-alkyl-C(=O)—NR$^{N1}$—$C_{1-3}$-alkyl-, HO—C(=O)—, $C_{1-6}$-alkyl-O—C(=O)—, heterocyclyl, heterocyclyl-O—, heterocyclyl-$C_{1-3}$-alkyl, heterocyclyl-$C_{1-3}$-alkyl-O—, heterocyclyl-C(=O)—, aryl, aryl-$C_{1-3}$-alkyl, aryl-O—, aryl-$C_{1-3}$-alkyl-O—, heteroaryl, heteroaryl-$C_{1-3}$-alkyl, heteroaryl-O— and heteroaryl-$C_{1-3}$-alkyl-O—,
wherein in each carbocyclyl and heterocyclyl a —$CH_2$- group may optionally be replaced by —C(=O)— or —C(=CR$^{Alk}_2$)—, and
wherein each carbocyclyl and heterocyclyl may be optionally substituted with one or more $C_{1-4}$-alkyl, which may be optionally substituted with one or more substituents $R^C$, and
wherein each alkyl, carbocyclyl and heterocyclyl may be optionally substituted with one or more substituents $R^C$, and
wherein each heterocyclyl may be optionally substituted with aryl or heteroaryl, and wherein each aryl and heteroaryl group may be optionally substituted with one or more substituents L, $R^C$ is selected from the group $R^C$-G1 consisting of F, Cl, Br, CN, OH, $C_{1-4}$-alkyl-O—, $C_{3-7}$-cycloalkyl-O—, $C_{3-7}$-cycloalkyl-$C_{1-4}$-alkyl-O—, $H_2N$—, ($C_{1-4}$-alkyl)NH—, ($C_{1-4}$-alkyl)$_2$N—, $C_{1-4}$-alkyl-C(=O)—, $C_{1-4}$-alkyl-S(=O)$_2$—, HO—C(=O)— and $C_{1-4}$-alkyl-O—C(=O)—, wherein each alkyl or cycloalkyl may be optionally substituted with one or more substituents selected from F and OH; and $R^{N1}$ is selected from the group $R^{N1}$-G1 consisting of H, $C_{1-6}$-alkyl, $C_{3-10}$-carbocyclyl, $C_{3-10}$-carbocyclyl-$C_{1-3}$-alkyl, $C_{3-6}$-alkenyl, $C_{3-6}$-alkynyl, heterocyclyl, heterocyclyl-$C_{1-3}$-alkyl, aryl, aryl-$C_{1-3}$-alkyl, heteroaryl and heteroaryl-$C_{1-3}$-alkyl, wherein each carbocyclyl and heterocyclyl may be optionally substituted with one or more $C_{1-4}$-alkyl, and wherein in each carbocyclyl and heterocyclyl a —CH$_2$- group may optionally be replaced by —C(=O)—, and wherein each alkyl, carbocyclyl and heterocyclyl may be optionally substituted with one or more substituents $R^C$, and wherein each aryl and heteroaryl group may be optionally substituted with one or more substituents L, $R^{N2}$ is selected from the group $R^{N2}$-G1 consisting of H and $C_{1-6}$-alkyl; and $R^{Alk}$ is selected from the group $R^{Alk}$-G1 consisting of H and $C_{1-6}$-alkyl which may be substituted with one or more F atoms; and $Ar^2$ is selected from the group $Ar^2$-G1 consisting of phenyl and a 5- or 6-membered monocyclic aromatic carbocyclic ring system containing 1, 2 or 3 heteroatoms selected from N, O, or S, wherein all of the before mentioned groups may be optionally substituted with one or more substituents L; and L is selected from the group L-G1 consisting of F, Cl, Br, CN, OH, $C_{1-4}$-alkyl-, $C_{1-4}$-alkyl-O—, $C_{1-4}$-alkyl-S—, $C_{1-4}$-alkyl-S(=O)$_2$—, $H_2N$—, ($C_{1-4}$-alkyl)NH—, ($C_{1-4}$-alkyl)$_2$N— and heterocyclyl, wherein each alkyl may be optionally substituted with one or more F-atoms and/or with a substituent selected from OH, $C_{1-3}$-alkyl-O— and CN; and wherein two substituents L attached to an aryl or heteroaryl group may be linked to each other and form a $C_{2-5}$-alkylene bridging group in which 1 or 2 —CH$_2$-groups may be replaced by a group independently of each other selected from O, S, NH and N($C_{1-4}$-alkyl)-, wherein the $C_{2-5}$-alkylene bridging group is optionally be substituted by 1 or 2 $C_{1-3}$-alkyl groups; and X is selected from the group X-G1 consisting of a straight chain $C_{1-3}$-alkylene group which may be optionally substituted with one or more groups selected from $C_{1-3}$-alkyl and $C_{1-3}$-alkyl-O—$C_{1-3}$-alkyl, and wherein two alkyl substituents may be connected with each other and together form a $C_{1-5}$-alkylene bridging group in which 1 or 2 —CH$_2$-groups may be replaced by a group independently of each other selected from O, S, NH or N($C_{1-4}$-alkyl)-, wherein the $C_{1-5}$-alkylene bridging group may be optionally substituted by 1 or 2 $C_{1-3}$-alkyl groups; and Y is selected from the group Y-G1 consisting of —C(=O)— and —S(=O)$_2$—;

$R^N$ is selected from the group $R^N$-G1 consisting of H and $C_{1-3}$-alkyl;

T is selected from the group T-G1 consisting of $C_{1-6}$-alkyl, $C_{2-6}$-alkenyl, $C_{2-6}$-alkynyl, $C_{3-10}$-carbocyclyl, $C_{3-10}$-carbocyclyl-$C_{1-3}$-alkyl, $C_{1-6}$-alkyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, $C_{1-4}$-alkyl-C(=O)—, $C_{1-4}$-alkyl-S(=O)$_2$—, $R^{N1}R^{N2}$N—, $R^{N1}R^{N2}$—N—$C_{1-3}$-alkyl-, $R^{N1}R^{N2}$—N—CO—, $C_{1-4}$-alkyl-C(=O)—$R^{N2}$N—$C_{1-3}$-alkyl, heterocyclyl, aryl and heteroaryl, wherein in each carbocyclyl and heterocyclyl a —CH$_2$- group may optionally be replaced by —C(=O)—, and wherein each carbocyclyl and heterocyclyl may be optionally substituted with one or more $C_{1-4}$-alkyl, which may be optionally substituted with one or more substituents $R^C$, and wherein each alkyl, carbocyclyl and heterocyclyl may be optionally substituted with one or more substituents $R^C$, and wherein each aryl and heteroaryl group may be optionally substituted with one or more substituents L, or the groups T and $R^N$ may be connected with each other and together form a group which is selected from the group T-$R^N$-G1 consisting of $C_{2-5}$-alkylene which may be optionally substituted with one or more substituents selected from F, Cl, Br, OH, CN, $C_{1-4}$-alkyl, $C_{3-10}$-carbocyclyl, $C_{3-10}$-carbocyclyl-$C_{1-3}$-alkyl, $C_{1-4}$-alkyl-O—, $C_{3-7}$-cycloalkyl-O—, $C_{3-10}$-carbocyclyl-$C_{1-3}$-alkyl-O—, $H_2N$—, ($C_{1-4}$-alkyl)NH—, ($C_{1-4}$-alkyl)$_2$N—, $C_{1-4}$-alkyl-C(=O)—, $C_{1-4}$-alkyl-S(=O)$_2$—, HO—C(=O)— and $C_{1-4}$-alkyl-O—C(=O)—, wherein each alkyl or carbocyclyl may be optionally substituted with one or more substituents selected from $R^C$, including any tautomers and stereoisomers thereof, or a salt thereof or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase enzyme(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a pharmaceutically acceptable salt thereof for the manufacture of a medicament for a therapeutic method as described hereinbefore and hereinafter.

According to another aspect of the invention, there is provided a compound of the general formula (I) or a pharmaceutically acceptable salt thereof for a therapeutic method as described hereinbefore and hereinafter.

In a further aspect this invention relates to a method for treating a disease or condition mediated by the inhibition of acetyl-CoA carboxylase enzyme(s) in a patient that includes the step of administering to the patient in need of such treatment a therapeutically effective amount of a compound of the general formula (I) or a pharmaceutically acceptable salt thereof in combination with a therapeutically effective amount of one or more additional therapeutic agents.

In a further aspect this invention relates to a use of a compound of the general formula (I) or a pharmaceutically acceptable salt thereof in combination with one or more additional therapeutic agents for the treatment or prevention of diseases or conditions which are mediated by the inhibition of the enzyme(s) acetyl-CoA carboxylase.

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $Ar^1$, $Ar^2$, X, Y, $R^N$, T, $R^A$, $R^C$, $R^{N1}$, $R^{N2}$, $R^{Alk}$, L, T, are defined as above and hereinafter. If residues, substituents, or groups occur several times in a compound, as for example $R^C$, $R^{N1}$, $R^{N2}$ or L, they may have the same or different meanings. Some preferred meanings of individual groups and substituents of the compounds according to the invention will be given hereinafter. Any and each of these definitions may be combined with each other.

$Ar^1$:

$Ar^1$-G1:

The group $Ar^1$ is preferably selected from the group $Ar^1$-G1 as defined hereinbefore and hereinafter.

$Ar^1$-G2:

In one embodiment the group $Ar^1$ is selected from the group $Ar^1$-G2 consisting of phenyl, dihydronaphthyl, tetrahydronaphthyl, naphthyl and a 5- or 6-membered monocyclic or 9- or 10-membered bicyclic-ring system containing 1, 2, 3 or 4 heteroatoms selected from N, O, S, or S(O)$_r$ with r=1 or 2 wherein at least one of the heteroatoms is part of an aromatic ring, and wherein all of the before mentioned groups may be optionally substituted with one or more substituents $R^A$, particularly wherein all of the before mentioned groups may be optionally substituted with a substituent $R^A$ and optionally one or more substituents L, and wherein two substituents $R^A$ linked to adjacent C-atoms of $Ar^1$ may be connected with each other and together form a $C_{3-5}$-alkylene bridging group in which 1, 2 or 3 CH$_2$-groups may be replaced by O, C(=O), S, S(=O), S(=O)$_2$, NH or N(C$_{1-4}$-alkyl)-, wherein the alkylene bridging group may optionally be substituted by one or two $C_{1-3}$-alkyl groups.

$Ar^1$-G3:

In another embodiment the group $Ar^1$ is selected from the group $Ar^1$-G3 consisting of phenyl, naphthyl, pyridyl, 2H-pyridin-2-onyl, pyrimidinyl, pyridazinyl, pyrazinyl, furanyl, thienyl, pyrrolyl, imidazolyl, triazolyl, oxazolyl, isoxazolyl, pyrazolyl, thiazolyl, quinolinyl, isoquinolinyl, indolyl, benzofuranyl, benzoimidazolyl, benzooxazolyl, benzotriazolyl, 2,3-dihydrobenzofuranyl, benzo[1,3]dioxolyl, 2,3-dihydrobenzo[1,4]dioxinyl and 3,4-dihydro-2H-benzo[b][1,4]dioxepinyl wherein the before mentioned bicyclic groups preferably are linked to the —C≡C— group of the core structure of the formula (I) via an aromatic or heteroaromatic ring of the bicyclic group, and wherein all of the before mentioned mono- and bicyclic groups may be optionally substituted with one or more substituents $R^A$, particularly wherein all of the before mentioned mono- or bicyclic groups may be optionally substituted with a substituent $R^A$ and optionally one or more substituents L.

$Ar^1$-G4:

In another embodiment the group $Ar^1$ is selected from the group $Ar^1$-G4 consisting of phenyl, naphthyl, pyridyl, 2H-pyridin-2-onyl, pyrimidinyl, pyridazinyl, pyrazinyl, furanyl, oxazolyl, isoxazolyl, pyrazolyl, thiazolyl, quinolinyl, indolyl, benzofuranyl, 2,3-dihydrobenzofuranyl, benzo[1,3]dioxolyl, 2,3-dihydro-benzo[1,4]dioxinyl and 3,4-dihydro-2H-benzo[b][1,4]dioxepinyl, wherein the before mentioned bicyclic groups preferably are linked to the —C≡C— group of the core structure of the formula (I) via an aromatic or heteroaromatic ring of the bicyclic group, and wherein all of the before mentioned mono- and bicyclic groups may be optionally substituted with one or more substituents $R^A$, particularly wherein all of the before mentioned mono- or bicyclic groups may be optionally substituted with a substituent $R^A$ and optionally one or more substituents L.

$Ar^1$-G5:

In another embodiment the group $Ar^1$ is selected from the group $Ar^1$-G5 consisting of:

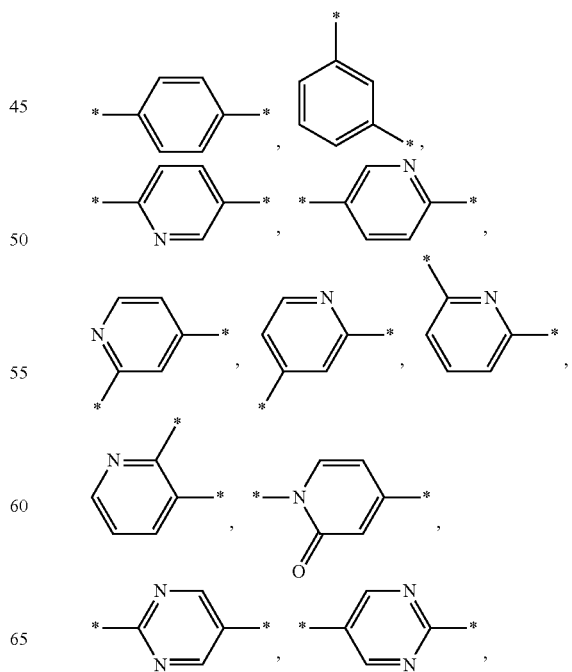

-continued

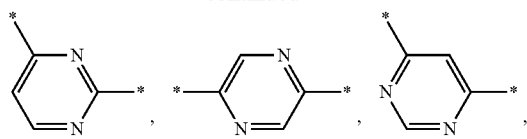
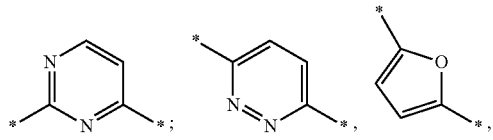
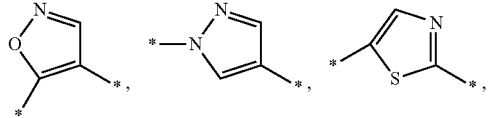
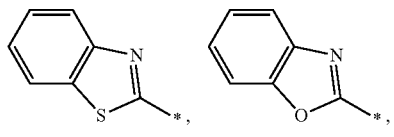
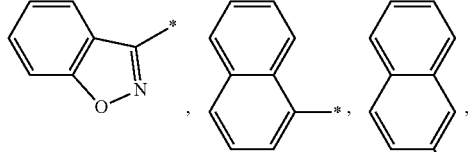
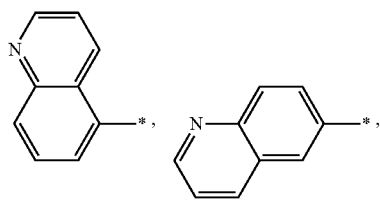

-continued

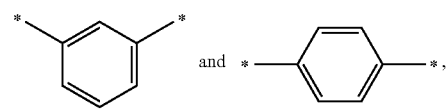

wherein the asterisk to the right side of each cyclic group indicates the bond which is connected to the —C≡C— group of the core structure of the formula (I), and if existing the asterisk to the left side of each cyclic group indicates the bond which is connected to a substituent $R^A$ or H, and in addition each of the before mentioned cyclic groups is optionally substituted with one or more further substituents $R^A$, in particular one or more substituents L, and the substituent $R^N$ is defined as hereinbefore and hereinafter.

$Ar^1$-G6:

In another embodiment the group $Ar^1$ is selected from the group $Ar^1$-G6 consisting of:

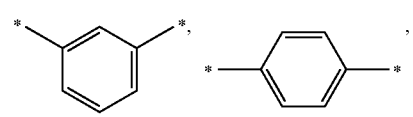

wherein the asterisk to the right side of the cyclic group indicates the bond which is connected to the —C≡C— group of the core structure of the formula (I), and the asterisk to the left side of the cyclic group indicates the bond which is connected to a substituent $R^A$ or H, and in addition the before mentioned cyclic group is optionally substituted with one or more further substituents $R^A$, in particular one or more substituents L.

Examples of members of the group $Ar^1$-G6 are without being limited to it:

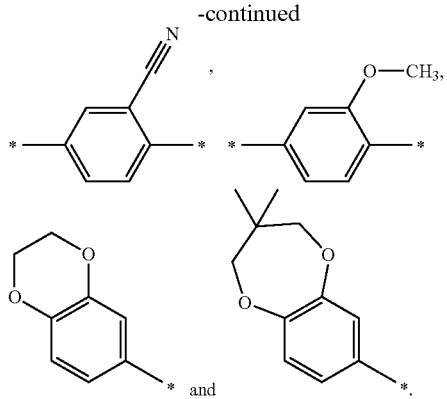

Ar¹-G7:

In another embodiment the group Ar¹ is selected from the group Ar¹-G7 consisting of 6-membered aromatic rings containing 1 or 2 N-atoms, wherein said rings may be optionally substituted with one or more substituents $R^A$, particularly wherein said rings may be optionally substituted with a substituent $R^A$ and optionally one or more substituents L. Examples of members of the group Ar¹-G7 are:

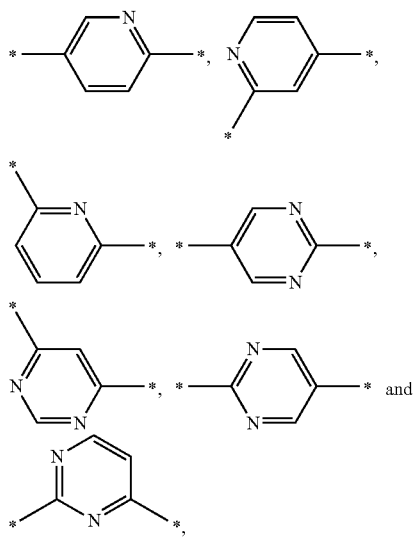

wherein the asterisk to the right side of each cyclic group indicates the bond which is connected to the —C≡C— group of the core structure of the formula (I), and the asterisk to the left side of each cyclic group indicates the bond which is connected to a substituent $R^A$, and in addition each of the before mentioned cyclic groups is optionally substituted with one or more further substituents $R^A$, in particular one or more substituents L.

Preferred examples of members of the group Ar¹-G7 are without being limited to it:

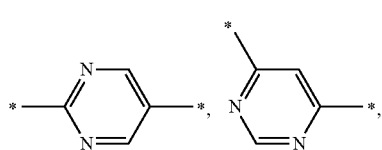

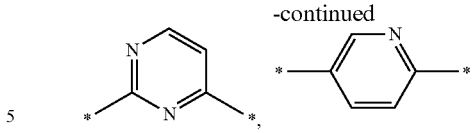

$R^A$:
$R^A$-G1:
The group $R^A$ is preferably selected from the group $R^A$-G1 as defined hereinbefore and hereinafter,
$R^A$-G2:

In another embodiment the group $R^A$ is selected from the group $R^A$-G2 consisting of H, F, Cl, Br, I, CN, OH, NO₂, $C_{1-6}$-alkyl, $C_{3-10}$-carbocyclyl, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, $C_{1-4}$-alkyl-C(=O)—, $R^{N1}R^{N2}N$—, $R^{N1}R^{N2}N$—$C_{2-3}$-alkyl-O—, $R^{N1}R^{N2}N$—C(=O)—, HO—C(=O)—, $C_{1-6}$-alkyl-O—C(=O)—, heterocyclyl, heterocyclyl-O—, heterocyclyl-$C_{1-3}$-alkyl, heterocyclyl-$C_{1-3}$-alkyl-O—, heterocyclyl-C(=O)—, aryl, aryl-$C_{1-3}$-alkyl, aryl-O—, aryl-$C_{1-3}$-alkyl-O—, heteroaryl, heteroaryl-$C_{1-3}$-alkyl, heteroaryl-O— and heteroaryl-$C_{1-3}$-alkyl-O—;

wherein heterocyclyl is defined as hereinbefore and hereinafter, or alternatively each heterocyclyl is selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroquinolinyl, dihydroisoquinolinyl, dihydroindolyl, dihydroisoindolyl, oxetanyl, tetrahydrofuranyl and tetrahydropyranyl, or from the group consisting of

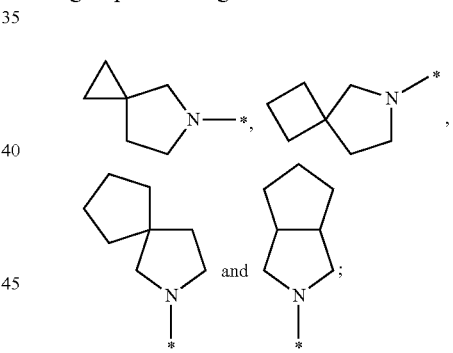

and
wherein carbocyclyl is defined as hereinbefore and hereinafter, or each carbocyclyl is preferably selected from $C_{3-7}$-cycloalkyl, indanyl and tetrahydronaphthyl; and
wherein heteroaryl is defined as hereinbefore and hereinafter, or each heteroaryl is preferably selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, benzofuranyl, indolyl, quinolinyl and indazolyl; and
wherein in each heterocyclyl and carbocyclyl a —CH₂-group may optionally be replaced by —C(=O)— or —C(=CR$^{Alk}$₂)—; and
wherein each carbocyclyl and heterocyclyl may be optionally substituted with one or more $C_{1-3}$-alkyl, which may be substituted as defined hereinafter, and
wherein each alkyl, carbocyclyl and heterocyclyl may be optionally substituted with one or more F atoms; and wherein each alkyl, carbocyclyl and heterocyclyl may be optionally substituted with 1, 2 or 3 substituents $R^C$, which are independently of each other selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH— and ($C_{1-3}$-alkyl)$_2$N—, HO—C(=O)— and $C_{1-4}$-alkyl-O—C(=O)—; and wherein each $R^{N1}$ is selected from the group $R^{N1}$-G1, $R^{N1}$-G2 or $R^{N1}$-G3 as defined hereinbefore and hereinafter; and each $R^{N2}$ is selected from the group $R^{N2}$-G1 or $R^{N2}$-G2 as defined hereinbefore and hereinafter; and wherein each carbocyclyl or heterocyclyl may be optionally substituted with an aryl or heteroaryl group, in particular with phenyl or pyridyl, and wherein each aryl and heteroaryl group may be optionally substituted with one or more substituents L, wherein L is selected from the groups L-G1, L-G2 or L-G3 as defined hereinbefore and hereinafter.

$R^A$-G2a:

In another embodiment the group $R^A$ is selected from the group $R^A$-G2a consisting of $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, heterocyclyl-O— and heterocyclyl-$C_{1-3}$-alkyl-O—;

wherein heterocyclyl is defined as hereinbefore and hereinafter, or each heterocyclyl is preferably selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroquinolinyl, dihydroisoquinolinyl, dihydroindolyl, dihydroisoindolyl, oxetanyl, tetrahydrofuranyl and tetrahydropyranyl, or from the group consisting of

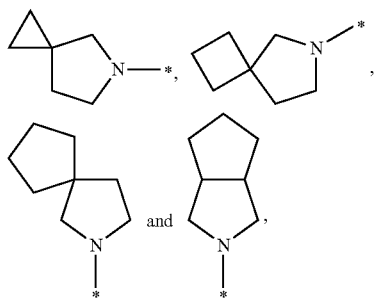

and wherein carbocyclyl is defined as hereinbefore and hereinafter, or each carbocyclyl is preferably selected from $C_{3-7}$-cycloalkyl, indanyl and tetrahydronaphthyl; and wherein in each heterocyclyl and carbocyclyl a $CH_2$-group may optionally be replaced by —C(=O)— or —C(=$CR^{Alk}_2$)—; and wherein each carbocyclyl and heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with 1, 2 or 3 substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH— and ($C_{1-3}$-alkyl)$_2$N—, HO—C(=O)— and $C_{1-4}$-alkyl-O—C(=O)—.

$R^A$-G2b:

In another embodiment the group $R^A$ is selected from the group $R^A$-G2b consisting of $C_{1-6}$-alkyl, $C_{3-10}$-carbocyclyl, $C_{3-10}$-carbocyclyl-$C_{1-3}$-alkyl, heterocyclyl, heterocyclyl-$C_{1-3}$-alkyl, aryl, aryl-$C_{1-3}$-alkyl, heteroaryl and heteroaryl-$C_{1-3}$-alkyl;

wherein heterocyclyl is defined as hereinbefore and hereinafter, or each heterocyclyl is preferably selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroquinolinyl, dihydroisoquinolinyl, dihydroindolyl, dihydroisoindolyl, oxetanyl, tetrahydrofuranyl and tetrahydropyranyl, or from the group consisting of

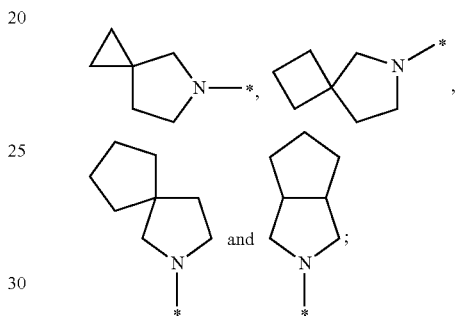

and wherein carbocyclyl is defined as hereinbefore and hereinafter, or each carbocyclyl is preferably selected from $C_{3-7}$-cycloalkyl, indanyl and tetrahydronaphthyl; and wherein heteroaryl is defined as hereinbefore and hereinafter, or each heteroaryl is preferably selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, benzofuranyl, indolyl, quinolinyl and indazolyl; and wherein in each heterocyclyl and carbocyclyl a $CH_2$-group may optionally be replaced by —C(=O)— or —C(=$CR^{Alk}_2$)—; and wherein each carbocyclyl and heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with 1, 2 or 3 substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH— and ($C_{1-3}$-alkyl)$_2$N—, HO—C(=O)— and $C_{1-4}$-alkyl-O—C(=O)—; and wherein each carbocyclyl or heterocyclyl may be optionally substituted with an aryl or heteroaryl group, in particular with phenyl or pyridyl; and wherein each aryl and heteroaryl group may be optionally substituted with one or more substituents L, wherein L is selected from the groups L-G1, L-G2 or L-G3 as defined hereinbefore and hereinafter.

R$^A$-G3:

In another embodiment the group R$^A$ is selected from the group R$^A$-G3 consisting of F, Cl, Br, I, CN, NO$_2$, C$_{1-6}$-alkyl, C$_{3-10}$-carbocyclyl-, C$_{3-10}$-carbocyclyl-C$_{1-3}$-alkyl, C$_{1-6}$-alkyl-O—, C$_{3-6}$-alkenyl-O—, C$_{3-6}$-alkynyl-O—, C$_{1-4}$-alkyl-S—, C$_{3-10}$-carbocyclyl-O—, C$_{3-10}$-carbocyclyl-C$_{1-3}$-alkyl-O—, C$_{1-4}$-alkyl-C(=O)—, R$^{N1}$R$^{N2}$N—, R$^{N1}$R$^{N2}$N—C$_{2-3}$-alkyl-O—, R$^{N1}$R$^{N2}$N—C(=O)—, HO—C(=O)—, C$_{1-4}$-alkyl-O—C(=O)—, heterocyclyl, heterocyclyl-C$_{1-3}$-alkyl, heterocyclyl-O—, heterocyclyl-C$_{1-3}$-alkyl-O—, heterocyclyl-C(=O)—, phenyl, phenyl-O—, phenyl-C$_{1-3}$-alkyl-, phenyl-C$_{1-3}$-alkyl-O—, heteroaryl, heteroaryl-C$_{1-3}$-alkyl, heteroaryl-O— and heteroaryl-C$_{1-3}$-alkyl-O—;

wherein each heterocyclyl is selected from the group consisting of azetidinyl, pyrrolidinyl, piperidinyl, piperazinyl, N—C$_{1-4}$-alkyl-piperazin-1-yl, N—C$_{1-4}$-alkylsulfonyl-piperazin-1-yl, morpholinyl, dihydroisoindolyl, oxetanyl, tetrahydrofuranyl and tetrahydropyranyl, or from the group consisting of

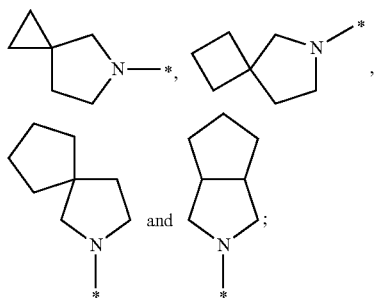

and wherein carbocyclyl is defined as hereinbefore and hereinafter, or each carbocyclyl is preferably selected from C$_{3-6}$-cycloalkyl, indanyl and tetrahydronaphthyl; most preferably carbocyclyl denotes C$_{3-6}$-cycloalkyl; and wherein in each carbocyclyl, pyrrolidinyl and piperidinyl a CH$_2$-group may optionally be replaced by —C(=O)— or —C(=CR$^{Alk}_2$)—; and wherein each heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, indazolyl, benzofuranyl, indolyl and quinolinyl; and wherein each carbocyclyl or heterocyclyl may be optionally substituted with one or more C$_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with one or two substituents R$^C$, which are selected from the group R$^C$-G1, R$^C$-G2 or R$^C$-G3 as defined hereinbefore and hereinafter; even more preferably R$^C$ is selected from Cl, Br, CN, OH, C$_{1-3}$-alkyl-O—, C$_{3-6}$-cycloalkyl-O—, HO—C$_{1-3}$-alkyl-O—, H$_2$N—, (C$_{1-3}$-alkyl)NH—, (C$_{1-3}$-alkyl)$_2$N—, HO—C(=O)— and C$_{1-4}$-alkyl-O—C(=O)—; and wherein each R$^{N1}$ is selected from the group R$^{N1}$-G1, R$^{N1}$-G2 or R$^{N1}$-G3; and each R$^{N2}$ is selected from the group R$^{N2}$-G1 or R$^{N2}$-G2 as defined hereinbefore and hereinafter; and wherein each carbocyclyl and heterocyclyl may be optionally substituted with an aryl or heteroaryl group, in particular with phenyl or pyridyl; and wherein each phenyl and heteroaryl group may be optionally substituted with one or more substituents L, wherein L is selected from the groups L-G1, L-G2 or L-G3 as defined hereinbefore and hereinafter.

R$^A$-G4:

In another embodiment the group R$^A$ is selected from the group R$^A$-G4 consisting of F, Cl, Br, I, CN, NO$_2$, C$_{1-6}$-alkyl, C$_{3-10}$-carbocyclyl-, C$_{3-10}$-carbocyclyl-C$_{1-3}$-alkyl, C$_{1-5}$-alkyl-O—, C$_{3-5}$-alkenyl-O—, C$_{3-5}$-alkynyl-O—, C$_{3-10}$-carbocyclyl-O—, C$_{3-10}$-carbocyclyl-C$_{1-3}$-alkyl-O—, R$^{N1}$R$^{N2}$N—, R$^{N1}$R$^{N2}$N—C(=O)—, heterocyclyl, heterocyclyl-C$_{1-3}$-alkyl, heterocyclyl-O—, heterocyclyl-C$_{1-3}$-alkyl-O—, heterocyclyl-C(=O)—, phenyl, phenyl-O—, phenyl-C$_{1-3}$-alkyl-, phenyl-C$_{1-3}$-alkyl-O—, heteroaryl, heteroaryl-C$_{1-3}$-alkyl, heteroaryl-O— and heteroaryl-C$_{1-3}$-alkyl-O—;

wherein carbocyclyl is defined as hereinbefore and hereinafter, or each carbocyclyl is preferably selected from C$_{3-6}$-cycloalkyl, indanyl and tetrahydronaphthyl; most preferably carbocyclyl denotes C$_{3-6}$-cycloalkyl; and wherein each heterocyclyl is selected from the group consisting of azetidinyl, pyrrolidinyl, piperidinyl, piperazinyl, N—C$_{1-4}$-alkyl-piperazin-1-yl, N—C$_{1-4}$-alkylsulfonyl-piperazin-1-yl, morpholinyl, dihydroisoindolyl, oxetanyl, tetrahydrofuranyl and tetrahydropyranyl, or from the group consisting of

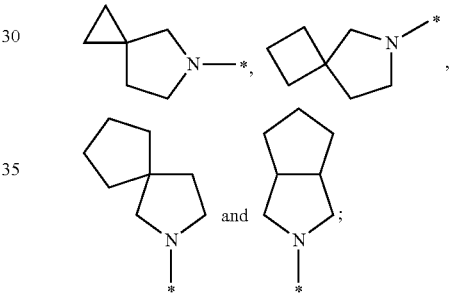

and wherein in each carbocyclyl and heterocyclyl a CH$_2$-group may optionally be replaced by —C(=O)— or —C(=CR$^{Alk}_2$)—; and wherein each heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, indazolyl, benzofuranyl, indolyl, and quinolinyl; and wherein each carbocyclyl and heterocyclyl may be optionally substituted with one or more C$_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with one or two substituents R$^C$, which are selected from the group R$^C$-G1, R$^C$-G2 or R$^C$-G3 as defined hereinbefore and hereinafter; even more preferably R$^C$ is selected from Cl, Br, CN, OH, C$_{1-3}$-alkyl-O—, C$_{3-6}$-cycloalkyl-O—, HO—C$_{1-3}$-alkyl-O—, H$_2$N—, (C$_{1-3}$-alkyl)NH—, (C$_{1-3}$-alkyl)$_2$N—, HO—C(=O)— and C$_{1-4}$-alkyl-O—C(=O)—; and wherein each R$^{N1}$ is selected from the group R$^{N1}$-G1, R$^{N1}$-G2 or R$^{N1}$-G3; and each R$^{N2}$ is selected from the group R$^{N2}$-G1 or R$^{N2}$-G2 as defined hereinbefore and hereinafter; and wherein each carbocyclyl and heterocyclyl may be optionally substituted with an aryl or heteroaryl group, in particular with phenyl or pyridyl; and wherein each phenyl and heteroaryl group may be optionally substituted with one or more substituents L, wherein L is selected from the groups L-G1, L-G2 or L-G3 as defined hereinbefore and hereinafter.

$R^A$-G5:

In another embodiment the group $R^A$ is selected from the group $R^A$-G5 consisting of F, Cl, Br, I, ON, $C_{1-5}$-alkyl, $C_{3-6}$-cycloalkyl, $C_{1-5}$-alkyl-O—, $C_{3-6}$-cycloalkyl-O—, $C_{3-6}$-cycloalkyl-$C_{1-3}$-alkyl-O—, $R^{N1}R^{N2}N$—, phenyl, phenyl-O—, phenyl-$CH_2$—O—, heteroaryl, heteroaryl-O— and heteroaryl-$CH_2$—O—; and wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a $CH_2$-group may optionally be replaced by —O—; and wherein each alkyl and cycloalkyl may be optionally substituted with one or two substituents $R^C$, wherein $R^C$ is defined as hereinbefore and hereinafter; preferably $R^C$ is selected from the group consisting of Cl, Br, ON, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-3}$-alkyl-O—C(=O)—; and wherein each $R^{N1}$ is selected from the group $R^{N1}$-G1, $R^{N1}$-G2 or $R^{N1}$-G3 as defined hereinbefore and hereinafter; preferably $R^{N1}$ is selected from the group consisting of H, $C_{1-6}$-alkyl, $C_{3-6}$-cycloalkyl, $C_{3-6}$-cycloalkyl-$CH_2$— and phenyl-$CH_2$—, wherein each cycloalkyl may be optionally substituted with one or more $C_{1-4}$-alkyl, and wherein each alkyl and cycloalkyl may be optionally substituted with one or more substituents selected from F, and wherein each alkyl and cycloalkyl may be optionally substituted with a substituent selected from OH, $C_{1-3}$-alkyl-O— and $H_2N$—; and wherein each $R^{N2}$ is selected from the group $R^{N2}$-G1 or $R^{N2}$-G2 as defined hereinbefore and hereinafter; and wherein heteroaryl is defined as hereinbefore and hereinafter; preferably heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, benzofuranyl, indolyl and quinolinyl; and wherein each phenyl and heteroaryl group may be optionally substituted with one or more substituents L, wherein L is selected from the groups L-G1, L-G2 or L-G3 as defined hereinbefore and hereinafter.

$R^A$-G5a:

In another embodiment the group $R^A$ is selected from the group $R^A$-G5a consisting of $C_{1-5}$-alkyl-O—, $C_{3-5}$-alkenyl-O—, $C_{3-5}$-alkynyl-O—, $C_{3-6}$-cycloalkyl-O— and $C_{3-6}$-cycloalkyl-$C_{1-3}$-alkyl-O—;

wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a $CH_2$-group may optionally be replaced by —O—; and wherein each alkyl and cycloalkyl may be optionally substituted with one or two substituents $R^C$, wherein $R^C$ is defined as hereinbefore and hereinafter; preferably $R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-3}$-alkyl-O—C(=O)—.

$R^A$-G5b:

In another embodiment the group $R^A$ is selected from the group $R^A$-G5b consisting of $C_{1-5}$-alkyl, $C_{3-6}$-cycloalkyl, phenyl and heteroaryl;

wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a $CH_2$-group may optionally be replaced by —O—; and wherein each alkyl and cycloalkyl may be optionally substituted with one or two substituents $R^C$, wherein $R^C$ is defined as hereinbefore and hereinafter; preferably $R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-3}$-alkyl-O—C(=O)—; and wherein heteroaryl is defined as hereinbefore and hereinafter; preferably heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, benzofuranyl, indolyl and quinolinyl; and wherein each phenyl and heteroaryl group may be optionally substituted with one or more substituents L, wherein L is selected from the groups L-G1, L-G2 or L-G3 as defined hereinbefore and hereinafter.

In the embodiments with regard to $R^A$ as described hereinbefore and hereinafter it is to be understood that the double or triple bond in the groups $C_{3-n}$-alkenyl-O— and $C_{3-n}$-alkynyl-O— (with n being an integer) is preferably not conjugated with the O-atom of that group.

$R^A$-G6:

In another embodiment the group $R^A$ is selected from the group $R^A$-G6 consisting of F, Cl, Br, I, CN, methyl, ethyl, n-propyl, i-propyl, n-butyl, t-butyl, $F_3C$—, HO—$CH_2CH_2$—,

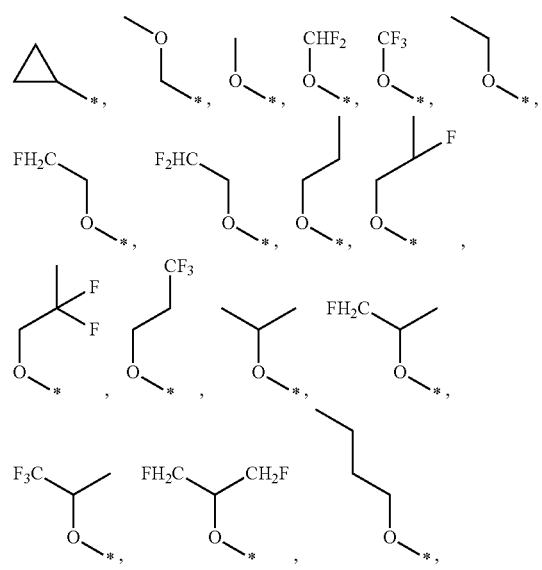

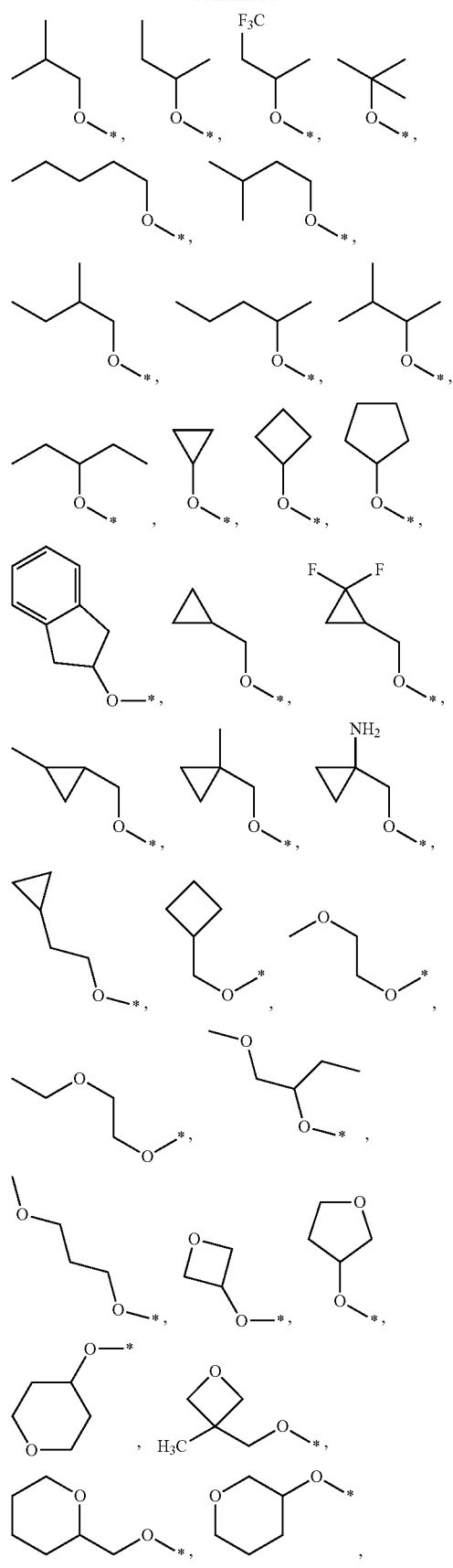
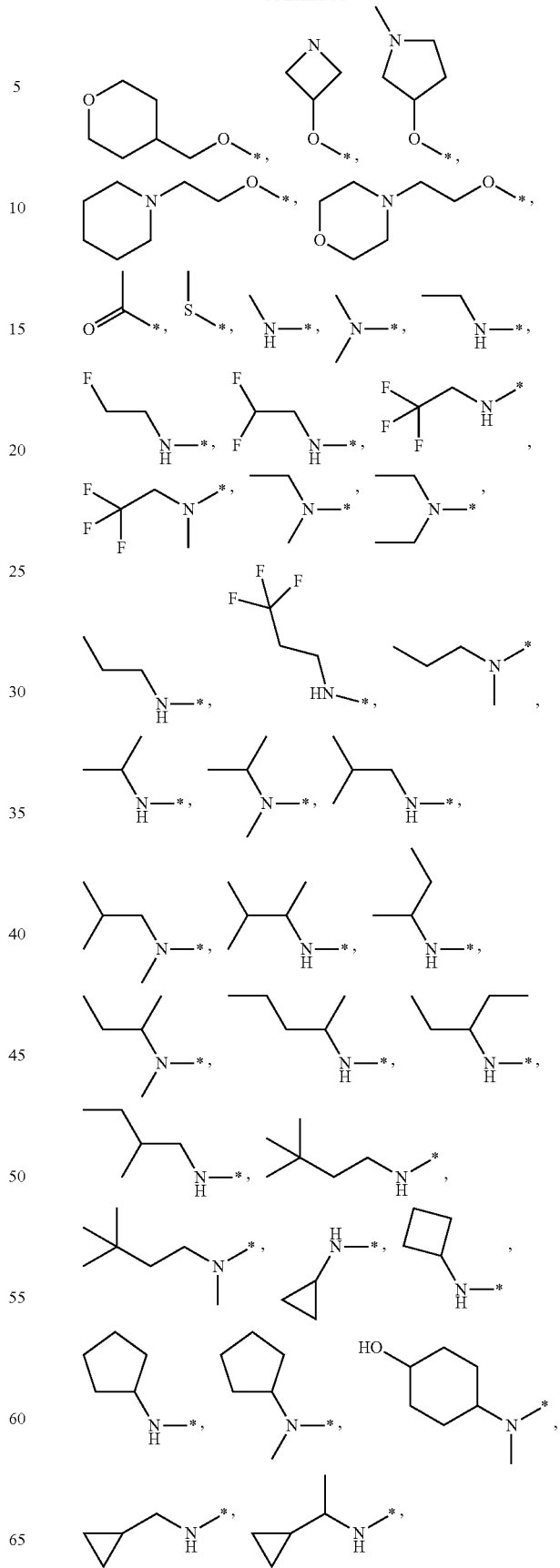

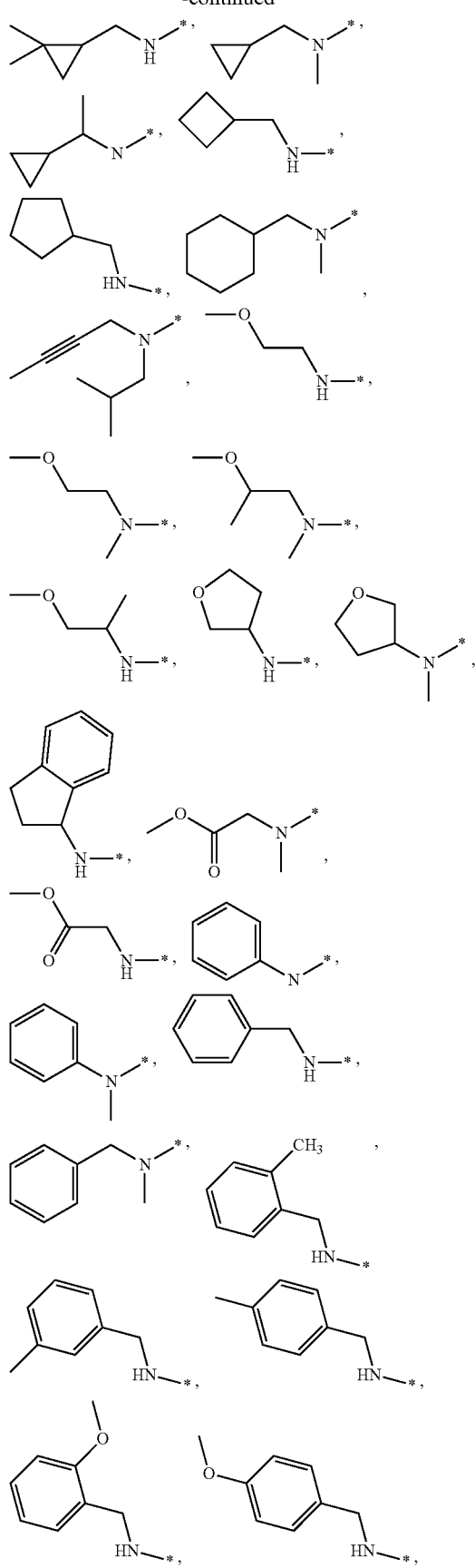
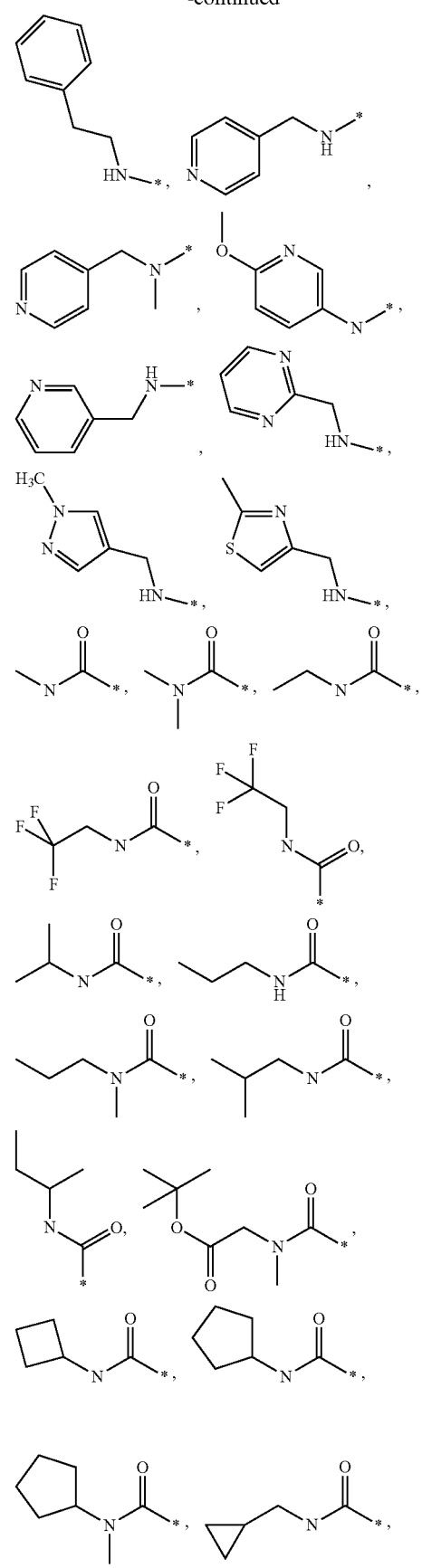

-continued
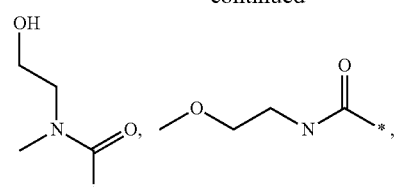
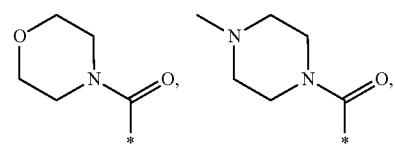
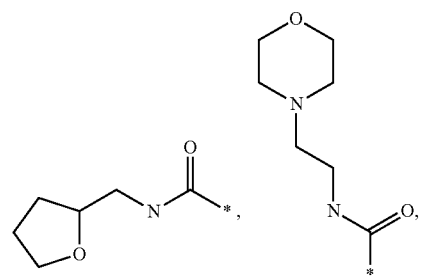
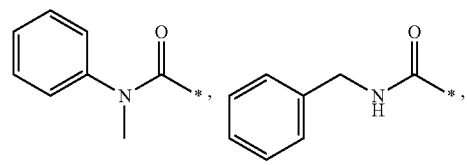
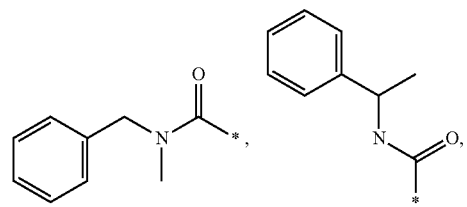
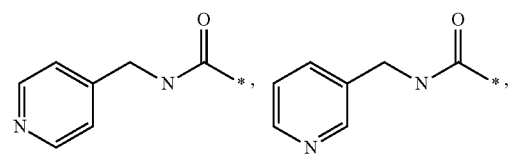
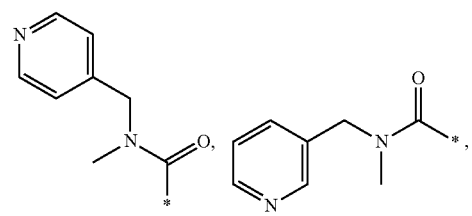
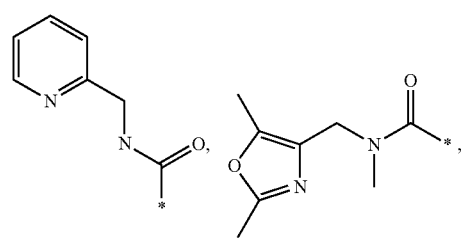
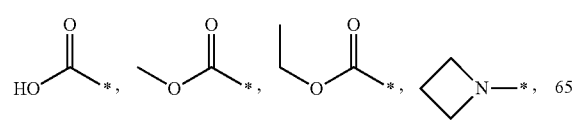
-continued
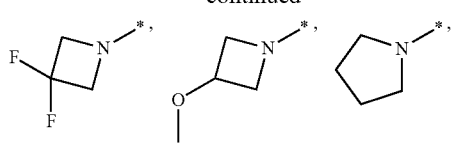
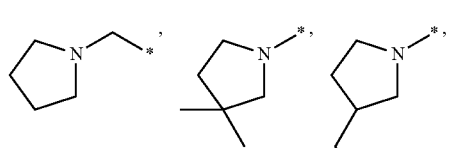
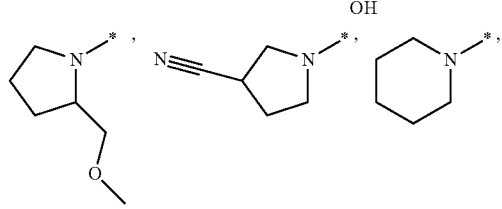
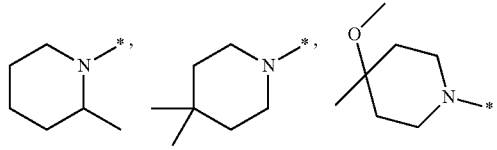
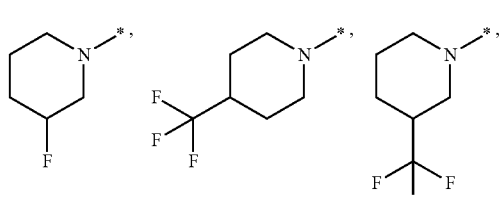
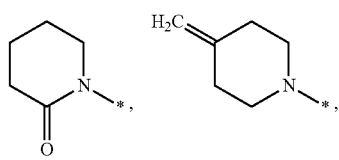
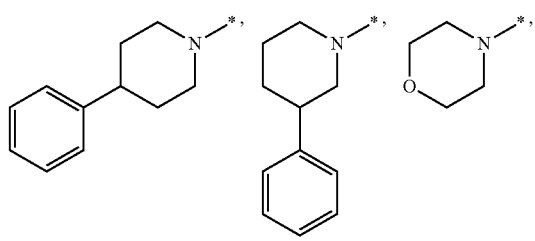
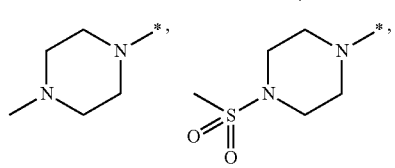
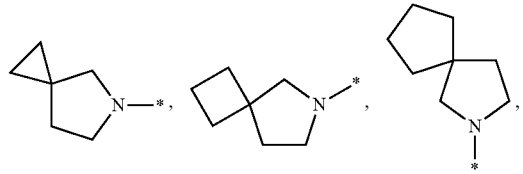

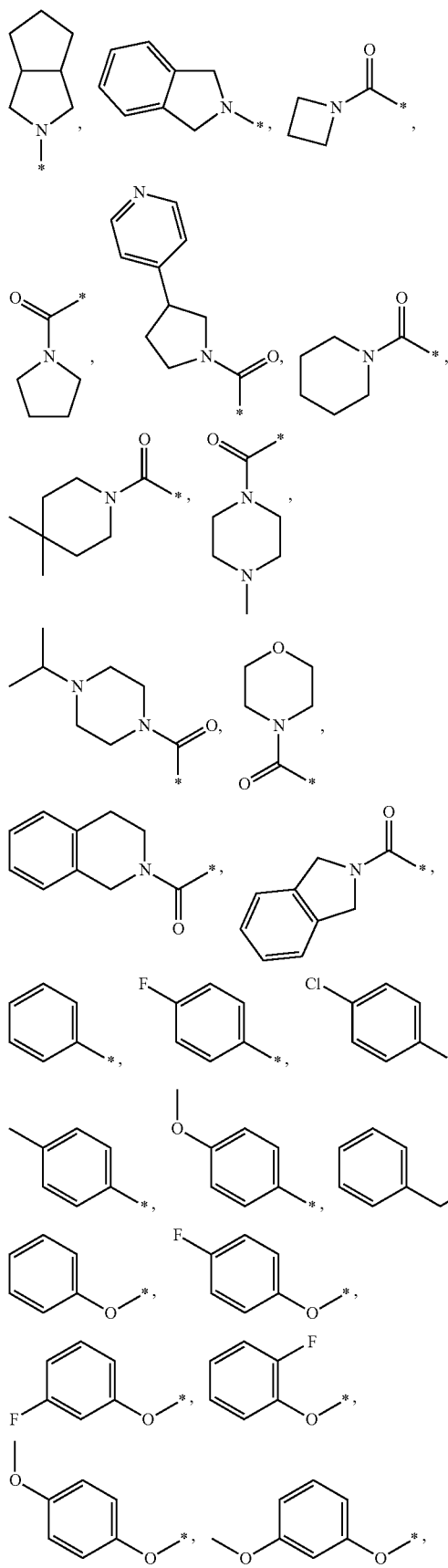
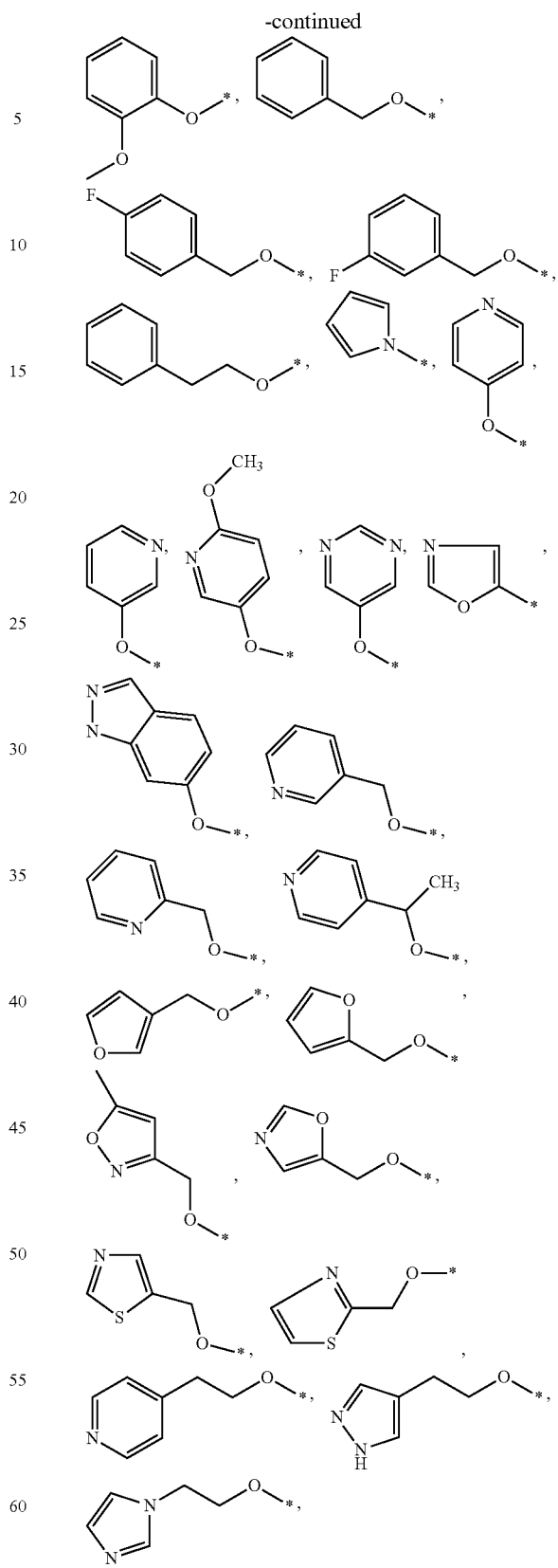
wherein each alkyl group and each cycloalkyl and heterocyclyl ring may be optionally substituted with one or more F atoms; and wherein each phenyl and heteroaryl ring may be optionally substituted with one or more substituents L.

$R^A$-G7:

In another preferred embodiment the group $R^A$ is selected from the group $R^A$-G7 consisting of

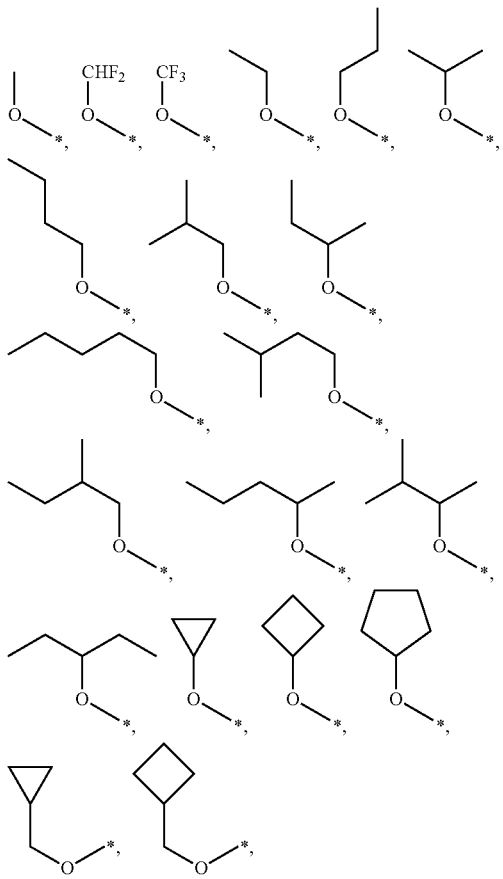

wherein each alkyl or cycloalkyl group may optionally be substituted with one or more F atoms.

$R^C$ $R^C$-G1:

The group $R^C$ is preferably selected from the group $R^C$-G1 as defined hereinbefore and hereinafter.

$R^C$-G2:

In another embodiment the group $R^C$ is selected from the group $R^C$-G2 consisting of F, Cl, Br, CN, OH, $C_{1-4}$-alkyl-O—, $C_{3-6}$-cycloalkyl-O—, $C_{3-6}$-cycloalkyl-CH$_2$—O—, $H_2N$—, $(C_{1-3}$-alkyl)NH—, $(C_{1-3}$-alkyl)$_2$N—, $C_{1-3}$-alkyl-C(=O)—, $C_{1-3}$-alkyl-S(=O)$_2$—, HO—C(=O)— and $C_{1-4}$-alkyl-O—C(=O)—, wherein each alkyl or cycloalkyl may be optionally substituted with one or more substituents selected from F and OH.

$R^C$-G3:

In another embodiment the group $R^C$ is selected from the group $R^C$-G3 consisting of F, Cl, Br, CN, OH, $C_{1-3}$-alkyl-O—, $C_{3-6}$-cycloalkyl-O—, $H_2N$—, $(C_{1-3}$-alkyl)NH—, $(C_{1-3}$-alkyl)$_2$N—, $C_{1-3}$-alkyl-C(=O)—, $C_{1-3}$-alkyl-S(=O)$_2$—, HO—C(=O)— and $C_{1-3}$-alkyl-O—C(=O)—, wherein each alkyl may be optionally substituted with one or more F-atoms and/or may be substituted with OH.

$R^{N1}$ $R^{N1}$-G1:

The group $R^{N1}$ is preferably selected from the group $R^{N1}$-G1 as defined hereinbefore and hereinafter.

$R^{N1}$-G2:

In another embodiment the group $R^{N1}$ is selected from the group $R^{N1}$-G2 consisting of H, $C_{1-6}$-alkyl, $C_{3-10}$-carbocyclyl, $C_{3-10}$-carbocyclyl-$C_{1-3}$-alkyl, $C_{3-6}$-alkynyl, heterocyclyl, heterocyclyl-$C_{1-3}$-alkyl, phenyl, phenyl-$C_{1-3}$-alkyl, heteroaryl and heteroaryl-$C_{1-3}$-alkyl;

wherein carbocyclyl is defined as hereinbefore and hereinafter, or each carbocyclyl is preferably selected from $C_{3-7}$-cycloalkyl, indanyl and tetrahydrofuranyl; and wherein heterocyclyl is defined as hereinbefore and hereinafter, or each heterocyclyl is preferably selected from tetrahydrofuranyl, tetrahydropyranyl, pyrrolidinyl, piperidinyl, piperazinyl and morpholinyl; and wherein heteroaryl is defined as hereinbefore and hereinafter, or heteroaryl preferably denotes pyridyl, pyrimidinyl, pyrazolyl and oxazolyl; and wherein each carbocyclyl and heterocyclyl, may be optionally substituted with one or more $C_{1-4}$-alkyl; and wherein each alkyl, carbocyclyl, heterocyclyl, including piperazinyl and morpholinyl, may be optionally substituted with one or more substituents selected from F; and wherein each alkyl, carbocyclyl, heterocyclyl, including piperazinyl and morpholinyl, may be optionally substituted with a substituent selected from OH, $C_{1-3}$-alkyl-O—, $H_2N$—, HO—C(=O)— and $C_{1-4}$-alkyl-O—C(=O)—: and wherein each phenyl and heteroaryl may be optionally substituted with one or more substituents L.

With regard to an alkenyl or alkynyl group, for example $R^{N1}$, attached to the N-atom of an amino-group it is to be understood that the double or triple bond is preferably not conjugated with the N-atom.

$R^{N1}$-G3:

In another embodiment the group $R^{N1}$ is selected from the group $R^{N1}$-G3 consisting of H, $C_{1-6}$-alkyl, $C_{3-6}$-cycloalkyl, $C_{3-6}$-cycloalkyl-CH$_2$—, heterocyclyl, heterocyclyl-CH$_2$—, phenyl, phenyl-CH$_2$—, pyridyl, pyridyl-CH$_2$— and oxazolyl-CH$_2$—;

wherein heterocyclyl is defined as hereinbefore and hereinafter, or each heterocyclyl is preferably selected from tetrahydrofuranyl, tetrahydropyranyl, pyrrolidinyl and piperidinyl; and wherein each cycloalkyl and heterocyclyl may be optionally substituted with one or more $C_{1-4}$-alkyl; and wherein each alkyl, cycloalkyl and heterocyclyl may be optionally substituted with one or more substituents selected from F; and wherein each alkyl, cycloalkyl and heterocyclyl may be optionally substituted with a substituent selected from OH, $C_{1-3}$-alkyl-O—, $H_2N$—, HO—C(=O)— and $C_{1-4}$-alkyl-O—C(=O)—; and wherein each phenyl and heteroaryl, including pyridyl, pyrazolyl and oxazolyl, may be optionally substituted with one or more substituents L.

With regard to an alkenyl or alkynyl group, for example $R^{N1}$, attached to the N-atom of an amino-group it is to be understood that the double or triple bond is preferably not conjugated with the N-atom.

$R^{N2}$ $R^{N2}$-G1:

The group $R^{N2}$ is preferably selected from the group $R^{N2}$-G1 as defined hereinbefore and hereinafter.

$R^{N2}$-G2:

In another embodiment the group $R^{N2}$ is selected from the group $R^{N2}$-G2 consisting of H and $C_{1-4}$-alkyl.

$R^{Alk}$:

$R^{Alk}$-G1:

The group $R^{Alk}$ is preferably selected from the group $R^{Alk}$-G1 as defined hereinbefore and hereinafter.

$R^{Alk}$-G2:

In another embodiment the group $R^{Alk}$ is selected from the group $R^{Alk}$-G2 consisting of H and $C_{1-3}$-alkyl which may be substituted with one or more F atoms.

$Ar^2$:

$Ar^2$-G1:

The group $Ar^2$ is preferably selected from the group $Ar^2$-G1 as defined hereinbefore and hereinafter.

$Ar^2$-G2:

In another embodiment the group $Ar^2$ is selected from the group $Ar^2$-G2 consisting of phenyl, pyridyl, pyrimidinyl, pyridazinyl, pyrazinyl, furanyl, thienyl, pyrrolyl, imidazolyl, triazolyl, oxazolyl, isoxazolyl, pyrazolyl and thiazolyl, wherein all of the before mentioned groups may be optionally substituted with one or more substituents L.

$Ar^2$-G3:

In another embodiment the group $Ar^2$ is selected from the group $Ar^2$-G3 consisting of phenyl and pyridyl, wherein all of the before mentioned groups may be optionally substituted with one or more substituents L.

$Ar^2$-G4:

In another embodiment the group $Ar^2$ is selected from the group $Ar^2$-G4 consisting of:

wherein the before mentioned group may be optionally substituted with one or more substituents L.

L:

L-G1:

The group L is preferably selected from the group L-G1 as defined hereinbefore and hereinafter.

L-G2:

In another embodiment the group L is selected from the group L-G2 consisting of F, Cl, Br, CN, OH, $C_{1-3}$-alkyl-, $C_{1-3}$-alkyl-O—, $C_{1-3}$-alkyl-S—, $H_2N$—, $(C_{1-3}$-alkyl)NH—, $(C_{1-3}$-alkyl)$_2$N— and heterocyclyl;

wherein each alkyl may be optionally substituted with one or more F-atoms and/or a substituent selected from OH, $C_{1-3}$-alkyl-O— and CN; and wherein heterocyclyl is defined as hereinbefore and hereinafter, or heterocyclyl preferably denotes a $C_{3-6}$-cycloalkyl ring wherein one or two —$CH_2$-groups are replaced by a group selected from —O—, —NH—, —N($C_{1-3}$-alkyl)-; and wherein two substituents L attached to an aryl or heteroaryl group may be linked to each other and form a $C_{2-5}$-alkylene bridging group in which 1 or 2 —$CH_2$-groups may be replaced by a group independently of each other selected from O, NH and N($C_{1-4}$-alkyl)-, wherein the $C_{2-5}$-alkylene bridging group is optionally be substituted by 1 or 2 $C_{1-3}$-alkyl groups.

L-G3:

In another embodiment the group L is selected from the group L-G3 consisting of F, Cl, CN, OH, $C_{1-3}$-alkyl-, $C_{1-3}$-alkyl-O—, $C_{1-3}$-alkyl-S—, $H_2N$—, $(C_{1-3}$-alkyl)NH—, $(C_{1-3}$-alkyl)$_2$N— and heterocyclyl;

wherein each alkyl may be optionally substituted with one or more F-atoms and/or a substituent selected from OH, $CH_3$—O— and CN; and wherein heterocyclyl is defined as hereinbefore and hereinafter or heterocyclyl preferably denotes a $C_{3-6}$-cycloalkyl ring wherein one or two —$CH_2$-groups are replaced by a group selected from —O—, —NH—, —N($C_{1-3}$-alkyl)-; and wherein two substituents L attached to adjacent C-atoms of an aryl or heteroaryl group may be linked to each other and form a —$CH_2$—$CH_2$—O—, —O—$CH_2$—$CH_2$—O— or —O—$CH_2$—O— bridging group which is optionally substituted by 1 or 2 $CH_3$— groups.

X:

X-G1:

The group X is preferably selected from the group X-G1 as defined hereinbefore and hereinafter, in particular from a group consisting of a straight chain $C_{1-3}$-alkylene group which may be optionally substituted with 1, 2 or 3 groups selected from $C_{1-3}$-alkyl and $C_{1-3}$-alkyl-O—$C_{1-3}$-alkyl; even more preferably optionally substituted with 1 or 2 groups independently selected from methyl, ethyl or methoxymethyl; and wherein two alkyl substituents may be connected with each other and together form a $C_{1-5}$-alkylene bridging group in which 1 or 2 —$CH_2$-groups may be replaced by O, S, NH or N($C_{1-4}$-alkyl)-, wherein the $C_{1-5}$-alkylene bridging group may optionally be substituted by one or two $C_{1-3}$-alkyl groups.

X-G2:

In another embodiment the group X is selected from the group X-G2 consisting of:

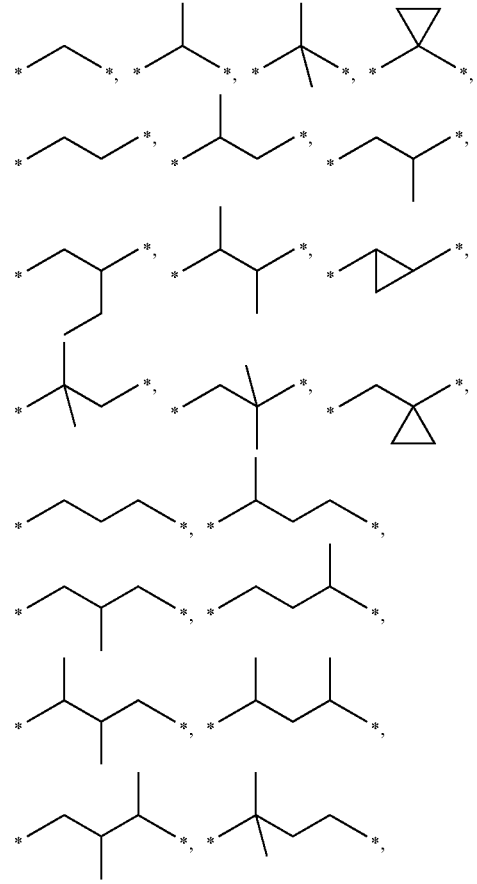

-continued

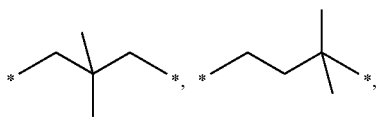

even more preferably selected from the group X-G3 consisting of:

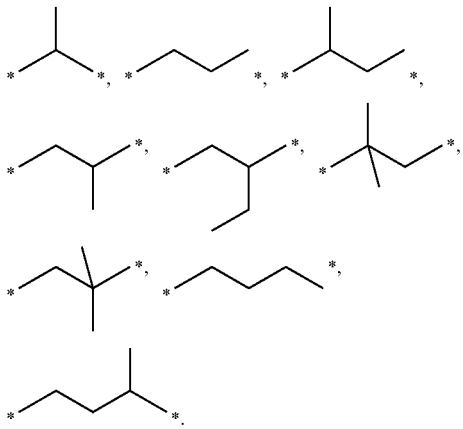

X-GC1:

According an embodiment X-GC1 the group X is —CH$_2$— which may be optionally substituted with one or two C$_{1-3}$-alkyl groups, preferably with one or two groups independently selected from methyl and ethyl, and wherein two alkyl substituents may be connected with each other and together form a C$_{2-5}$-alkylene bridging group in which 1 or 2 —CH$_2$-groups may be replaced by O, S, NH or N(C$_{1-4}$-alkyl)-, wherein the C$_{1-5}$-alkylene bridging group may optionally be substituted by one or two C$_{1-3}$-alkyl groups.

Examples of this embodiment are:

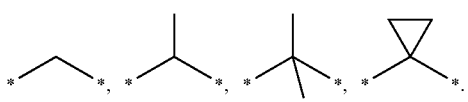

X-GC1a:

According an embodiment X-GC1a the group X is

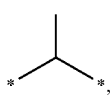

embracing

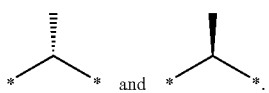

A preferred example of the group X-GC1a is

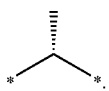

X-GC2:

According to another embodiment X-GC2 the group X is —CH$_2$—CH$_2$— which may be optionally substituted with one or more C$_{1-3}$-alkyl groups, preferably with one or two groups independently selected from methyl and ethyl, and wherein two alkyl substituents may be connected with each other and together form a C$_{1-5}$-alkylene bridging group in which 1 or 2 —CH$_2$-groups may be replaced by O, S, NH or N(C$_{1-4}$-alkyl)-, wherein the C$_{1-5}$-alkylene bridging group may optionally be substituted by one or two C$_{1-3}$-alkyl groups.

Examples of this embodiment are:

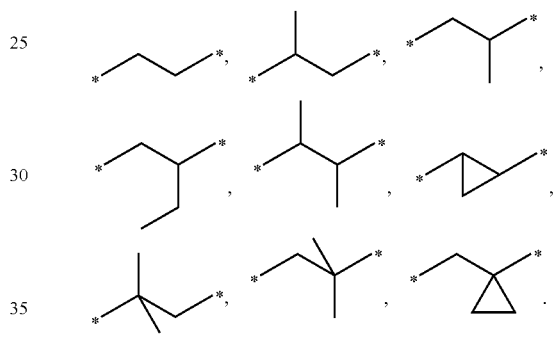

Preferred examples are:

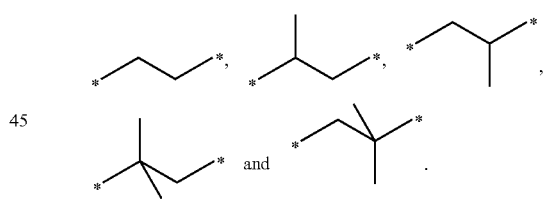

X-GC2a:

According an embodiment X-GC2a the group X is

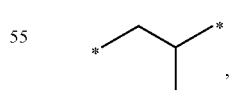

embracing

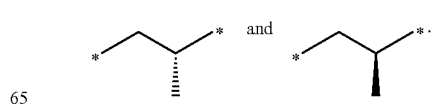

A preferred example of the group X-GC2a is

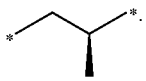

X-GC3:

According another embodiment X-GC3 the group X is —CH$_2$—CH$_2$—CH$_2$— which may be optionally substituted with one or more C$_{1-3}$-alkyl groups, preferably with one or two groups independently selected from methyl and ethyl, and wherein two alkyl substituents may be connected with each other and together form a C$_{1-5}$-alkylene bridging group in which 1 or 2 —CH$_2$-groups may be replaced by O, S, NH or N(C$_{1-4}$-alkyl)-, wherein the C$_{1-5}$-alkylene bridging group may optionally be substituted by one or two C$_{1-3}$-alkyl groups.

Examples of this embodiment are:

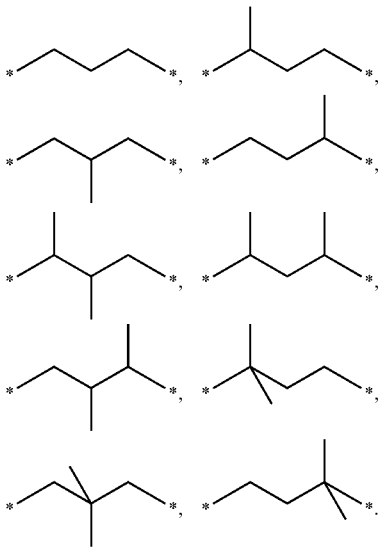

Y:
Y-G1:
The group Y is preferably selected from the group Y-G1 as defined hereinbefore and hereinafter.
Y-G2:
In another embodiment the group Y is selected from the group Y-G2 consisting of —C(=O)—.
Y-G3:
In another embodiment the group Y is selected from the group Y-G3 consisting of —S(=O)$_2$—.
R$^N$:
R$^N$-G1:
The group R$^N$ is preferably selected from the group R$^N$-G1 as defined hereinbefore and hereinafter.
R$^N$-G2:
In another embodiment the group R$^N$ is selected from the group R$^N$-G2 consisting of H, methyl and ethyl.
T:
T-G1:
The group T is preferably selected from the group T-G1 as defined hereinbefore and hereinafter.

T-G2:
In another embodiment the group T is selected from the group T-G2 consisting of C$_{1-6}$-alkyl, C$_{2-6}$-alkenyl, C$_{2-6}$-alkynyl, C$_{3-7}$-cycloalkyl, C$_{1-6}$-alkyl-O—, C$_{3-7}$-cycloalkyl-O—, C$_{3-7}$-cycloalkyl-C$_{1-3}$-alkyl-O—, C$_{1-6}$-alkyl-S—, C$_{3-7}$-cycloalkyl-S—, C$_{3-7}$-cycloalkyl-C$_{1-3}$alkyl-S—, C$_{1-4}$-alkyl-C(=O)—, C$_{1-4}$-alkyl-S(=O)$_2$—, R$^{T1}$R$^{T2}$—N—, R$^{T1}$R$^{T2}$—N—CO—, C$_{1-4}$-alkyl-C(=O)—R$^{T2}$N—C$_{1-3}$-alkyl, heterocyclyl, phenyl and heteroaryl;
wherein in each cycloalkyl and heterocyclyl a —CH$_2$-group may optionally be replaced by —C(=O)—; and
wherein each cycloalkyl and heterocyclyl may be optionally substituted with one or more C$_{1-4}$-alkyl, which may be optionally substituted with one or more substituents R$^C$; and
wherein each alkyl, cycloalkyl and heterocyclyl may be optionally substituted with one or more substituents R$^C$; and
wherein R$^C$ is selected from the group consisting of R$^C$-G1, R$^C$-G2 or R$^C$-G3 as defined hereinbefore and hereinafter,
wherein R$^{T1}$ is selected from the group R$^{T1}$-G1 or R$^{T1}$-G2 as defined as hereinbefore and hereinafter; and
wherein R$^{T2}$ is selected from the group R$^{T2}$-G1 or R$^{T2}$-G2 as defined as hereinbefore and hereinafter; and
wherein heterocyclyl is defined as hereinbefore and hereinafter; preferably heterocyclyl is azetidinyl, pyrrolidinyl, piperidinyl, oxetanyl, tetrahydrofuranyl or tetrahydropyranyl; and
wherein heteroaryl is selected from the group consisting of phenyl, pyridyl, pyrimidinyl, pyridazinyl, pyrazinyl, furanyl, thienyl, pyrrolyl, imidazolyl, pyrazolyl, triazolyl, oxazolyl, isoxazolyl and thiazolyl; and
wherein each aryl and heteroaryl group may be optionally substituted with one or more substituents L.
T-G3:
In another embodiment the group T is selected from the group T-G3 consisting of C$_{1-4}$-alkyl, C$_{3-6}$-cycloalkyl, C$_{1-4}$-alkyl-O—, R$^{T1}$R$^{T2}$—N—, heterocyclyl, phenyl and heteroaryl,
wherein in each cycloalkyl and heterocyclyl a CH$_2$-group may optionally be replaced by —C(=O)—; and
wherein each cycloalkyl and heterocyclyl may be optionally substituted with one or more C$_{1-4}$-alkyl, which may be optionally substituted with one or more substituents R$^C$; and
wherein each alkyl, cycloalkyl and heterocyclyl may be optionally substituted with one or more substituents R$^C$; and
wherein R$^C$ is selected from the group consisting of R$^C$-G1, R$^C$-G2 or R$^C$-G3 as defined hereinbefore and hereinafter; and
wherein R$^{T1}$ is selected from the group R$^{T1}$-G1 or R$^{T1}$-G2 as defined as hereinbefore and hereinafter; preferably R$^{T1}$ denotes H, C$_{1-4}$-alkyl, C$_{3-6}$-cycloalkyl or C$_{3-6}$-cycloalkyl-C$_{1-3}$-alkyl; and
wherein R$^{T2}$ is selected from the group R$^{T2}$-G1 or R$^{T2}$-G2 as defined as hereinbefore and hereinafter; preferably R$^{T2}$ denotes H or C$_{1-4}$-alkyl; and
wherein heterocyclyl is defined as hereinbefore and hereinafter, preferably heterocyclyl is selected from the group consisting of

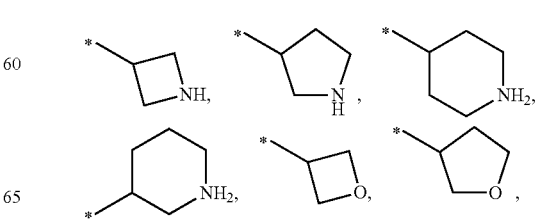

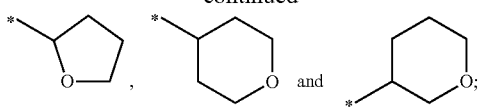

and wherein heteroaryl is selected from the group consisting of phenyl, pyridyl, pyrimidinyl, pyridazinyl, pyrazinyl, furanyl, thienyl, pyrrolyl, imidazolyl, pyrazolyl, triazolyl, oxazolyl, isoxazolyl and thiazolyl; and wherein each heteroaryl group may be optionally substituted with one or more substituents L.

T-G4:

In another embodiment the group T is selected from the group T-G4 consisting of $C_{1-3}$-alkyl, $C_{3-5}$-cycloalkyl, $C_{1-3}$-alkyl-O— and $R^{T1}R^{T2}$—N—;

wherein each cycloalkyl may be optionally substituted with one or more $C_{1-3}$-alkyl;

and wherein $R^{T1}$ and $R^{T2}$ are independently of each other selected from H and $C_{1-3}$-alkyl.

Preferred examples of the group T-G4 are $H_3C$—, $H_3C$—O—, $(H_3C)_2N$—,

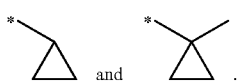

T-G5:

In another embodiment the group T is selected from the group T-G5 consisting of $H_3C$—, $H_2FC$—, $HF_2C$—, NC—$CH_2$—, $F_3C$—$CH_2$—, $(H_3C)_2CF$—, $H_5C_2$—, n-propyl, i-propyl, n-butyl, i-butyl, $H_3C$—$(H_3CO)CH$—, $H_3C$—$(HO)CH$—, NC—$CH_2$—, NC—$CH_2$—$CH_2$—, cyclopropyl, cyclobutyl, cyclopropyl-$CH_2$—,

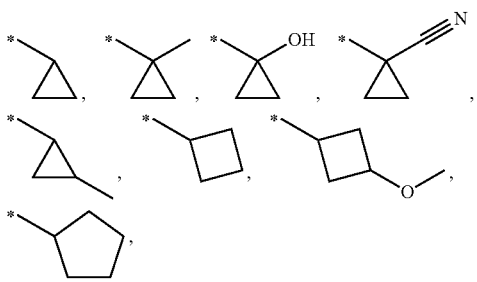

$H_2C$=CH—, $H_3C$—CH=CH—, $(H_3C)_2C$=CH—, $H_2C$=CH—$CH_2$—, HO—$CH_2$—, HO—$CH_2$—$CH_2$—, $(CH_3)_2CH$—(HO)CH—, $H_3C$—(HO)CH—, $H_3C$—O—$CH_2$—, $H_3C$—O—$CH_2$—$CH_2$—, $H_3C$—O—, $H_3C$—$CH_2$—CO—, $H_3C$—$SO_2$—$CH_2$—,

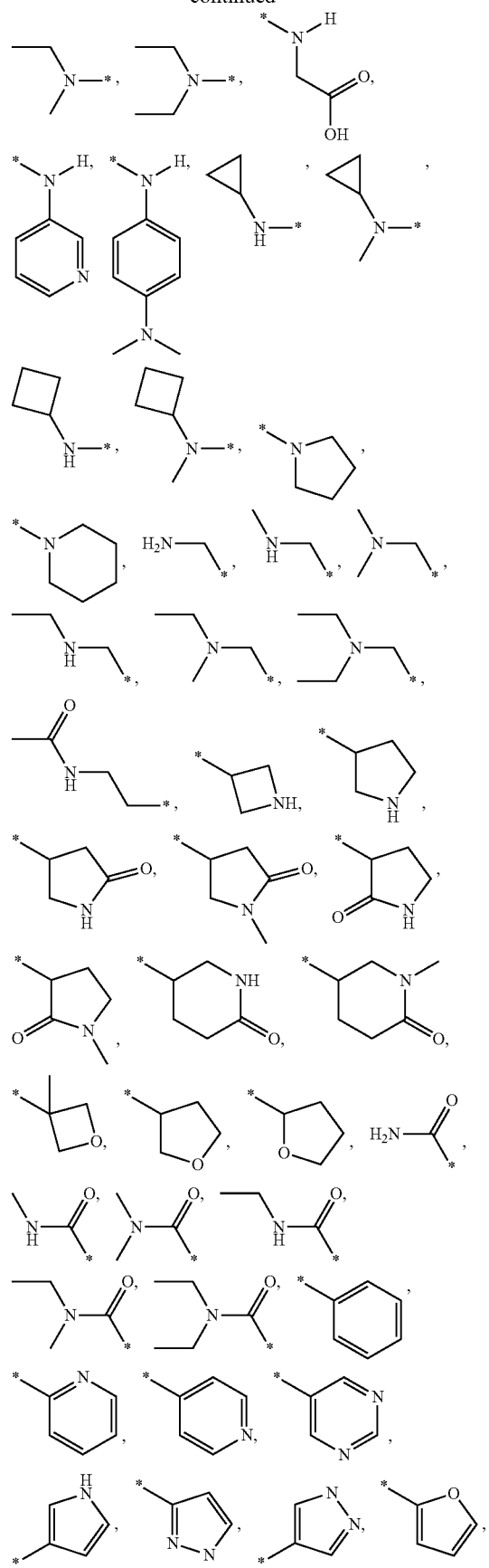

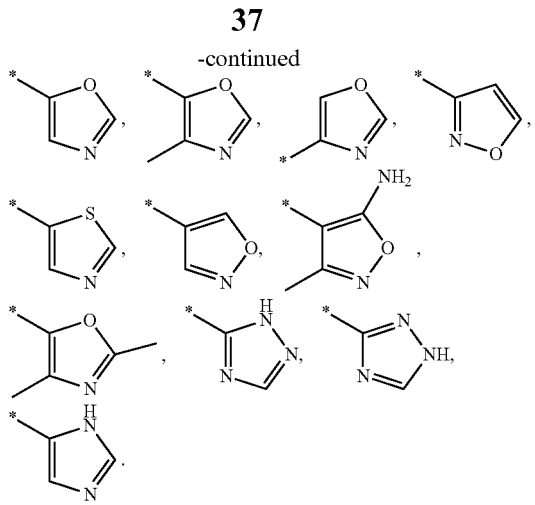

T-G6:

In another preferred embodiment the group T is preferably selected from the group T-G6 consisting of $H_3C-$, $H_2FC-$, $HF_2C-$, $NC-CH_2-$, $F_3C-CH_2-$, $(H_3C)_2CF-$, $H_5C_2-$, n-propyl, i-propyl, n-butyl, i-butyl, $H_3C-(H_3CO)CH-$, $H_3C-(HO)CH-$, $NC-CH_2-$, $NC-CH_2-CH_2-$, cyclopropyl, cyclobutyl, cyclopropyl-$CH_2-$,

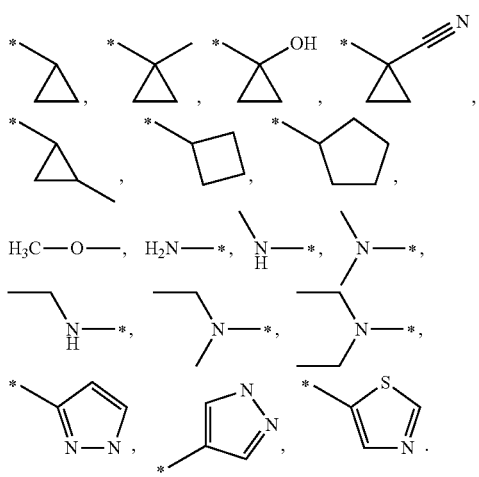

$T-R^N$:

$T-R^N-G1$:

In an embodiment the groups T and $R^N$ are connected with each other and together form a group which is preferably selected from the group $T-R^N-G1$ as defined hereinbefore and hereinafter.

$T-R^N-G2$:

In another embodiment the groups T and $R^N$ are connected with each other such that the group

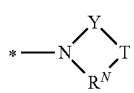

is selected from the group $T-R^N-G2$ consisting of:

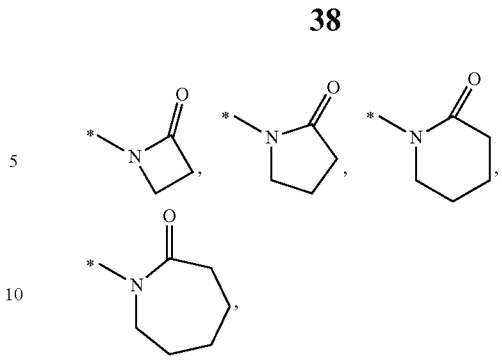

all of which may be optionally substituted with one or more substituents selected from F, Cl, Br, OH, CN, $C_{1-4}$-alkyl, $C_{3-6}$-cycloalkyl, $C_{3-6}$-cycloalkyl-$C_{1-3}$-alkyl, $C_{1-4}$-alkyl-O—, $C_{3-6}$-cycloalkyl-O—, $C_{3-6}$-cycloalkyl-$C_{1-3}$-alkyl-O—, $H_2N-$, $(C_{1-4}$-alkyl)NH—, $(C_{1-4}$-alkyl)$_2$N—, $C_{1-4}$-alkyl-C(=O)—, $C_{1-4}$-alkyl-S(=O)$_2$—, HO—C(=O)— and $C_{1-4}$-alkyl-O—C(=O)—, wherein each alkyl or cycloalkyl may be optionally substituted with one or more substituents selected from F, and wherein each alkyl or cycloalkyl may be optionally substituted with a substituent selected from Cl, Br, OH, CN, $C_{1-3}$-alkyl-O—, $C_{3-6}$-cycloalkyl-O—, $C_{3-6}$-cycloalkyl-$C_{1-3}$-alkyl-O—, $H_2N-$, $(C_{1-3}$-alkyl)NH—, $(C_{1-3}$-alkyl)$_2$N—, $C_{1-4}$-alkyl-C(=O)—, $C_{1-4}$-alkyl-S(=O)$_2$—, HO—C(=O)— and $C_{1-4}$-alkyl-O—C(=O)—.

$T-R^N-G3$:

In another embodiment the groups T and $R^N$ are connected with each other such that the group

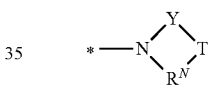

is selected from the group $T-R^N-G3$ consisting of:

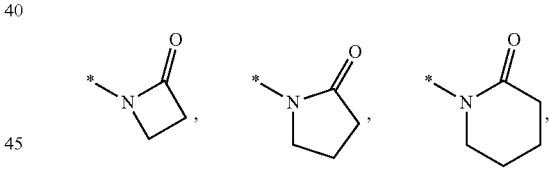

all of which may be substituted with one or more F atoms and/or $C_{1-3}$-alkyl.

$R^{T1}$ $R^{T1}$-G1:

The group $R^{T1}$ is preferably selected from the group $R^{T1}$-G1 consisting of H, $C_{1-6}$-alkyl, $C_{3-6}$-cycloalkyl, $C_{3-6}$-cycloalkyl-$C_{1-3}$-alkyl, phenyl and pyridyl, wherein each cycloalkyl may be optionally substituted with one or more $C_{1-4}$-alkyl, and wherein each alkyl and cycloalkyl may be optionally substituted with one or more F atoms, and wherein each alkyl and cycloalkyl may be optionally substituted with a substituent selected from OH, $C_{1-3}$-alkyl-O—, $C_{1-3}$-alkyl-C(=O)—, HO—C(=O)— and $C_{1-4}$-alkyl-O—C(=O)—; and wherein each phenyl and pyridyl group may be optionally substituted with one or more substituents L.

$R^{T1}$-G2:

In another embodiment the group $R^{T1}$ is selected from the group $R^{T1}$-G2 consisting of methyl, ethyl, n-propyl, isopropyl, HOOC—CH₂—, H₃C—CO—, phenyl and pyridinyl, wherein the groups phenyl and pyridyl may be substituted with one or more substituents L.

$R^{T2}$ $R^{T2}$-G1:

The group $R^{T2}$ is preferably selected from the group $R^{T2}$-G1 consisting of H and $C_{1-4}$-alkyl.

$R^{T2}$-G2:

In another embodiment the group $R^{T2}$ is selected from the group $R^{T2}$-G2 consisting of H, methyl, ethyl, n-propyl and isopropyl.

Examples of preferred subgeneric embodiments according to the present invention are set forth in the following table, wherein each substituent group of each embodiment is defined according to the definitions set forth hereinbefore and wherein all other substituents of the formula (I) are defined according to the definitions set forth hereinbefore:

| Embodiment | Ar¹ | R⁴ | Ar² | X | Y | R^N and T |
|---|---|---|---|---|---|---|
| E-1 | Ar¹-G1 | R⁴-G1 | Ar²-G1 | X-G1 | Y-G1 | R^N-G1, T-G1 or T-R^N-G1 |
| E-2 | Ar¹-G2 | R⁴-G2 | Ar²-G2 | X-G1 | Y-G1 | R^N-G1, T-G2 or T-R^N-G2 |
| E-3 | Ar¹-G3 | R⁴-G3 | Ar²-G2 | X-G1 | Y-G1 | R^N-G1, T-G2 or T-R^N-G2 |
| E-4 | Ar¹-G4 | R⁴-G4 | Ar²-G3 | X-G1 | Y-G1 | R^N-G1, T-G2 |
| E-5 | Ar¹-G4 | R⁴-G4 | Ar²-G3 | X-G1 | Y-G1 | T-R^N-G2 |
| E-6 | Ar¹-G6 | R⁴-G4 | Ar²-G3 | X-G1 | Y-G1 | R^N-G1, T-G3 or T-R^N-G2 |
| E-7 | Ar¹-G7 | R⁴-G4 | Ar²-G3 | X-G1 | Y-G1 | R^N-G1, T-G3 or T-R^N-G2 |
| E-8 | Ar¹-G6 | R⁴-G5 | Ar²-G4 | X-G1 | Y-G1 | R^N-G1, T-G3 or T-R^N-G2 |
| E-9 | Ar¹-G7 | R⁴-G5 | Ar²-G4 | X-G1 | Y-G1 | R^N-G1, T-G3 or T-R^N-G2 |
| E-10 | Ar¹-G5 | R⁴-G6 | Ar²-G3 | X-G2 | Y-G1 | R^N-G1, T-G4 or T-R^N-G3 |
| E-11 | Ar¹-G1 | R⁴-G1 | Ar²-G1 | X-GC1 | —C(=O)— | R^N-G1, T-G1 or T-R^N-G1 |
| E-12 | Ar¹-G1 | R⁴-G1 | Ar²-G1 | X-GC2 | —C(=O)— | R^N-G1, T-G1 or T-R^N-G1 |
| E-13 | Ar¹-G1 | R⁴-G1 | Ar²-G1 | X-GC3 | —C(=O)— | R^N-G1, T-G1 or T-R^N-G1 |
| E-14 | Ar¹-G6 | R⁴-G4 | Ar²-G3 | X-GC1 | —C(=O)— | R^N-G1, T-G3 or T-R^N-G2 |
| E-15 | Ar¹-G6 | R⁴-G4 | Ar²-G3 | X-GC2 | —C(=O)— | R^N-G1, T-G3 or T-R^N-G2 |
| E-16 | Ar¹-G6 | R⁴-G4 | Ar²-G3 | X-GC3 | —C(=O)— | R^N-G1, T-G3 or T-R^N-G2 |
| E-17 | Ar¹-G7 | R⁴-G4 | Ar²-G3 | X-GC1 | —C(=O)— | R^N-G1, T-G3 or T-R^N-G2 |
| E-18 | Ar¹-G7 | R⁴-G4 | Ar²-G3 | X-GC2 | —C(=O)— | R^N-G1, T-G3 or T-R^N-G2 |
| E-19 | Ar¹-G7 | R⁴-G4 | Ar²-G3 | X-GC3 | —C(=O)— | R^N-G1, T-G3 or T-R^N-G2 |
| E-20 | Ar¹-G1 | R⁴-G1 | Ar²-G1 | X-GC1 | —S(=O)₂— | R^N-G1, T-G1 or T-R^N-G1 |
| E-21 | Ar¹-G1 | R⁴-G1 | Ar²-G1 | X-GC2 | —S(=O)₂— | R^N-G1, T-G1 or T-R^N-G1 |
| E-22 | Ar¹-G1 | R⁴-G1 | Ar²-G1 | X-GC3 | —S(=O)₂— | R^N-G1, T-G1 or T-R^N-G1 |
| E-23 | Ar¹-G6 | R⁴-G4 | Ar²-G3 | X-GC1 | —S(=O)₂— | R^N-G1, T-G3 or T-R^N-G2 |
| E-24 | Ar¹-G6 | R⁴-G4 | Ar²-G3 | X-GC2 | —S(=O)₂— | R^N-G1, T-G3 or T-R^N-G2 |
| E-25 | Ar¹-G6 | R⁴-G4 | Ar²-G3 | X-GC3 | —S(=O)₂— | R^N-G1, T-G3 or T-R^N-G2 |
| E-26 | Ar¹-G7 | R⁴-G4 | Ar²-G3 | X-GC1 | —S(=O)₂— | R^N-G1, T-G3 or T-R^N-G2 |
| E-27 | Ar¹-G7 | R⁴-G4 | Ar²-G3 | X-GC2 | —S(=O)₂— | R^N-G1, T-G3 or T-R^N-G2 |
| E-28 | Ar¹-G7 | R⁴-G4 | Ar²-G3 | X-GC3 | —S(=O)₂— | R^N-G1, T-G3 or T-R^N-G2 |

The following preferred embodiments of compounds of the formula (I) are described using generic formulas (I.1a) to (I.1f) and (I.1) to (I.5), wherein any tautomers and stereoisomers, solvates, hydrates and salts thereof, in particular the pharmaceutically acceptable salts thereof, are encompassed.

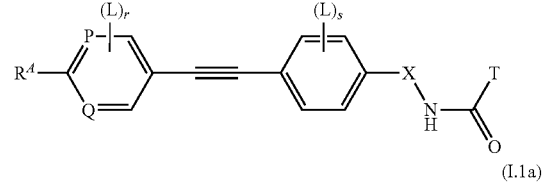

(I.1)

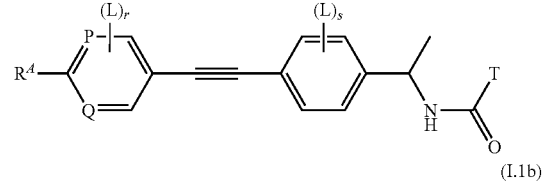

(I.1a)

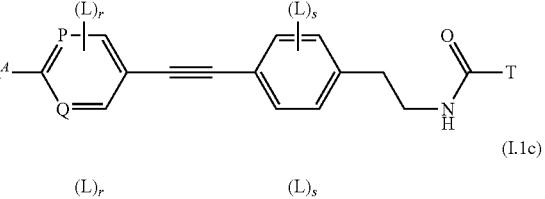

(I.1b)

(I.1c)

-continued

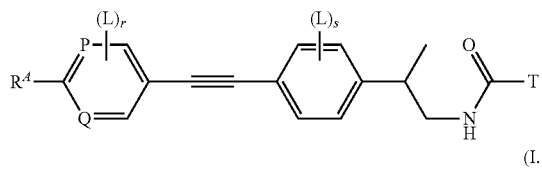
(I.1d)

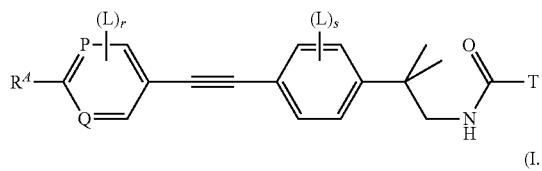
(I.1e)

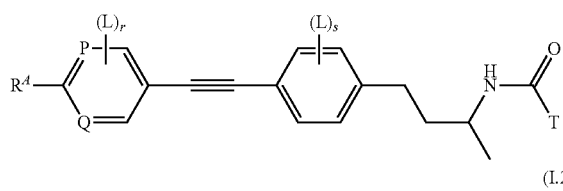
(I.1f)

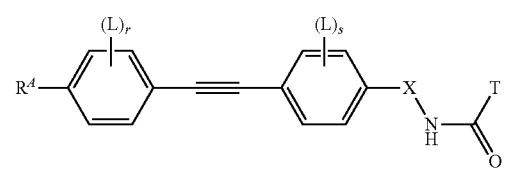
(I.2)

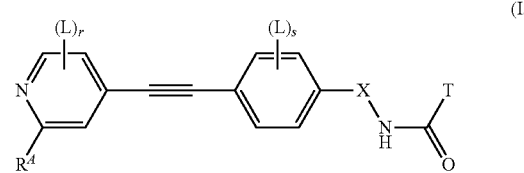
(I.3)

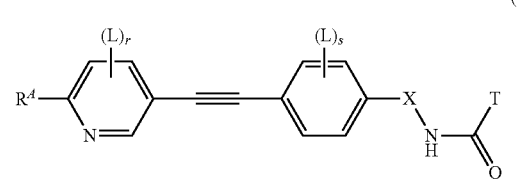
(I.4)

(I.5)

wherein in each of the above formulas (I.1a) to (I.1f) and (I.1) to (I.5), the groups
$R^A$, L, X and T are defined as hereinbefore and hereinafter; and
P is N or CH, wherein CH may be optionally substituted by L as defined; and
Q is N or CH, wherein CH may be optionally substituted by L as defined; and
r is 0, 1 or 2; and
s is 0, 1 or 2.

Preferred embodiments of the above formulas (I.1a) to (I.1f) and (I.1) to (I.5) according to the present invention are set forth in the following table, wherein each group $R^A$, X, T, L of each embodiment is defined according to the definitions set forth hereinbefore and wherein all other substituents of the formula (I) are defined according to the definitions set forth hereinbefore and P, Q, r and s are defined as hereinbefore:

| Embodiment | Formula | $R^A$ | X | T | L |
|---|---|---|---|---|---|
| E-A | (I.1) | RA-G2 | X-G1 | T-G2 | L-G2 |
| E-B | (I.1) | RA-G4 | X-G2 | T-G3 | L-G2 |
| E-C | (I.1a) | RA-G2 | X-G1 | T-G2 | L-G2 |
| E-D | (I.1a) | RA-G4 | X-G2 | T-G3 | L-G2 |
| E-E | (I.1b) | RA-G2 | X-G1 | T-G2 | L-G2 |
| E-F | (I.1b) | RA-G4 | X-G2 | T-G3 | L-G2 |
| E-G | (I.1e) | RA-G2 | X-G1 | T-G2 | L-G2 |
| E-H | (I.1e) | RA-G4 | X-G2 | T-G3 | L-G2 |
| E-I | (I.1d) | RA-G2 | X-G1 | T-G2 | L-G2 |
| E-J | (I.1d) | RA-G4 | X-G2 | T-G3 | L-G2 |
| E-K | (I.1e) | RA-G2 | X-G1 | T-G2 | L-G2 |
| E-L | (I.1e) | RA-G4 | X-G2 | T-G3 | L-G2 |
| E-M | (I.1f) | RA-G2 | X-G1 | T-G2 | L-G2 |
| E-N | (I.1f) | RA-G4 | X-G2 | T-G3 | L-G2 |
| E-O | (I.2) | RA-G2 | X-G1 | T-G2 | L-G2 |
| E-P | (I.2) | RA-G4 | X-G2 | T-G3 | L-G2 |
| E-Q | (I.3) | RA-G2 | X-G1 | T-G2 | L-G2 |
| E-R | (I.3) | RA-G4 | X-G2 | T-G3 | L-G2 |
| E-S | (I.4) | RA-G2 | X-G1 | T-G2 | L-G2 |
| E-T | (I.4) | RA-G4 | X-G2 | T-G3 | L-G2 |
| E-U | (I.5) | RA-G2 | X-G1 | T-G2 | L-G2 |
| E-V | (I.5) | RA-G4 | X-G2 | T-G3 | L-G2 | including any tautomers and stereoisomers, solvates, hydrates and salts thereof, in particular the pharmaceutically acceptable salts thereof.

Particularly preferred compounds, including their tautomers and stereoisomers, the salts thereof, or any solvates or hydrates thereof, are described in the experimental section hereinafter.

The compounds according to the invention may be obtained using methods of synthesis which are known to the one skilled in the art and described in the literature of organic synthesis. Preferably the compounds are obtained analogously to the methods of preparation explained more fully hereinafter, in particular as described in the experimental section.

Compounds of the general formula (I) can be prepared by the following methods:

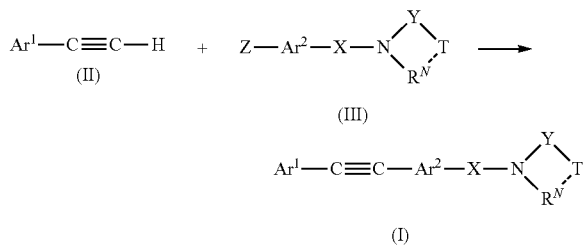

Compounds of general formula (I) may be prepared by a palladium-catalyzed Sonogashira reaction of alkynes (II) with aryl halogenides or aryl triflates (III) wherein Z is a leaving group which for example denotes Cl, Br, I or OTf (triflate).

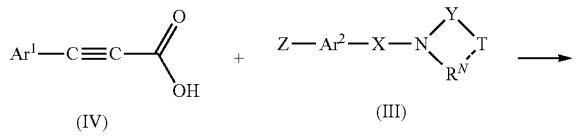

-continued

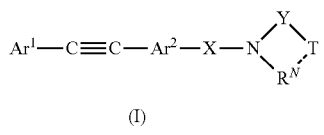

(I)

In an alternative approach compounds of general formula (I) may be prepared by a palladium-catalyzed decarbonylative Sonogashira reaction of propynoic acids (IV) with aryl halogenides or aryl triflates (III) wherein Z is a leaving group which for example denotes Cl, Br, I or OTf (triflate).

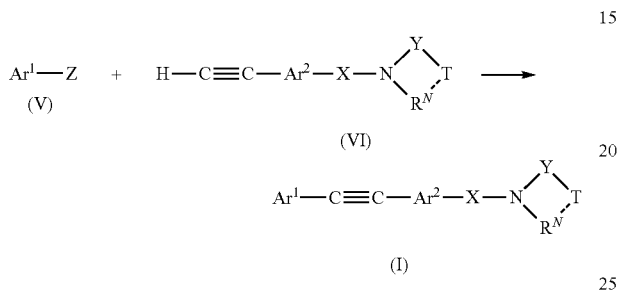

Compounds of general formula (I) may be prepared by a palladium-catalyzed Sonogashira reaction of alkynes (VI) with aryl halogenides or aryl triflates (V) wherein Z is a leaving group which for example denotes Cl, Br, I or OTf (triflate).

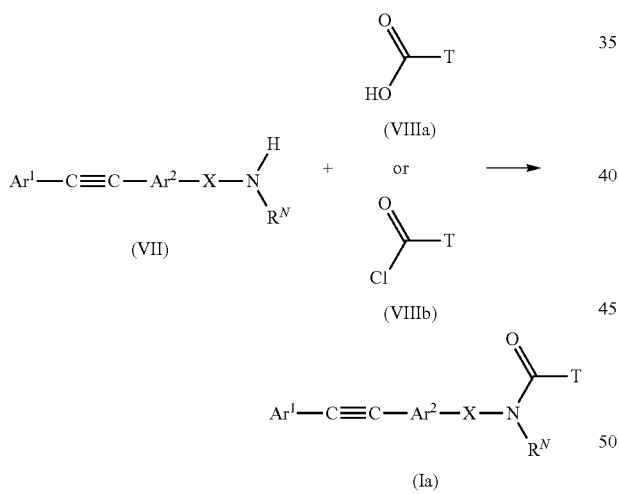

Compounds of general formula (Ia) may be prepared by amide coupling reactions of amines (VII) with either carboxylic acids (VIIIa) mediated by coupling reagents such as e.g. TBTU, HOBt or HATU or carboxylic acid chlorides (VIIIb).

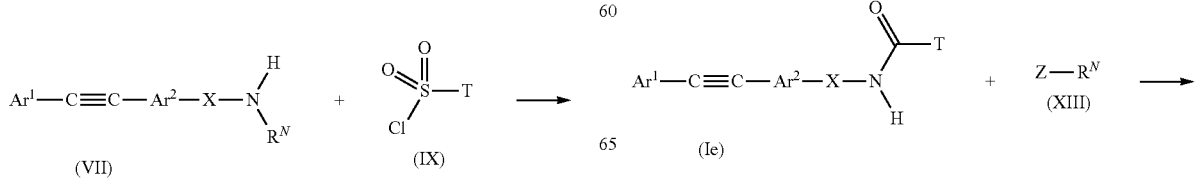

-continued

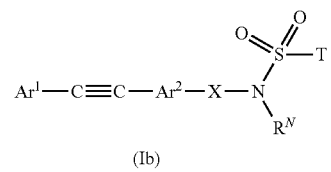

(Ib)

Compounds of general formula (Ib) may be prepared by sulfonylation of amines (VII) with sulfonyl chlorides (IX).

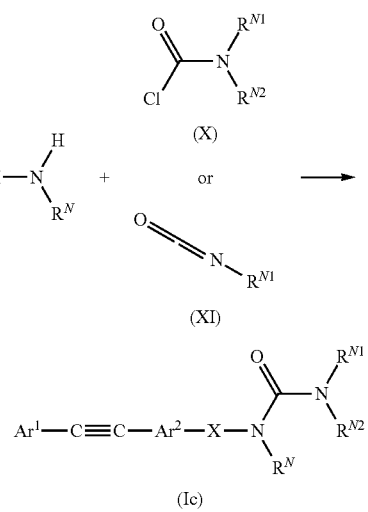

Compounds of general formula (Ic) may be prepared by urea forming reactions such as reaction of amines (VII) with carbamoyl chlorides (X) or isocyanates (XI).

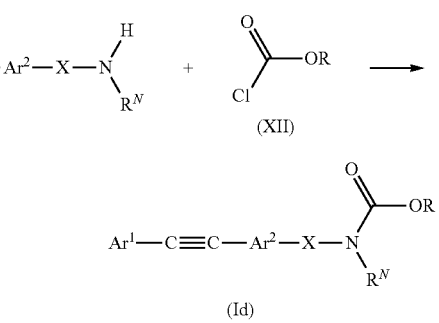

Compounds of general formula (Id) may be prepared by urethane forming reactions such as reaction of amines (VII) with chloro formates (XII).

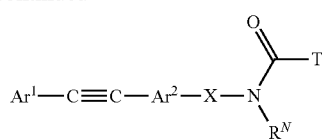

(If)

Compounds of general formula (If) may be prepared by alkylation reactions of secondary amides (Ie) with alkylating reagents (XIII) wherein Z denotes leaving groups such as Cl, Br, I, OTf (triflate), sulfonate or sulfate.

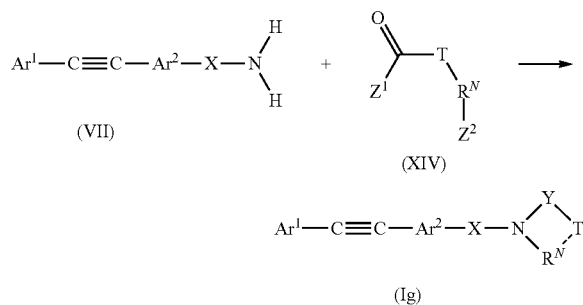

(Ig)

Compounds of general formula (Ig) may be prepared by ring-closing reactions of amines (VII) with double electrophiles (XIV) combining an acylating and an alkylating step in a one-pot reaction. $Z^1$ denotes leaving groups such as Cl, Br or I, $Z^2$ denotes leaving groups such as Cl, Br, I, OTf (triflate), sulfonate or sulfate.

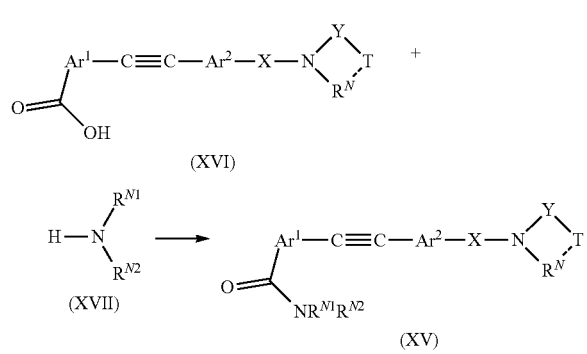

Compounds of general formula (XV) may be prepared by amide coupling reactions of carboxylic acids (XVI) with amines (XVII) with mediated by coupling reagents such as eg TBTU, HOBt or HATU.

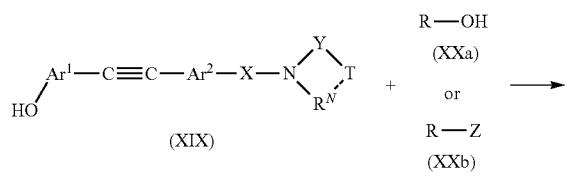

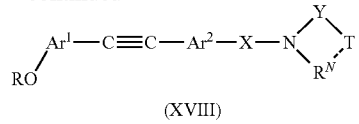

(XVIII)

Compounds of general formula (XVIII) may be prepared by Mitsunobu reactions of aromatic alcohols (XIX) with alcohols (XXa) mediated by coupling reagents such as azodicarboxylates (e.g. DEAD, DIAD etc.) and phosphines (e.g. triphenylphosphine) or by a nucleophilic substitution reaction of the phenol (XIX) with electrophiles (XXb) wherein Z is a leaving group which for example denotes Cl, Br, I, mesylate, tosylate or triflate in the presence of a base, such as e.g. $K_2CO_3$ or NaH.

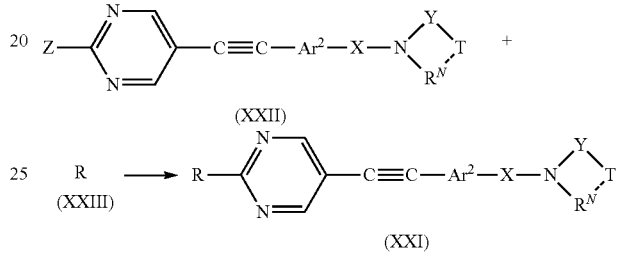

Compounds of general formula (XXI) may be prepared by nucleophilic aromatic substitution reactions ($S_NAr$) of pyrimidines (XXII) with nucleophiles R (XXIII), wherein Z is a leaving group which for example denotes Cl, Br, I, S(=O)$CH_3$ or triflate and wherein R is a nucleophile, such as for example an alcohol or an amine and wherein the reaction may be performed with other regioisomers of pyrimidine or other hetaryls also.

TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy.

In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of the Acetyl-CoA carboxylases (ACC) enzyme(s) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

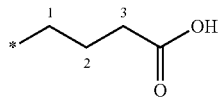

wherein the carboxy group is attached to the third carbon atom of the propyl group. The terms "1-methylpropyl-", "2,2-dimethylpropyl-" or "cyclopropylmethyl-" group represent the following groups:

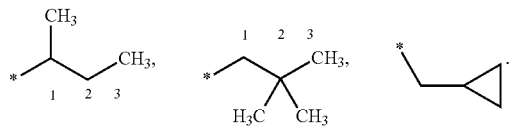

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methyl nitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear 7 hydrocarbon radical with 1 to n C atoms. For example the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term $C_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —CH=CH$_2$, —CH=CH—CH$_3$, —CH$_2$—CH=CH$_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —CH=CH—, —CH=CH—CH$_2$—, —CH$_2$—CH=CH—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —CH$_2$—C≡CH.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes —C≡C—, —C≡C—CH$_2$—, —CH$_2$—C≡C—.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cylcoalkyl, $C_{3-10}$-cycloalkenyl, octahydropentalenyl, octahydroindenyl, decahydronaphthyl, indanyl, tetrahydronaphthyl. Most preferably the term $C_{3-n}$-carbocyclyl denotes $C_{3-n}$-cylcoalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)$_r$ with r=0, 1 or 2 which in addition may have a carbonyl group. The term "heterocyclyl is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

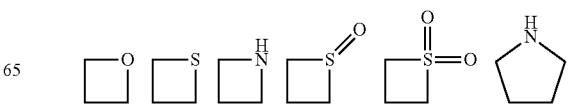

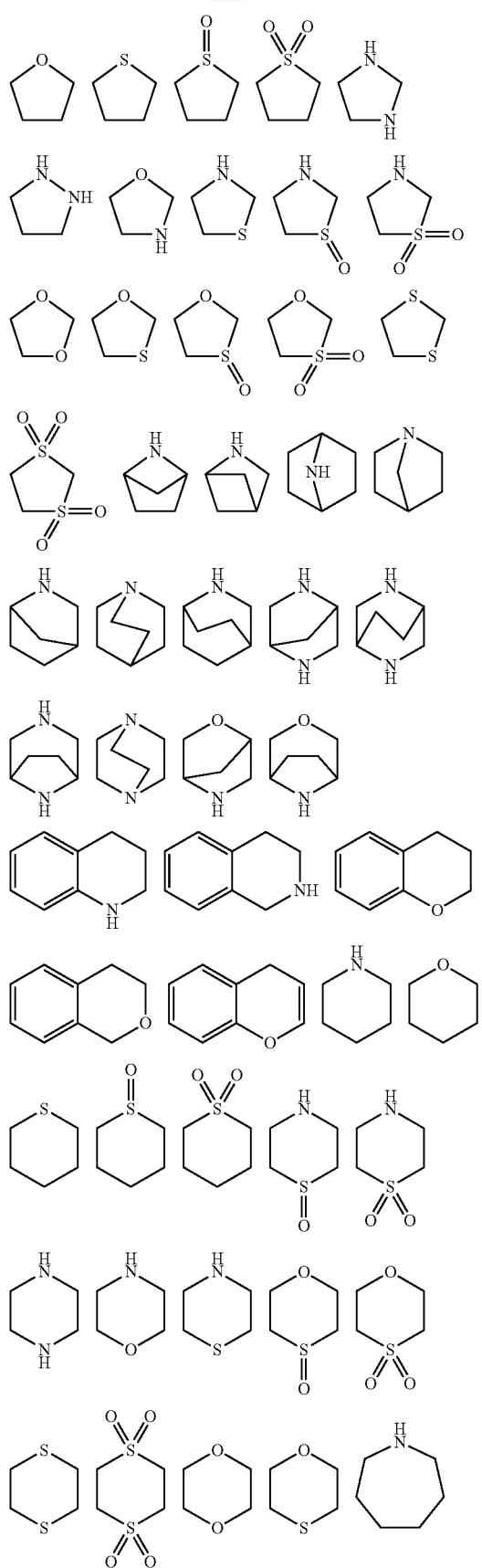
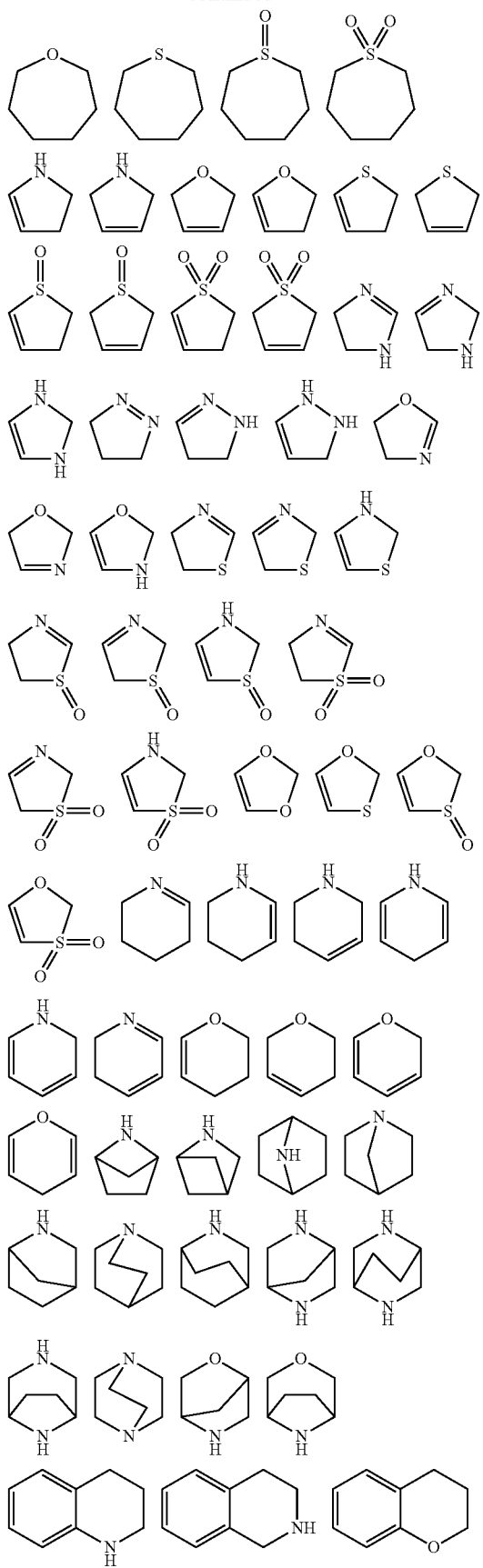

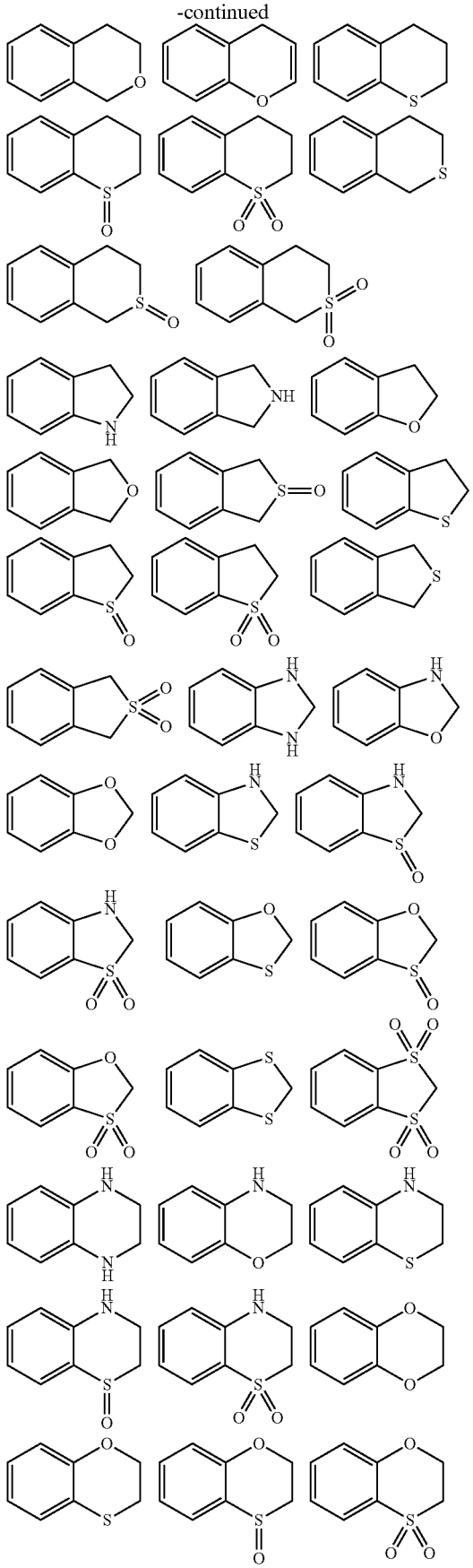

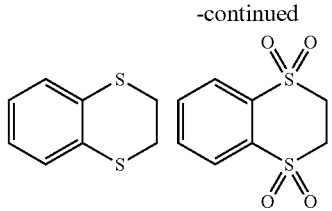

The term "heteroaryl" means a mono- or polycyclic, preferably mono- or bicyclic-ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

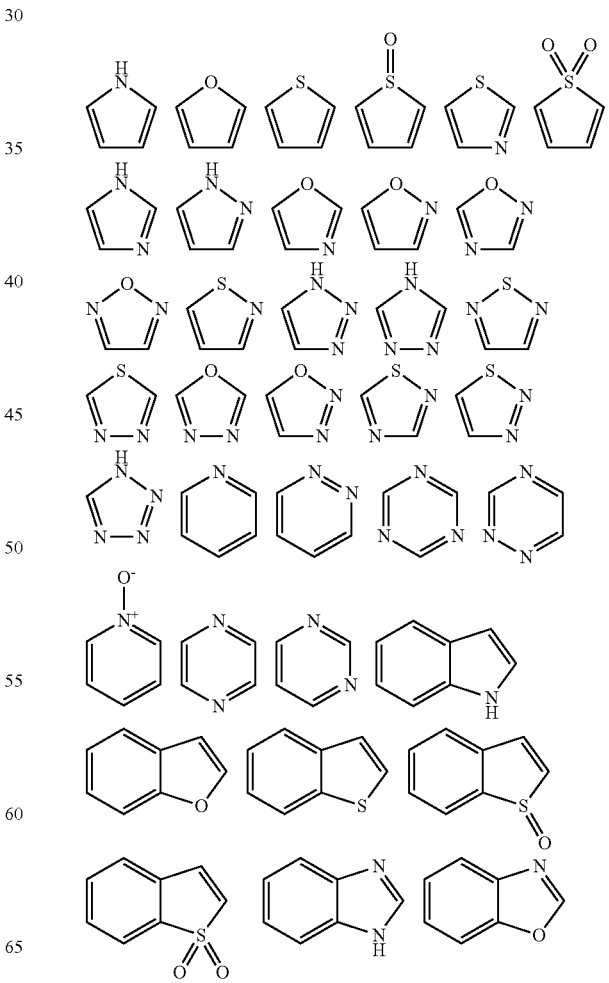

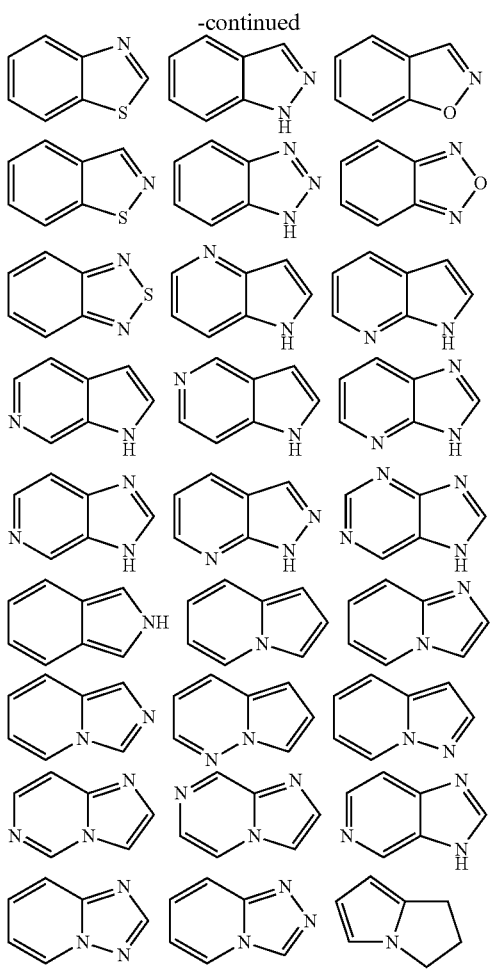

Many of the terms given above may be used repeatedly in the definition of a formula or group and in each case have one of the meanings given above, independently of one another.

Pharmacological Activity

The activity of the compounds of the invention may be demonstrated using the following ACC2 assay:

Spectrophotometric 384 Well Assay

Malonyl CoA formation by acetyl CoA carboxylases is stoichometrically linked to the consumption of ATP. ACC2 activity is measured in a NADH-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM KHCO$_3$, 10 mM MgCl$_2$, 0.5 mg/mL BSA, 3.75 mM reduced L-glutathione, 15 U/mL lactate dehydrogenase, 0.5 mM phosphoenolpyruvate, 15 U/mL pyruvate kinase, compounds at different concentrations at final DMSO concentrations of 1%.

The enzymatic reaction is then started by addition of a mixture of NADH, acetyl Coenzyme A (both 200 µM f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW').

The slope S is used for calculation of % CTL=(S(compound)−S('LOW'))/(S('HIGH')−S('LOW'))*100. Compounds will give values between 100% CTL (no inhibition) and 0% CTL (complete inhibition).

For IC50 value determination, the sample slope in the presence of the test compound after subtraction of the low controls (S(compound)−S('LOW')) are used. An IC50 value is derived from the compound slopes at different dosages after subtraction of the low controls (S(compound)−S('LOW')) by non-linear regression curve fitting (equation $y=(A+((B-A)/(1+((C/x)^D)))))$.

The compounds of general formula (I) according to the invention for example have IC$_{50}$ values below 30000 nM, particularly below 1000 nM, preferably below 300 nM.

In the following table the activity expressed as IC50 (µM) of compounds according to the invention is presented wherein the IC50 values are determined in the ACC2 assay as described hereinbefore. The term "Ex." refers to the example numbers according to the following experimental section.

| Ex. | IC50 [µM] |
|---|---|
| 1.1 | 0.53 |
| 1.2 | 0.81 |
| 1.3 | 0.69 |
| 1.4 | 2.0 |
| 1.5 | 2.4 |
| 1.6 | 0.88 |
| 1.7 | 4.9 |
| 1.8 | 0.20 |
| 1.9 | 8.4 |
| 1.10 | 5.5 |
| 1.11 | 1.7 |
| 1.12 | 2.3 |
| 1.13 | 1.1 |
| 1.14 | 0.20 |
| 1.15 | 1.8 |
| 1.16 | 0.12 |
| 1.17 | 0.39 |
| 1.18 | 0.99 |
| 1.19 | 1.5 |
| 1.20 | 0.61 |
| 1.21 | 0.40 |
| 1.22 | 0.29 |
| 1.23 | 1.0 |
| 1.24 | 1.1 |
| 1.25 | 5.1 |
| 1.26 | 0.32 |
| 1.27 | 0.55 |
| 1.28 | 0.12 |
| 1.29 | 0.25 |
| 1.30 | 2.1 |
| 1.31 | 0.45 |
| 1.32 | 16.9 |
| 2.1 | 0.46 |
| 2.2 | 0.39 |
| 2.3 | 1.4 |
| 2.4 | 3.3 |
| 2.5 | 0.82 |
| 2.6 | 1.4 |
| 2.7 | 0.76 |
| 2.8 | 0.73 |

| Ex. | IC50 [μM] |
|---|---|
| 2.9 | 1.5 |
| 2.10 | 7.5 |
| 2.11 | 0.27 |
| 2.12 | 6.7 |
| 2.13 | 5.3 |
| 2.14 | 0.13 |
| 2.15 | 0.56 |
| 2.16 | 0.12 |
| 2.17 | 0.11 |
| 2.18 | 2.2 |
| 2.19 | 3.6 |
| 2.20 | 0.30 |
| 2.21 | 0.24 |
| 2.22 | 0.72 |
| 2.23 | 0.32 |
| 2.24 | 0.76 |
| 2.25 | 0.17 |
| 2.26 | 0.93 |
| 2.27 | 0.28 |
| 2.28 | 0.27 |
| 2.29 | 1.6 |
| 2.30 | 0.33 |
| 2.31 | 0.28 |
| 2.32 | 0.16 |
| 2.33 | 0.27 |
| 2.34 | 0.18 |
| 2.35 | 0.13 |
| 2.36 | 0.14 |
| 2.37 | 0.10 |
| 2.38 | 10.1 |
| 2.39 | 21.6 |
| 2.40 | 11.8 |
| 2.41 | 25.0 |
| 2.42 | 24.6 |
| 2.43 | 0.45 |
| 2.44 | 0.42 |
| 2.45 | 0.25 |
| 2.46 | 0.41 |
| 2.47 | 0.36 |
| 2.48 | 0.26 |
| 2.49 | 0.25 |
| 2.50 | 0.90 |
| 2.51 | 1.3 |
| 2.52 | 0.19 |
| 2.53 | 0.12 |
| 2.54 | 1.2 |
| 2.55 | 0.07 |
| 2.56 | 0.96 |
| 2.57 | 0.57 |
| 2.58 | 3.7 |
| 2.59 | 2.1 |
| 2.60 | 0.69 |
| 2.61 | 2.0 |
| 2.62 | 0.74 |
| 2.63 | 0.46 |
| 2.64 | 2.8 |
| 2.65 | 0.48 |
| 2.66 | 0.23 |
| 2.67 | 7.2 |
| 2.68 | 0.25 |
| 2.69 | 2.0 |
| 2.70 | 0.80 |
| 2.71 | 3.4 |
| 2.72 | 0.91 |
| 2.73 | 0.64 |
| 2.74 | 1.1 |
| 2.75 | 0.10 |
| 2.76 | 5.8 |
| 2.77 | 1.5 |
| 2.78 | 0.75 |
| 2.79 | 0.45 |
| 2.80 | 0.74 |
| 2.81 | 4.0 |
| 2.82 | 1.6 |
| 2.83 | 17.7 |
| 2.84 | 5.8 |
| 2.85 | 1.1 |
| 2.86 | 0.93 |
| 2.87 | 12.9 |
| 2.88 | 0.88 |
| 2.89 | 16.4 |
| 2.90 | 5.2 |
| 2.91 | 0.40 |
| 2.92 | 0.17 |
| 2.93 | 0.08 |
| 2.94 | 0.26 |
| 2.95 | 0.11 |
| 2.96 | 0.13 |
| 2.97 | 0.14 |
| 2.98 | 0.15 |
| 2.99 | 7.4 |
| 2.100 | 0.12 |
| 2.101 | 0.35 |
| 2.102 | 0.58 |
| 2.103 | 0.50 |
| 2.104 | 1.5 |
| 2.105 | 0.93 |
| 2.106 | 8.2 |
| 2.107 | 4.9 |
| 2.108 | 0.30 |
| 2.109 | 0.79 |
| 3.1 | 0.40 |
| 3.2 | 0.27 |
| 3.3 | 1.3 |
| 3.4 | 0.56 |
| 3.5 | 0.66 |
| 3.6 | 2.3 |
| 3.7 | 10.6 |
| 3.8 | 0.69 |
| 3.9 | 0.26 |
| 3.10 | 4.5 |
| 3.11 | 4.3 |
| 3.12 | 1.2 |
| 3.13 | 1.7 |
| 3.14 | 0.22 |
| 3.15 | 0.35 |
| 3.16 | 4.7 |
| 3.17 | 0.88 |
| 4.1 | 0.21 |
| 4.2 | 0.19 |
| 4.3 | 0.22 |
| 4.4 | 0.15 |
| 4.5 | 1.5 |
| 4.6 | 0.97 |
| 4.7 | 0.12 |
| 4.8 | 0.46 |
| 4.9 | 0.40 |
| 4.10 | 1.1 |
| 4.11 | 1.4 |
| 4.12 | 0.56 |
| 4.13 | 0.68 |
| 4.14 | 1.2 |
| 4.15 | 0.78 |
| 4.16 | 1.6 |
| 4.17 | 0.47 |
| 4.18 | 0.46 |
| 4.19 | 2.8 |
| 4.20 | 0.18 |
| 4.21 | 0.14 |
| 4.22 | 0.93 |
| 4.23 | 0.31 |
| 4.24 | 1.0 |
| 4.25 | 0.54 |
| 4.26 | 0.23 |
| 4.27 | 13.3 |
| 4.28 | 0.79 |
| 4.29 | 2.7 |
| 4.30 | 1.7 |
| 4.31 | 0.41 |
| 4.32 | 0.44 |
| 4.33 | 0.49 |
| 4.34 | 0.60 |

| Ex. | IC50 [μM] |
|---|---|
| 4.35 | 0.38 |
| 4.36 | 0.86 |
| 4.37 | 0.90 |
| 4.38 | 0.17 |
| 4.39 | 0.71 |
| 4.40 | 3.7 |
| 4.41 | 2.0 |
| 4.42 | — |
| 4.43 | 11.0 |
| 4.44 | 1.5 |
| 4.45 | 0.53 |
| 4.46 | 8.5 |
| 4.47 | 2.7 |
| 4.48 | 3.9 |
| 4.49 | 8.7 |
| 4.50 | 6.3 |
| 4.51 | 0.51 |
| 4.52 | 5.1 |
| 4.53 | 0.37 |
| 4.54 | 30.0 |
| 4.55 | 0.33 |
| 4.56 | 5.6 |
| 4.57 | 0.99 |
| 4.58 | 0.68 |
| 4.59 | 0.11 |
| 4.60 | 24.7 |
| 4.61 | 10.1 |
| 4.62 | 3.7 |
| 4.63 | 0.92 |
| 4.64 | 5.1 |
| 4.65 | 1.1 |
| 4.66 | 4.7 |
| 4.67 | 0.07 |
| 4.68 | 0.45 |
| 4.69 | 0.07 |
| 4.70 | 1.3 |
| 4.71 | 0.43 |
| 4.72 | 0.94 |
| 4.73 | 19.2 |
| 4.74 | 2.8 |
| 4.75 | 15.4 |
| 4.76 | 0.66 |
| 4.77 | 0.46 |
| 4.78 | 0.29 |
| 4.79 | 0.16 |
| 4.80 | 7.7 |
| 5.1 | 0.25 |
| 5.2 | 7.2 |
| 5.3 | 1.2 |
| 5.4 | 0.33 |
| 6.1 | 30.0 |
| 6.2 | 2.2 |
| 6.3 | 0.23 |
| 6.4 | 9.6 |
| 7.1 | 0.62 |
| 7.2 | 0.19 |
| 7.3 | 0.36 |
| 8.1 | 0.50 |
| 8.2 | 5.6 |
| 8.3 | 13.0 |
| 8.4 | 1.6 |
| 8.5 | — |
| 8.6 | 1.5 |
| 8.7 | 26.3 |
| 8.8 | 4.2 |
| 8.9 | 3.7 |
| 8.10 | 1.1 |
| 8.11 | 16.6 |
| 8.12 | 1.5 |
| 8.13 | 2.4 |
| 8.14 | 11.5 |
| 8.15 | 2.2 |
| 8.16 | 1.9 |
| 8.17 | 4.4 |
| 8.18 | 7.7 |
| 8.19 | 4.6 |
| 8.20 | 4.4 |
| 8.21 | 1.4 |
| 8.22 | 6.5 |
| 8.23 | 10.9 |
| 8.24 | 30.0 |
| 8.25 | 2.4 |
| 8.26 | 1.5 |
| 8.27 | 11.1 |
| 8.28 | 5.0 |
| 8.29 | 4.5 |
| 8.30 | 2.8 |
| 8.31 | 14.5 |
| 8.32 | 2.1 |
| 8.33 | 2.0 |
| 8.34 | 1.2 |
| 8.35 | 2.4 |
| 8.36 | 2.1 |
| 8.37 | 1.6 |
| 8.38 | 14.3 |
| 8.39 | 13.4 |
| 8.40 | 6.7 |
| 8.41 | 23.3 |
| 8.42 | 30.0 |
| 8.43 | 3.9 |
| 8.44 | 22.1 |
| 8.45 | 1.4 |
| 8.46 | 11.3 |
| 8.47 | 12.1 |
| 8.48 | 6.2 |
| 8.49 | 22.0 |
| 8.50 | — |
| 8.51 | 30.0 |
| 8.52 | — |
| 8.53 | — |
| 8.54 | 25.1 |
| 9.1 | 0.22 |
| 9.2 | 0.10 |
| 9.3 | 0.09 |
| 9.4 | 0.61 |
| 9.5 | 22.1 |
| 9.6 | 9.4 |
| 9.7 | 1.9 |
| 9.8 | 0.81 |
| 9.9 | 9.2 |
| 9.10 | 12.2 |
| 9.11 | 0.18 |
| 9.12 | 0.16 |
| 9.13 | 0.63 |
| 9.14 | 1.6 |
| 9.15 | 2.1 |
| 9.16 | 0.26 |
| 9.17 | 0.61 |
| 9.18 | 14.9 |
| 9.19 | 0.28 |
| 9.20 | 0.08 |
| 9.21 | 0.06 |
| 9.22 | 0.24 |
| 9.23 | 0.40 |
| 9.24 | 0.20 |
| 9.25 | 2.5 |
| 9.26 | 0.25 |
| 9.27 | 0.64 |
| 9.28 | 0.69 |
| 9.29 | 0.19 |
| 9.30 | 0.23 |
| 9.31 | 0.55 |
| 9.32 | 0.10 |
| 9.33 | 0.34 |
| 9.34 | 6.4 |
| 9.35 | 0.66 |
| 9.36 | 0.42 |
| 9.37 | 0.52 |
| 9.38 | 2.6 |
| 9.39 | 0.18 |
| 9.40 | 0.05 |
| 9.41 | 0.50 |

| Ex. | IC50 [μM] |
|---|---|
| 9.42 | 0.63 |
| 10.1 | 0.19 |
| 10.2 | 1.2 |
| 10.3 | 1.8 |
| 11.1 | 1.2 |
| 11.2 | 30.0 |
| 11.3 | 2.3 |
| 11.4 | 0.53 |
| 11.5 | 7.2 |
| 11.6 | 0.93 |
| 11.7 | 12.7 |
| 11.8 | 0.75 |
| 11.9 | 4.0 |
| 11.10 | 16.7 |
| 11.11 | 0.26 |
| 11.12 | 5.6 |
| 11.13 | 1.9 |
| 11.14 | 13.8 |
| 11.15 | 0.33 |
| 11.16 | 0.68 |
| 11.17 | 1.7 |
| 11.18 | 0.51 |
| 11.19 | 5.9 |
| 11.20 | 9.9 |
| 11.21 | 0.25 |
| 11.22 | 8.1 |
| 11.23 | 0.37 |
| 11.24 | 0.39 |
| 11.25 | 1.8 |
| 11.26 | 0.43 |
| 11.27 | 0.40 |
| 11.28 | 0.38 |
| 11.29 | 4.5 |
| 11.30 | 0.48 |
| 11.31 | 2.0 |
| 11.32 | 0.35 |
| 11.33 | 0.68 |
| 11.34 | 13.9 |
| 11.35 | 2.4 |
| 11.36 | 0.69 |
| 11.37 | 14.3 |
| 11.38 | 0.43 |
| 11.39 | 0.72 |
| 11.40 | 1.1 |
| 11.41 | 2.7 |
| 11.42 | 0.62 |
| 11.43 | 0.93 |
| 11.44 | 1.3 |
| 11.45 | 0.53 |
| 11.46 | 0.29 |
| 11.47 | 7.4 |
| 11.48 | 10.3 |
| 11.49 | 0.46 |
| 12.1 | 8.5 |
| 12.2 | 4.3 |
| 12.3 | 1.3 |
| 12.4 | 0.98 |
| 12.5 | 1.6 |
| 12.6 | 1.1 |
| 12.7 | 3.6 |
| 12.8 | 2.2 |
| 12.9 | 2.1 |
| 12.10 | 0.63 |
| 12.11 | 0.67 |
| 12.12 | 0.09 |
| 12.13 | 0.43 |
| 12.14 | 2.5 |
| 12.15 | 0.23 |
| 12.16 | 0.17 |
| 12.17 | 0.38 |
| 12.18 | 7.1 |
| 12.19 | 1.2 |
| 12.20 | 0.53 |
| 12.21 | 0.38 |
| 12.22 | 0.64 |
| 12.23 | 1.1 |
| 12.24 | 0.59 |
| 12.25 | 2.4 |
| 12.26 | 1.0 |
| 12.27 | 0.86 |
| 12.28 | 1.1 |
| 12.29 | 0.07 |
| 12.30 | 0.19 |
| 12.31 | 1.1 |
| 12.32 | 0.32 |
| 12.33 | 0.32 |
| 12.34 | 0.28 |
| 12.35 | 2.3 |
| 12.36 | 1.5 |
| 12.37 | 1.1 |
| 12.38 | 0.26 |
| 12.39 | 3.2 |
| 12.40 | 0.63 |
| 12.41 | 0.52 |
| 12.42 | 0.35 |
| 12.43 | 2.6 |
| 12.44 | 1.0 |
| 12.45 | 0.18 |
| 12.46 | 1.0 |
| 12.47 | 0.13 |
| 12.48 | 0.32 |
| 12.49 | 0.23 |
| 12.50 | 0.53 |
| 12.51 | 1.5 |
| 12.52 | 0.43 |
| 12.53 | 9.0 |
| 12.54 | 0.23 |
| 12.55 | 0.17 |
| 12.56 | 4.9 |
| 12.57 | 1.8 |
| 12.58 | 4.5 |
| 12.59 | 1.6 |
| 12.60 | 0.54 |
| 12.61 | 0.79 |
| 12.62 | 0.24 |
| 12.63 | 1.1 |
| 12.64 | 0.55 |
| 12.65 | 0.45 |
| 12.66 | 2.1 |
| 12.67 | 3.9 |
| 12.68 | 0.98 |
| 12.69 | 2.6 |
| 13.1 | 3.2 |
| 13.2 | 0.21 |
| 13.3 | 1.0 |
| 13.4 | 0.17 |
| 13.5 | 1.4 |
| 13.6 | 0.10 |
| 13.7 | 0.26 |
| 13.8 | 0.22 |
| 13.9 | 0.81 |
| 13.10 | 0.45 |
| 13.11 | 0.23 |
| 13.12 | 0.11 |
| 13.13 | 0.23 |
| 13.14 | 1.9 |
| 13.15 | 0.16 |
| 13.16 | 0.19 |
| 13.17 | 0.18 |
| 13.18 | 0.13 |
| 13.19 | 0.67 |
| 13.20 | 0.26 |
| 13.21 | 0.21 |
| 13.22 | 0.73 |
| 13.23 | 1.2 |
| 13.24 | 0.20 |
| 13.25 | 0.22 |
| 13.26 | 0.20 |
| 13.27 | 0.12 |
| 13.28 | 3.4 |
| 13.29 | 0.61 |
| 13.30 | 0.36 |

-continued

| Ex. | IC50 [μM] |
|---|---|
| 13.31 | 0.50 |
| 13.32 | 0.41 |
| 13.33 | 1.8 |
| 13.34 | 4.7 |
| 13.35 | 0.29 |
| 13.36 | 1.6 |
| 13.37 | 2.6 |
| 13.38 | 0.69 |
| 13.39 | 0.64 |
| 13.40 | 2.2 |
| 13.41 | 2.4 |
| 13.42 | 4.5 |
| 13.43 | 0.58 |
| 13.44 | 0.32 |
| 13.45 | 0.91 |
| 13.46 | 2.7 |
| 13.47 | 0.60 |
| 13.48 | 1.3 |
| 13.49 | 2.6 |
| 13.50 | 1.5 |
| 13.51 | 2.2 |
| 13.52 | 5.2 |
| 13.53 | 5.2 |
| 13.54 | 0.20 |
| 13.55 | 0.13 |
| 13.56 | 0.97 |
| 13.57 | 0.22 |
| 13.58 | 1.2 |
| 13.59 | 0.36 |
| 13.60 | 0.25 |
| 13.61 | 3.8 |
| 13.62 | 0.33 |
| 13.63 | 0.20 |
| 13.64 | 0.80 |
| 13.65 | 1.6 |
| 13.66 | 0.15 |
| 13.67 | 0.66 |
| 13.68 | 0.23 |
| 13.69 | 5.0 |
| 13.70 | 6.8 |
| 13.71 | 0.21 |
| 13.72 | 0.19 |
| 13.73 | 0.28 |
| 13.74 | 1.7 |
| 13.75 | 0.17 |
| 13.76 | 0.60 |
| 13.77 | 0.22 |
| 13.78 | 0.13 |
| 13.79 | 0.11 |
| 13.80 | 0.48 |
| 13.81 | 0.33 |
| 13.82 | 1.2 |
| 13.83 | 0.19 |
| 13.84 | 1.0 |
| 13.85 | 0.08 |
| 13.86 | 0.12 |
| 13.87 | 1.0 |
| 13.88 | 3.1 |
| 13.89 | 1.0 |
| 13.90 | 0.96 |
| 13.91 | 2.9 |
| 13.92 | 7.3 |
| 13.93 | 0.27 |
| 13.94 | 3.6 |
| 13.95 | 2.8 |
| 14.1 | 1.2 |
| 14.2 | 5.9 |
| 14.3 | 0.45 |
| 14.4 | 1.5 |
| 14.5 | 4.1 |
| 14.6 | 0.12 |
| 14.7 | 0.07 |
| 14.8 | 1.3 |
| 14.9 | 0.18 |
| 14.10 | 0.10 |
| 14.11 | 0.13 |

-continued

| Ex. | IC50 [μM] |
|---|---|
| 14.12 | 0.17 |
| 14.13 | 0.22 |
| 14.14 | 0.16 |
| 14.15 | 0.14 |
| 14.16 | 0.12 |
| 14.17 | 0.51 |
| 14.18 | 0.14 |
| 14.19 | 0.19 |
| 14.20 | 0.51 |
| 14.21 | 3.1 |
| 14.22 | 13.4 |
| 14.23 | 0.14 |
| 14.24 | 0.20 |
| 14.25 | 1.8 |
| 14.26 | 0.14 |
| 14.27 | 3.7 |
| 14.28 | 3.4 |
| 14.29 | 0.68 |
| 14.30 | 0.15 |
| 14.31 | 0.09 |
| 14.32 | 0.71 |
| 14.33 | 1.6 |
| 14.34 | 0.60 |
| 14.35 | 0.73 |
| 14.36 | 2.3 |
| 14.37 | 0.17 |
| 14.38 | 1.4 |
| 14.39 | 1.1 |
| 14.40 | 0.08 |
| 14.41 | 0.44 |
| 14.42 | 0.83 |
| 14.43 | 0.36 |
| 14.44 | 0.36 |
| 14.45 | 1.0 |
| 14.46 | 0.21 |
| 14.47 | 0.08 |
| 14.48 | 0.58 |
| 14.49 | 0.32 |
| 14.50 | 1.5 |
| 14.51 | 0.40 |
| 14.52 | 3.8 |
| 14.53 | 0.28 |
| 14.54 | 0.24 |
| 14.55 | 0.12 |
| 15.1 | 0.16 |
| 16.1 | 1.1 |
| 16.2 | 3.2 |
| 16.3 | 0.43 |
| 17.1 | 1.9 |
| 18.1 | 13.7 |
| 18.2 | 4.4 |
| 19.1 | 1.8 |
| 20.1 | 0.98 |
| 20.2 | 0.60 |
| 21.1 | 0.13 |
| 22.1 | 1.6 |
| 23.1 | 0.23 |
| 23.2 | 0.13 |
| 23.3 | 0.40 |
| 23.4 | 0.09 |
| 23.5 | 0.08 |
| 23.6 | 0.07 |
| 23.7 | 1.6 |
| 23.8 | 0.18 |
| 23.9 | 0.14 |
| 23.10 | 0.22 |
| 23.11 | 1.4 |
| 23.12 | 0.65 |
| 23.13 | 0.45 |
| 23.14 | 0.65 |
| 23.15 | 21.5 |
| 24.1 | 0.07 |
| 24.2 | 0.08 |
| 24.3 | 0.17 |
| 25.1 | 0.14 |
| 26.1 | 7.2 |

-continued

| Ex. | IC50 [µM] |
|---|---|
| 27.1 | 0.20 |
| 27.2 | 1.2 |
| 27.3 | 0.15 |
| 28.1 | 24.4 |
| 29.1 | 13.1 |
| 29.2 | 0.31 |
| 30.1 | 0.33 |
| 31.1 | 1.7 |
| 31.2 | 0.20 |
| 32.1 | 0.07 |
| 32.2 | 0.20 |
| 32.3 | 0.07 |
| 32.4 | 0.81 |
| 33.1 | 0.16 |
| 33.2 | 0.13 |
| 33.3 | 2.3 |
| 33.4 | 0.52 |
| 34.1 | 0.17 |
| 35.1 | 0.07 |
| 35.2 | 0.33 |
| 35.3 | 26.9 |

In view of their ability to inhibit the enzyme(s) acetyl-CoA carboxylase, the compounds of general formula (I) according to the invention and the correspon-ding salts thereof are theoretically suitable for the treatment, including preventative treatment of all those diseases or conditions which may be affected or which are mediated by the inhibition of the enzyme(s) acetyl-CoA carboxylase, in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase enzyme(s), in particular ACC2, in a patient, preferably in a human.

In yet another aspect the present invention relates a method for treating, including preventing a disease or condition mediated by the inhibition of acetyl-CoA carboxylase enzyme(s) in a mammal that includes the step of administering to a patient, preferably a human, in need of such treatment a therapeutically effective amount of a compound of the present invention, or a pharmaceutical composition thereof.

Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as is hyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, microalbuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or greater.

According to another aspect the compounds of the present invention are particularly suitable for treating, including preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:

A. disorders of fatty acid metabolism and glucose utilization disorders; disorders in which insulin resistance is involved;

B. hepatic disorders and conditions related thereto, including: fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;

C. skin disorders and conditions and those associated with polyunsaturated fatty acids, such as
   eczema, acne, sebaceous gland diseases, psoriasis, keloid scar formation or prevention, other diseases related to mucous membrane fatty acid composition;

D. primary hypertriglyceridemia or secondary hypertriglyceridemias following familial histiocytic reticulosis, lipoprotein lipase deficiency, hyperlipo-proteinemias, apolipoprotein deficiency (e.g. apoCII or apoE deficiency);

E. diseases or conditions related to neoplastic cellular proliferation, for example benign or malignant tumors, cancer, neoplasias, metastases, carcinogenesis;

F. diseases or conditions related to neurological, psychiatric or immune disorders or conditions;

G. other diseases or conditions in which inflammatory reactions, cell differentiation and/or other ACC-mediated aspects may for example be involved:

atherosclerosis such as, for example (but not restricted thereto), coronary sclerosis including angina pectoris or myocardial infarction, stroke, ischemic, stroke and transient ischemic attack (TIA),
peripheral occlusive disease,
vascular restenosis or reocclusion,
chronic inflammatory bowel diseases such as, for example, Crohn's disease and ulcerative colitis,
pancreatitis,
sinusitis,
retinopathy, ischemic retinopathy,
adipose cell tumors,
lipomatous carcinomas such as, for example, liposarcomas,
solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc.,
tumors in which ACC is up regulated,
acute and chronic myeloproliferative disorders and lymphomas, angiogenesis
neurodegenerative disorders including Alzheimer's disease, multiple sclerosis, Parkinson's disease, epilepsy,
erythemato-squamous dermatoses such as, for example, psoriasis,
acne vulgaris,
other skin disorders and dermatological conditions which are modulated by PPAR,
eczemas and neurodermatitis,
dermatitis such as, for example, seborrheic dermatitis or photodermatitis,
keratitis and keratoses such as, for example, seborrheic keratoses, senile keratoses, actinic keratoses, photo-induced keratoses or keratosis follicularis,
keloids and keloid prophylaxis,
bacterial infections,
fungal infections,
warts, including condylomata or condylomata acuminata
viral infections such as, for example, human hepatitis B virus (HBV), hepatitis C virus (HCV), West Nile virus (WNV) or Dengue virus, human Immunodeficiency virus (HIV), poxvirus and Vaccinia virus (VV), HCMV, influenza A, human papilloma viral (HPV) venereal papillomata, viral warts such as, for example, molluscum contagiosum, leukoplakia,
papular dermatoses such as, for example, lichen planus,
skin cancer such as, for example, basal-cell carcinomas, melanomas or cutaneous T-cell lymphomas,
localized benign epidermal tumors such as, for example, keratoderma, epidermal naevi,
chilblains;
high blood pressure,
polycystic ovary syndrome (PCOS),
asthma,
cystic fibrosis,
osteoarthritis,
lupus erythematosus (LE) or inflammatory rheumatic disorders such as, for example rheumatoid arthritis,
vasculitis,
wasting (cachexia),
gout,
ischemia/reperfusion syndrome,
acute respiratory distress syndrome (ARDS)
viral diseases and infections
lipodystrophy and lipodystrophic conditions, also for treating adverse drug effect;
myophathies and lipid myopathis (such as carnitine palm itoyltransferase I or II deficiency);
H. formation of muscles and a lean body or muscle mass formation.

The dose range of the compounds of general formula (I) applicable per day is usually from 0.001 to 10 mg, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11beta-hydroxy steroid dehydrogenase-1 (11beta-HSD type 1) inhibitors, stearoyl-CoA desaturase-1 (SCD-1) inhibitors, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-Y antagonists (e.g., NPY Y5 antagonists), $PY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, GOAT (Ghrelin O-Acyltransferase) inhibitors, histamine 3 antagonists or inverse agonists, neuromedin U agonists, MTP/ApoB inhibitors (e.g., gut-selective MTP inhibitors), opioid antagonists, orexin antagonists, and the like.

Preferred anti-obesity agents for use in the combination aspects of the present invention include gut-selective MTP inhibitors CCKa agonists, 5HT2c agonists, MCR4 agonists, lipase inhibitors, opioid antagonists, oleoyl-estrone, obinepitide, pramlintide (Symlin®), tesofensine (NS2330), leptin, liraglutide, bromocriptine, orlistat, exenatide (Byetta®), AOD-9604 (CAS No. 221231-10-3) and sibutramine.

Suitable anti-diabetic agents include sodium-glucose co-transporter (SGLT) inhibitors, 11beta-hydroxy steroid dehydrogenase-1 (11beta-HSD type 1) inhibitors, phosphodiesterase (PDE) 10 inhibitors, diacylglycerol acyltransferase (DGAT) 1 or 2 inhibitors, sulfonylureas (e.g., acetohexamide, chlorpropamide, diabinese, glibenclamide, glipizide, glyburide, glimepiride, gliclazide, glipentide, gliquidone, glisolamide, tolazamide, and tolbutamide), meglitinides, alpha-amylase inhibitors (e.g., tendamistat, trestatin and AL-3688), alpha-glucoside hydrolase inhibitors (e.g., acarbose), alpha-glucosidase inhibitors (e.g., adiposine, camiglibose, emiglitate, miglitol, voglibose, pradimicin-Q, and salbostatin), PPAR gamma agonists (e.g., balaglitazone, ciglitazone, darglitazone, englitazone, isaglitazone, pioglitazone, rosiglitazone and troglitazone), PPAR alpha/gamma agonists (e.g., CLX-0940, GW-1536, GW-20 1929, GW-2433, KRP-297, L-796449, LR-90, MK-0767 and SB-219994), biguanides (e.g., metformin), GLP-1 derivatives, glucagon-like peptide 1 (GLP-1) agonists (e.g., Byetta™, exendin-3 and exendin-4), GLP-1 receptor and glucagon receptor co-agonists, glucagon receptor antagonists, GIP receptor antagonists, protein tyrosine phosphatase-1 B (PTP-1 B) inhibitors (e.g., trodusquemine, hyrtiosal extract), SIRT-1 activators (e.g. reservatrol), dipeptidyl peptidease IV (DPP-IV) inhibitors (e.g., sitagliptin, vildagliptin, alogliptin, linagliptin and saxagliptin), insulin secretagogues, GPR119 agonists, GPR40 agonists, TGR5 agonists, MNK2 inhibitors, GOAT (Ghrelin O-Acyltransferase) inhibitors, fatty acid oxidation inhibitors, A2 antagonists, c-jun amino-terminal kinase (JNK) inhibitors, insulins, insulin derivatives, fast acting insulins, inhalable insulins, oral insulins, insulin mimetics, glycogen phosphorylase inhibitors, VPAC2 receptor agonists and glucokinase activators.

Preferred anti-diabetic agents are metformin, a glucagon-like peptide 1 (GLP-1) agonists (e.g., Byetta™), GLP-1 receptor and glucagon receptor co-agonists, sodium-glucose co-transporter (SGLT) inhibitors, 11beta-hydroxy steroid dehydrogenase-1 (11beta-HSD type 1) inhibitors and DPP-IV inhibitors (e.g. sitagliptin, vildagliptin, alogliptin, linagliptin and saxagliptin).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of the enzyme(s) acetyl-CoA carboxylase, in particular ACC2, in particular diseases or conditions as described hereinbefore and hereinafter.

In yet another aspect the present invention relates a method for treating, including preventing a disease or condition mediated by the inhibition of acetyl-CoA carboxylase enzyme(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

EXAMPLES

The Examples that follow are intended to illustrate the present invention without restricting it. The terms "ambient temperature" and "room temperature" are used interchangeably and designate a temperature of about 20° C.

Preliminary Remarks:

As a rule, 1H-NMR and/or mass spectra have been obtained for the compounds prepared. The $R_f$ values are determined using Merck silica gel 60 $F_{254}$ plates and UV light at 254 nm.

Experimental Part

The following abbreviations are used above and hereinafter:

| | |
|---|---|
| aq. | aqueous |
| ACN | acetonitrile |
| AcOH | acetic acid |
| BOC | tert-butoxy-Carbonyl- |
| BuLi | butyllithium |
| CDI | N,N-carbonyldiimidazole |
| CDT | N,N-carbonylditriazole |
| CyH | cyclohexane |
| DBAD | di-tert-butyl azodicarboxylate |
| DCM | dichloromethane |
| DIAD | diisopropyl azodicarboxylate |
| DIBAlH | diisobutyl aluminium hydride |
| DIPE | diisopropyl ether |

| | |
|---|---|
| DIPEA | N,N-diisopropylethylamine |
| DMAP | 4-dimethylaminopyridine |
| DMF | N,N-dimethylformamide |
| DMSO | dimethyl sulfoxide |
| EtOAc | ethyl acetate |
| EtOH | ethanol |
| Ex | example |
| FA | formic acid |
| HATU | 2-(1H-7-azabenzotriazol-1-yl)-1,1,3,3-tetramethyluronium hexafluorophosphate |
| HOBt | hydroxybenzotriazole |
| LAH | lithium aluminium hydride |
| MeOH | methanol |
| m.p. | melting point |
| MsCl | methanesulfonyl chloride |
| n.d. | not determined |
| NMP | N-methyl-2-pyrrolidone |
| Pd/C | palladium on activated carbon |
| PE | petroleum ether |
| PG | protecting group |
| r.t. | room temperature (about 20° C.) |
| sat. | saturated |
| TBME | tert-butyl methyl ether |
| TEA | triethylamine |
| TF/TFA | trifluoroacetic acid |
| THF | tetrahydrofuran |
| TBAF | tetrabutylammonium fluoride |
| TBTU | 2-(1H-benzotriazol-1-yl)-1,1,3,3-tetramethyluronium tetrafluoroborat |

Analytical Methods

1. HPLC

Method A

| time (min) | Vol % water (incl. 0.1% FA) | Vol % acetonitrile (incl. 0.1% FA) |
|---|---|---|
| 0.0 | 95 | 5 |
| 2.0 | 0 | 100 |
| 2.5 | 0 | 100 |
| 2.6 | 95 | 5 |

Analytical column: Sunfire C18 (Waters); 2.5 μm; 2.1×50 mm; column temperature: 60° C.; flow: 1.5 mL/min; detection 210-500 nm.

Method B

| time (min) | Vol % water (incl. 0.1% FA) | Vol % acetonitrile (incl. 0.1% FA) |
|---|---|---|
| 0.0 | 95 | 5 |
| 0.1 | 95 | 5 |
| 3.1 | 2 | 98 |
| 4.5 | 2 | 98 |
| 5.0 | 95 | 5 |

Analytical column: X-terra™ MS C18 (Waters); 2.5 μm; 4.6×30 mm; column temperature: r.t.; flow: 1.0 mL/min; detection 210-420 nm.

Method C

| time (min) | Vol % water (incl. 0.032% NH$_4$OH) | Vol % acetonitrile |
|---|---|---|
| 0.0 | 95 | 5 |
| 2.0 | 0 | 100 |
| 2.5 | 0 | 100 |
| 2.6 | 95 | 5 |

Analytical column: XBridge C18 (Waters); 1.7 μm; 2.1×50 mm; column temperature: 60° C.; flow: 1.3 mL/min; detection 210-500 nm.

Method D

| time (min) | Vol % water (incl. 0.032% NH$_4$OH) | Vol % methanol |
|---|---|---|
| 0.0 | 95 | 5 |
| 2.0 | 0 | 100 |

Analytical column: XBridge C18 (Waters); 3.5 μm; 4.6×50 mm; column temperature: 40° C.; flow: 1.5 mL/min; detection 210-500 nm.

Method E

| time (min) | Vol % water (incl. 0.2% NH$_4$OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters); 2.5 μm; 3.0×30 mm; column temperature: 40° C.; flow: 1.3 mL/min;

Method F

| time (min) | Vol % water (incl. 0.1% FA) | Vol % acetonitrile (incl. 0.1% FA) |
|---|---|---|
| 0.0 | 95 | 5 |
| 4.5 | 10 | 90 |
| 5.0 | 10 | 90 |
| 5.5 | 95 | 5 |

Analytical column: StableBond C18 (Agilent); 3.5 μm; 4.6×75 mm; column temperature: r.t.; flow: 1.6 mL/min; detection 230-254 nm.

Method G

| time (min) | Vol % water (incl. 0.1% FA) | Vol % acetonitrile (incl. 0.1% FA) |
|---|---|---|
| 0.0 | 95 | 5 |
| 2.0 | 10 | 90 |
| 5.0 | 10 | 90 |
| 5.5 | 95 | 5 |

Analytical column: Zorbax StableBond C18 (Agilent); 3.5 μm; 4.6×75 mm; column temperature: r.t.; flow: 1.6 mL/min; detection 230-254 nm.

Method H

| time (min) | Vol % water (incl. 0.13% TFA) | Vol % acetonitrile |
|---|---|---|
| 0.18 | 95 | 5 |
| 2.00 | 2 | 98 |
| 2.20 | 2 | 98 |
| 2.30 | 95 | 5 |

Analytical column: Microsorb 100-3 C18 (Varian); 3.0 μm; 4.6×30 mm; column temperature: r.t.; flow: 3.5 mL/min; detection 210-380 nm.

Method I

| time (min) | Vol % water (incl. 0.1% FA) | Vol % acetonitrile (incl. 0.1% FA) |
|---|---|---|
| 0.0 | 95 | 5 |
| 4.0 | 10 | 90 |
| 10.0 | 10 | 90 |
| 11.0 | 95 | 5 |

Analytical column: Zorbax StableBond C18 (Agilent); 3.5 µm; 4.6×75 mm; column temperature: r.t.; flow: 0.8 mL/min; detection 230-254 nm.

Method J

| time (min) | Vol % water (incl. 0.1% TFA) | Vol % acetonitrile (incl. 0.1% TFA) |
|---|---|---|
| 0.0 | 95 | 5 |
| 0.1 | 95 | 5 |
| 5.1 | 2 | 98 |
| 6.5 | 2 | 98 |
| 7.0 | 95 | 5 |

Analytical column: XTerra C18 (Waters); 4.6×50 mm; 3.5 µm; column temperature: 40° C.; flow: 1.0 mL/min; detection 230-254 nm.

Method K

| time (min) | Vol % water (incl. 0.1% TFA) | Vol % methanol |
|---|---|---|
| 0.0 | 95 | 5 |
| 1.3 | 0 | 100 |
| 2.5 | 0 | 100 |
| 2.6 | 95 | 5 |

Analytical column: Sunfire C18 (Waters); 3.5 µm; 4.6×50 mm; column temperature: 40° C.; flow: 1.5 mL/min; detection 210-500 nm.

Method L

| time (min) | Vol % water (incl. 0.032% NH$_4$OH) | Vol % methanol |
|---|---|---|
| 0.0 | 95 | 5 |
| 1.3 | 0 | 100 |
| 2.5 | 0 | 100 |
| 2.6 | 95 | 5 |

Analytical column: XBridge C18 (Waters); 1.7 µm; 2.1×50 mm; column temperature: 60° C.; flow: 1.0 mL/min; detection 210-500 nm.

Method M

| time (min) | Vol % water (incl. 0.1% TFA) | Vol % methanol |
|---|---|---|
| 0.0 | 95 | 5 |
| 1.3 | 0 | 100 |
| 3.0 | 0 | 100 |
| 3.4 | 95 | 5 |

Analytical column: Sunfire C18 (Waters); 3.5 µm; 4.6×50 mm; column temperature: 40° C.; flow: 1.5 mL/min; detection 210-500 nm.

Method N

| time (min) | Vol % water (incl. 0.1% TFA) | Vol % acetonitrile (incl. 0.08% TFA) |
|---|---|---|
| 0.0 | 95 | 5 |
| 2.0 | 0 | 100 |
| 2.5 | 0 | 100 |
| 2.6 | 95 | 5 |

Analytical column: Sunfire C18 (Waters); 3.5 µm; 4.6×50 mm; column temperature: 40° C.; flow: 1.5 mL/min; detection 210-500 nm.

Method O

| time (min) | Vol % water (incl. 0.2% NH$_4$OH) | Vol % methanol (incl. 3% water) |
|---|---|---|
| 0.0 | 95 | 5 |
| 1.0 | 10 | 90 |
| 2.2 | 10 | 90 |
| 2.3 | 0 | 100 |
| 2.5 | 0 | 100 |

Analytical column: XBridge C18 (Waters); 2.5 µm; 3.0×30 mm; column temperature: 40° C.; flow: 1.3 mL/min;

Method P

| time (min) | Vol % water (incl. 0.1% TFA) | Vol % acetonitrile (incl. 0.08% TFA) |
|---|---|---|
| 0.0 | 95 | 5 |
| 2.0 | 0 | 100 |
| 3.0 | 0 | 100 |
| 3.4 | 95 | 5 |

Analytical column: Sunfire C18 (Waters); 3.5 µm; 4.6×50 mm; column temperature: 40° C.; flow: 1.5 mL/min; detection 210-500 nm.

Method Q

| time (min) | Vol % water (incl. 0.1% FA) | Vol % methanol (incl. 0.1% FA) |
|---|---|---|
| 0.0 | 90 | 10 |
| 2.5 | 2 | 98 |
| 6.0 | 2 | 98 |

Analytical column: XBridge C18 (Waters); 3.5 µm; 2.1×50 mm; column temperature: 35° C.; flow: 0.8 mL/min; detection 220-320 nm.

Method R

| time (min) | Vol % 10 mM (NH$_4$)HCO$_3$ in water | Vol % methanol (incl. 10 mM (NH4)HCO3) |
|---|---|---|
| 0.0 | 90 | 10 |
| 2.5 | 2 | 98 |
| 6.0 | 2 | 98 |

Analytical column: XBridge C18 (Waters); 3.5 µm; 2.1×50 mm; column temperature: 25° C.; flow: 1.0 mL/min; detection 220-320 nm.

Method S

| time (min) | Vol % water (incl. 0.1% FA) | Vol % methanol (incl. 0.1% FA) |
|---|---|---|
| 0.00 | 90 | 10 |
| 1.25 | 2 | 98 |
| 3.00 | 2 | 98 |

Analytical column: XBridge C18 (Waters); 3.5 µm; 2.1×30 mm; column temperature: 35° C.; flow: 1.0 mL/min; detection 220-320 nm.

Method T

| time (min) | Vol % water (incl. 0.1% TFA) | Vol % methanol |
|---|---|---|
| 0.0 | 95 | 5 |
| 1.3 | 0 | 100 |
| 3.0 | 0 | 100 |
| 3.4 | 95 | 5 |

Analytical column: Sunfire C18 (Waters); 3.5 µm; 4.6×50 mm; column temperature: 40° C.; flow: 1.5 mL/min; detection 210-500 nm.

Method U

| time (min) | Vol % water (incl. 0.2% FA) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: Zorbax StableBond C18 (Agilent); 1.8 µm; 3.0×30 mm; column temperature: 40° C.; flow: 1.3 mL/min;

Method V

| time (min) | Vol % water (incl. 0.1% TFA) | Vol % acetonitrile (incl. 0.08% TFA) |
|---|---|---|
| 0.0 | 95 | 5 |
| 2.0 | 0 | 100 |
| 2.5 | 0 | 100 |
| 2.6 | 95 | 5 |

Analytical column: Sunfire C18 (Waters); 3.5 µm; 4.6×50 mm; column temperature: 40° C.; flow: 1.5 mL/min; detection 210-500 nm.

Method W

| time (min) | Vol % water (incl. 0.1% TFA) | Vol % methanol |
|---|---|---|
| 0.0 | 95 | 5 |
| 1.3 | 0 | 100 |
| 2.5 | 0 | 100 |
| 2.6 | 95 | 5 |

Analytical column: Sunfire C18 (Waters); 3.5 µm; 4.6×50 mm; column temperature: 40° C.; flow: 1.5 mL/min; detection 210-500 nm.

Method X

| time (min) | Vol % water (incl. 0.2% FA) | Vol % methanol (incl. 3% water) |
|---|---|---|
| 0.0 | 95 | 5 |
| 1.0 | 10 | 90 |
| 2.2 | 10 | 90 |
| 2.3 | 0 | 100 |
| 2.5 | 0 | 100 |

Analytical column: Zorbax StableBond C18 (Agilent); 1.8 µm; 3.0×30 mm; column temperature: 40° C.; flow: 1.3 mL/min;

Method Y

| time (min) | Vol % water (incl. 0.1% FA) | Vol % acetonitrile (incl. 0.1% FA) |
|---|---|---|
| 0.0 | 95 | 5 |
| 0.1 | 95 | 5 |
| 7.1 | 2 | 98 |
| 7.9 | 2 | 98 |
| 8.0 | 95 | 5 |

Analytical column: XTerra C18 (Waters); 4.6×50 mm; 3.5 µm; column temperature: r.t.; flow: 1.0 mL/min; detection 210-420 nm.

Method Z

| time (min) | Vol % water (incl. 0.1% FA) | Vol % acetonitrile (incl. 0.1% FA) |
|---|---|---|
| 0.00 | 95 | 5 |
| 1.00 | 10 | 90 |
| 2.50 | 10 | 90 |
| 2.75 | 95 | 5 |

Analytical column: Zorbax StableBond C18 (Agilent); 1.8 µm; 3.0×30 mm; column temperature: r.t.; flow: 1.6 mL/min;

Method AA

| time (min) | Vol % water (incl. 0.1% TFA) | Vol % methanol |
|---|---|---|
| 0.0 | 80 | 20 |
| 1.7 | 0 | 100 |
| 2.5 | 0 | 100 |
| 2.6 | 80 | 20 |

Analytical column: Sunfire C18 (Waters); 3.5 µm; 4.6×50 mm; column temperature: 60° C.; flow: 2 mL/min;

Method AB

| time (min) | Vol % water (incl. 0.2% NH$_4$OH) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: Gemini C18 (Phenomenex); 2.5 µm; 3.0×30 mm; column temperature: 40° C.; flow: 1.3 mL/min Method AC

| time (min) | Vol % water (incl. 0.032% NH₃) | Vol % acetonitrile |
| --- | --- | --- |
| 0.01 | 5 | 95 |
| 0.89 | 98 | 2 |
| 0.90 | 98 | 2 |
| 0.95 | 5 | 95 |

Analytical column: XBridge C18 (Waters); 3.0 μm; 4.6×20 mm; column temperature: r.t.; flow: 3.5 mL/min;

Method AD

| time (min) | Vol % water (incl. 0.2% NH₄OH) | Vol % methanol (incl. 3% water) |
| --- | --- | --- |
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters); 2.5 μm; 3.0×30 mm; column temperature: 60° C.; flow: 1.3 mL/min;

Method AE

| time (min) | Vol % water | Vol % ACN |
| --- | --- | --- |
| 0.0 | 80 | 20 |
| 15.0 | 20 | 80 |
| 20.0 | 20 | 80 |

Analytical column: Zorbax 300SB-C8 (Agilent); 3.5 μm; 4.6×150 mm; column temperature: 35° C.; flow: 1.0 mL/min;

Method AF

| time (min) | Vol % water (incl. 0.1% NH₄OH) | Vol % methanol |
| --- | --- | --- |
| 0.0 | 90 | 10 |
| 0.15 | 90 | 10 |
| 4.0 | 0 | 100 |
| 4.4 | 0 | 100 |
| 4.55 | 90 | 10 |
| 5.0 | 90 | 10 |

Analytical column: XBridge C18 (Waters) 2.5 μm; 3.0×30 mm; column temperature: r.t.; flow: 1.6 ml/min.

2. GC

Method A

Analytical column: SLB-5MS 15 m, ID 100 μM, df 0.10 μM.
Average velocity 45 cm/s, carrier gas:He, split ratio: 300:1, injector temp: 250° C.,
injection volume: 1 μL.
Initial temp: 60° C., initial time: 1.0 min, solvent delay: 0.6 min, rate: 50° C./min,
final temp: 250° C., final time: 1.0 min.

Preparation of Starting Compounds

Intermediate 1

4-Iodo-1H-pyridin-2-one

To 10.0 g (41.8 mmol) 2-chloro-4-iodopyridine in 100 mL AcOH are added 17.1 g (208 mmol) NaOAc and the reaction mixture is heated at 180° C. for 2 h in a microwave oven. DCM and water are added to the reaction mixture and the layers are separated. The organic layer is washed with water, dried with Na₂SO₄ and the solvent is removed in vacuo. The crude product is triturated with TBME.

$C_5H_4INO$ (M=221.0 g/mol),
ESI-MS: 222 [M+H]⁺
$R_f$ (TLC): 0.3 (silica gel DCM/MeOH 9/1)

Intermediate 2

Example I2.1

General Route

4-Iodo-N-propyl-2-pyridone

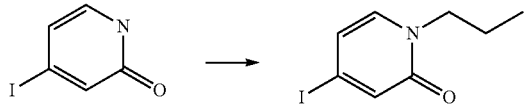

To 2.0 g (9.05 mmol) 4-iodo-2-pyridone in 10 mL DMF are added 1.00 mL (10.9 mmol) 1-bromopropane and 3.13 g (22.6 mmol) K₂CO₃. The reaction mixture is stirred at r.t. over night. The reaction is quenched by the addition of water. The resulting mixture is extracted with EtOAc. The organic layer is washed with aq. NaHCO₃ solution, dried with Na₂SO₄ and the solvent is removed in vacuo. The residue is purified by column chromatography (silica gel, heptane/EtOAc. 70/30→50/50)

$C_8H_{10}INO$ (M=263.1 g/mol)
ESI-MS: 264 [M+H]⁺
$R_t$ (HPLC): 1.51 min (method E)

The following compounds are prepared analogously to example I2.1

| Ex. | Starting material | Structure | Mass spec result | HPLC retention time (method) |
| --- | --- | --- | --- | --- |
| I2.1 | | 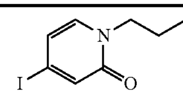 | 264 [M+H]⁺ | 1.51 (E) |

-continued

| Ex. | Starting material | Structure | Mass spec result | HPLC retention time (method) |
|---|---|---|---|---|
| I2.2 | (pyridinone with I, NH) | (N-isobutyl pyridinone with I) | 278 [M + H]+ | 2.99 (Q) |
| I2.3 | (pyridinone with I, NH) | (N-ethyl pyridinone with I) | 250 [M + H]+ | 2.46 (Q) |
| I2.4 | (pyridinone with I, NH) | (N-propyl pyridinone with I) | 278 [M + H]+ | 3.03 (Q) |
| I2.5 | (pyridinone with I, NH) | (N-methoxyethyl pyridinone with I) | 280 [M + H]+ | 2.53 (Q) |
| I2.6 | (pyridinone with I, NH) | (N-isopropyl pyridinone with I) | 264 [M + H]+ | 2.74 (Q) |

Intermediate 3

5-Isopropoxypicolinaldehyde

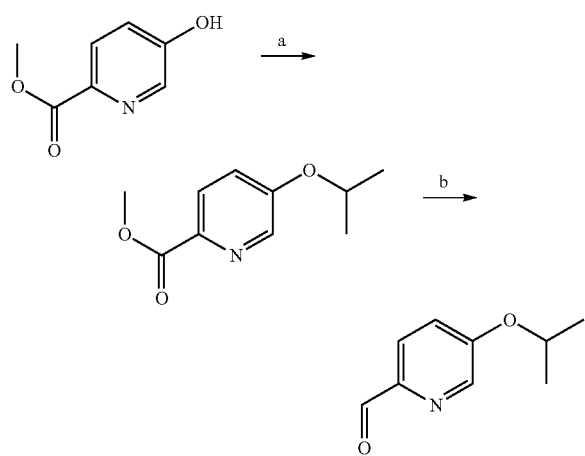

I3a Methyl 5-isopropoxypicolinate

To 2.7 g (17.6 mmol) methyl 5-hydroxypicolinate in 20 mL ACN and 5 mL DMF are added 6.09 g (44.1 mmol) $K_2CO_3$ and 5.0 mL (52.9 mmol) 2-bromopropane. The reaction mixture is stirred at reflux for 5 h and at r.t. over night. The mixture is filtered and the solvent is removed under vacuo. The residue is partitioned between EtOAc and water. The organic layer is dried with $Na_2SO_4$ and the solvent is removed in vacuo.

$C_{10}H_{13}NO_3$ (M=195.2 g/mol)

ESI-MS: 196 [M+H]+

$R_t$ (HPLC): 3.34 min (method F)

I3b 5-Isopropoxypicolinaldehyde 1.3 g (6.56 mmol) methyl 5-isopropoxypicolinate are added to 10 mL toluene and cooled down to −70° C. Then 9.84 mL (9.84 mmol) DIBAlH (1 mol/l in toluene) are added and stirring is continued for 1 h at −70° C. The reaction is quenched by the addition of a pH7 buffer solution and extracted with TBME. The organic layer is washed with water, dried with $Na_2SO_4$ and the solvent is removed in vacuo.

$C_9H_{11}NO_2$ (M=165.2 g/mol)

ESI-MS: 166 [M+H]+

Rf (TLC): 0.79 (silica gel; PE/EtOAc=1/1)

Intermediate 4

Example I4.1

General Route

2-Ethynyl-5-isopropoxypyridine

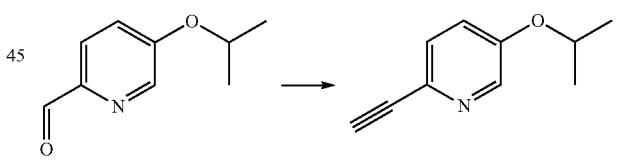

To 1.00 g (6.05 mmol) 5-isopropoxypicolinaldehyde in 20 mL methanol are added 1.67 g (12.1 mmol) $K_2CO_3$ followed by 1.4 g (7.26 mmol) dimethyl 1-diazo-2-oxopropylphosphonate. After stirring at r.t. over the weekend the reaction mixture is diluted with EtOAc and washed consecutively with $NaHCO_3$ solution and water. The organic layer is dried with $Na_2SO_4$ and the solvent is removed in vacuo.

$C_{10}H_{11}NO$ (M=161.2 g/mol)

ESI-MS: 162 [M+H]+

Rf (TLC): 0.28 (silica gel, PE/EtOAc 8/2)

The following compounds are prepared analogously to example I4.1

For example I4.2 the reaction conditions are 4 h at r.t.

For examples I4.3 and I4.4 the reaction conditions are 16 h at r.t.

| Ex. | Starting material | Product structure | Mass spec result | TLC retention factor (method) |
|---|---|---|---|---|
| I4.1 | | | 162 [M + H]⁺ | 0.28 (silica gel, PE/EtOAc 8/2) |
| I4.2 | | | 196 [M + H]⁺ | 0.75 (silica gel, PE/EtOAc 6/4) |
| I4.3 | | | 160 [M]⁺ | 0.45 (silica gel, PE/EtOAc 8/2) |
| I4.4 | | | 160 [M]⁺ | n.d. |

Intermediate 5

Example I5.1

General Route 5-tert-Butyl-2-iodobenzonitrile

To 1.0 g (5.74 mmol) 2-amino-5-tert-butylbenzonitrile in 7.5 mL 4 M aq. HCl at 0° C. is added 0.4 g (5.80 mmol) sodium nitrite in 2 mL water followed by 1.60 g (9.64 mmol) KI in 2 mL water. The reaction mixture is warmed to r.t. and extracted with EtOAc. The organic layer is washed with 10% aq. Na₂S₂O₅ solution and sat. NaCl solution, dried with MgSO₄ and the solvent is removed in vacuo. The crude product is purified by column chromatography (silica gel, CyH/EtOAc 100/0→90/10).

$C_{11}H_{12}IN$ (M=285.1 g/mol)

ESI-MS: 286 [M+H]⁺

$R_t$ (HPLC): 1.77 min (method H)

The following compounds are prepared analogously to example I5.1

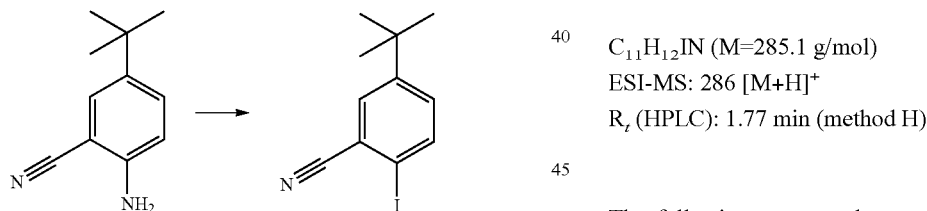

| Ex. | Starting material | Product structure | Mass spec result | HPLC retention time (method) |
|---|---|---|---|---|
| I5.1 | | | 286 [M + H]⁺ | 1.77 (H) |
| I5.2 | | | 314 [M + H]⁺ | 1.60 (H) |

Intermediate 6

Example I6.1

General Route

2-Ethoxy-4-iodopyridine

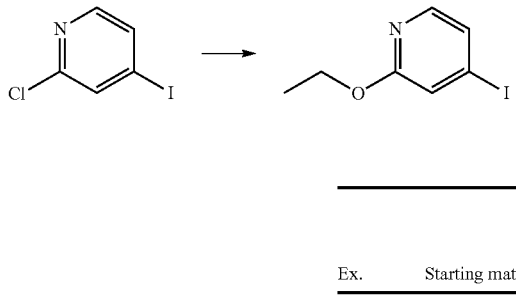

2.0 g (8.35 mmol) 2-chloro-4-iodopyridine and 3.4 mL (9.19 mmol) sodium ethoxide are added to 15 mL ethanol and stirred at reflux over night. The solvent is evaporated in vacuo and the residue is partitioned between water and DCM. The organic layer is dried ($Na_2SO_4$) and the solvent is removed in vacuo. The crude product is purified by column chromatography (silica gel, DCM/MeOH 100/0→96/4).

$C_7H_8INO$ (M=249.1 g/mol)
ESI-MS: 250 [M+H]$^+$
$R_t$ (HPLC): 3.43 (method B)

The following compounds are prepared analogously to example I6.1

For example I6.3 the reaction mixture is stirred at r.t. over night.

For example I6.4 tBuOH is used as solvent and KOtBu is used for deprotonation of the benzylic alcohol. The reaction conditions are 16 h at 50° C.

| Ex. | Starting material | Product structure | Mass spec result | HPLC retention time (method) |
|---|---|---|---|---|
| I6.1 | | | 250 [M + H]$^+$ | 3.43 (B) |
| I6.2 | | | 251 [M + H]$^+$ | 2.67 (B) |
| I6.3 | | | 251 [M + H]$^+$ | TLC $R_f$ = 0.5 (silica gel; DCM/MeOH 50/1) |
| I6.4 | | | 265 [M + H]$^+$ | TLC $R_f$ = 0.6 (silica gel; PE/EtOAc 10/1) |

Intermediate 7

4-Iodo-2-propoxy-pyridine

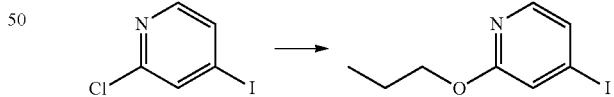

0.58 g (25.06 mmol) sodium are carefully added to 40 mL n-propanol by several portions. The mixture is stirred until the metal is dissolved completely (ca. 45 min). Then 6.00 g (25.1 mmol) 2-chloro-4-iodo-pyridine are slowly added to the mixture. The mixture is stirred at reflux for 3 h. The reaction is quenched by the addition of some water. The solvent is removed in vacuo and to the residue are added 20 mL DMF/MeOH. The mixture is filtrated and the filtrate is purified by HPLC (MeOH/$H_2$O/$NH_3$).

$C_8H_{10}INO$ (M=263.1 g/mol)
ESI-MS: 264 [M+H]$^+$
$R_t$ (HPLC): 2.15 min (method E)

Intermediate 8

4-Iodo-2-(2-methoxy-ethoxy)-pyridine

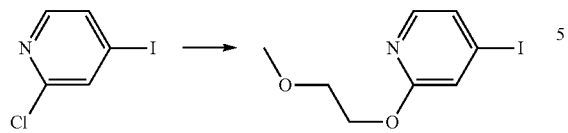

2.00 g (8.35 mmol) 3-iodo-1-chloropyridine are added to 5.00 mL (63.3 mmol) anhydrous 2-methoxyethanol. Then 316 mg (12.5 mmol) sodium hydride are added carefully. The reaction mixture is stirred at reflux over night. The mixture is allowed to cool to r.t., quenched with water and extracted with DCM. The organic layer is dried with $Na_2SO_4$ and the solvent is evaporated in vacuo. The crude product is purified by column chromatography (silica gel; DCM/MeOH 100/0→90/10).

$C_8H_{10}INO_2$ (M=279.1 g/mol)
ESI-MS: 280 [M+H]$^+$
$R_f$ (TLC): 0.9 (silica gel, DCM/MeOH 9/1)

Intermediate 9

Example I9.1

General Route

5-Bromo-2-(2-methoxyethoxy)pyridine

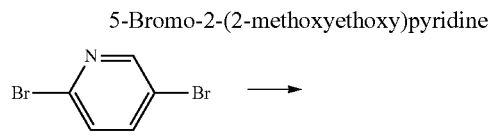

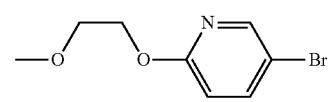

0.25 mL 2-methoxyethanol (3.17 mmol) are added to a mixture of 80 mg (3.17 mmol) sodium hydride in 5 mL THF. The reaction mixture is stirred at r.t. for 10 min before 500 mg (2.11 mmol) 2,5-dibromopyridine are added. After 5 h at 75° C. the reaction mixture is diluted with half sat.aq. NaHCO$_3$ solution and extracted with EtOAc. The organic layer is dried with MgSO$_4$ and the solvent is removed in vacuo. The crude product is purified by column chromatography (silica gel, PE/EtOAc 85/15).

$C_8H_{10}BrNO_2$ (M=232.1 g/mol)
ESI-MS: 232 [M+H]$^+$
$R_t$ (HPLC): 1.72 min (method E)

The following compounds are prepared analogously to example I9.1

For examples I9.2-5 the reaction mixture is stirred at 50° C. over night.

For example I9.4 and I9.5 DMF is used as solvent.

| Ex. | Starting material | Product structure | Mass spec result | HPLC retention time (method) |
|---|---|---|---|---|
| I9.1 | | | 232 [M + H]$^+$ | 1.72 (E). |
| I9.2 | | | 236 [M + H]$^+$ | 3.25 (Q) |
| I9.3 | | | 278 [M + H]$^+$ | 4.00 (Q) |
| I9.4 | | | 298 [M + H]$^+$ | 3.64 (Q) |
| I9.5 | | | 300 [M + H]$^+$ | 2.87 (Q) |

Intermediate 10

4-Iodo-2-isopropoxy-pyridine

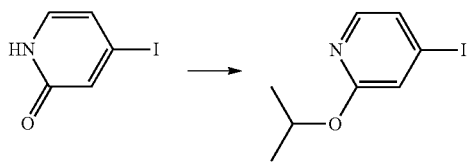

To 2.30 g (10.4 mmol) 4-iodo-1H-pyridin-2-one in 130 mL DCM are added 0.88 mL (11.4 mmol) 2-propanol and 3.00 (11.4 mmol) triphenylphosphine. After cooling down to 0° C. 2.23 mL (11.4 mmol) DIAD are added dropwise. After 5 min the cooling is removed and the mixture is stirred at r.t. for 2 h. The reaction mixture is washed with water and brine, dried with $Na_2SO_4$ and the solvent is removed in vacuo. The crude product is purified by column chromatography (silica gel, heptane/EtOAc 90/10).

$C_8H_{10}INO$ (M=263.1 g/mol)
ESI-MS: 264 $[M+H]^+$
$R_t$ (HPLC): 3.72 (method Q)

Intermediate 11

Example I11.1

General Route

2-Bromo-5-ethoxy-pyridine

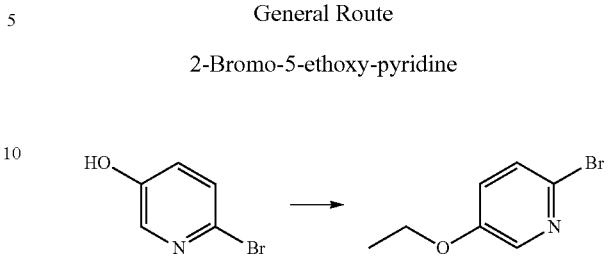

2.51 g (22.99 mmol) 1-bromoethane and 1.99 g (14.37 mmol) $K_2CO_3$ are added to a mixture of 1.0 g (5.75 mmol) 2-bromo-5-hydroxypyridine in 100 mL ACN. The mixture is stirred at reflux over night. Then the reaction mixture is poured onto water and extracted with TBME. The organic layer is dried with $Na_2SO_4$ and the solvent is removed under vacuo. The residue is purified by column chromatography (silica gel, PE/EtOAC 1/1).

$C_7H_8BrNO$ (M=202.1 g/mol)
ESI-MS: 202 $[M+H]^+$
$R_t$ (HPLC): 1.7 min (method AB)

The following compounds are prepared analogously to example I11.1

For example I11.4 DMF is used as solvent and the reaction mixture is stirred at 140° C. for 16 h.

| Ex. | Starting material | Product structure | Mass spec result | HPLC retention time (method) |
|---|---|---|---|---|
| I11.1 | HO-pyridine-Br | EtO-pyridine-Br | 202 $[M+H]^+$ | 1.7 (AB) |
| I11.2 | HO-pyridine-Br | n-PrO-pyridine-Br | 216 $[M+H]^+$ | 1.7 (AB) |
| I11.3 | HO-pyridine-Br | iBuO-pyridine-Br | 230 $[M+H]^+$ | 2.0 (E) |
| I11.4 | 4-bromocatechol | 3,3-dimethyl-7-bromo-benzo[b][1,4]dioxepine | 257 $[M]^+$ | TLC: $R_f$ = 0.90 (silica gel, PE/EtOAc 8/2) |

Intermediate 12

5-Hydroxy-pyrimidine

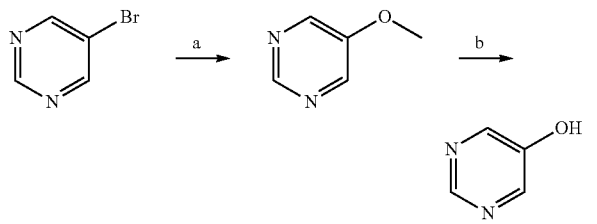

a)

10.0 g (63.0 mmol) 5-bromopyridine, 6.80 g (125 mmol) sodium methoxide and 200 mL MeOH are stirred in a sealed tube at 110° C. over night. The reaction mixture is allowed to cool to r.t. and the solvent is removed in vacuo. The residue is dissolved in water and extracted with DCM. The organic layer is dried with Na$_2$SO$_4$ and the solvent is removed under reduced pressure. The crude product is used without further purification.

C$_5$H$_6$N$_2$O (M=110.1 g/mol)
ESI-MS: 111 [M+H]$^+$
R$_t$ (HPLC): 0.32 min (method AC)

b)

An autoclave is charged with 13.1 g (119 mmol) 5-methoxy-pyrimidine and 250 ml Methanol. 66.8 g (1.19 mol) KOH are added and the mixture is stirred at 125° C. over night. After this the mixture is neutralized with AcOH to pH 6-7 and then concentrated under vacuo. The residue is triturated four times with hot MeCN and the combined extracts are concentrated under vacuum. The resulting crude product is purified by flash chromatography (EtOAc 100%).

C$_4$H$_4$N$_2$O (M=96.09 g/mol)
ESI-MS: 95 [M−H]−

Intermediate 13

5-(4-Hydroxy-phenoxy)-pyrimidine

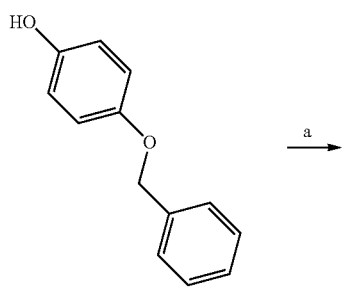

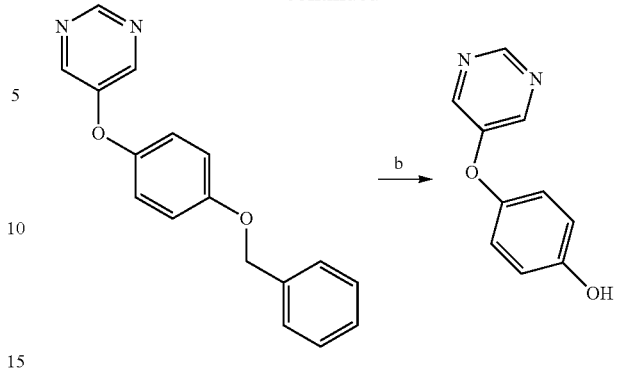

a)

To 1.00 g (4.99 mmol) 4-(benzyloxy)phenol and 794 mg (4.99 mmol) 5-bromo-pyrimidine in 5 mL DMF are added 3.25 g (9.99 mmol) Cs$_2$CO$_3$ and the reaction mixture is stirred at 120° C. for 6 h in a microwave oven. Then the reaction mixture is diluted with water and extracted with EtOAc. The organic layer is dried with Na$_2$SO$_4$ and the solvent is removed in vacuo. The residue is purified by HPLC (MeOH/H$_2$O/NH$_3$).

C$_{17}$H$_{14}$N$_2$O$_2$ (M=278.3 g/mol)
ESI-MS: 279 [M+H]$^+$
R$_t$ (HPLC): 2.02 min (method E)

b)

A mixture of 250 mg (0.898 mmol) 5-(4-benzyloxy-phenoxy)-pyrimidine and 20 mL THF is charged with 20 mg Pd/C and stirred under an atmosphere of hydrogen (5 bar) at 25° C. for 5.5 h. Then the reaction mixture is filtrated, and the solvent is removed in vacuo. The crude product is used without further purification.

C$_{10}$H$_8$N$_2$O$_2$ (M=188.2 g/mol)
ESI-MS: 189 [M+H]$^+$
R$_t$ (HPLC): 1.16 min (method E)

Intermediate 14

Example I14.1

General Route

5-Bromo-2-cyclopentyloxy-pyrimidine

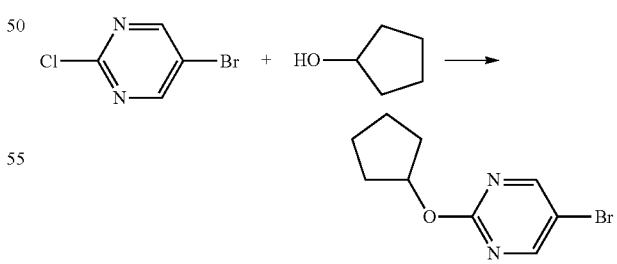

36.3 μL (0.40 mmol) cyclopentanol and 38.7 mg (0.20 mmol) 5-bromo-2-chloro-pyrimidine are added to 1.5 mL dioxane and cooled down to 0° C. Then the reaction mixture is charged with 24.0 mg NaH. After removing of the cooling bath the reaction mixture is stirred at r.t. over night. The reaction is quenched by the addition of water. The solvent is removed under vacuo and the residue is dissolved in DCM, washed with water and dried with MgSO4. The solvent is removed under reduced pressure. The crude product is used without further purification.

$C_9H_{11}BrN_2O$ (M=243.1 g/mol)

ESI-MS: 243 [M+H]$^+$

R$_f$ (TLC): 2.07 (method AA)

The following compounds are prepared analogously to example I14.1

For example I14.3 the crude product is purified by column chromatography (silica gel, PE/EtOAc 9/1);

For examples I14.4-7 THF is used as solvent and the product is purified by column chromatography.

| Ex. | Starting material | Product structure | Mass spec result | HPLC retention time (method) |
|---|---|---|---|---|
| I14.1 | | | 243 [M + H]$^+$ | 2.07 (AA) |
| I14.2 | | | 229 [M + H]$^+$ | 1.95 (E) |
| I14.3 | | | 293 [M + H]$^+$ | TLC: R$_f$ = 0.90 (silica gel, PE/EtOAc 9/1) |
| I14.4 | | | 279 [M + H]$^+$ | 3.35 (Q) |
| I14.5 | | | 265 [M + H]$^+$ | 3.14 (Q) |
| I14.6 | | | 299 [M + H]$^+$ | 3.12 (Q) |
| I14.7 | | | 281 [M + H]$^+$ | 2.47 (Q) |
| I14.8 | | | 281 [M + H]$^+$ | 3.86 (AF) |

Intermediate 15

Example I15.1

General Route 5-(5-Iodopyridin-2-yloxy)pyrimidine

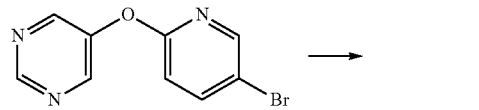

A mixture of 550 mg (2.18 mmol) 5-(5-bromopyridin-2-yloxy)pyrimidine and 2.5 mL 1,4-dioxane is charged with 42 mg (0.22 mmol) CuI, 650 mg (4.36 mmol) NaI and 50 µl (0.44 mmo) N,N-dimethylethylendiamine. The reaction mixture is stirred at 110° C. over night. The mixture is allowed to cool down to r.t. and diluted with EtOAc. The mixture is washed with 5% aq. ammonia solution and water. The organic layer is dried with $Na_2SO_4$ and the solvent is removed in vacuo to yield the desired product without further purification.

$C_9H_6IN_3O$ (M=299.1 g/mol)

ESI-MS: 300 $[M+H]^+$ $R_t$ (HPLC): 1.63 min (method E)

The following compounds are prepared analogously to example I15.1

| Ex. | Starting material | Product structure | Mass spec result | HPLC retention time (method) |
|---|---|---|---|---|
| I15.1 | | | 300 $[M + H]^+$ | 1.63 (E) |
| I15.2 | | | 280 $[M + H]^+$ | 1.79 (E) |
| I15.3 | | | 264 $[M + H]^+$ | 2.14 (E) |
| I15.4 | | | 277 $[M + H]^+$ | 1.96 (E) |
| I15.5 | | | 276 $[M + H]^+$ | 1.86 (E) |
| I15.4 | | | 272 $[M + H]^+$ | 2.00 (AB) |
| I15.5 | | | 304 $[M]^+$ | 2.30 (E) |

| Ex. | Starting material | Product structure | Mass spec result | HPLC retention time (method) |
|---|---|---|---|---|
| I15.6 | 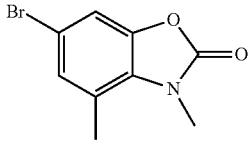 | 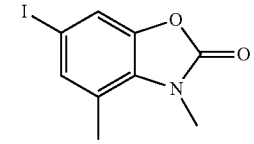 | 290 [M + H]⁺ | TLC: $R_f$ = 0.72 (silica gel, toluene/ EtOH 8/2) |

* the used aryl-bromide can be synthesized accordingly to U.S. 2006/0252931

Intermediate 16

Example I16.1

General Route

1-Iodo-4-isobutoxybenzene

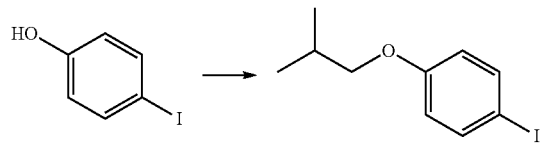

3.0 g (13.64 mmol) 4-iodophenol, 1.6 mL (15.00 mmol) 1-bromo-2-methylpropane and 7.5 g (54.54 mmol) $K_2CO_3$ are added to 30 mL DMF and stirred at 80° C. for 4 h. Afterwards the reaction mixture is diluted with water and extracted with EtOAc. The organic layer is washed with diluted aq. NaOH (2×) and water (2×), dried with $MgSO_4$ and the solvent is removed in vacuo. The crude product is used without further purification.

$C_{10}H_{13}IO$ (M=276.1 g/mol)

ESI-MS: 276 [M*]⁺

$R_t$ (HPLC): 1.39 min (method X)

The following compounds are prepared analogously to example I16.1

For example I16.2 the reaction conditions are 2 d at 120° C.

For example I16.9 the reaction time is 24 h.

| Ex. | Starting material | Product structure | Mass spec result | HPLC retention time (method) |
|---|---|---|---|---|
| I16.1 |  |  | 276 [M + H]⁺ | 1.39 (Z) |
| I16.2 |  |  | 274 [M]⁺ | 2.29 (E) |
| I16.3 |  |  | 219 [M − $C_4H_9$]⁻ | 2.30 (E) |
| I16.4 |  |  | 262 [M]⁺ | 1.29 (Z) |
| I16.5 |  |  | 290 [M]⁺ | n.d. |
| I16.6 |  |  | 262 [M]⁺ | 2.43 (U) |

| Ex. | Starting material | Product structure | Mass spec result | HPLC retention time (method) |
|---|---|---|---|---|
| I16.7 | HO-C6H4-I | cyclopropylmethyl-O-C6H4-I | 219 [M − C4H9]− | 2.22 (E) |
| I16.8 | HO-C6H4-I | cyclopentyl-O-C6H4-I | 219 [M − C5H9]− | 2.36 (E) |
| I16.9 | HO-C6H4-I | n-butyl-O-C6H4-I | 219 [M − C4H9]− | 2.54 (AA) |
| I16.10 | HO-C6H4-I (meta) | isopropyl-O-C6H4-I (meta) | 219 [M − C3H7]− | 2.22 (E) |

Intermediate 17

4-(Pyrimidin-5-yloxy)-phenyl trifluoromethanesulfonate

A mixture of 620 mg (3.30 mmol) of the phenol and 1.29 g (3.62 mmol) N-phenyltrifluoromethanesulfonimide in 10 mL DCM is cooled down to 0° C. 502 µl (3.62 mmol) TEA are added dropwise and stirring is continued for 1 h at constant temperature. Then the cooling is removed and the reaction mixture is stirred at r.t. over night. The reaction is quenched by the addition of water and extracted with DCM. The organic layer is washed with sat. aq. NaHCO$_3$ solution, dried with Na$_2$SO$_4$ and the solvent is removed in vacuo. The crude product is purified by flash chromatography (silica gel, CyH/EtOAc 70/30→60/40).

C$_{11}$H$_7$F$_3$N$_2$O$_4$S (M=320.3 g/mol)

ESI-MS: 321 [M+H]$^+$

R$_t$ (HPLC): 1.88 min (method E)

Intermediate 18

Example I18.1

General Route

2-Iodo-5-(4-methoxyphenyl)pyrazine

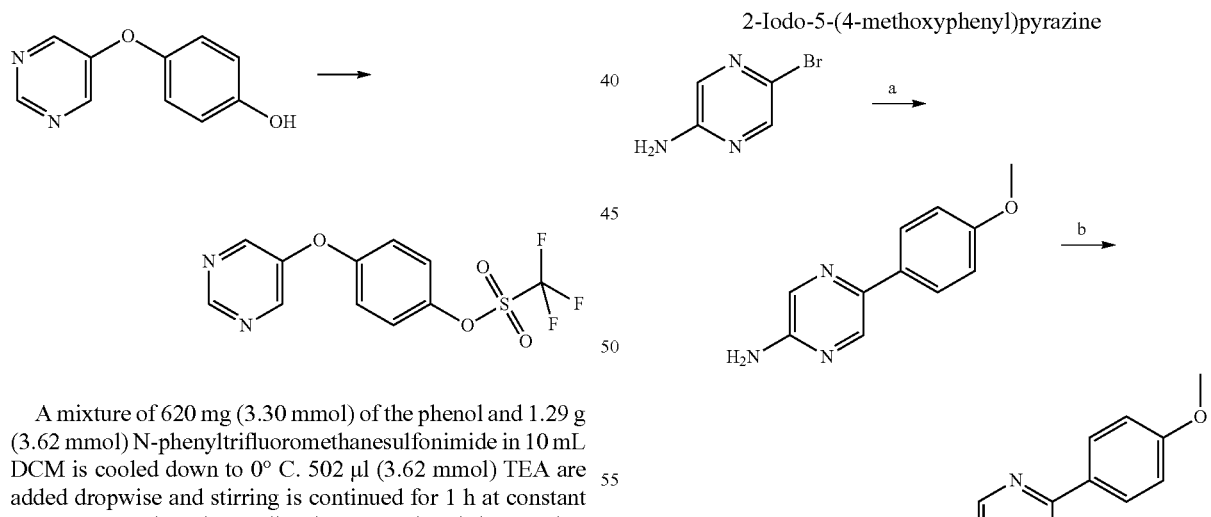

a)

To 5.00 g (28.7 mmol) 5-bromo-pyrazine-2-ylamine in 150 mL dioxane and 50 mL MeOH are added 4.58 g (30.2 mmol) 4-methoxyphenyl boronic acid, 0.13 g (0.17 mmol) PdCl$_2$(dppf)xCH$_2$Cl$_2$ and 28.7 mL (57.5 mmol) aq. 2N Na$_2$CO$_3$ solution and the reaction mixture is stirred under reflux for 7 h. The amount of solvent is reduced to some extent and EtOAc and water are added and the layers are separated. The org. layer is washed with aq. NaHCO₃ solution, dried with MgSO₄ and the solvent is removed in vacuo. The residue is triturated with TBME.

b)

In a light protected flask, 4.10 g (20.4 mmol) 5-(4-methoxyphenyl)-pyrazin-2-amine are added to 140 mL carbon tetrachloride. After cooling down to 0° C. 4.12 mL (34.6 mmol) tert-butyl nitrite and 6.72 g (26.5 mmol) iodine are added sequently. Then cooling is removed and the reaction mixture is stirred at ambient temperature over night. The reaction mixture is diluted with DCM and washed sequently with aq. Na₂S₂O₅ solution and water. The organic layer is dried with MgSO₄ and the solvent is removed in vacuo. The residue is triturated with TBME and purified by column chromatography (silica gel, PE/EtOAc 6/4).

$C_{11}H_9IN_2O$ (M=312.1 g/mol)
ESI-MS: 313 [M+H]⁺
$R_t$ (HPLC): 3.10 min (method G)

The following compounds are prepared analogously to example I18.1

| Ex. | Starting material | Product structure | Mass spec result | HPLC retention time (method) |
|---|---|---|---|---|
| I18.1 | {H₂N-pyrazine-Br} | {I-pyrazine-phenyl-OMe} | 313 [M + H]⁺ | 3.10 (G) |
| I18.2 | {H₂N-pyrazine-Br} | {I-pyrazine-phenyl-Cl} | 317 [M + H]⁺ | TLC: $R_f$= 0.55 (silica gel, PE/EtOAc 9/1) |

Intermediate 19

Example I19.1

General Route

1-Iodo-2-methyl-4-propoxybenzene

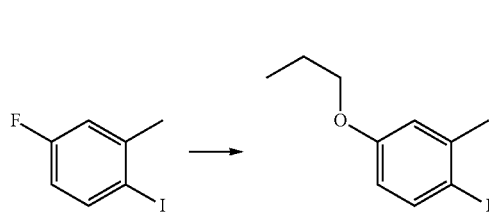

3.44 mL (45.8 mmol) 1-propanol is added to an ice cold mixture of 3.42 g (30.5 mmol) KOtBu in 18 mL DMF. After stirring the mixture for 10 min 1.80 g (7.63 mmol) 4-fluoro-1-iodo-2-methylbenzene are added and the reaction mixture is stirred at 80° C. for 3 h. The reaction is quenched by the addition of a sat. aq. NH₄Cl solution and extracted with EtOAc (2×). The combined organic layers are washed with sat. aq. NH₄Cl solution and brine, dried with Na₂SO₄ and the solvent is removed in vacuo. The crude product is purified by column chromatography (silica gel, heptane/EtOAc 9/1).

$C_{10}H_{13}IO$ (M=276.1 g/mol)
EI-MS: 276 [M]⁺
$R_t$ (GC): 4.31 min (method A)

The following compounds are prepared analogously to example I19.1

For example I16.2 the reaction mixture is stirred at r.t. for 3 h.

| Ex. | Starting material | Product structure | Mass spec result | GC retention time (method) |
|---|---|---|---|---|
| I19.1 | {F-phenyl-Me-I} | {propyl-O-phenyl-Me-I} | 276 [M + H]⁺ | 4.31 (A) |

-continued

| Ex. | Starting material | Product structure | Mass spec result | GC retention time (method) |
|---|---|---|---|---|
| I19.2 | {F-phenyl-Cl-I} | {propyl-O-phenyl-Cl-I} | 296 [M]⁺ | 4.56 (A) |

Intermediate 20

1-Iodo-2-methoxy-4-propoxybenzene

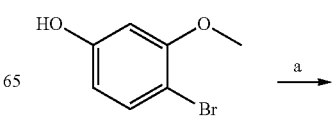

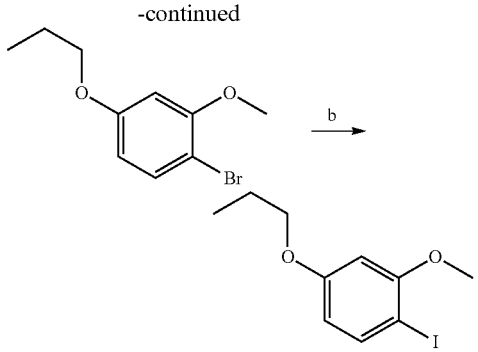

a)

To 1.50 g (7.39 mmol) 4-bromo-3-methoxy-phenol and 1.36 g (11.1 mmol) 1-bromopropane in 10 mL DMF are added 2.04 g (14.8 mmol) $K_2CO_3$ and the reaction mixture is stirred at 80° C. over night. The reaction mixture is diluted with water and extracted with DCM. The organic layer is dried with $Na_2SO_4$ and the solvent is removed in vacuo.

$C_{10}H_{13}BrO$ (M=245.1 g/mol)
ESI-MS: 245 [M+H]+.
$R_t$ (HPLC): 2.12 (method E)

b)

A mixture of 3.64 g (14.9 mmol) 1-bromo-2-methoxy-4-propoxybenzene and 100 mL THF is cooled down to −78° C. 11.1 mL (17.8 mmol) BuLi (1.6M solution in hexane) are added via a syringe. The mixture is stirred for 5 min at constant temperature. Then a mixture of 5.65 g (22.3 mmol) $I_2$ in 10 mL THF is added via a syringe until a yellow color persisted. The mixture is allowed to reach r.t. The solvent is removed in vacuo and the residue is purified by column chromatography (silica gel, heptane/EtOAc 1/1).

$C_{10}H_{13}IO_2$ (M=292.1 g/mol)
EI-MS: 292 [M]+.
$R_t$ (GC): 4.64 (method A)

Intermediate 21

2-Iodo-5-propoxy-benzamide

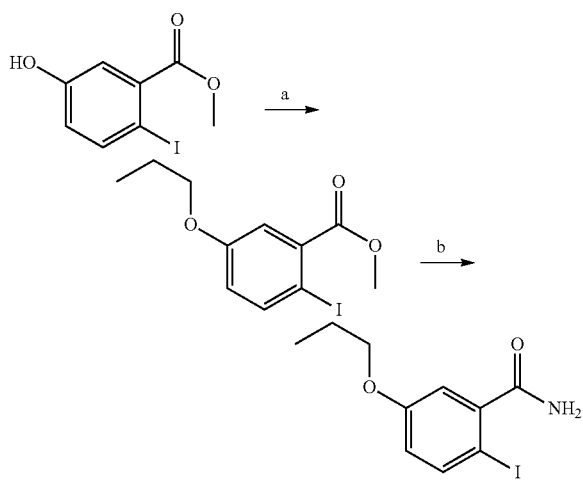

a)

2.97 mL 32.7 mmol) 1-bromopropane and 299 mg (1.80 mmol) KI are added to a mixture of 3.39 g (24.5 mmol) $K_2CO_3$ and 200 mL acetone. The mixture is stirred for 30 min under reflux. Then 5.00 g (18.0 mmol) methyl-5-hydroxy-2-iodobenzoate are added and the resulting mixture is refluxed for 2 h. One more equivalent of 1-bromopropane and $K_2CO_3$ is added and refluxing is continued over night. The reaction is quenched by the addition of water and extracted with EtOAc. The organic layer is dried with $Na_2SO_4$ and the solvent is removed in vacuo. The crude product is purified by column chromatography (silica gel, heptane/EtOAc 100/0→60/40).

The product is used without further characterization.

b)

A mixture of 4.12 g (12.9 mmol) methyl-5-propoxy-2-iodobenzoate and 60 mL MeOH is charged with 129 mL (258 mmol) 2N aq. NaOH solution. The resulting mixture is stirred at 50° C. for 3 h. Then the mixture was acidified to pH5 with 1 M aq. HCl and extracted with EtOAc (2×). The combined organic layers are washed with water and brine, dried with $Na_2SO_4$ and the solvent is removed in vacuo. The crude product from the previous saponification is added to 30 mL THF, charged with 2.04 g (12.6 mmol) CDI and stirred at r.t. for 1 h. More 0.5 eq CDI are added and stirring is continued for 20 min. To this mixture are added dropwise 20 mL of 35% ammonia in water and the resulting reaction mixture is stirred at r.t. for 5 min. The solvent is partly removed in vacuo until precipitation of a white solid occurs. The product is filtered and dried at 40° C. in vacuo.

$C_{10}H_{12}NIO_2$ (M=305.1 g/mol)
ESI-MS: 306 [M+H]+
$R_t$ (HPLC): 2.98 (method Q)

Intermediate 22

1-Iodo-2-cyano-4-propoxy-benzene

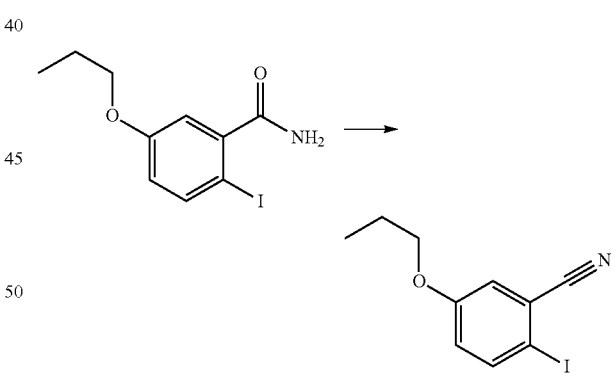

To 1.40 g (4.59 mmol) 2-iodo-5-propoxy-benzamide in 40 mL DMF are added 1.67 mL (22.9 mmol) $SOCl_2$ and the reaction mixture is stirred at 115° C. for 1 h. The reaction is quenched by the addition of water and extracted with EtOAc (3×). The combined organic layers are washed with water and brine, dried with $Na_2SO_4$ and the solvent is removed in vacuo. The crude product is purified by column chromatography (silica gel, heptane/EtOAc 100/0→60/40).

$C_{10}H_{10}INO$ (M=287.1 g/mol)
EI-MS: 287 [M]+
$R_t$ (GC): 4.84 (method A)

Intermediate 23

Example I23.1

General Route 2-(4-Methoxyphenyl)-5-((trimethylsilyl)ethynyl)pyrazine

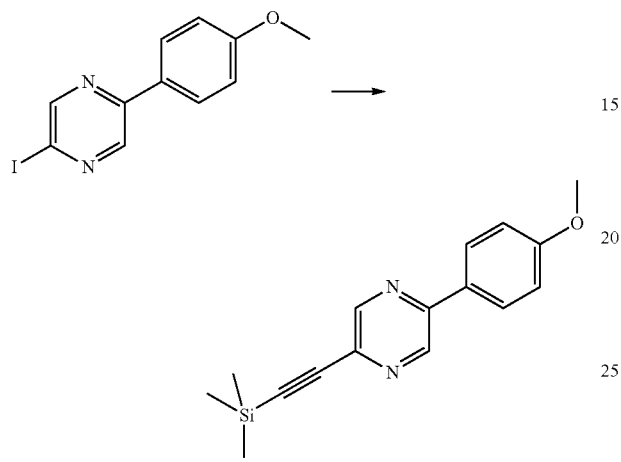

A mixture of 2.30 g (7.37 mmol) 2-iodo-5-(4-methoxyphenyl)pyrazine and 1.56 mL (11.1 mmol) ethynyltrimethylsilane in 30 mL THF is charged with 0.12 g (0.15 mmol) bis(triphenylphosphine)dichloropalladium, 0.03 g (15.0 mmol) CuI and 3.01 mL (22.1 mmol) TEA. After stirring at r.t. for 4 h the reaction mixture is diluted with DCM and washed with 50 mL aq. 5% ammonia solution (1×) and 50 mL water (1×). The organic layer is dried with $MgSO_4$ and the solvent is removed in vacuo. The residue is treated with PE/EtOAc (8/2), filtered through a plug of silica gel and the solvent is again removed in vacuo. The product is used without further purification.

$C_{16}H_{18}N_2OSi$ (M=282.4 g/mol)

ESI-MS: 283 $[M+H]^+$

Rf (TLC): 0.6 (silica gel; PE/EtOAc 8/2)

The following compounds are prepared analogously to example I23.1

For examples I23.2, I23.3 and I23.7 $PdCl_2(dppf)xCH_2Cl_2$ is used as catalyst.

For example I23.4-6 and I23.8 the silane is added under cooling.

For examples I23.5 and I23.8 purification by flash chromatography is necessary.

| Ex. | Starting material | Product structure | Mass spec result | TLC retention factor (method) |
|---|---|---|---|---|
| I23.1 | | | 283 [M + H]⁺ | 0.60 (silica gel, PE/EtOAc 8/2;) |
| I23.2 | | | 287/9 [M + H]⁺ | 0.70 (silica gel, PE/EtOAc 8/2) |
| I23.3 | | | 329 [M + H]⁺ | 0.70 (silica gel, PE/DCM/EtOAc 5/4/1) |
| I23.4 | | | n.d. | 0.65 (silica gel, PE/EtOAc 9/1) |
| I23.5 | | | 233 [M + H]⁺ | 0.75 (silica gel, CyH/EtOAc 2/1) |
| I23.6 | | | 247 [M + H]⁺ | HPLC: $R_t$ = 2.47 (method AA) |

| Ex. | Starting material | Product structure | Mass spec result | TLC retention factor (method) |
|---|---|---|---|---|
| I23.7 | [structure: 4-bromo-2-methyl-benzoyl pyrrolidine]* | [structure: TMS-alkynyl-2-methyl-benzoyl pyrrolidine] | 286 [M + H]⁺ | HPLC: $R_t$ = 5.20 (method J) |
| I23.8 | [structure: 1-(2-hydroxyethyl)-5-iodoindole]** | [structure: 1-(2-hydroxyethyl)-5-(TMS-ethynyl)indole] | 258 [M + H]⁺ | 0.25 (silica gel, CyH/EtOAc 2/1) |

\* the used aryl-bromide can be synthesized accordingly to WO2008/148867
\*\* the used aryl-iodide can be synthesized accordingly to WO2004/039780

Intermediate 24

Example I24.1

General Route 2-((tert-Butyldimethylsilyl)ethynyl)-5-p-tolylpyridine

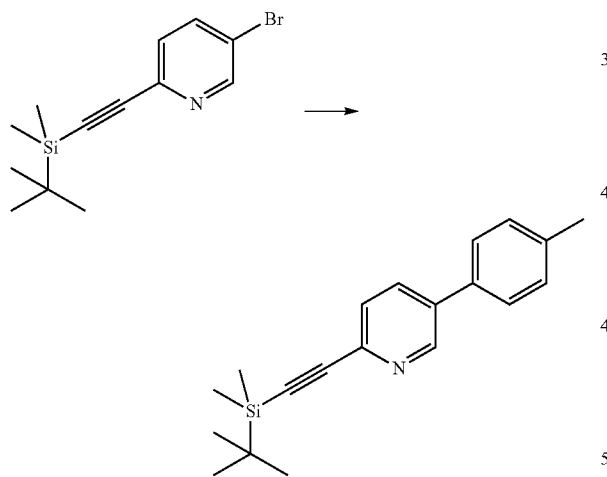

4.6 g (15.00 mmol) 5-bromo-2-((tert-butyldimethylsilyl)ethynyl)pyridine are added to 12 mL methanol and 50 mL 1,4-dioxane. Then the mixture is charged with 2.40 g (17.3 mmol) p-tolyl-boronic acid, 0.1 g (0.15 mmol) bis(triphenyphosphine)-dichloropalladium and 16.5 mL (33.0 mmol) of a 2N aq. Na₂CO₃ solution. The reaction mixture is stirred at reflux for 2 h. Then the solvent is removed in vacuo to some extent and the residue is diluted with EtOAc and water. The organic layer is sequently washed with 50 mL half sat. Na₂CO₃ solution (1×) and 50 mL water (1×). The organic layer is dried with MgSO₄ and the solvent is removed in vacuo. The residue is treated with DIPE and PE to receive a precipitate which is filtered and dried to yield the desired product.

$C_{20}H_{25}NSi$ (M=307.5 g/mol)
ESI-MS: 308 [M+H]⁺
Rf (TLC): 0.4 (silica gel, PE/DCM 1/1)

The following compounds are prepared analogously to example I24.1

For examples I24.2 and I24.3 Pd(dppf)Cl₂ is used as catalyst

| Ex. | Starting material | Product structure | Mass spec result | TLC retention factor (method) |
|---|---|---|---|---|
| I24.1 | [structure: TBS-ethynyl-5-bromopyridine] | [structure: TBS-ethynyl-5-(4-tolyl)pyridine] | 308 [M + H]⁺ | 0.40 (silica gel, PE/EtOAc 1/1) |
| I24.2 | [structure: TBS-ethynyl-5-bromopyridine] | [structure: TBS-ethynyl-5-(4-fluorophenyl)pyridine] | 198 [M + H]⁺ | 0.30 (silica gel, PE/EtOAc 1/1) |

Intermediate 25

Example I25.1

General Route

2-Ethynyl-5-(4-methoxyphenyl)pyrazine

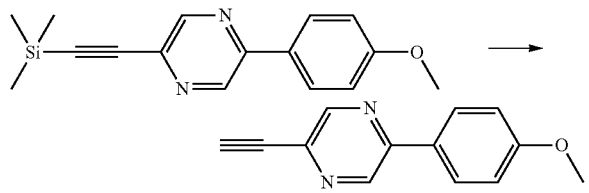

To 2.00 g (7.08 mmol) 2-(4-methoxyphenyl)-5-((trimethylsilyl)ethynyl)pyrazine in 50 mL DCM are added 2.08 g (7.44 mmol) TBAF*H$_2$O and the reaction mixture is stirred at r.t. for 30 min. The mixture is washed with 50 mL water (3×) and the organic layer is dried with MgSO$_4$ and the solvent is removed in vacuo. The crude product is purified by column chromatography (silica gel, PE/EtOAc 100/0→80/20).

C$_{13}$H$_{10}$N$_2$O (M=210.2 g/mol)

ESI-MS: 211 [M+H]$^+$

Rf (TLC): 0.3 (silica gel, PE/EtOAc 8/2)

The following compounds are prepared analogously to example I25.1

For example I25.7 TBAF*3H$_2$O is added at 0° C. and stirred at r.t. for 1 h.

For examples I25.6 and I25.8 THF is used as solvent.

| Ex. | Starting material | Product structure | Mass spec result | TLC retention factor (method) |
|---|---|---|---|---|
| I24.3 | (structure) | (structure) | 324 [M + H]$^+$ | 0.40 (silica gel, PE/EtOAc 8/2) |
| I25.1 | (structure) | (structure) | 211 [M + H]$^+$ | 0.30 (silica gel, PE/EtOAc 8/2) |
| I25.2 | (structure) | (structure) | 213/5 [M + H]$^+$ | 0.40 (silica gel, PE/EtOAc 8/2) |
| I25.3 | (structure) | (structure) | 210 [M + H]$^+$ | 0.20 (silica gel, PE/EtOAc 8/2) |
| I25.4 | (structure) | (structure) | 198 [M + H]$^+$ | 0.10 (PE/DCM 1/1) |
| I25.5 | (structure) | (structure) | 194 [M + H]$^+$ | 0.15 (silica gel, PE/DCM 1:1) |
| I25.6 | (structure) | (structure) | 215/7 [M + H]$^+$ | 0.40 (silica gel, PE/DCM/EtOAc 5/4/1) |

-continued

| Ex. | Starting material | Product structure | Mass spec result | TLC retention factor (method) |
|---|---|---|---|---|
| I25.7 | | | 175 [M + H]+ | HPLC: R_t = 2.05 (method AA) |
| I25.8 | | | 186 [M + H]+ | 0.20 (silica gel, EtOAc/ MeOH/NH_3 9/1/0.1) |

Intermediate 26

Example I26.1

General Route

4-Ethynyl-benzoic acid methyl ester

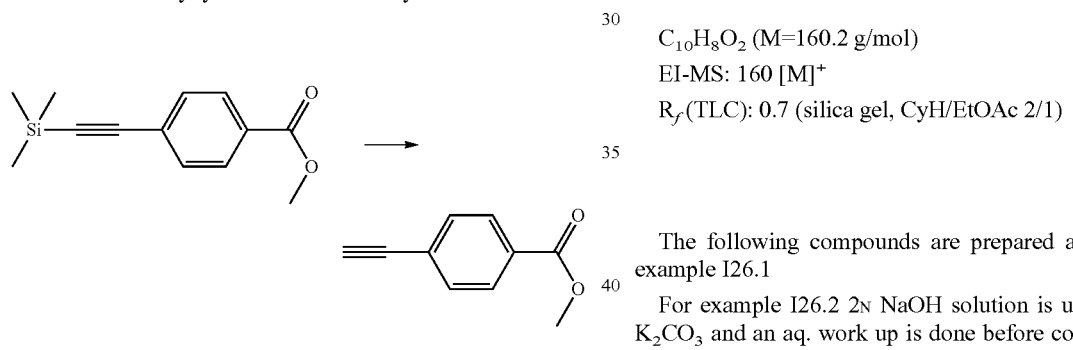

18.1 g (77.9 mmol) 4-trimethylsilanylethynyl-benzoic acid methyl ester are added to 400 mL MeOH, cooled down to 0° C. and charged with 3.24 g (23.4 mmol) $K_2CO_3$. The reaction mixture is stirred for 3 h, then the solvent is removed in vacuo and the resulting residue is purified by column chromatography (silica gel, hexane/TBME 10/1).

$C_{10}H_8O_2$ (M=160.2 g/mol)

EI-MS: 160 [M]+

$R_f$(TLC): 0.7 (silica gel, CyH/EtOAc 2/1)

The following compounds are prepared analogously to example I26.1

For example I26.2 2N NaOH solution is used instead of $K_2CO_3$ and an aq. work up is done before column chromatography.

| Ex. | Starting material | Product structure | Mass spec result | TLC retention factor (method) |
|---|---|---|---|---|
| I26.1 | | | 160 [M]+ | 0.7 (silica gel, CyH/EtOAc 2/1) |
| I26.2 | | | 214 [M + H]+ | HPLC: R_t = 3.91 (J) |

Intermediate 27

3-Biphenyl-4-yl-2,3-dibromo-propionic acid

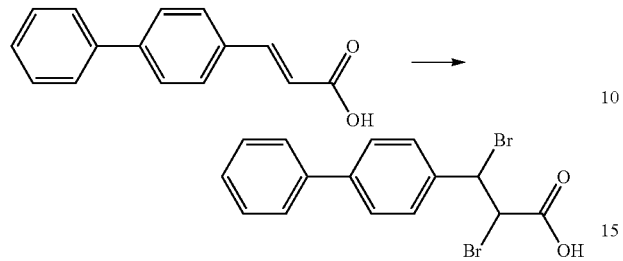

0.81 mL (15.7 mmol) bromine are added dropwise to a mixture of 3.20 g (14.3 mmol) 3-biphenyl-4-yl-acrylic acid and 100 mL tetrachloro-methane. After finishing the addition the reaction mixture is stirred at r.t. for additional 3 h. Afterwards the solvent is removed in vacuo and the crude product is crystallized from PE.

$C_{15}H_{12}Br_2O_2$ (M=384.1 g/mol)
m.p.: 200-203° C.
Rf (TLC): 0.4 (silica gel, DCM/MeOH/AcOH 9/1/0.01)

Intermediate 28

Biphenyl-4-yl-propynoic acid

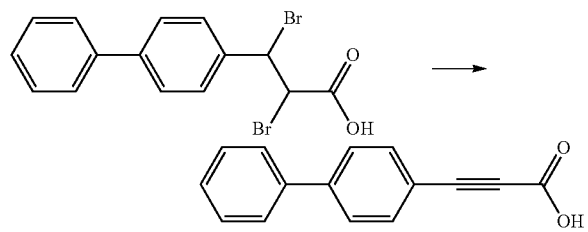

5.00 g (13.0 mmol) 3-biphenyl-4-yl-2,3-dibromo-propionic acid are added to 40 mL tBuOH. Over a period of 25 min 5.80 g (52.1 mmol) KOtBu are added in several portions while keeping the temperature below 35° C. Then the reaction mixture is stirred at 40° C. for 2 h. Again 1.40 g (12.5 mmol) potassium tert-butoxide are added and the mixture is stirred for additional 2 h at 40° C. Then the mixture is allowed to cool to r.t. and poured onto icewater/concentrated HCl. The precipitate is filtered and partitioned between EtOAc and water. The organic layer is washed with water, dried and the solvent is removed in vacuo. The crude product is triturated with PE, filtered and dried at 80° C. in vacuo.

$C_{15}H_{10}O_2$ (M=222.2 g/mol)
ESI-MS: 223 [M+H]$^+$
$R_f$(TLC): 0.4 (silica gel, DCM/MeOH/AcOH 5/1/0.01)

Intermediate 29

Example I29.1

General Route

1-(4-Bromophenyl)propane-2-amine

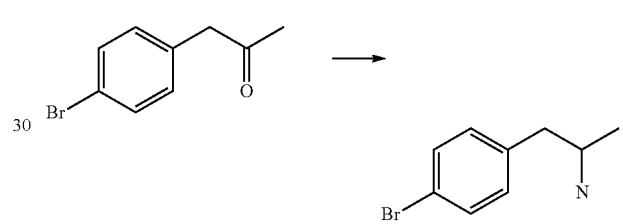

A mixture of 25.0 g (0.12 mol) 4-bromophenylacetone and 400 mL 7N ammonia in MeOH is charged with 1.20 g Raney nickel. The mixture is stirred in an hydrogen atmosphere (15 psi) at r.t. over night. Again 0.6 g Raney nickel are added and the mixture is stirred again for 3.5 h. After complete reaction, the mixture is filtrated. The residue is washed with MeOH and the solvent of the filtrate is removed in vacuo. The crude product is used without further purification.

$C_9H_{12}BrN$ (M=214.1 g/mol)
ESI-MS: 214 [M+H]$^+$
Rf (TLC): 0.3 (silica gel, DCM/MeOH 9/1)

The following compounds are prepared analogously to example I29.1

| Ex. | Starting material | Product structure | Mass spec result | TLC retention factor (method) |
|---|---|---|---|---|
| I29.1 | Br-C6H4-CH2-CO-CH3 | Br-C6H4-CH2-CH(NH2)-CH3 | 214 [M + H]$^+$ | 0.3 (silica gel; DCM/MeOH 9/1) |
| I29.2 | HO-C6H4-CH2-CO-CH3 | HO-C6H4-CH2-CH(NH2)-CH3 | 152 [M + H]$^+$ | 0.2 (silica gel; DCM/MeOH/NH$_3$ 9/1/0.02) |

| Ex. | Starting material | Product structure | Mass spec result | TLC retention factor (method) |
|---|---|---|---|---|
| I29.3 | ![sm] | ![prod] | 288 [M + H]+ | n.d. |

Intermediate 30

2-(4-Bromo-phenyl)-propionitrile

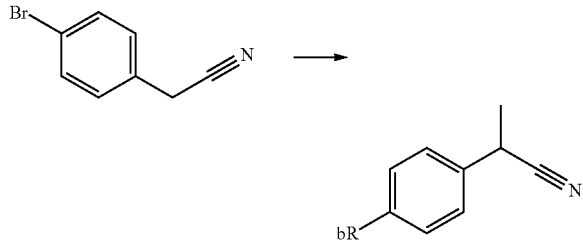

An autoclave is charged with 25.0 g (128 mmol) 4-bromobenzylcyanide, 190 mL dimethylcarbonate and 0.900 g (6.51 mmol) $K_2CO_3$ and stirred for 16 h at 180° C. Then the reaction mixture is allowed to cool to r.t., the mixture is diluted with EtOAc and washed with water (1×), aq. 10% $Na_2S_2O_3$ solution (1×) and brine (1×). The organic layer is dried with $MgSO_4$ and the solvent is removed in vacuo. The residue is purified by destillation (bath temperature 204° C., head temperature 153° C.).

$C_9H_8BrN$ (M=210.1 g/mol)

$R_f$ (TLC): 0.25 (silica gel, CyH/EtOAc 9/1)

Intermediate 31

2-(4-Bromo-phenyl)-propylamine

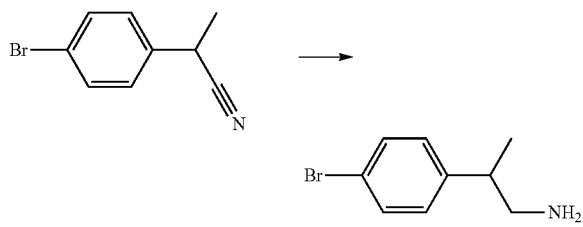

A mixture of 3.00 g (14.3 mmol) 2-(4-bromo-phenyl)-propionitrile and 40 mL ammonia solution (7N in methanol) is charged with 0.30 g Raney nickel. The mixture is stirred under an atmosphere of hydrogen (50 psi) at r.t. for 34 h. The mixture is filtered and the solvent is removed in vacuo. The crude product is used without further purification.

$C_9H_{12}BrN$ (M=214.1 g/mol)

ESI-MS: 214 [M+H]+

$R_t$ (HPLC): 1.63 min (method E)

Intermediate 32

2-(6-Chloropyridin-3-yl)-acetamide

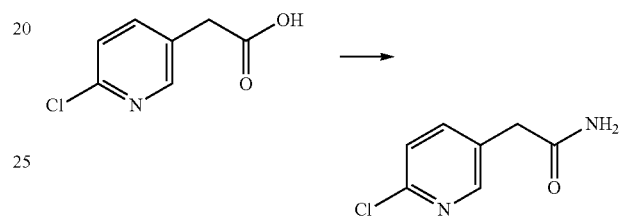

To 10.0 g (58.3 mmol) (2-chloropyridyl)-5-acetic acid in 150 mL THF are added 9.45 g (58.3 mmol) CDI and the mixture is stirred at 45° C. for 1 h. Then 28.0 g (291 mmol) $NH_4CO_3$ are added and the mixture is stirred at r.t. over night. The reaction mixture is poured onto water and extracted with EtOAc. The organic layer is dried with $MgSO_4$ and the solvent is removed in vacuo. The residue is triturated with TBME and recrystallized from EtOH.

$C_7H_7ClN_2O$ (M=170.6 g/mol)

ESI-MS: 171 M+H]+

Rf (TLC): 0.45 (silica gel, DCM/MeOH 9/1)

Intermediate 33

2-(6-Chloropyridin-3-yl)-ethanamine

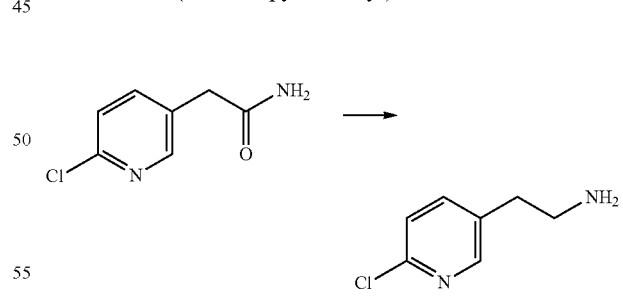

To 2.00 g (11.7 mmol) 2-(6-chloropyridin-3-yl)-acetamide in 50 mL THF at 0° C. are added 12.9 ml LAH (c=1 mol/l in THF) by a dropping funnel. Cooling is removed and the reaction mixture is stirred for 1 h at r.t., then 8 ml LAH (c=1 mol/l in THF) are added and the reaction mixture is stirred at r.t. over night. The reaction is carefully quenched by the addition of 2 ml of an aq. $NaHCO_3$ solution (10%). The mixture is filtrated and the solvent is removed under reduced pressure. The crude product is used without further purification.

$C_7H_9ClN_2$ (M=156.6 g/mol)
ESI-MS: 157 [M+H]$^+$
$R_t$ (HPLC): 1.12 min (method AB)

Intermediate 34

N-(1,1-Dimethyl-2-phenyl-ethyl)-formamide

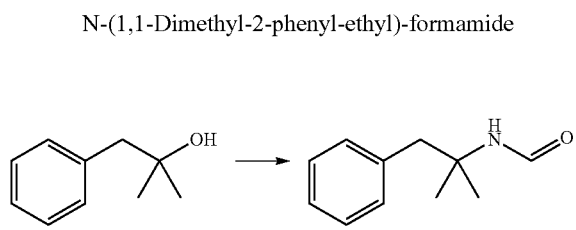

11.3 g (230 mmol) NaCN are added to 60 mL AcOH. A combination of 30 mL AcOH and 60 mL concentrated sulfuric acid is carefully dropped into the NaCN/AcOH mixture while maintaining the temperature below 20° C. Then 30 mL (195 mmol) 2-methyl-1-phenyl-2-propanol, in 30 mL acetic acid, are added dropwise to the reaction mixture, again keeping the temperature below 20° C. After having finished the addition, the reaction mixture is stirred for an additional hour at r.t., poured onto ice water and is finally neutralised with an aq. Na$_2$CO$_3$ solution. The resulting mixture is extracted with diethylether. The organic layer is dried with MgSO$_4$, filtered and the solvent is removed under reduced pressure. The crude product is used without further purification.

$C_{11}H_{15}NO$ (M=177.2 g/mol)
ESI-MS: 178 [M+H]$^+$
$R_f$ (TLC): 0.62 (silica gel, DCM/MeOH 9/1)

Intermediate 35

N-[2-(4-Bromo-phenyl)-1,1-dimethyl-ethyl]-formamide

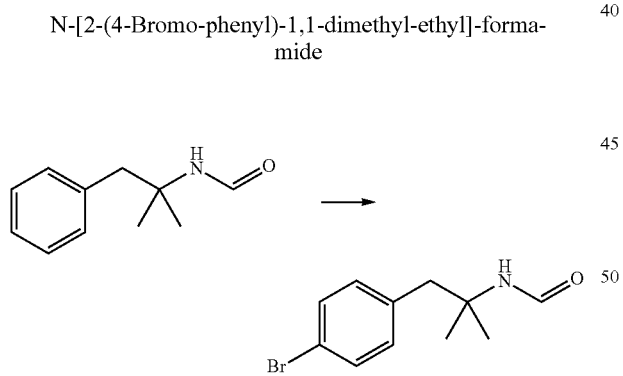

1.00 g (5.64 mmol) N-(1,1-dimethyl-2-phenyl-ethyl)-formamide (I34) is added to 8 mL DCM and cooled down to −5° C. Then 1.50 g (11.3 mmol) aluminium chloride is added by several portions, stirred for 5 min, before 0.9 g (5.64) bromine is added over a period of 1 min. Having finished the addition, the mixture is stirred for two more minutes at 0° C., poured onto ice water and extracted with DCM. The organic layer is dried with MgSO$_4$ and the solvent is removed in vacuo.

$C_{11}H_{14}BrNO$ (M=256.1 g/mol)
ESI-MS: 256 [M+H]$^+$
Rf (TLC): 0.62 (silica gel, DCM/MeOH 9/1)

Intermediate 36

2-(4-Bromo-phenyl)-1,1-dimethyl-ethylamine

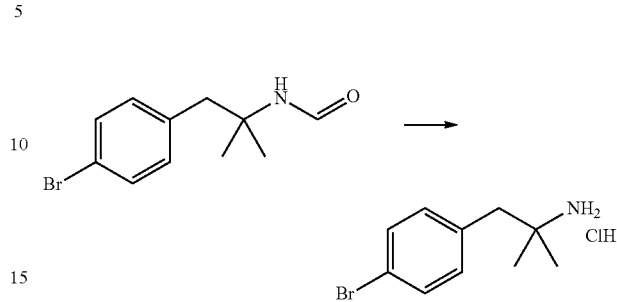

28.0 g (109 mmol) N-[2-(4-bromo-phenyl)-1,1-dimethyl-ethyl]-formamide (I35) are added to 102 mL water and 101 mL (1218 mmol) conc. HCl and stirred at reflux for 8 h. Then heating is stopped and the mixture is stirred at r.t. over night. The precipitate is filtered, washed with TBME and dried in vacuo.

$C_{10}H_{14}BrN$*HCl (M=264.6 g/mol)
ESI-MS: 228/300 [M+H]$^+$
$R_f$(TLC): 0.30 (silica gel, DCM/MeOH/NH$_3$ 9/1/0.1)

Intermediate 37

4-(2-(1-Phenylethylamino)-propyl)phenol

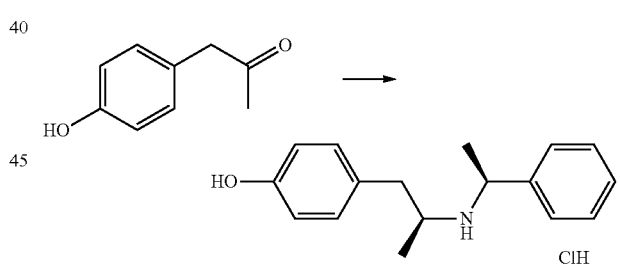

A mixture of 15.0 g (100 mmol) 4-hydroxyphenylaceton and 15.0 mL (120 mmol) S-(−)-alpha-methylbenzylamine in 400 mL EtOH is charged with 3.00 g Raney nickel. The mixture is stirred in a hydrogen atmosphere (50 psi) at r.t. for 2 days. Then the mixture is filtrated and the solvent is removed in vacuo. The residue is purified by column chromatography (silica gel, DCM/MeOH/NH$_3$ 9/1/0.01). The resulting product is recrystallized from PE. Then the product is dissolved in a 1/1 mixture of EtOAc and diethylether and cooled down to 0° C. HCl (solution in diethylether) is added and the precipitate is filtered, washed with diethylether and dried at 70° C. in vacuo.

$C_{17}H_{21}NO$*HCl (M=291.8 g/mol)
ESI-MS: 256 [M+H]$^+$
$R_t$ (HPLC): 1.83 min (method B)

Intermediate 38

4-(2-Amino-propyl)-phenol

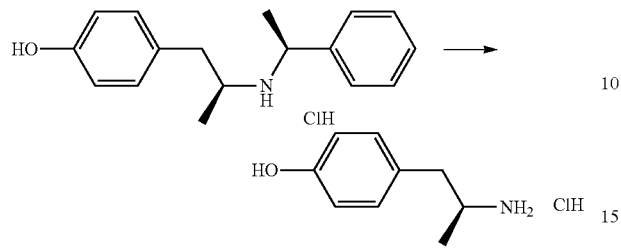

5.80 g (20.0 mmol) 4-[2-(1-phenyl-ethylamino)-propyl]-phenol (I37) are added to 300 mL MeOH and charged with 0.60 g palladiumhydroxide (20%) on activated carbon. The mixture is stirred in a hydrogen atmosphere (50 psi) at 50° C. for 1 h 15 min. Then the mixture is filtrated, the solvent is removed in vacuo and the residue is triturated diethylether. The residue is dried at 80° C. in vacuo.

$C_9H_{13}NO*HCl$ (M=187.7 g/mol)

ESI-MS: 152 [M+H]$^+$ $R_f$(TLC): 0.1 (silica gel, DCM/MeOH/NH$_3$ 9/1/0.01)

Intermediate 39

1-(4-Iodophenyl)-butane-2-one

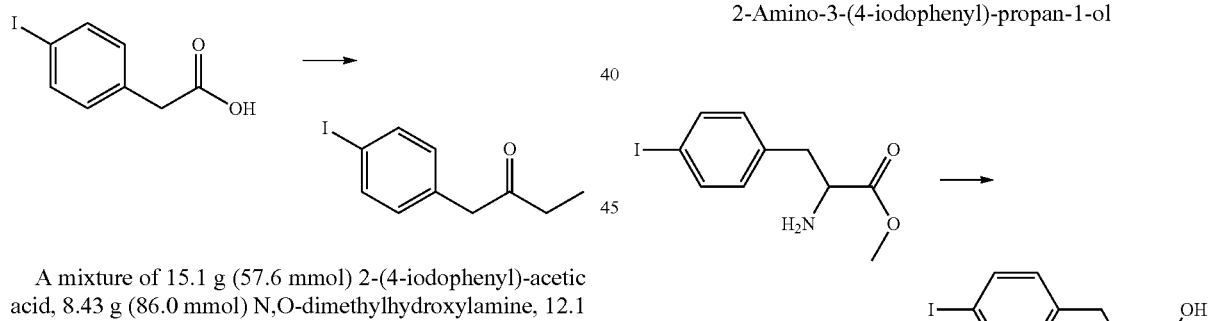

A mixture of 15.1 g (57.6 mmol) 2-(4-iodophenyl)-acetic acid, 8.43 g (86.0 mmol) N,O-dimethylhydroxylamine, 12.1 g (63.3 mmol) EDC and 1.57 g (11.5 mmol) 1-hydroxy-7-azabenzotriazole in 140 mL DMF is cooled down to 0° C. 30.2 mL (173 mmol) DIPEA are added slowly and after removing of the ice bath the reaction mixture is stirred at r.t. over night. It is poured onto 1N aq. HCl and the solids are filtered off and dried in vacuo.

11.7 g (36 mmol) of the above mentioned product are added to 180 mL THF and cooled down to 0° C. 180 mL (180 mmol) ethylmagnesium bromide (1 mol/l) are added dropwise and the reaction is stirred at 0° C. for 1 h. The reaction is quenched by the addition of a sat. aq. NH$_4$Cl solution and extracted with EtOAc. The combined organic layers are washed with brine and dried with Na$_2$SO$_4$. The solvent is removed in vacuo and the crude product is purified by column chromatography (silica gel, heptane/EtOAc 100/0→95/5).

$C_{10}H_{11}IO$ (M=274.1 g/mol)

EI-MS: 274 [M]$^+$

Intermediate 40

1-(4-Iodobenzyl)-propylamine

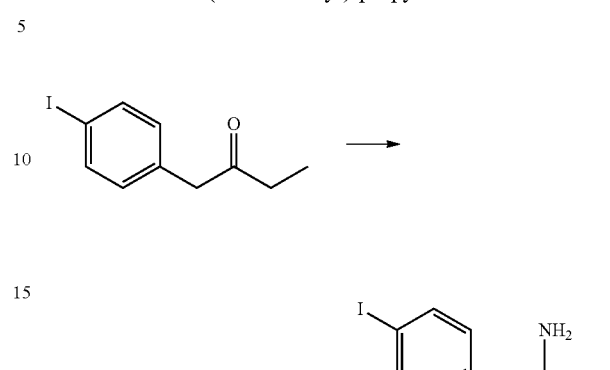

5.95 g (21.7 mmol) 1-(4-iodophenyl)-butane-2-one (I39) are added to 150 mL 2-propanol and transferred into an autoclav. 25.1 g (326 mmol) NH$_4$OAc and 4.09 g (65.1 mmol) NaCNBH$_3$ are added and the mixture is stirred at 90° C. over night. The reaction is quenched by the addition of sat. aq. NaHCO$_3$ solution and extracted with EtOAc (3×). The combined organic layers are washed with brine, dried with Na$_2$SO$_4$ and the solvent is removed in vacuo. The compound is used without further purification.

$C_{10}H_{14}IN$ (M=275.1 g/mol)

ESI-MS: 276 [M+H]$^+$

Intermediate 41

2-Amino-3-(4-iodophenyl)-propan-1-ol

A mixture of 28.5 g (75.0 mmol) 2-amino-3-(4-iodophenyl)propanoate hydrochloride in 300 mL ethanol and 300 mL water is added to a mixture of 14.2 g (375 mmol) NaBH$_4$ and 600 mL water (gas evolution!) and the resulting mixture is stirred at reflux for 2 h. The ethanol is evaporated in vacuo and the remaining aq. Phase is extracted with DCM (4×). The combined organic layers are dried with Na$_2$SO$_4$ and the solvent is removed in vacuo. The compound is used without further purification.

$C_9H_{12}INO$ (M=277.1 g/mol)

ESI-MS: 278 [M+H]$^+$ $R_t$ (HPLC): 2.40 (method AD)

Intermediate 42

2-(4-Iodophenyl)-1-methoxymethyl-ethylamine

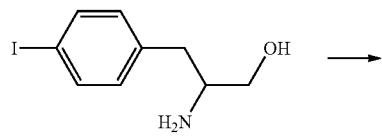

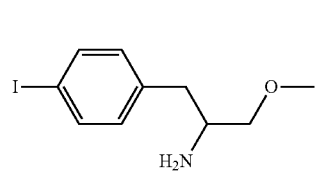

A mixture of 12.0 g (43.3 mmol) 2-amino-3-(4-iodophenyl)-propan-1-ol (I41) and 350 mL THF is cooled down to 0° C. 3.81 g (95 mmol) NAH (60% in min. oil) are carefully added and the mixture is stirred at 0° C. for 30 min. 3.25 mL (52.0 mmol) iodomethane are added and cooling is removed. The reaction mixture is stirred at r.t. for 1 h. The mixture is poured onto water and extracted with EtOAc (2×). The combined organic layers are washed with brine, dried with $Na_2SO_4$ and the solvent is removed in vacuo. The compound is used without further purification.

$C_9H_{12}INO$ (M=291.1 g/mol)

ESI-MS: 292 [M+H]$^+$

Intermediate 43

1-(4-Iodobenzyl)pyrrolidin-2-one

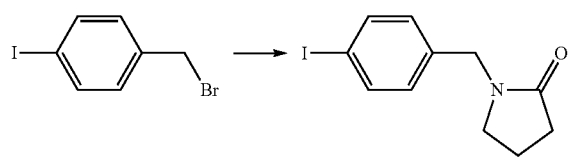 [SMILES: BrCc1ccc(I)cc1 ; O=C1CCCN1Cc1ccc(I)cc1]

To 140 μl (1.68 mmol) 2-pyrrolidone in 5 mL DMF are added 110 mg (2.53 mmol) sodium hydride. Then 500 mg (1.68 mmol) 4-iodobenzyl bromide are added by several portions and the resulting mixture is stirred at r.t. over night. The solvent is removed in vacuo and the residue is resolved in DCM and water. The layers are separated and the organic layer is dried with $Na_2SO_4$, filtrated and the solvent is removed in vacuo. The crude product is purified by HPLC.

$C_{11}H_{12}INO$ (M=301.1 g/mol)

ESI-MS: 302 [M+H]$^+$ $R_f$ (TLC): 0.6 (silica gel, DCM/MeOH 9/1)

Intermediate 44

Example I44.1

General Route

N-(1-(4-Bromophenyl)propan-2-yl)acetamide

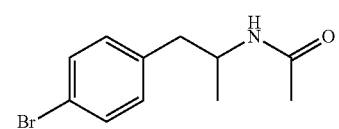

Method I:

A mixture of 24.7 g (115 mmol) 1-(4-bromophenyl)propane-2-amine and 24.2 ml (174 mmol) TEA in 250 mL DCM are cooled down to 0° C. 12.4 ml (174 mmol) acetyl chloride are dropped in slowly and the mixture is stirred for 15 min at constant temperature. The reaction mixture is allowed to warm up to r.t. and stirred for additional 2.5 h. The reaction mixture is washed with water, dried with $Na_2SO_4$ and the solvent is removed in vacuo. The crude product is triturated with diethylether, filtered and dried at 45° C. in vacuo.

$C_{11}H_{14}BrNO$ (M=256.1 g/mol)

ESI-MS: 256 [M+H]$^+$ $R_t$ (HPLC): 2.60 min (method B)

Method II:

17.0 mL (179.7 mmol) acetic anhydride are added to a mixture of 24.2 g (113.03 mmol) 1-(4-bromophenyl)propane-2-amine and 20 mL AcOH and the reaction mixture is stirred at r.t. over night. The solvent is evaporated in vacuo, and the residue partitonated between TBME and a saturated aq. $NaHCO_3$ solution. The layers are separated and the organic layer is washed with water, dried with $Na_2SO_4$ and the solvent is removed in vacuo. The crude product is triturated with DIPE.

The following compounds are prepared analogously to example I44.1.

For examples I44.6 and I44.9 and I44.10 DIPEA is used as base.

For example I44.11 dimethylcarbamyl chloride is used as acylating agent.

For examples I44.12 and I44.13 Acetic anhydride is used as acylating agent and the crude products are purified by column chromatography (silica gel, heptane/EtOAc).

For examples I44.14 and I44.15 no amine base is used and the reaction is stirred at r.t. over night.

| Ex. | Starting material | Product structure | Method | Mass spec result | HPLC retention time (method) |
|---|---|---|---|---|---|
| I44.1 | 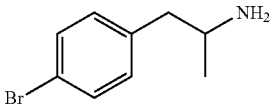 | 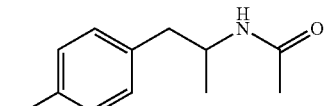 | I + II | 256 [M + H]+ | 2.60 (B) |
| I44.2 | 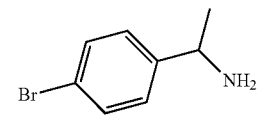 | 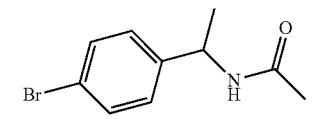 | II | 242 [M + H]+ | 2.47 (B) |
| I44.3 | 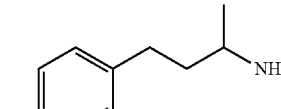 | 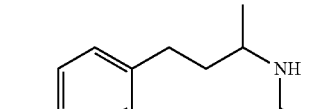 | I + II | 270 [M + H]+ | 2.11 (E) |
| I44.4 | 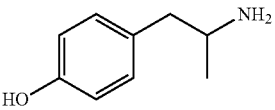 | 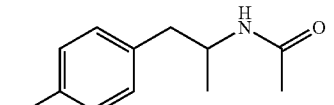 | II | 194 [M + H]+ | 1.80 (E) |
| I44.5 | 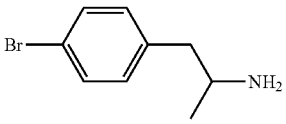 | 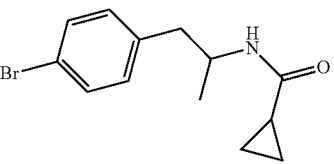 [SMILES: CC(Cc1ccc(Br)cc1)NC(=O)C1CC1] | I | 282 [M + H]+ | 1.87 (E) |
| I44.6 | 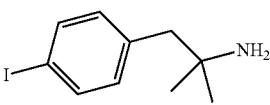 |  | I | 344 [M + H]+ | 2.07 (E) |
| I44.7 | 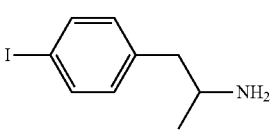 | 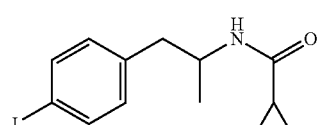 | I | 330 [M + H]+ | 3.38 (A). |
| I44.8 | 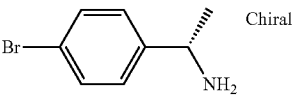 Chiral | 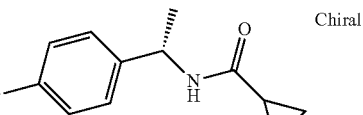 Chiral | I | 268 [M + H]+ | 2.76 (B) |
| I44.9 | 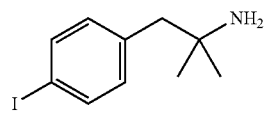 | 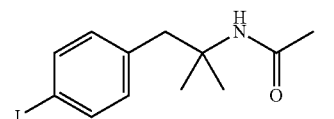 | I | 318 [M + H]+ | 1.97 (E) |
| I44.10 | 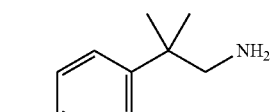 | 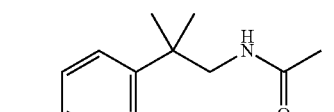 | I | 270 [M + H]+ | 2.11 (E) |

| Ex. | Starting material | Product structure | Method | Mass spec result | HPLC retention time (method) |
|---|---|---|---|---|---|
| I44.11 | 4-bromophenyl-CH2-CH(NH2)-CH3 | 4-bromophenyl-CH2-CH(CH3)-NH-C(=O)-N(CH3)2 | I | 285 [M + H]+ | TLC: 0.6 (silica gel; DCM:MEOH 9:1) |
| I44.12 | 4-iodophenyl-CH2-CH(NH2)-CH2CH3 | 4-iodophenyl-CH2-CH(CH2CH3)-NH-C(=O)-CH3 | I | 318 [M + H]+ | 3.17 (Q) |
| I44.13 | 4-iodophenyl-CH2-CH(NH2)-CH2-OCH3 | 4-iodophenyl-CH2-CH(CH2OCH3)-NH-C(=O)-CH3 | I | 334 [M + H]+ | 2.98 (Q) |
| I44.14 | 4-bromophenyl-CH(CH3)-NH2 Chiral | 4-bromophenyl-CH(CH3)-NH-C(=O)-CH3 Chiral | I + II | 242 [M + H]+ | 1.65 (E) |
| I44.15 | 4-bromophenyl-CH(CH3)-NH2 Chiral | 4-bromophenyl-CH(CH3)-NH-C(=O)-CH3 Chiral | I + II | 242 [M + H]+ | 1.65 (E) |

Intermediate 45

Methyl 1-(4-iodophenyl)propan-2-ylcarbamate

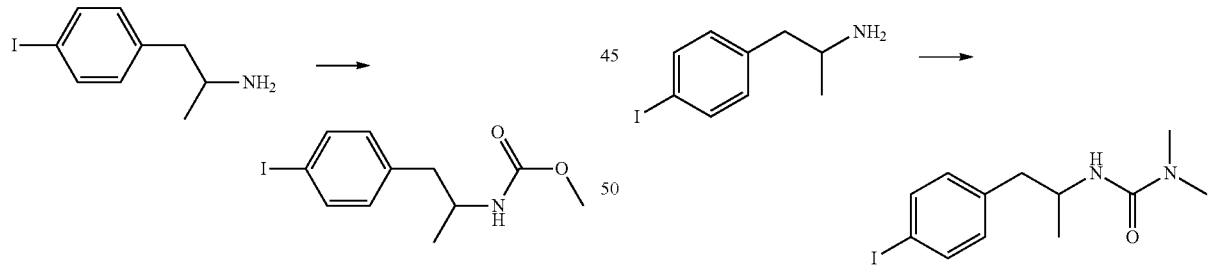

0.53 ml (6.89 mmol) methyl chloroformate are added to a mixture of 1.50 g (5.75 mmol) 1-(4-iodophenyl)propane-2-amine and 1.16 ml pyridine (14.3 mmol) in 30 ml DCM at 0° C. and the reaction mixture is stirred for 1 h at constant temperature. Further DCM is added and the organic solution is consecutively washed with aq. HCl-solution (0.5 mol/l) and water, dried with MgSO$_4$ and the solvent is removed under reduced pressure. The crude product is used without further purification.

$C_{11}H_{14}INO_2$ (M=319.1 g/mol)

ESI-MS: 320 [M+H]+

R$_t$ (HPLC): 1.96 min (method E)

Intermediate 46

3-[2-(4-Iodo-phenyl)-1-methyl-ethyl]-1,1-dimethyl-urea 2.70 g (10.3 mmol) 2-(4-iodo-phenyl)-1-methyl-ethylamine and 1.82 mL (12.9 mmol) TEA are added to 40 mL DCM and cooled down to 0° C. The mixture is charged with 1.78 g (10.9 mmol) CDT stirred at 0-5° C. for 15 min. 1.40 g (31.0 mmol) dimethylamine (gas cylinder) are added and the mixture is stirred at r.t. over night. The mixture is diluted with DCM, washed with a 1N aq. KHSO$_4$ (2×) solution and water (1×). The organic layer is dried with MgSO$_4$ and the solvent is removed in vacuo.

$C_{12}H_{17}IN_2O$ (M=332.18 g/mol)

ESI-MS: 333 [M+H]+

R$_t$ (HPLC): 1.88 min (method E)

Intermediate 47

Example I47.1

General Route

N-(4-iodophenethyl)acetamide

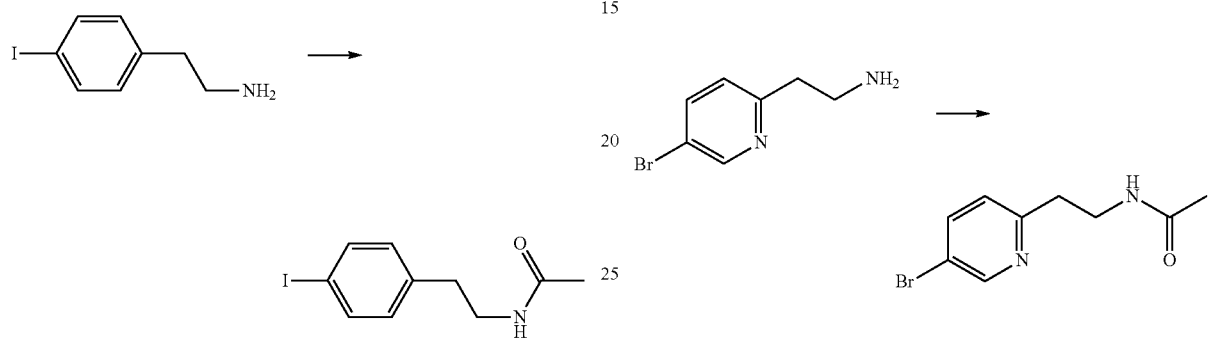

3.00 g (12.1 mmol) 4-iodophenethylamine and 0.37 g (3.03 mmol) DMAP in 50 mL THF are cooled down to 0° C. 4.95 g (48.5 mmol) acetic anhydride are added and, after removing of the cooling bath, the reaction mixture is stirred for 5 h at r.t. The reaction mixture is quenched in ice cold water and extracted with EtOAc. The organic layer is dried with $Na_2SO_4$ and the solvent is removed in vacuo. The crude product is purified by column chromatography (silica gel, DCM/MeOH 98.5/1.5).

$C_{10}H_{12}INO$ (M=289.1 g/mol)
ESI-MS: 290 $[M+H]^+$
$R_t$ (HPLC): 1.75 min (method E)

The following compounds are prepared analogously to example I47.1

Intermediate 48

Example I48.1

General Route

N-[2-(5-Bromo-pyridin-2-yl)-ethyl]-acetamide

A mixture of 200 mg (1.00 mmol) 2-(5-bromopyridin-2-yl)ethanamine, 86.6 µL (1.09 mmol) pyridine and 2 mL DCM is charged with 103 µL (1.09 mmol) acetic anhydride and stirred at r.t. over night. The mixture is treated with saturated aq. $NaHCO_3$ solution and extracted with DCM. The organic layer is dried with $Na_2SO_4$ and the solvent is evaporated in vacuo.

$C_9H_{11}BrN_2O$ (M=243.1 g/mol)
ESI-MS: 243 $[M+H]^+$
$R_t$ (HPLC): 1.25 min (method E)

The following compounds are prepared analogously to example I48.1

For example I48.2 pyridine and acetic anhydride are added at 0° C. and the crude product is purified by HPLC (MeOH/$H_2O$/$NH_3$).

| Ex. | Starting material | Product Structure | Mass spec result | TLC retention factor (method) |
|---|---|---|---|---|
| I47.1 | I-C6H4-CH2CH2-NH2 | I-C6H4-CH2CH2-NH-C(O)CH3 | 290 $[M+H]^+$ | 0.5 (silica gel, DCM/MeOH 9/1) |
| I47.2 | I-C6H4-CH2CH2-NH2 | I-C6H4-CH2CH2-NH-C(O)CH2CH3 | 304 $[M+H]^+$ | 0.6 (silica gel, DCM/MeOH 9/1) |

| Ex. | Starting material | Product structure | Mass spec result | HPLC retention time method |
|---|---|---|---|---|
| I48.1 | Br-pyridine-CH2CH2NH2 | Br-pyridine-CH2CH2NHC(O)CH3 | n.d. | n.d. |
| I48.2 | Cl-pyridine-CH2CH2NH2 | Cl-pyridine-CH2CH2NHC(O)CH3 | 199 [M + H]+ | 1.09 (E) |

Intermediate 49

N-[2-(4-Hydroxy-phenyl)-1-methyl-ethyl]-acetamide

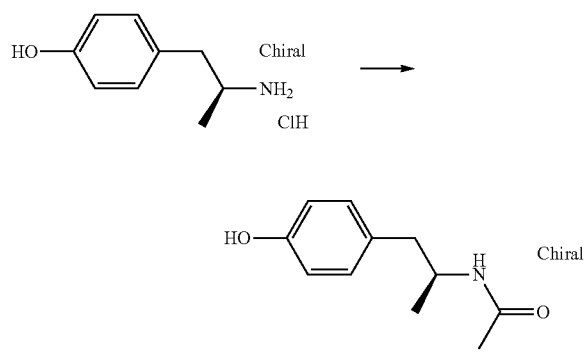

1.88 g (10.0 mmol) 4-(2-amino-propyl)-phenol*HCl and 1.80 g (21.0 mmol) NaHCO₃ are combined in 50 mL water and cooled down to 0° C. 0.95 mL (10.0 mmol) acetic anhydride, dissolved in 50 mL ACN, are dropped into the mixture over a period of 1.5 h. The reaction mixture is stirred at r.t. for 72 h. The ACN is evaporated in vacuo and the aq. residue is acidified with HCl (1N). The mixture is extracted several times with EtOAc. The organic layers are combined, dried with Na₂SO₄ and the solvent is removed in vacuo. The crude product is purified by column chromatography (silica gel, DCM/MeOH 95/5).

C₁₁H₁₅NO₂ (M=193.2 g/mol)
ESI-MS: 194 [M+H]⁺
R_t (HPLC): 1.85 min (method B)

Intermediate 50

Example I50.1

General Route tert-Butyl 1-(4-bromophenyl)propan-2-ylcarbamate

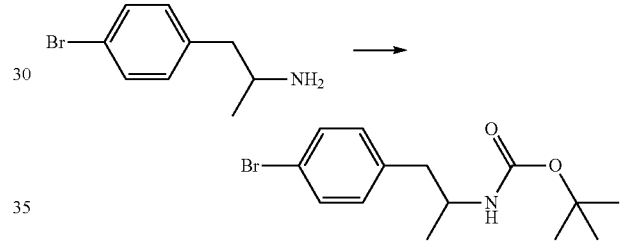

To 25.0 g (117 mmol) 1-(4-bromophenyl)propan-2-amine in 500 mL DCM are added 73 mL of a 2N aq. Na₂CO₃ solution followed by 26.9 g (123 mmol) di-tert-butyl dicarbonate (in 50 mL DCM) and the resulting mixture is stirred at r.t. for 2 h. 250 mL water are added and the layers are separated. The organic layer is washed with water (2x), dried with MgSO₄ and the solvent is removed in vacuo. The crude product is triturated with DIPE and PE.

C₁₄H₂₀BrNO₂ (M=314.2 g/mol)
ESI-MS: 314 [M+H]⁺
R_t (HPLC): 1.64 min (method O)

The following compounds are prepared analogously to example I50.1

For example I50.2 and I50.4 TEA is used as base.

| Ex. | Starting material | Product structure | Mass spec result | HPLC retention time (method) |
|---|---|---|---|---|
| I50.1 | Br-C6H4-CH2CH(CH3)NH2 | Br-C6H4-CH2CH(CH3)NHBoc | 314 [M + H]+ | 1.64 (O) |

-continued

| Ex. | Starting material | Product structure | Mass spec result | HPLC retention time (method) |
|---|---|---|---|---|
| I50.2 | Br-C6H4-CH(NH2)CH3 | Br-C6H4-CH(CH3)-NH-C(O)-O-C(CH3)3 | 298 [M − H]⁻ | 4.08 (R) |
| I50.3 | Br-C6H4-CH(NH2)CH3 Chiral | Br-C6H4-CH(CH3)-NH-C(O)-O-C(CH3)3 Chiral | 300 [M + H]⁺ | TLC: $R_f$ = 0.56 (silica gel, DCM/MeOH 98/2) |
| I50.4 | Br-C6H4-CH(CH3)-CH2-NH2 | Br-C6H4-CH(CH3)-CH2-NH-C(O)-O-C(CH3)3 | 314 [M + H]⁺ | 2.15 (E) |

Intermediate 51

N-(1-(4-Bromophenyl)-1-methyl-ethyl)-acetamide

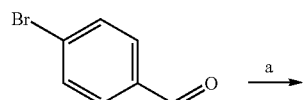

a) 2-(4-Bromophenyl)-propan-2-ol 20.0 g (100 mmol) 4-bromoacetophenone are added to 300 mL diethylether and cooled down to 0° C. 35.2 mL MeMgBr (3M in diethylether) are added by a dropping funnel. Cooling is removed and the mixture is stirred at r.t. over night. The reaction quenched by careful addition of 150 mL sat. aq. NH₄Cl solution and 150 mL water. The resulting mixture is stirred for 20 min. The layers are separated and the org. layer is washed with water (2×), dried with MgSO₄ and the solvent is removed in vacuo.

$C_9H_{11}BrO$ (M=215.1 g/mol)
EI-MS: 214 [M+H]⁺
$R_f$ (TLC): 0.5 min (silica gel, DCM)

b) N-(1-(4-Bromophenyl)-1-methyl-ethyl)-acetamide

To 21.0 g (97.6 mmol) 2-(4-bromophenyl)-propan-2-ol in 1 L ACN are added 16.1 mL conc. H₂SO₄ dropwise while keeping the temperature at 20° C. The resulting mixture is stirred at r.t. over night. The solvent is removed in vacuo and the residue is partitioned between water and diethylether. The organic layer is washed with water (2×), sat. aq. NaHCO₃ solution (2×) and water again (1×). The solution is dried with MgSO₄ and the solvent is removed in vacuo. The crude product is triturated with PE.

$C_{11}H_{14}BrNO$ (M=256.1 g/mol)
EI-MS: 256 [M+H]⁺
$R_t$ (HPLC): 1.08 min (method O)

Intermediate 52

Example I52.1

General Route

N-(1-(4-iodophenyl)propan-2-yl)acetamide

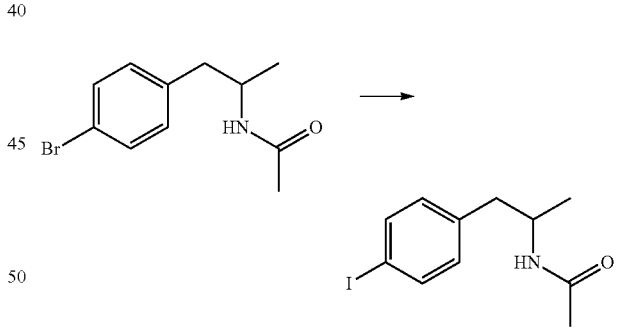

To 6.00 g (23.4 mmol) N-(1-(4-bromophenyl)propan-2-yl) acetamide (I44.1) in 65 mL dioxan are added 0.45 g (2.34 mmol) CuI, 0.50 mL (4.70 mmol) N,N'-dimethylethylendiamine and 7.02 g (46.9 mmol) NaI. The reaction mixture is stirred at 120° C. for 70 h. The mixture is allowed to cool to r.t. and half of the solvent is removed in vacuo. EtOAc and diluted aq. ammonia solution are added and the layers are separated. The aq. layer is once more extracted with EtOAc. The organic layers are combined, dried with Na₂SO₄ and the solvent is removed in vacuo. The crude product is triturated with diethylether and dried at 50° C. in vacuo.

$C_{11}H_{14}INO$ (M=303.1 g/mol)
ESI-MS: 304 [M+H]+
$R_t$ (HPLC): 2.69 min (method Y)

The following compounds are prepared analogously to example I52.1

For the examples I52.5, I52.7 and I52.9 the crude product is purified by column chromatography. For example I52.5 the reaction time is 5 h at 110° C.

For examples I52.10-11 the reaction time is 16 h at 120° C.

| Ex. | Starting material | Product structure | Mass spec result | HPLC retention time (method) |
|---|---|---|---|---|
| I52.1 | | | 304 [M + H]$^+$ | 2.69 (Y) |
| I52.2 | Chiral | Chiral | 316 [M + H]$^+$ | 1.82 (E) |
| I52.3 | | | 330 [M + H]$^+$ | 3.38 (B) |
| I52.4 | | | 318 [M + H]$^+$ | 2.17 (E) |
| I52.5 | | | 362 [M + H]$^+$ | 2.25 (E) |
| I52.6 | | | 290 [M + H]$^+$ | 2.55 (B) |
| I52.7 | | | 333 [M + H]$^+$ | 1.88 (E) |
| I52.8 | | | 362 [M + H]$^+$ | 2.19 (E) |

-continued

| Ex. | Starting material | Product structure | Mass spec result | HPLC retention time (method) |
|---|---|---|---|---|
| I52.9 | | | 376 [M + H]+ | 2.31 (E) |
| I52.10 | | | 318 [M + H]+ | 1.98 (E) |
| I52.11 | | | 304 [M + H]+ | 1.11 (O) |
| I52.12 | Chiral | Chiral | 290 [M + H]+ | TLC: Rf = 0.57 (silica gel, DCM/MeOH 9/1) |
| I52.13 | Chiral | Chiral | 290 [M + H]+ | TLC: Rf = 0.57 (silica gel, DCM/MeOH 9/1) |

Intermediate 53

Example I53.1

General Route

Trifluoromethanesulfonic acid
4-(2-acetylamino-propyl)-phenyl ester

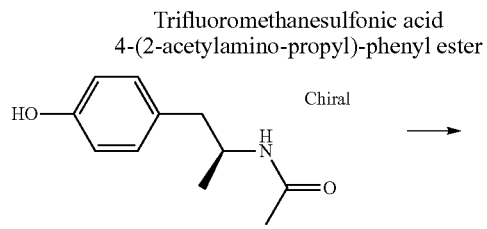

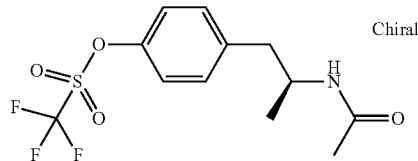

To 1.00 g (5.18 mmol) N-[2-(4-hydroxy-phenyl)-1-methyl-ethyl]-acetamide (149) and 1.88 g (5.25 mmol) N-phenyltrifluoromethanesulfonimide in 50 mL DCM are added 0.76 mL (5.50 mmol) TEA at 0° C. The reaction mixture is stirred at 0° C. for 1 h and at r.t. for 6 h. Further 0.1 g (0.280 mmol) N-phenyltrifluoromethane-sulfonimide are added and the mixture is stirred at r.t. over night. The mixture is washed with water and sat. aq. NaHCO₃ solution, dried with Na₂SO₄ and the solvent is removed in vacuo. The residue is purified by column chromatography (silica gel, EtOAc 100%) and the resulting product is further crystallized from PE and dried at 45° C. in vacuo.

$C_{12}H_{14}F_3NO_4S$ (M=325.3 g/mol)
ESI-MS: 326 [M+H]+
$R_t$ (HPLC): 2.75 min (method B)

The following compounds are prepared analogously to example I53.1

| Ex. | Starting material | Product structure | | Mass spec result | HPLC retention time (method) |
|---|---|---|---|---|---|
| I53.1 | I49 | 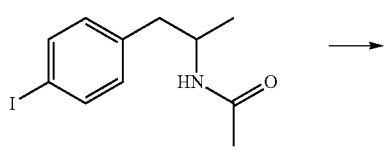 | Chiral | 326 [M + H]⁺ | 2.75 (B) |
| I53.2 | I44.4 | 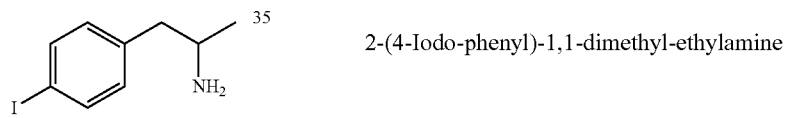 | | 326 [M + H]⁺ | 2.73 (B) |

Intermediate 54

2-(4-Iodo-phenyl)-1-methyl-ethylamine

Method I:

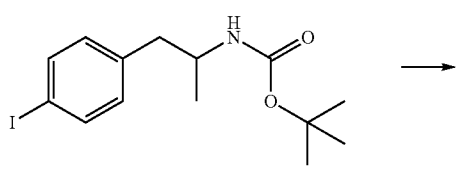

9.00 g (29.69 mmol) N-[2-(4-iodo-phenyl)-1-methyl-ethyl]-acetamide (I52.1) are added to 150 mL HCl (4N) and the reaction mixture is stirred at reflux over night. Then the mixture is diluted with soda lye and extracted with EtOAc. The organic layer is dried with $Na_2SO_4$ and the solvent is removed in vacuo.

$C_9H_{12}IN$ (M=261.1 g/mol)

ESI-MS: 262 [M+H]⁺

$R_t$ (HPLC): 1.44 (method AA)

Method II:

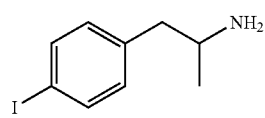

To 6 g (16.6 mmol) [2-(4-iodo-phenyl)-1-methyl-ethyl]-carbamic acid tert-butyl ester (I52.5) in 40 ml DCM are added 46.5 ml HCl (1.25 mol/l in EtOH) and the solution is stirred at 70° C. over night. The solvent is removed in vacuo and the residue is resolved in water and washed with DCM. The aqueous layer is basified with 4N aq. NaOH solution and extracted two times with DCM. The org. layers are combined, dried with $Na_2SO_4$ and the solvent is removed in vacuo.

Intermediate 55

2-(4-Iodo-phenyl)-1,1-dimethyl-ethylamine

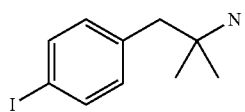

To 1.10 g (2.93 mmol) [2-(4-iodophenyl)-1,1-dimethyl-ethyl]-carbamic acid tert-butyl ester (I52.9) in 8 ml methanol are added 7.04 ml HCl (1.25 mol/l in MeOH) and the solution is stirred at 50° C. for 3 h. The solvent is removed under reduced pressure and the resulting crude product is purified by HPLC ($H_2O$/MeOH/$NH_3$).

$C_{10}H_{14}IN$ (M=275.1 g/mol)

ESI-MS: 276 [M+H]⁺

$R_t$ (HPLC): 1.77 (method E)

Intermediate 56

Example I56.1

General Route

N-(4-((tert-Butyldimethylsilyl)ethynyl)phenethyl)acetamide

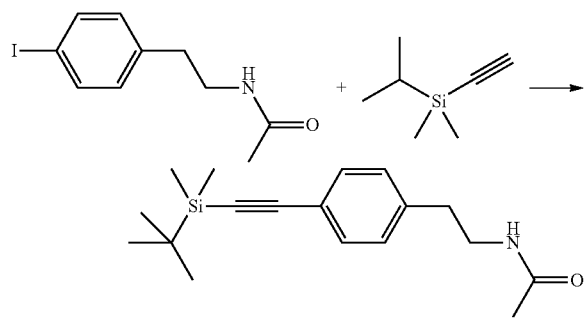

To 2.40 g (8.30 mmol) of the iodide I47.1 in 50 ml of THF are added 1.28 g (9.15 mmol) ethynyl-tert-butyldimethylsilane and 2.33 ml (16.6 mmol) diisopropylamine. After cooling down to 0° C. 0.58 g (0.83 mmol) bis(triphenyl-phosphine)dichloro-palladium and 158 mg (0.83 mmol) CuI are added and the solution is stirred at r.t. over night. The reaction mixture is filtrated and the solvent is removed in vacuo. The residue is resolved in EtOAc and washed with water. The organic layer is dried with MgSO4, filtrated and solvent is removed in vacuo. The residue is purified by column chromatography (silica gel, DCM/MeOH 10/0→20/1).

$C_{18}H_{27}NOSi$ (M=301.5 g/mol)

ESI-MS: 302 [M+H]+

$R_t$ (HPLC): 2.32 min (method E)

The following compounds are prepared analogously to example I56.1

For example I56.8 the acetylene is added on latest stage and the reaction time is 1 h at r.t. For example I56.5 the reaction time 1 h at 0° C.

| Ex. | Starting material | Product structure | Mass spec result | HPLC retention time (method) |
|---|---|---|---|---|
| I56.1 | I47.1 | | 302 [M + H]+ | 2.32 (E) |
| I56.2 | I52.1 | | 274 [M + H]+ | 1.69 (H) |
| I56.3 | I52.1 | | 316 [M + H]+ | 2.45 (M) |
| I56.4 | I52.10 | | 288 [M + H]+ | 2.25 (E) |
| I56.5 | I52.11 | | 316 [M + H]+ | 2.38 (E) |
| I56.6 | I45 | | 290 [M + H]+ | 2.23 (E) |

-continued

| Ex. | Starting material | Product structure | Mass spec result | HPLC retention time (method) |
|---|---|---|---|---|
| I56.7 | I52.7 | | 303 [M + H]+ | 2.19 (E) |
| I56.8 | I52.5 | | 332 [M + H]+ | 2.42 (E) |
| I56.9 | I52.8 | | 332 [M + H]+ | 2.49 (E) |
| I56.10 | I52.12 | Chiral | n.d. | TLC: R$_f$ = 0.68 (silica gel, DCM/MeOH 9/1) |
| I56.11 | I52.13 | Chiral | n.d. | TLC: R$_f$ = 0.68 (silica gel, DCM/MeOH 9/1) |

Intermediate 57

N-(2-{4-[(tert-Butyldimethylsilanyl)-ethynyl]-phenyl}-1-methyl-ethyl)-acetamide

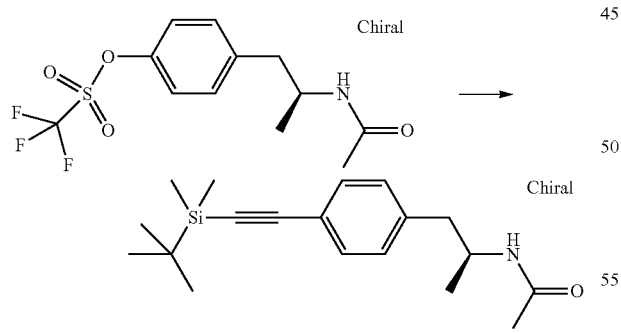

To 2.40 g (7.38 mmol) trifluoromethanesulfonic acid 4-(2-acetylamino-propyl)-phenyl ester (I53.1), 1.52 mL (8.12 mmol) (tert-butyldimethylsilyl)acetylene and 2.56 mL (18.4 mmol) diisopropylamine in 25 mL ACN are added 72.3 mg (0.089 mmol) [1,1'bis(diphenylphosphino)ferrocene]dichloropalladium(II), complex with dichloromethane and 17.2 mg (0.09 mmol) CuI, and the mixture is stirred at r.t. for 24 h. Again 0.69 mL (3.69 mmol) (tert-butyldimethyl-silyl)acetylene are added and stirring is continued for additional 24 h.

The mixture is poured onto aq. ammonia solution (5%), diluted with EtOAc and the organic layer is separated. The organic layer is washed with diluted aq. ammonia solution (1×) and water (1×), dried with MgSO$_4$ and the solvent is removed in vacuo. The residue is purified by column chromatography (silica gel; PE/EtOAc 2/8).

$C_{19}H_{29}NOSi$ (M=315.5 g/mol)

ESI-MS: 316 [M+H]+

R$_f$(TLC): 0.4 (silica gel, PE/EtOAc 2/8)

Intermediate 58

Example I58.1

General Route

N-(4-Ethynylphenethyl)acetamide

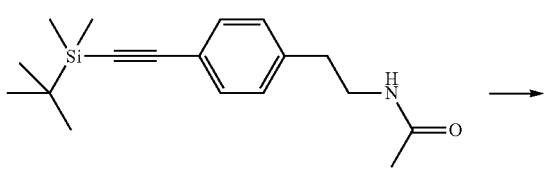

-continued

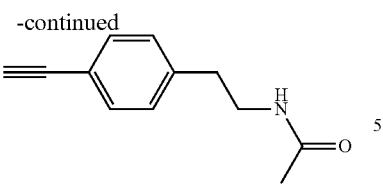

To 2.20 g (7.30 mmol) N-(4-((tert-butyldimethylsilyl)ethynyl)phenethyl)acetamide (I56.1) in 30 mL DCM are added 2.24 g (8.03 mmol) TBAF*H$_2$O and the mixture is stirred at r.t. over night. The mixture is washed with water (2×). The organic layer is dried with Na$_2$SO$_4$ and the solvent is removed in vacuo. The crude product is purified by column chromatography (silica gel, DCM/MeOH 10/0→20/1).

C$_{12}$H$_{13}$NO (M=187.2 g/mol)
ESI-MS: 188 [M+H]$^+$
R$_t$ (HPLC): 1.48 min (method E)

The following compounds are prepared analogously to example I58.1

For examples I58.4-9 TBAF*3H$_2$O is added at 0° C. The reaction times are 1 h at r.t.

For examples I58.10 and I58.11 the desilylation is done with K$_2$CO$_3$ (0.1 eq) in MeOH. The reaction conditions are 3 h at r.t.

| Ex. | Starting material | Product structure | Mass spec result | HPLC retention time (method) |
|---|---|---|---|---|
| I58.1 | I56.1 | | 188 [M + H]$^+$ | 1.48 (E) |
| I58.2 | I57 | Chiral | 202 [M + H]$^+$ | 1.60 (E) |
| I58.3 | I56.3 | | 202 [M + H]$^+$ | 2.04 (M) |
| I58.4 | I56.4 | | 216 [M + H]$^+$ | 1.76 (E) |
| I58.5 | I56.5 | | 202 [M + H]$^+$ | 0.97 (O) |
| I58.6 | I56.7 | | 231 [M + H]$^+$ | 1.66 (E) |
| I58.7 | I56.6 | | 218 [M + H]$^+$ | 1.75 (E) |
| I58.8 | I56.8 | | 260 [M + H]$^+$ | 2.09 (E) |

| Ex. | Starting material | Product structure | Mass spec result | HPLC retention time (method) |
|---|---|---|---|---|
| I58.9 | I56.9 | 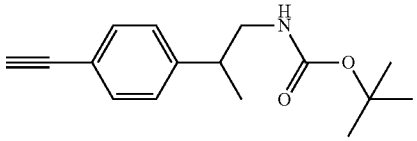 [SMILES: C#Cc1ccc(C(C)CNC(=O)OC(C)(C)C)cc1] | 260 [M + H]⁺ | 2.11 (E) |
| I58.10 | I56.10 | 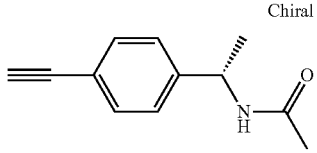 Chiral | n.d. | TLC: $R_f$ = 0.68 (silica gel, DCM/MeOH 9/1) |
| I58.11 | I56.11 | 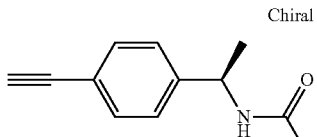 Chiral | n.d. | TLC: $R_f$ = 0.68 (silica gel, DCM/MeOH 9/1) |

Intermediate 59

Example I59.1

General Route

N-(1-(4-Ethynylphenyl)propan-2-yl)cyclopropanecarboxamide

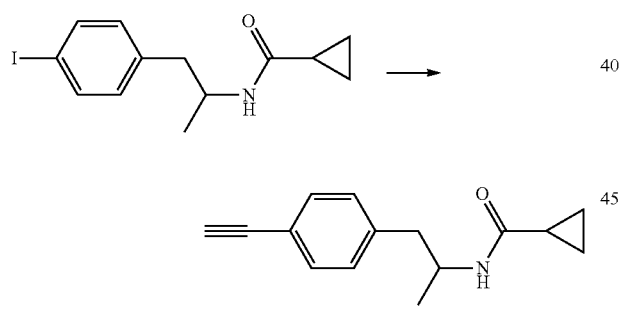

To 900 mg (2.73 mmol) N-(1-(4-iodophenyl)propan-2-yl)cyclopropanecarboxamide (I52.3) and 0.56 mL (3.01 mmol) (tert-butyldimethylsilyl)acetylene in 5 mL THF at 0° C. are added 0.77 mL (5.48 mmol) DIPEA, 96.1 mg (0.14 mmol) bis(triphenyl-phosphine)dichloropalladium and 53.1 mg (0.28 mmol) CuI, and the reaction mixture is stirred at r.t. overnight. The mixture is diluted with water and extracted with DCM (2×). The organic layer is dried with Na₂SO₄ and the solvent is removed in vacuo. The residue is purified by column chromatography (silica gel, DCM/MeOH 98/2) to yield the silylated compound. To this substance in DCM are added 949 mg (3.01 mmol) TBAF*3H₂O and the mixture is stirred at r.t. for 3 h. The mixture is diluted with water and extracted with DCM. The organic layer is dried with Na₂SO₄ and the solvent is removed in vacuo. The crude product is purified by column chromatography (silica gel, DCM/MeOH 98/2).

$C_{15}H_{17}NO$ (M=227.3 g/mol)

ESI-MS: 228 [M+H]⁺

$R_t$ (HPLC): 3.41 min (method B)

The following compounds are prepared analogously to example I59.1

| Ex. | Starting material | Product structure | Mass spec result | HPLC retention time (method) |
|---|---|---|---|---|
| I59.1 | I52.3 | 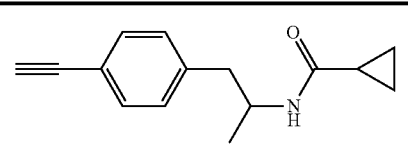 | 228 [M + H]⁺ | 3.41 (B) |

-continued

| Ex. | Starting material | Product structure | Mass spec result | HPLC retention time (method) |
|---|---|---|---|---|
| I59.2 | I52.2 | Chiral structure with ethynyl-phenyl, cyclopropyl carboxamide | 214 (M + H)+ | 1.58 (E) |
| I59.3 | I52.4 | ethynyl-phenyl-propyl-acetamide | 216 (M + H)+ | 1.72 (E) |
| I59.4 | I52.6 | ethynyl-phenyl-ethyl-acetamide | 188 (M + H)+ | 2.35 (B) |

Intermediate 60

{2-[4-(4-Ethoxy-phenylethynyl)-phenyl]-1-methyl-ethyl}-carbamic acid tert-butyl ester

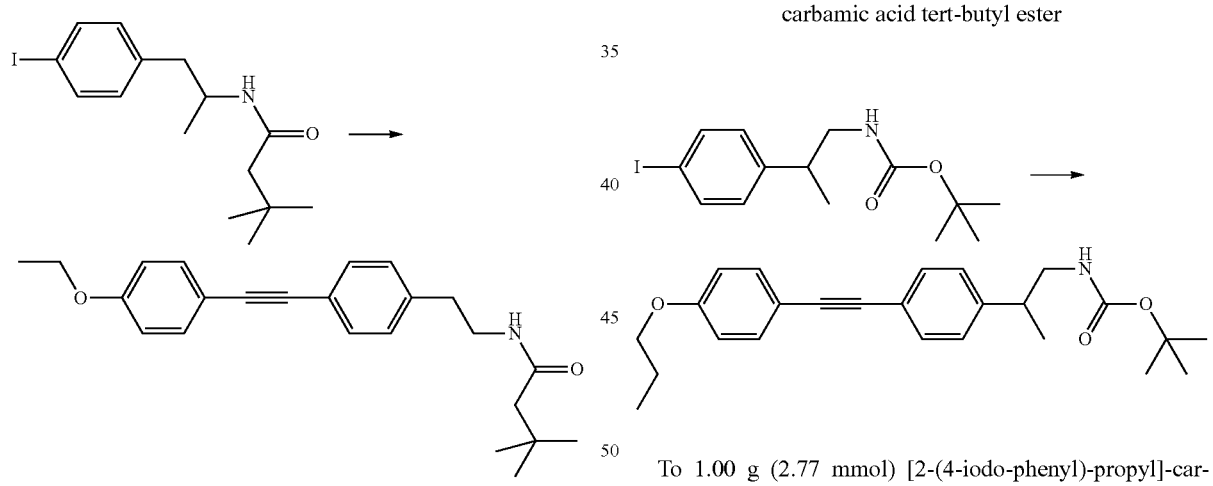

To 5.00 g (13.8 mmol) [2-(4-iodo-phenyl)-1-methyl-ethyl]-carbamic acid tert-butyl ester (I52.5) and 2.02 g (13.8 mmol) 4-ethoxyphenylacetylene in 80 mL ACN are added 4.46 mL (32.2 mmol) TEA, 135.6 mg (0.17 mmol) [1,1'-bis(diphenyl-phosphino)ferrocene]dichloropalladium(II) complex with dichloromethane and 32.3 mg (0.17 mmol) CuI, and the reaction mixture is stirred at r.t. over night. The precipitate is filtered and washed with ACN. The resulting crude product is purified by column chromatography (CyH/EtOAc 100/0→90/10).

$C_{24}H_{29}NO_3$ (M=379.5 g/mol)
ESI-MS: 380 [M+H]+
$R_t$ (HPLC): 1.47 min (method E)

Intermediate 61

Example I61.1

General Route

{2-[4-(4-Propoxy-phenylethynyl)-phenyl]propyl}-carbamic acid tert-butyl ester

To 1.00 g (2.77 mmol) [2-(4-iodo-phenyl)-propyl]-carbamic acid tert-butyl ester (I52.8) and 0.44 g (2.77 mmol) 1-ethinyl-4-propoxybenzene in 25 mL THF are added 0.78 mL (5.54 mmol) DIPEA, 40.5 mg (0.06 mmol) [1,1'-bis(diphenyl-phosphino)ferrocene]dichloropalladium(II) and 10.6 mg (0.055 mmol) CuI. The reaction mixture is stirred at r.t. for 3 h. EtOAc is added and the mixture is washed with diluted aq. ammonia solution (1×) and water (1×), dried with MgSO4 and the solvent is removed in vacuo. The crude product is purified by column chromatography (silica gel, PE/EtOAc 9/1).

$C_{25}H_{31}NO_3$ (M=393.5 g/mol)
ESI-MS: 394 [M+H]+
$R_t$ (HPLC): 2.40 min (method E)

The following compounds are prepared analogously to example I61.1

For example I61.2 diisopropylamine is used as base.

| Ex. | Starting material(s) | Product structure | Mass spec result | HPLC retention time (method) |
|---|---|---|---|---|
| I61.1 | I52.8 | 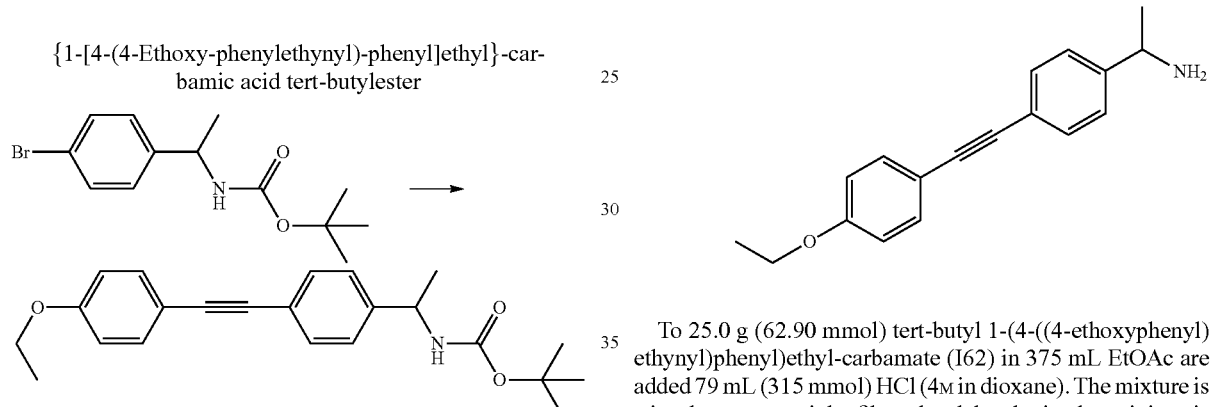 | 394 [M + H]+ | 2.40 (E) |
| I61.2 | I58.9 I15.4 | | 214 (M + H)+ | 1.58 (E) |

Intermediate 62

{1-[4-(4-Ethoxy-phenylethynyl)-phenyl]ethyl}-carbamic acid tert-butylester 24.6 g (168 mmol) 1-ethoxy-4-ethynyl-benzene, 52.8 g (176 mmol) [1-(4-Bromo-phenyl)-ethyl]-carbamic acid tert-butyl ester (I50.2) and 42.6 mL (307 mmol) TEA are added to 400 mL ACN. The mixture is warmed to 65° C. 8.84 g (7.65 mmol) Pd(PPh$_3$)$_4$ and 2.91 g (15.3 mmol) CuI are added and the reaction mixture is stirred at reflux for 2 h. The mixture is cooled to r.t. and the solvent is removed in vacuo. The crude product is purified by column chromatography (hexane/EtOAC 9:1→3:1).

$C_{23}H_{27}NO_3$ (M=365.5 g/mol)

ESI-MS: 388 [M+Na]+

R$_t$ (HPLC): 2.30 min (method S)

Intermediate 63

1-(4-((4-Ethoxyphenyl)ethynyl)phenyl)ethanamine

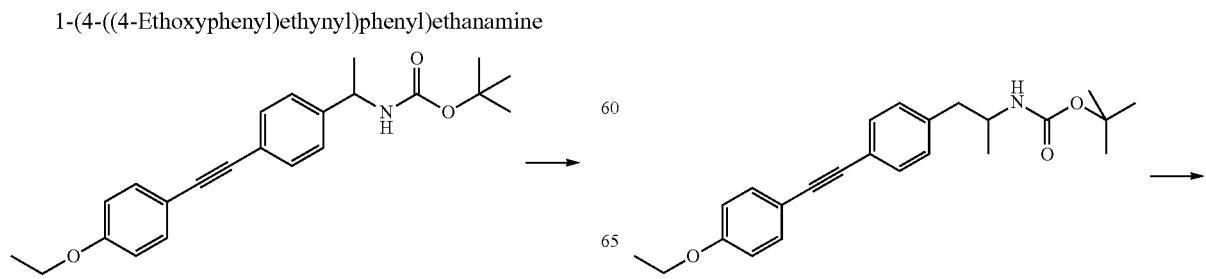

To 25.0 g (62.90 mmol) tert-butyl 1-(4-((4-ethoxyphenyl)ethynyl)phenyl)ethyl-carbamate (I62) in 375 mL EtOAc are added 79 mL (315 mmol) HCl (4M in dioxane). The mixture is stirred at r.t. over night, filtered and the obtained precipitate is dried. The crude product is suspended in DCM and sat. NaHCO$_3$ is added until a clear solution is obtained. The layers are separated and the aqueous layer is extracted two more times with DCM. The organic layers are combined, washed with brine (1×), dried with Na$_2$SO$_4$ and the solvent is removed in vacuo. The residue is purified by column chromatography (silica gel, heptane/EtOAc/TEA 75/25/1→0/100/1).

$C_{18}H_{19}NO$ (M=265.4 g/mol)

ESI-MS: 249 [M+H−NH$_3$]+

R$_t$ (HPLC): 3.14 min (method Q)

Intermediate 64

1-(4-((4-Ethoxyphenyl)ethynyl)phenyl)propan-2-amine hydrochloride

-continued

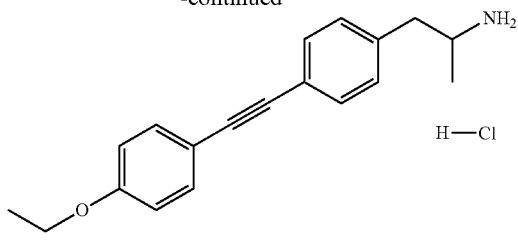

To 3.30 g (8.70 mmol) tert-butyl 1-(4-((4-ethoxyphenyl)ethynyl)phenyl)propan-2-yl-carbamate (I60) in 40 mL MeOH are added 20 mL (25 mmol) HCl (1.25M in MeOH). The mixture is stirred at 70° C. for 7 h. The solvent is removed in vacuo and the crude product is triturated with DIPE and dried in normal atmosphere.

$C_{18}H_{19}NO*HCl$ (M=315.9 g/mol)
ESI-MS: 280 [M+H]$^+$
R$_t$ (HPLC): 2.00 min (method M)

Intermediate 65

2-(4-((4-Propoxyphenyl)ethynyl)phenyl)propan-1-amine

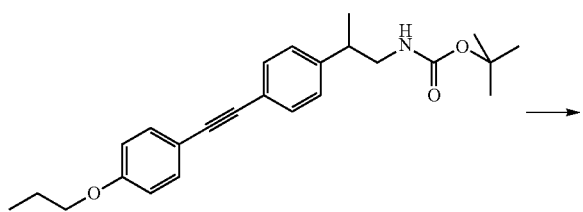

To 0.70 g (1.78 mmol) tert-butyl 2-(4-((4-propoxyphenyl)ethynyl)phenyl)propyl-carbamate (I61.1) in 5 mL MeOH are added 4.27 mL (5.34 mmol) HCl (1.25M in MeOH). The mixture is stirred at r.t. over night. The solvent is removed in vacuo and the crude product is treated with aq. NaHCO$_3$ solution. The precipitate is filtered, washed with water and dried at 50° C. in vacuo.

$C_{18}H_{19}NO*HCl$ (M=293.4 g/mol)
ESI-MS: 294 [M+H]$^+$
R$_t$ (HPLC): 2.26 min (method E)

Intermediate 66

2-(4-((2-Cyclobutoxy-pyrimidin-5-ylethynyl)-phenyl]-propylamine

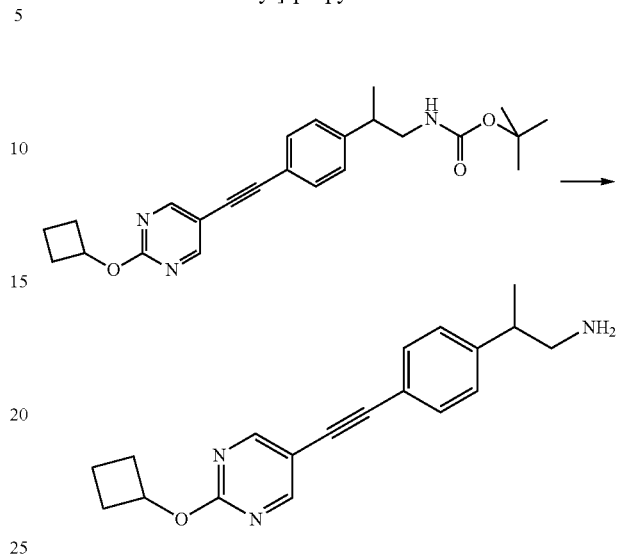

To 0.90 g (2.21 mmol) 2-(4-((2-cyclobutoxy-pyrimidin-5-ylethynyl)-phenyl]-propyl carbamic acid tert-butyl ester (I61.2) in 5 mL dioxane are added 5.30 mL (6.63 mmol) HCl (1.25M in dioxane). The mixture is stirred at r.t. for 2 h. The mixture is basified with 1M aq. NaOH solution and extracted with DCM (2×). The org. layers are combined, washed with water (1×), dried with MgSO$_4$ and the solvent is removed in vacuo.

$C_{19}H_{21}N_3O$ (M=307.4 g/mol)
ESI-MS: 308 [M+H]$^+$
R$_t$ (HPLC): 2.15 min (method E)

Intermediate 67

2-(4-((2-Methoxy-pyrimidin-5-ylethynyl)-phenyl]-propylamine

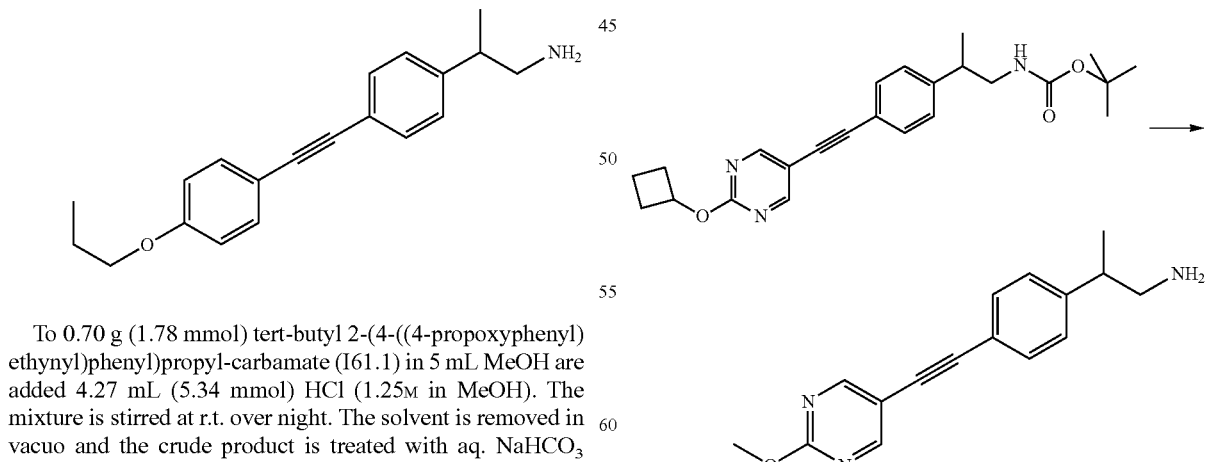

To 0.14 g (0.34 mmol) 2-(4-((2-cyclobutoxy-pyrimidin-5-yl-ethynyl)-phenyl]-propyl carbamic acid tert-butyl ester (I61.2) in 1 mL MeOH are added 0.82 mL (1.03 mmol) HCl (1.25M in MeOH). The mixture is stirred at r.t. over night and 2 h at 40° C. Then additional 0.82 mL (1.03 mmol) HCl (1.25M in MeOH) are added and the reaction mixture is again stirred for 2 h at 40° C. The solvent is removed in vacuo and the residue is purified by HPLC (MeOH/H₂O/NH₃).

C$_{16}$H$_{17}$N$_3$O (M=267.3 g/mol)
ESI-MS: 268 [M+H]$^+$
R$_t$ (HPLC): 1.06 min (method O)

Intermediate 68

2-(4-Iodophenyl)-1,1-dimethyl-ethylamine

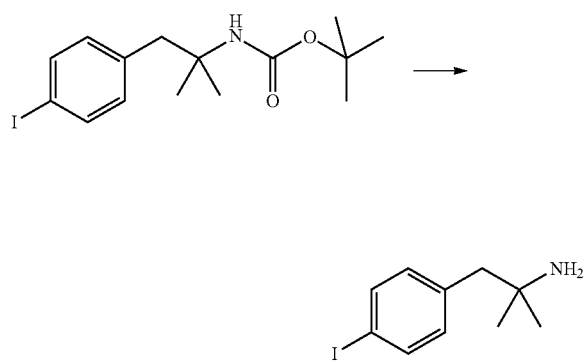

To 1.10 g (2.93 mmol) 2-(4-iodophenyl)-1,1-dimethyl-ethyl-carbamic acid tert-butyl ester (I52.9) in 10 mL MeOH are added 7.04 mL (8.80 mmol) HCl (1.25M in MeOH). The mixture is stirred at 50° C. for 3 h. The solvent is removed in vacuo and the residue is purified by HPLC (MeOH/H₂O/NH₃).

C$_9$H$_{12}$IN (M=275.1 g/mol)
ESI-MS: 276 [M+H]$^+$
R$_t$ (HPLC): 1.77 min (method E)

Intermediate 69

Example I69.1

General Route

N-(1-(4-((2-Chloropyrimidin-5-yl)ethynyl)phenyl)propan-2-yl)acetamide

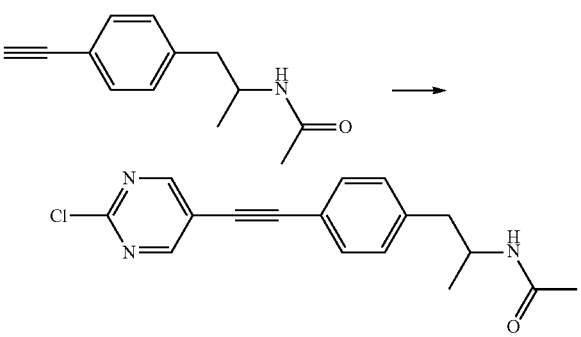

To 1.20 g (5.96 mmol) N-(1-(4-ethynylphenyl)propan-2-yl)acetamide (I58.3) in 10 mL THF are added 1.43 g (5.96 mmol) 2-chloro-5-iodopyrimidine, 418 mg (0.60 mmol) bis(triphenylphosphine)dichloropalladium, 56.8 mg (0.30 mmol) CuI and 2.03 mL (11.9 mmol) DIPEA. The reaction mixture is stirred at r.t. for 4 h. The solvent is removed in vacuo and the residue is purified by column chromatography (silica gel, DCM/MeOH 98/2).

C$_{17}$H$_{16}$ClN$_3$O (M=313.8 g/mol)
ESI-MS: 314 [M+H]$^+$
R$_t$ (HPLC): 2.12 min (method AA)

The following compounds are prepared analogously to example I69.1

For examples I69.3 and I69.4 additional purification by prep. HPLC is necessary.

For examples I69.5 and I69.6 the reaction mixture is stirred at r.t. over night.

| Ex. | Starting material | Product structure | Mass spec result | HPLC ret. time method |
|---|---|---|---|---|
| I69.1 | I58.3 | | 314 [M + H]$^+$ | 2.12 (AA) |
| I69.2 | I58.6 | | 343 [M + H]+ | 2.18 (AA) |
| I69.3 | I59.1 | | 340 [M + H]$^+$ | 2.19 (AA) |

-continued

| Ex. | Starting material | Product structure | | Mass spec result | HPLC ret. time method |
|---|---|---|---|---|---|
| I69.4 | I58.7 | (2-chloropyrimidin-5-yl-ethynyl-phenyl with methyl carbamate propan-2-yl) | | 330 [M + H]⁺ | 2.04 (AA) |
| I69.5 | I59.2 | (2-chloropyrimidin-5-yl-ethynyl-phenyl with cyclopropanecarboxamide) | Chiral | 326 [M + H]⁺ | 1.85 (E) |
| I69.6 | I58.10 | (2-chloropyrimidin-5-yl-ethynyl-phenyl with acetamide) | Chiral | 300 [M + H]⁺ | 1.89 (E) |

Intermediate 70

N-(1-(4-((2-Chloropyrimidin-5-yl)ethynyl)phenyl)propan-2-yl)acetamide

To 3.30 g (16.4 mmol) N-(1-(4-ethynylphenyl)propan-2-yl)acetamide (I58.3) in 40 mL THF are added 2.44 g (16.4 mmol) 2,4-dichloropyrimidine, 57.5 mg (82.0 µmol) bis(triphenyphosphine)dichloropalladium and 9.10 mL (65.7 mmol) TEA. The reaction mixture is stirred under reflux for 4 h and at r.t. over night. The reaction mixture is filtrated and the solvent is removed in vacuo. The residue is triturated with water and afterwards with diethylether.

$C_{17}H_{16}ClN_3O$ (M=313.8 g/mol)
ESI-MS: 314 [M+H]⁺
$R_t$ (HPLC): 2.11 min (method M)

Intermediate 71

Example I71.1

General Route

Methyl 3-((4-(2-acetamidopropyl)phenyl)ethynyl)benzoate

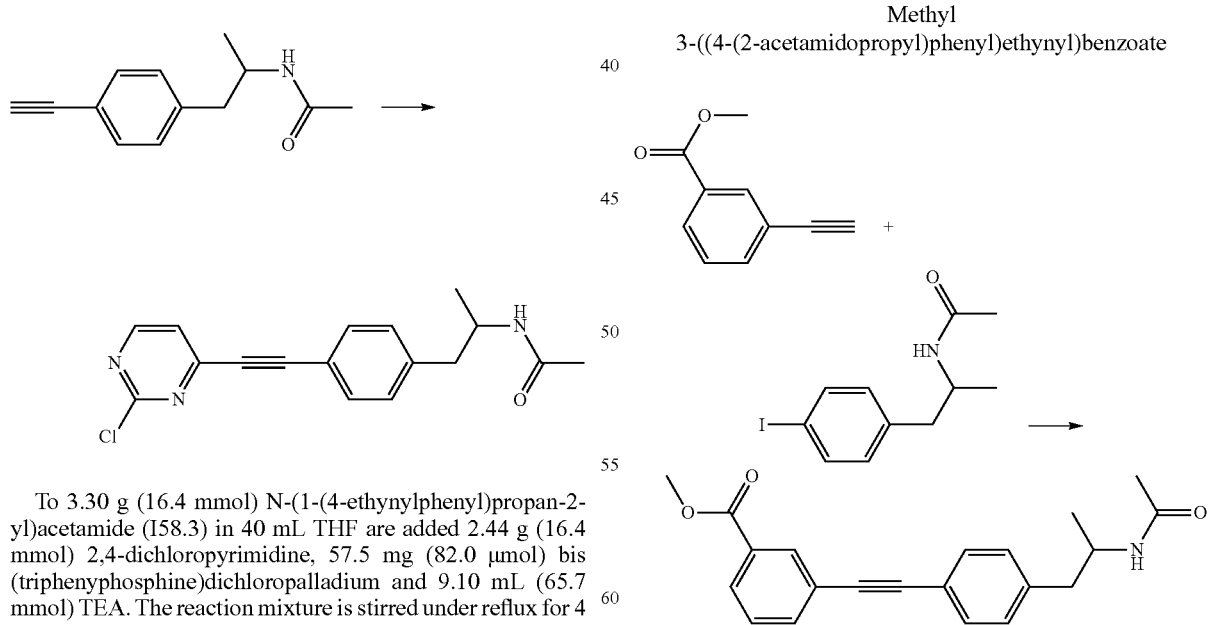

To 10.0 g (63.4 mmol) methyl 3-ethynylbenzoate (J. Org. Chem. 1981, 46, 2280-6) and 7.00 g (23.1 mmol) N-(1-(4-iodo-phenyl)propan-2-yl)acetamide (I52.1) in 80 mL DMF are added 100 mL TEA, 250 mg (1.31 mmol) CuI and 1.20 g (1.71 mmol) bis(triphenylphosphine)-palladium (II) chloride. After stirring over night r.t. the solvents are removed under reduced pressure. The residue is partitioned between EtOAc and diluted aq. NH$_4$Cl solution. The organic layer is separated and the aq. layer is extracted with EtOAc (2×). The org. layers are combined, washed with brine, dried with Na$_2$SO$_4$ and the solvent is removed in vacuo. The residue is purified by column chromatography (silica gel, EtOAc 100%).

C$_{17}$H$_{16}$ClN$_3$O M=313.8 g/mol
R$_t$ (HPLC): 8.75 min (method AE)

The following compounds are prepared analogously to example I71.1

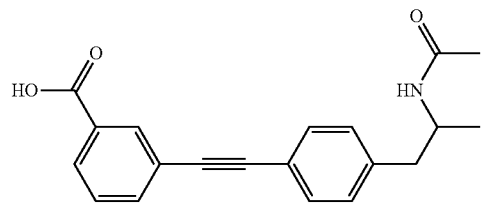

| Ex. | Starting material(s) | Product structure | HPLC retention time (method) |
|---|---|---|---|
| I71.1 | I52.1 | | 8.75 (AE) |
| I71.2 | I52.1 I26.1 | | 8.83 (AE) |

Intermediate 72

Example I72.1

General Route 3-((4-(2-Acetamidopropyl)phenyl)ethynyl)benzoic acid

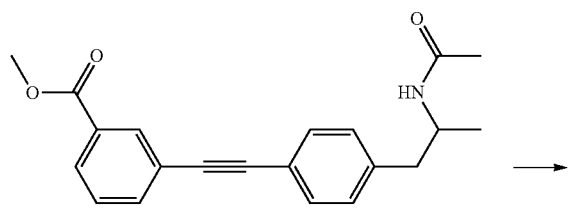

To a mixture of 6.00 g (17.9 mmol) methyl 3-((4-(2-acetamido-propyl)phenyl)ethynyl)-benzoate (I71.1) in 150 mL MeOH are added at 0° C. 18 mL LiOH solution (3 M in water). The reaction mixture is stirred at r.t. over night. The MeOH is removed in vacuo and the desired product is precipitated by acidification with 2N aq. HCl. The resulting solid is filtered, washed with pentane and dried in vacuo.

C$_{17}$H$_{16}$ClN$_3$O M=313.8 g/mol
ESI-MS: 322 [M+H]$^+$
R$_t$ (HPLC): 7.01 min (method AE)

The following compounds are prepared analogously to example I72.1

| Ex. | Starting material | Product structure | Mass spec result | HPLC retention time (method) |
|---|---|---|---|---|
| I72.1 | I71.1 | | 322 [M + H]$^+$ | 7.01 (AE) |

| Ex. | Starting material | Product structure | Mass spec result | HPLC retention time (method) |
|---|---|---|---|---|
| I72.2 | I71.2 | 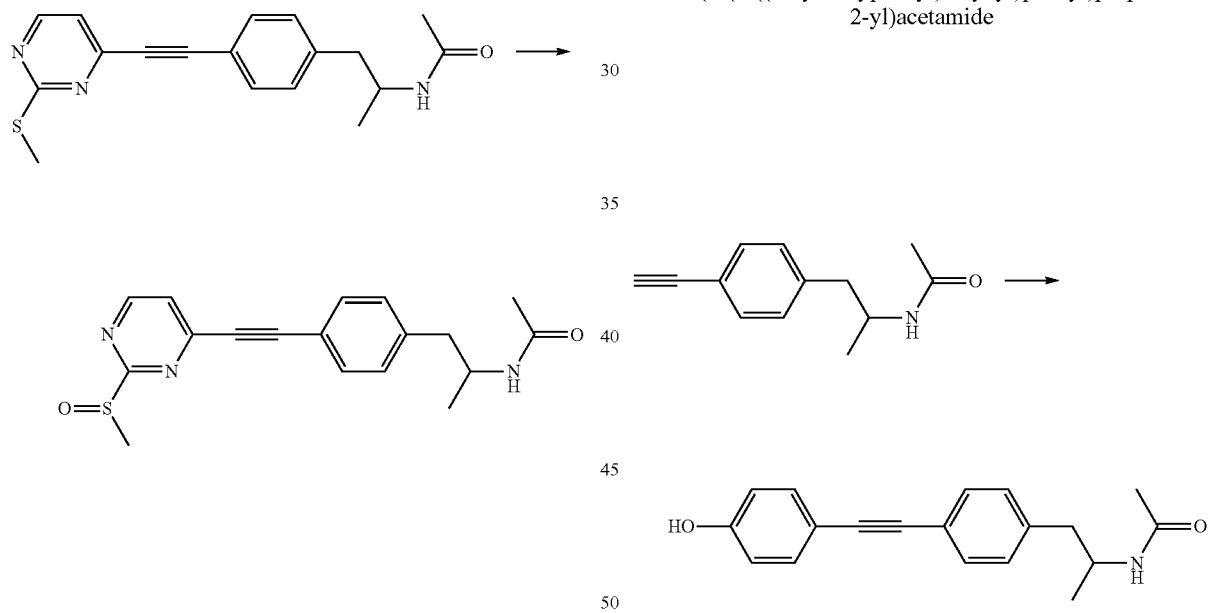 | 326 [M + H]+ | 6.90 (AE) |

Intermediate 73

N-{2-[4-(2-Methanesulfinyl-pyrimidin-4-ylethynyl)-phenyl]-1-methyl-ethyl}-acetamide A mixture of 0.30 g (0.922 mmol) N-{1-methyl-2-[4-(2-methylsulfanyl-pyrimidin-4-ylethynyl)-phenyl]-ethyl}-acetamide (example 14.1) in 9 mL DCM is cooled down to 0° C. and charged with 0.27 g (1.10 mmol; 70% purity) 3-chloroperoxybenzoic acid. The mixture is stirred for 30 min at constant temperature. The mixture is poured onto sat. aq. NaHCO₃ solution. The organic layer is separated, dried with Na₂SO₄ and filtered. The resulting mixture can be used directly used in the following reaction.

$C_{18}H_{19}N_3O_2S$ (M=341.4 g/mol)
ESI-MS: 342 [M+H]+
$R_t$ (HPLC): 2.20 min (method B)

Intermediate 74

Example I74.1

General Route

N-(1-(4-((4-hydroxyphenyl)ethynyl)phenyl)propan-2-yl)acetamide 4.00 g (19.9 mmol) of N-(1-(4-ethynylphenyl)propan-2-yl)acetamide (I58.3) and 5.25 g (23.9 mmol) 4-iodophenol are added to 125 ml of a 1:1 mixture of DMF and TEA. After cooling down to 0° C. 189 mg (0.99 mmol) CuI and 976 mg (1.39 mmol) Pd(PPh₃)₄ are added. After stirring over night at r.t. the mixture is treated with EtOAc and sat. NH₄Cl solution. The organic layer is washed with brine, dried with Na₂SO₄ and the solvent is removed in vacuo. The residue is purified by column chromatography (silica gel, EtOAc).

$C_{19}H_{19}NO_2$ (M=293.4 g/mol)
ESI-MS: 294 [M+H]+
$R_t$ (HPLC): 1.27 min (Method U)

The following compounds are prepared analogously to example I74.1

| Ex. | Starting material | Product structure | Mass spec result | HPLC retention time (method) |
|---|---|---|---|---|
| I74.1 | I58.3 | ![structure] | 294 [M + H]+ | 1.27 (U) |
| I74.2 | I58.3 | ![structure] | 294 [M + H]+ | 6.95 (AE) |

Intermediate 75

2-Oxo-pyrrolidine-3-carboxylic acid

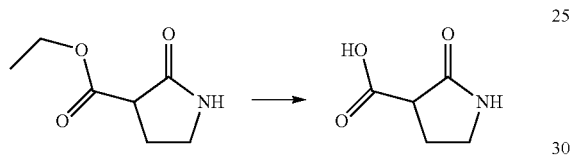

To 0.50 g (3.18 mmol) 2-oxo-pyrollidine-carboxylic acid ethyl ester in 10 mL EtOH are added 5 mL aq. NaOH (1M) solution. The reaction mixture is stirred at r.t. for 3 h. The EtOH is removed in vacuo and the residue is diluted with water and acidified with aq. HCl (2M) solution. The resulting precipitate is filtered and dried.

$C_5H_7NO_3$ (M=129.1 g/mol)

ESI-MS: 130 [M+H]+

Intermediate 76

Thiazole-5-carboxylic acid (2-(4-iodophenyl)-1-methylethyl)-amide

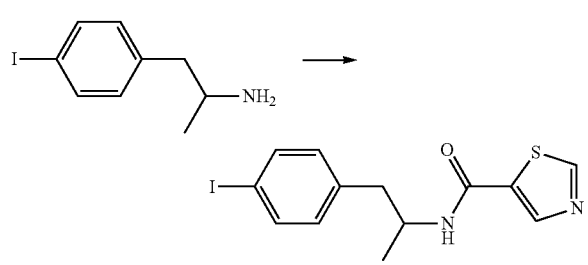

To 109 mg (0.84 mmol) thiazole-5-carboxylic acid (I54) in 10 mL DMF are added 267 µL (1.53 mmo.) DIPEA and 246 mg (0.77 mmol) TBTU. After stirring at r.t. for 10 min 200 mg (0.77 mmol) of intermediate 54 are added and stirring is continued for 5 h. The reaction mixture is purified directly by HPLC (MeOH/H₂O/TFA).

$C_{13}H_{13}IN_2O_3S$ (M=372.2 g/mol)

ESI-MS: 373 [M+H]+

$R_t$ (HPLC): 2.14 min (method AA)

Intermediate 77

Example I77.1

General Route (4-Ethynylphenyl)-morpholin-4-yl-methanone

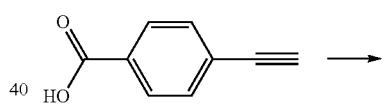

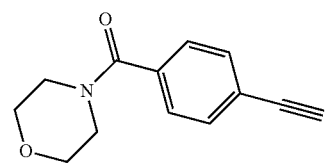

To 3.50 g (23.9 mmol) 4-ethynylphenyl benzoic acid in 20 mL THF are added 3.88 g (23.9 mmol) CDI. The mixture is stirred at 60° C. for 30 min and then charged with 2.11 mL (23.9 mmol) morpholine. The complete mixture is stirred under reflux for 5 h and at r.t. for 24 h. The solvent is removed in vacuo and the residue is purified by column chromatography (silica gel, EtOAc 100%).

$C_{13}H_{13}NO_2$ (M=215.2 g/mol)

ESI-MS: 216 [M+H]+

The following compounds are prepared analogously to example I77.1

For example I77.4 the crude product is purified by HPLC and the resulting product is isolated as TFA salt.

| Ex. | Starting material | Product structure | Mass spec result |
|---|---|---|---|
| I77.1 | | | 216 [M + H]⁺ |
| I77.2 | | | 228 [M + H]⁺ |
| I77.3 | | | 236 [M + H]⁺ |
| I77.4 | | | 257 [M + H]⁺ |
| I77.5 | | | 216 [M + H]⁺ |

Preparation of Final Compounds

Example 1

Example 1.1

General Route

N-(1-(4-((4-Chlorophenyl)ethynyl)phenyl)propan-2-yl)acetamide

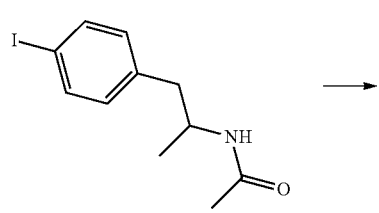

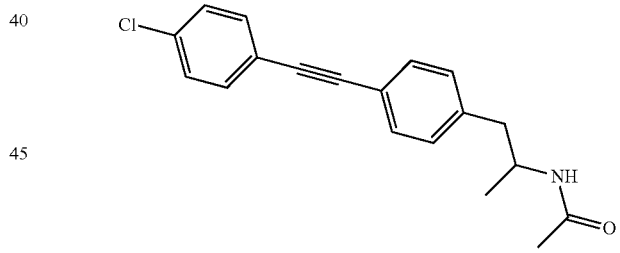

To 45.5 mg (0.15 mmol) N-(1-(4-iodophenyl)propan-2-yl) acetamide (I52.1) and 27.3 mg (0.20 mmol) 1-chloro-4-ethynylbenzene in 750 µl sec-butylamine are added 14.3 (0.02 mmol) bis(triphenyphosphine)dichloropalladium (in 400 µl sec-butylamine) followed by 1.0 mL water. The reaction mixture is stirred at r.t. overnight. The solvent is removed in vacuo and the residue is purified by HPLC (ACN/H$_2$O/TFA).

$C_{16}H_{18}ClNO$ (M=311.1 g/mol)

ESI-MS: 312 [M+H]⁺

$R_t$ (HPLC): 1.35 min (method B)

The following compounds are prepared analogously to example 1.1

| Ex. | Starting material(s) | Structure | Mass spec result | HPLC retention time (method) |
|---|---|---|---|---|
| 1.1 | I52.1 | 4-Cl-C6H4-C≡C-C6H4-CH2-CH(CH3)-NH-C(O)-CH3 | 312 [M + H]+ | 1.35 (A) |
| 1.2 | I52.1 | 4-CH3-C6H4-C≡C-C6H4-CH2-CH(CH3)-NH-C(O)-CH3 | 292 [M + H]+ | 1.31 (A) |
| 1.3 | I52.1, I25.6 | 4-Cl-C6H4-(pyridazine)-C≡C-C6H4-CH2-CH(CH3)-NH-C(O)-CH3 | 390 [M + H]+ | 1.23 (A) |
| 1.4 | I52.1 | 1-naphthyl-C≡C-C6H4-CH2-CH(CH3)-NH-C(O)-CH3 | 328 [M + H]+ | 1.39 (A) |
| 1.5 | I52.1 | 4-HOOC-C6H4-C≡C-C6H4-CH2-CH(CH3)-NH-C(O)-CH3 | 322 [M + H]+ | 0.94 (A) |
| 1.6 | I52.1 | 2-naphthyl-C≡C-C6H4-CH2-CH(CH3)-NH-C(O)-CH3 | 328 [M + H]+ | 1.40 (A) |
| 1.7 | I52.1 | 3-(CHF2O)-C6H4-C≡C-C6H4-CH2-CH(CH3)-NH-C(O)-CH3 | 344 [M + H]+ | 1.29 (A) |
| 1.8 | I52.1, I4.2 | 6-phenoxy-pyridin-3-yl-C≡C-C6H4-CH2-CH(CH3)-NH-C(O)-CH3 | 371 [M + H]+ | 1.35 (A) |
| 1.9 | I52.1, I77.4 | 3-(4-isopropylpiperazine-1-carbonyl)-C6H4-C≡C-C6H4-CH2-CH(CH3)-NH-C(O)-CH3 | 432 [M + H]+ | 0.55 (A) |

-continued

| Ex. | Starting material(s) | Structure | Mass spec result | HPLC retention time (method) |
|---|---|---|---|---|
| 1.10 | I52.1 I77.2 | 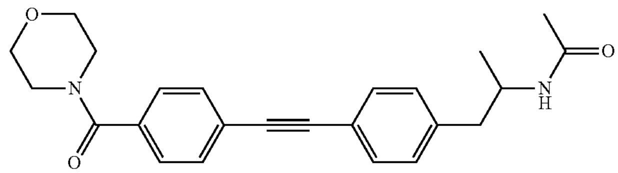 [SMILES: CC(=O)NC(C)Cc1ccc(C#Cc2ccc(C(=O)N3CCOCC3)cc2)cc1] | 391 [M + H]+ | 0.92 (A) |
| 1.11 | I52.1 I77.2 | 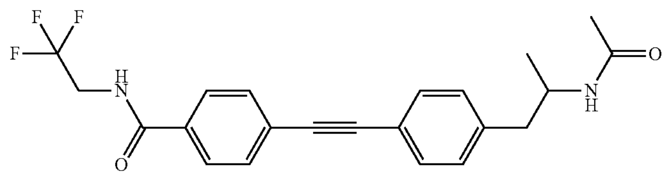 [SMILES: CC(=O)NC(C)Cc1ccc(C#Cc2ccc(C(=O)NCC(F)(F)F)cc2)cc1] | 403 [M + H]+ | 1.09 (A) |
| 1.12 | I52.1 I77.3 | 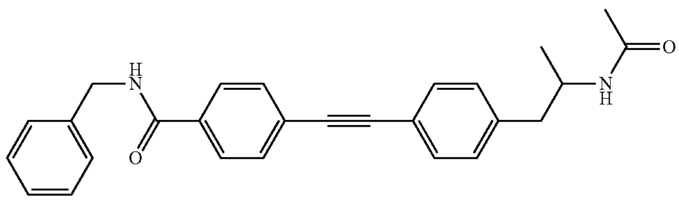 [SMILES: CC(=O)NC(C)Cc1ccc(C#Cc2ccc(C(=O)NCc3ccccc3)cc2)cc1] | 411 [M + H]+ | 1.16 (A) |
| 1.13 | I52.1 I25.1 | 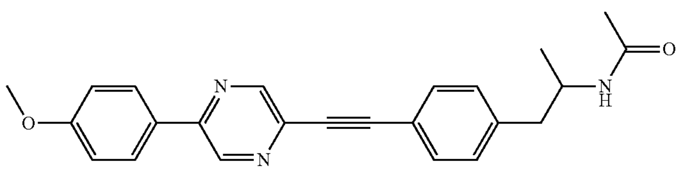 [SMILES: COc1ccc(-c2cnc(C#Cc3ccc(CC(C)NC(C)=O)cc3)cn2)cc1] | 386 [M + H]+ | 1.23 (A) |
| 1.14 | I52.1 I25.2 | 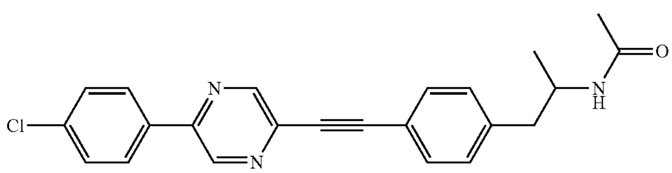 [SMILES: CC(=O)NC(C)Cc1ccc(C#Cc2cnc(-c3ccc(Cl)cc3)cn2)cc1] | 390 [M + H]+ | 1.38 (A) |
| 1.15 | I52.1 I25.3 | 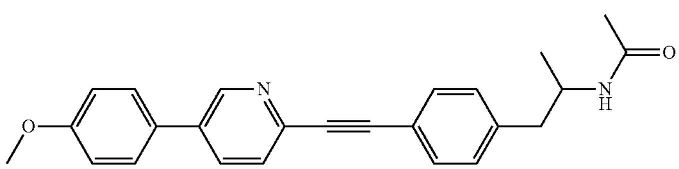 | 358 [M + H]+ | 1.19 (A) |
| 1.16 | I52.1 I25.4 | 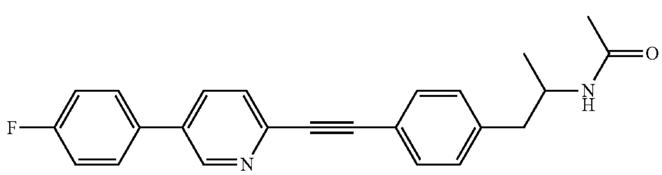 [SMILES: CC(=O)NC(C)Cc1ccc(C#Cc2ccc(-c3ccc(F)cc3)cn2)cc1] | 373 [M + H]+ | 1.25 (A) |
| 1.17 | I52.1 I25.5 | 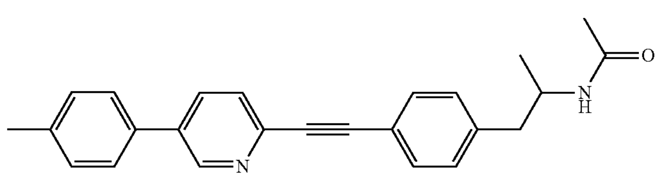 [SMILES: CC(=O)NC(C)Cc1ccc(C#Cc2ccc(-c3ccc(C)cc3)cn2)cc1] | 369 [M + H]+ | 1.30 (A) |

-continued

| Ex. | Starting material(s) | Structure | Mass spec result | HPLC retention time (method) |
|---|---|---|---|---|
| 1.18 | I52.1 I26.2 | 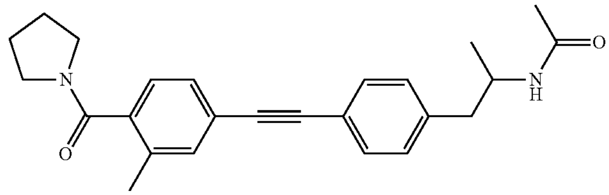 [SMILES: CC(=O)NC(C)Cc1ccc(C#Cc2ccc(C(=O)N3CCCC3)c(C)c2)cc1] | 389 [M + H]+ | 1.10 (A) |
| 1.19 | I52.1 | 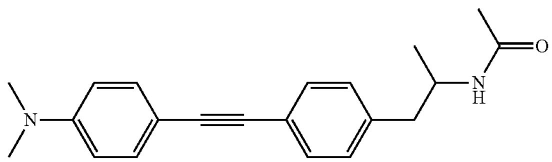 | 321 [M + H]+ | 1.24 (A) |
| 1.20 | I52.1 I5.1 | 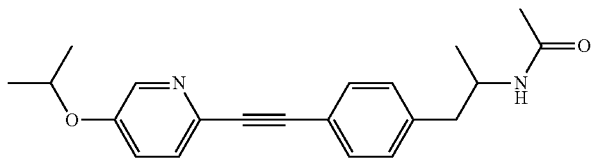 [SMILES: CC(=O)NC(C)Cc1ccc(C#Cc2ccc(OC(C)C)cn2)cc1] | 337 [M + H]+ | 1.15 (A) |
| 1.21 | I52.1 | 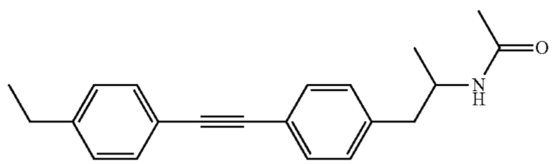 [SMILES: CCc1ccc(C#Cc2ccc(CC(C)NC(C)=O)cc2)cc1] | 306 [M + H]+ | 1.43 (A) |
| 1.22 | I52.1 | 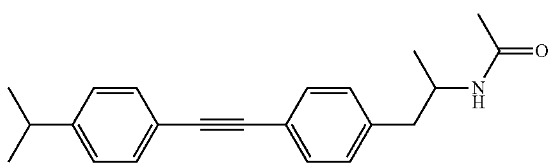 [SMILES: CC(=O)NC(C)Cc1ccc(C#Cc2ccc(C(C)C)cc2)cc1] | 320 [M + H]+ | 1.51 (A) |
| 1.23 | I52.1 | 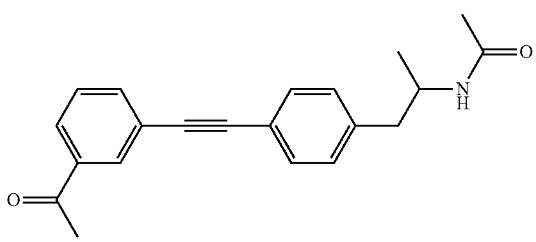 [SMILES: CC(=O)NC(C)Cc1ccc(C#Cc2cccc(C(C)=O)c2)cc1] | 320 [M + H]+ | 1.11 (A) |
| 1.24 | I52.1 | 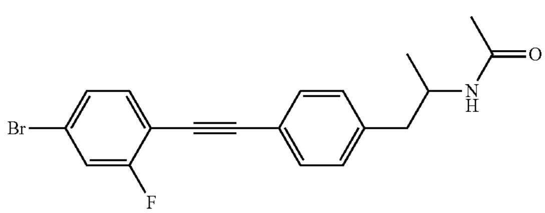 [SMILES: CC(=O)NC(C)Cc1ccc(C#Cc2ccc(Br)cc2F)cc1] | 374 [M + H]+ | 1.39 (A) |
| 1.25 | I52.1 I25.8 | 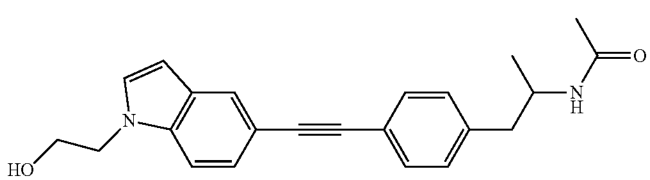 [SMILES: CC(=O)NC(C)Cc1ccc(C#Cc2ccc3c(ccn3CCO)c2)cc1] | 361 [M + H]+ | 1.02 (A) |

-continued

| Ex. | Starting material(s) | Structure | Mass spec result | HPLC retention time (method) |
|---|---|---|---|---|
| 1.26 | I52.1 | 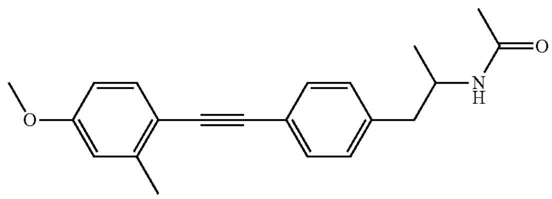 [SMILES: COc1ccc(C#Cc2ccc(CC(C)NC(C)=O)cc2)c(C)c1] | 322 [M + H]+ | 1.28 (A) |
| 1.27 | I52.1 I4.4 | 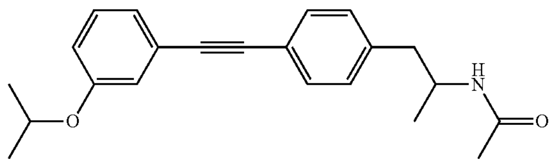 | 336 [M + H]+ | 3.43 (B) |
| 1.28 | I52.1 | 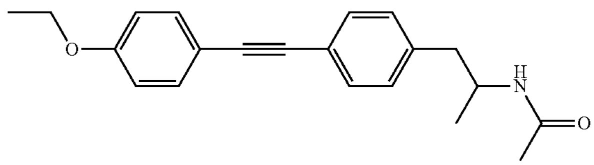 | 322 [M + H]+ | 3.35 (B) |
| 1.29 | I52.1 I4.3 | 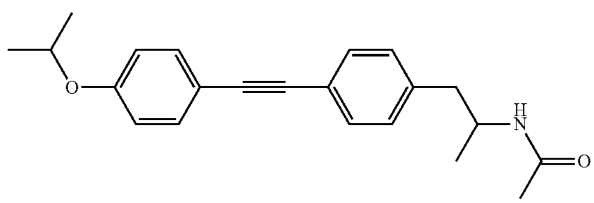 [SMILES: CC(=O)NC(C)Cc1ccc(C#Cc2ccc(OC(C)C)cc2)cc1] | 336 [M + H]+ | 3.47 (B) |
| 1.30 | I59.4 | 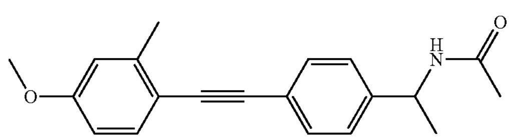 [SMILES: COc1ccc(C#Cc2ccc(C(C)NC(C)=O)cc2)c(C)c1] | 308 [M + H]+ | 3.03 (B) |
| 1.31 | I52.3 I25.4 | 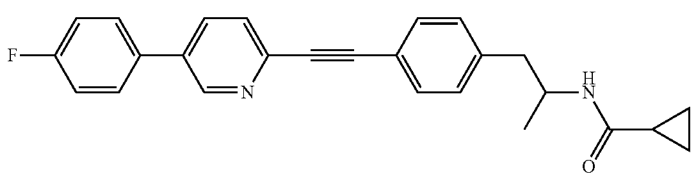 [SMILES: CC(Cc1ccc(C#Cc2ccc(-c3ccc(F)cc3)cn2)cc1)NC(=O)C1CC1] | 399 [M + H]+ | 2.14 (E) |
| 1.32 | I52.1 I77.5 | 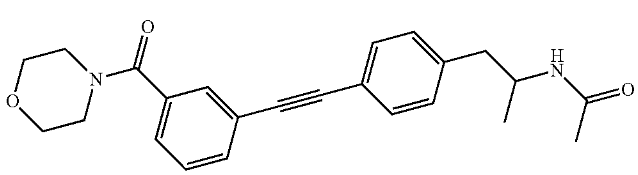 [SMILES: CC(=O)NC(C)Cc1ccc(C#Cc2cccc(C(=O)N3CCOCC3)c2)cc1] | 391 [M + H]+ | 0.93 (A) |

Example 2

Example 2.1

General Route

N-(1-(4-((4-(1H-Pyrrol-1-yl)phenyl)ethynyl)phenyl)propan-2-yl)acetamide

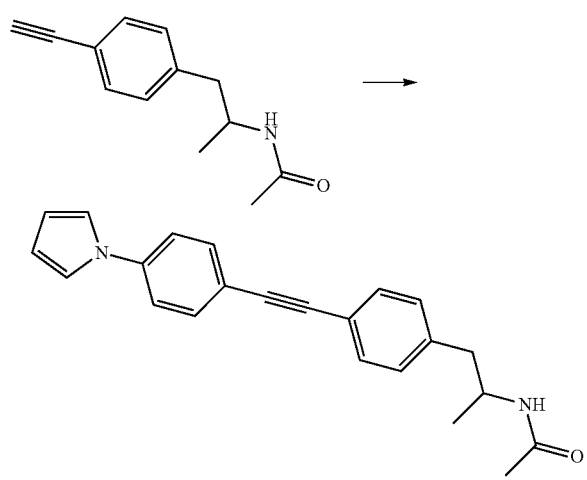

To 40.4 mg (0.15 mmol) 1-(4-iodophenyl)-H-pyrrole and 40.3 mg (0.20 mmol) N-(1-(4-ethynylphenyl)propan-2-yl)acetamide (I58.3) in 750 μl sec-butylamine are added 14.3 mg (0.02 mmol) bis(triphenylphosphine)dichloropalladium (in 400 μl sec-butylamine) followed by 1.0 mL water. The reaction mixture is stirred at r.t. for 72 h. The solvent is removed in vacuo and the residue is purified by HPLC (ACN/H$_2$O/TFA).

$C_{23}H_{22}N_2O$ (M=342.1 g/mol)
ESI-MS: 343 [M+H]$^+$
$R_t$ (HPLC): 1.35 min (method C)

The following compounds are prepared analogously to example 2.1

For example 2.32 additional purification by column chromatography (silica gel, DCM/MeOH 10/0→8/2) is necessary.

For examples 2.43-100 the alkyne is dissolved in THF before use. Reaction conditions 5 h at 80° C. (alkyne/aryliodide-ratio=1/1).

| Ex. | Starting material(s) | Structure | Mass spec result | HPLC retention time (method) |
|---|---|---|---|---|
| 2.1 | I58.3 | 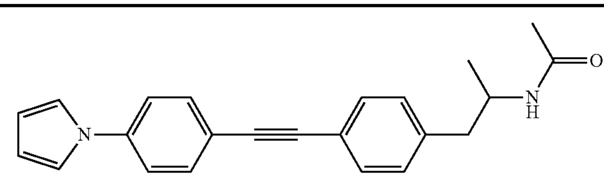 | 343 [M + H]$^+$ | 1.35 (C) |
| 2.2 | I58.3 | 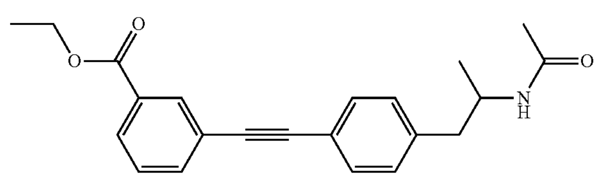 [SMILES: CCOC(=O)c1cccc(C#Cc2ccc(CC(C)NC(C)=O)cc2)c1] | 350 [M + H]$^+$ | 1.30 (C) |
| 2.3 | I58.3 | 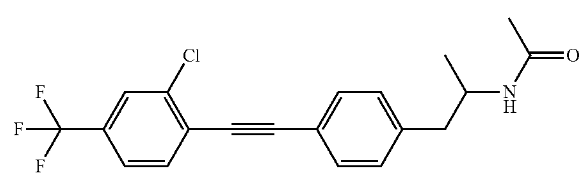 [SMILES: CC(=O)NC(C)Cc1ccc(C#Cc2ccc(C(F)(F)F)cc2Cl)cc1] | 380 [M + H]$^+$ | 1.46 (C) |
| 2.4 | I58.3 | 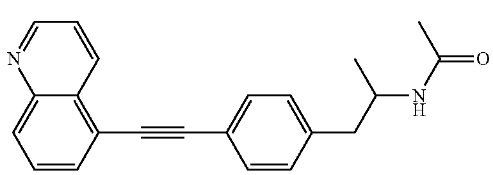 [SMILES: CC(=O)NC(C)Cc1ccc(C#Cc2cccc3ncccc23)cc1] | 329 [M + H]$^+$ | 1.06 (C) |

-continued

| Ex. | Starting material(s) | Structure | Mass spec result | HPLC retention time (method) |
|---|---|---|---|---|
| 2.5 | I58.3* | 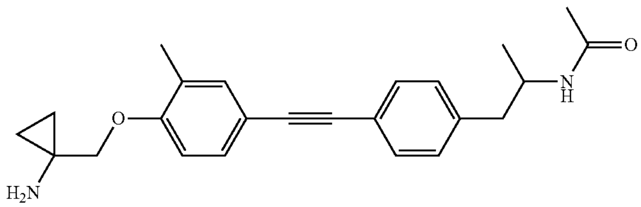 [SMILES: CC(=O)NC(C)Cc1ccc(C#Cc2ccc(OCC3(N)CC3)c(C)c2)cc1] | 377 [M + H]+ | 1.14 (C) |
| 2.6 | I58.3 | 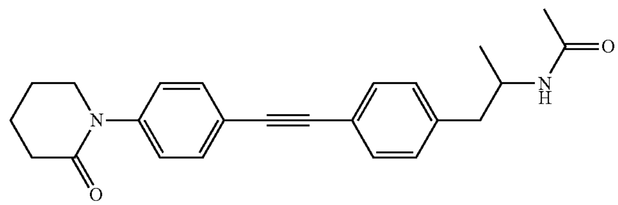 [SMILES: CC(=O)NC(C)Cc1ccc(C#Cc2ccc(N3CCCCC3=O)cc2)cc1] | 375 [M + H]+ | 1.02 (C) |
| 2.7 | I58.3 | 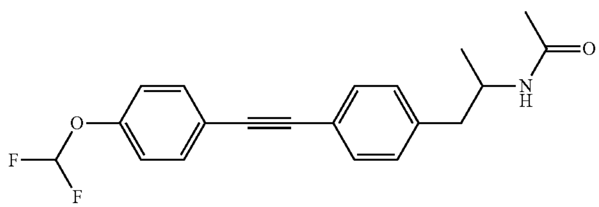 [SMILES: CC(=O)NC(C)Cc1ccc(C#Cc2ccc(OC(F)F)cc2)cc1] | 344 [M + H]+ | 1.24 (C) |
| 2.8 | I58.3 | 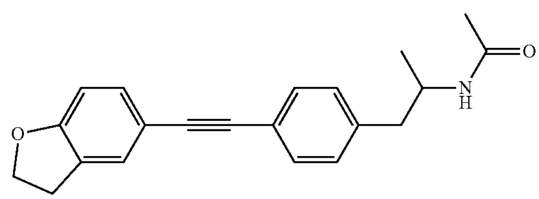 [SMILES: CC(=O)NC(C)Cc1ccc(C#Cc2ccc3c(c2)CCO3)cc1] | 320 [M + H]+ | 1.19 (C) |
| 2.9 | I58.3 | 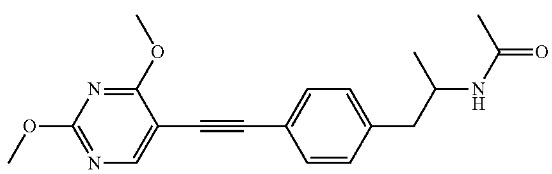 [SMILES: COc1ncc(C#Cc2ccc(CC(C)NC(C)=O)cc2)c(OC)n1] | 340 [M + H]+ | 0.72 (C) |
| 2.10 | I58.3 I5.2 | 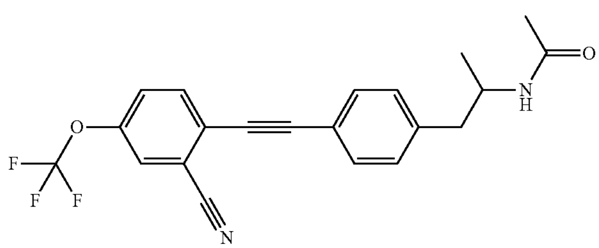 [SMILES: CC(=O)NC(C)Cc1ccc(C#Cc2ccc(OC(F)(F)F)cc2C#N)cc1] | 387 [M + H]+ | 1.31 (C) |
| 2.11 | I58.3 I5.1 | 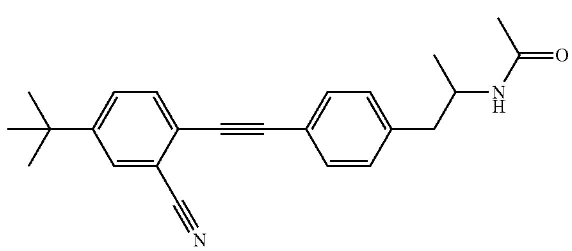 [SMILES: CC(=O)NC(C)Cc1ccc(C#Cc2ccc(C(C)(C)C)cc2C#N)cc1] | 359 [M + H]+ | 1.44 (C) |

-continued

| Ex. | Starting material(s) | Structure | Mass spec result | HPLC retention time (method) |
|---|---|---|---|---|
| 2.12 | I58.3 | 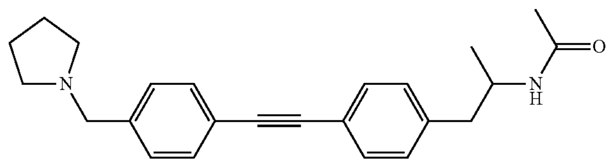 [SMILES: CC(=O)NC(C)Cc1ccc(C#Cc2ccc(CN3CCCC3)cc2)cc1] | 361 [M + H]+ | 1.32 (C) |
| 2.13 | I58.3 | 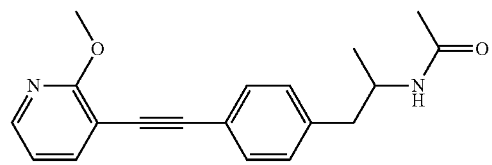 [SMILES: COc1ncccc1C#Cc1ccc(CC(C)NC(C)=O)cc1] | 309 [M + H]+ | 1.05 (C) |
| 2.14 | I58.3 I7 | 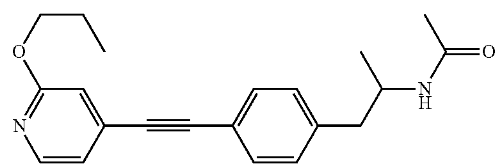 [SMILES: CCCOc1cc(C#Cc2ccc(CC(C)NC(C)=O)cc2)ccn1] | 337 [M + H]+ | 1.32 (C) |
| 2.15 | I58.3 | 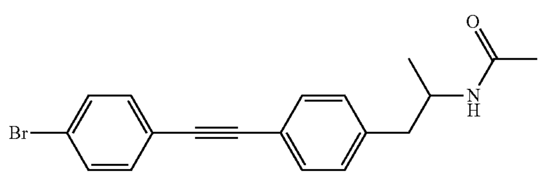 [SMILES: CC(=O)NC(C)Cc1ccc(C#Cc2ccc(Br)cc2)cc1] | 356 [M + H]+ | 1.67 (U) |
| 2.16 | I58.3 | 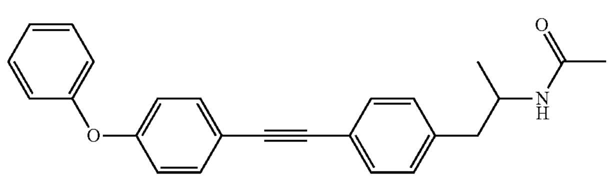 [SMILES: CC(=O)NC(C)Cc1ccc(C#Cc2ccc(Oc3ccccc3)cc2)cc1] | 370 [M + H]+ | 1.76 (U) |
| 2.17 | I58.3 I16.1 | 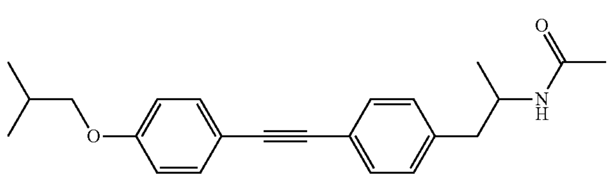 [SMILES: CC(=O)NC(C)Cc1ccc(C#Cc2ccc(OCC(C)C)cc2)cc1] | 350 [M + H]+ | 1.80 (U) |
| 2.18 | I58.3 | 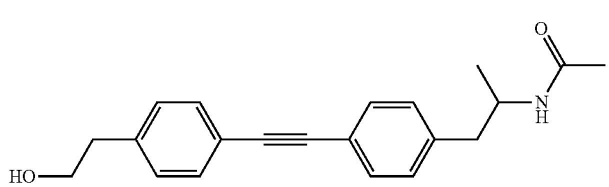 [SMILES: CC(=O)NC(C)Cc1ccc(C#Cc2ccc(CCO)cc2)cc1] | 322 [M + H]+ | 1.28 (U) |
| 2.19 | I58.3 | 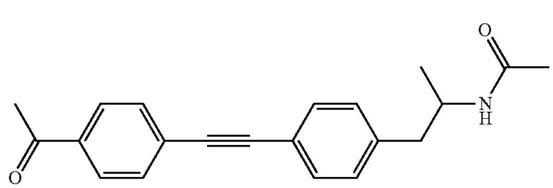 [SMILES: CC(=O)NC(C)Cc1ccc(C#Cc2ccc(C(C)=O)cc2)cc1] | 320 [M + H]+ | 1.42 (U) |

-continued

| Ex. | Starting material(s) | Structure | Mass spec result | HPLC retention time (method) |
|---|---|---|---|---|
| 2.20 | I58.3 | 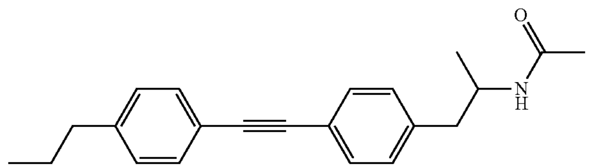 [SMILES: CCCc1ccc(C#Cc2ccc(CC(C)NC(C)=O)cc2)cc1] | 320 [M + H]⁺ | 1.79 (U) |
| 2.21 | I58.3 | 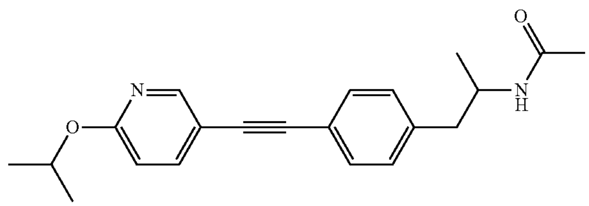 [SMILES: CC(=O)NC(C)Cc1ccc(C#Cc2ccc(OC(C)C)nc2)cc1] | 337 [M + H]+ | 2.18 (E) |
| 2.22 | I58.3 | 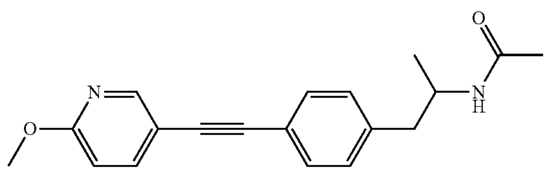 [SMILES: COc1ccc(C#Cc2ccc(CC(C)NC(C)=O)cc2)cn1] | 309 [M + H]⁺ | 1.99 (E) |
| 2.23 | I58.3 | 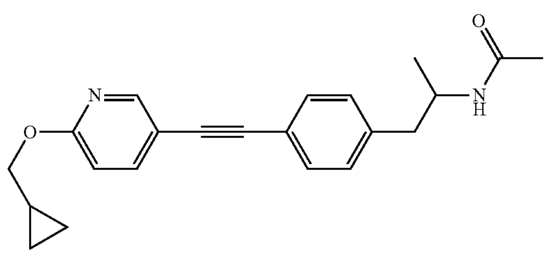 [SMILES: CC(=O)NC(C)Cc1ccc(C#Cc2ccc(OCC3CC3)nc2)cc1] | 349 [M + H]⁺ | 2.19 (E) |
| 2.24 | I58.3 | 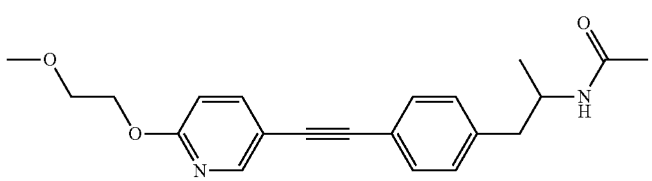 [SMILES: COCCOc1ccc(C#Cc2ccc(CC(C)NC(C)=O)cc2)cn1] | 353 [M + H]⁺ | 1.95 (E) |
| 2.25 | I58.3 | 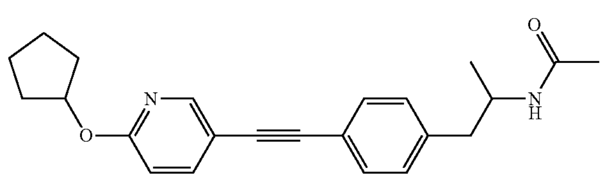 [SMILES: CC(=O)NC(C)Cc1ccc(C#Cc2ccc(OC3CCCC3)nc2)cc1] | 363 [M + H]⁺ | 2.28 (E) |
| 2.26 | I58.3 | 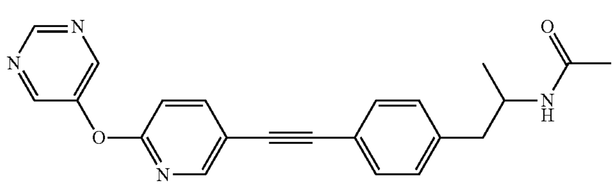 [SMILES: CC(=O)NC(C)Cc1ccc(C#Cc2ccc(Oc3cncnc3)nc2)cc1] | 373 [M + H]⁺ | 1.87 (E) |
| 2.27 | I58.3 | 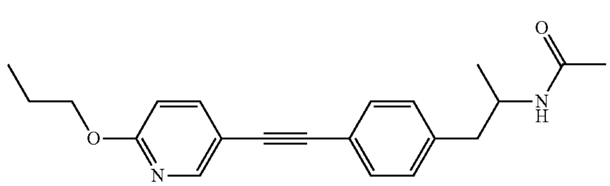 [SMILES: CCCOc1ccc(C#Cc2ccc(CC(C)NC(C)=O)cc2)cn1] | 337 [M + H]⁺ | 2.19 (E) |

-continued

| Ex. | Starting material(s) | Structure | Mass spec result | HPLC retention time (method) |
|---|---|---|---|---|
| 2.28 | I58.3 I6.1 | 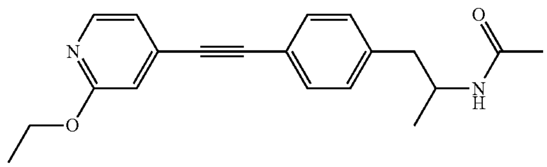 [SMILES: CCOc1cc(C#Cc2ccc(CC(C)NC(C)=O)cc2)ccn1] | 323 [M + H]+ | 1.47 (H) |
| 2.29 | I58.3 | 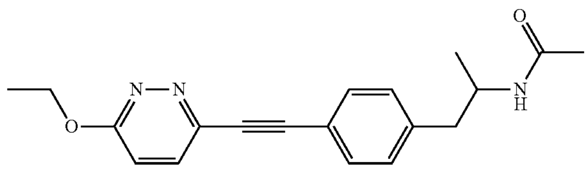 [SMILES: CCOc1ccc(C#Cc2ccc(CC(C)NC(C)=O)cc2)nn1] | 324 [M + H]+ | 1.84 (E) |
| 2.30 | I58.3 | 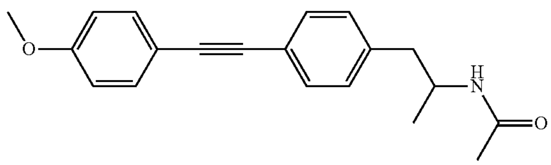 [SMILES: COc1ccc(C#Cc2ccc(CC(C)NC(C)=O)cc2)cc1] | 308 [M + H]+ | 3.12 (B) |
| 2.31 | I58.3 | 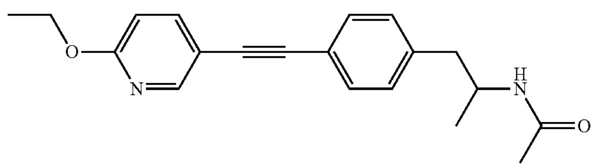 | 323 [M + H]+ | 3.15 (B) |
| 2.32 | I58.3 I20 | 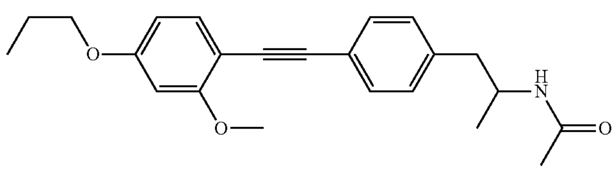 [SMILES: CCCOc1ccc(C#Cc2ccc(CC(C)NC(C)=O)cc2)c(OC)c1] | 366 [M + H]+ | 2.41 (E) |
| 2.33 | I58.4 I15.5 | 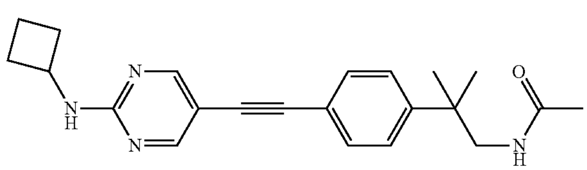 [SMILES: CC(=O)NCC(C)(C)c1ccc(C#Cc2cnc(NC3CCC3)nc2)cc1] | 363 [M + H]+ | 2.36 (E) |
| 2.34 | I58.4 I15.4 | 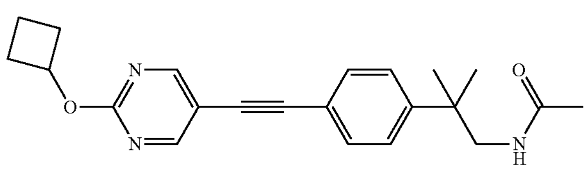 [SMILES: CC(=O)NCC(C)(C)c1ccc(C#Cc2cnc(OC3CCC3)nc2)cc1] | 364 [M + H]+ | 2.40 (E) |
| 2.35 | I58.4 I15.3 | 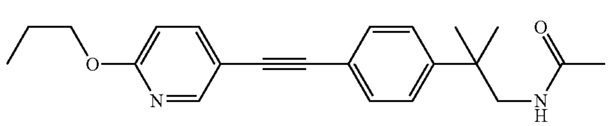 [SMILES: CCCOc1ccc(C#Cc2ccc(C(C)(C)CNC(C)=O)cc2)cn1] | 351 [M + H]+ | 2.49 (E) |
| 2.36 | I58.4 I16.6 | 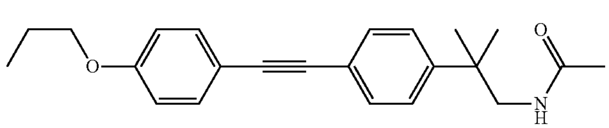 [SMILES: CCCOc1ccc(C#Cc2ccc(C(C)(C)CNC(C)=O)cc2)cc1] | 350 [M + H]+ | 2.53 (E) |

-continued
| Ex. | Starting material(s) | Structure | Mass spec result | HPLC retention time (method) |
|---|---|---|---|---|
| 2.37 | I58.4 I16.7 | 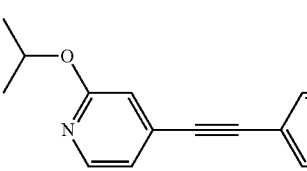 | 362 [M + H]+ | 2.51 (E) |
| 2.38 | I58.5 I10 | 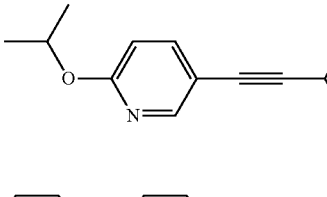 | 337 [M + H]+ | 2.38 (E) |
| 2.39 | I58.5 | 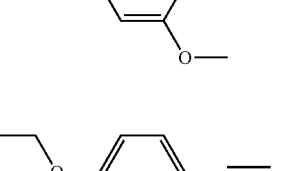 | 337 [M + H]+ | 2.41 (E) |
| 2.40 | I58.5 I20 | 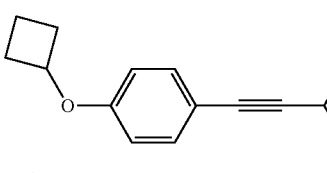 | 366 [M + H]+ | 2.28 (E) |
| 2.41 | I58.5 I16.6 | 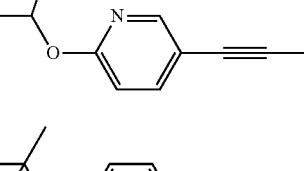 | 336 [M + H]+ | 2.47 (E) |
| 2.42 | I58.5 I16.2 | 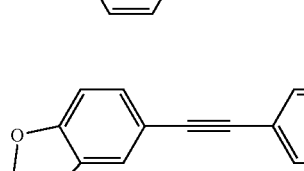 | 348 [M + H]+ | 2.46 (E) |
| 2.43 | I59.4 | 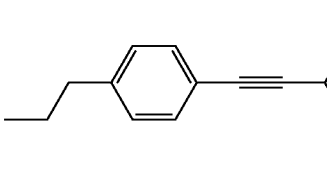 | 349 [M + H]+ | 2.21 (AA) |
| 2.44 | I59.4** | 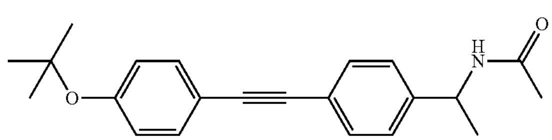 [SMILES: CC(=O)NC(C)c1ccc(C#Cc2ccc(OC(C)(C)C)cc2)cc1] | 336 [M + H]+ | 2.15 (AA) |
| 2.45 | I59.4 | 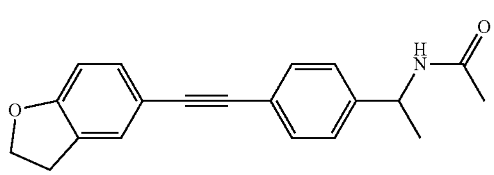 [SMILES: CC(=O)NC(C)c1ccc(C#Cc2ccc3c(c2)CCO3)cc1] | 306 [M + H]+ | 2.01 (AA) |
| 2.46 | I59.4 | 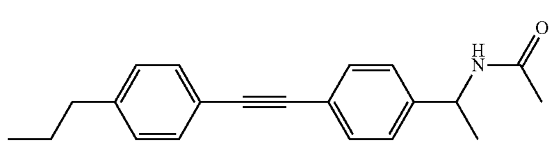 [SMILES: CCCc1ccc(C#Cc2ccc(C(C)NC(C)=O)cc2)cc1] | 306 [M + H]+ | 2.23 (AA) |

-continued

| Ex. | Starting material(s) | Structure | Mass spec result | HPLC retention time (method) |
|---|---|---|---|---|
| 2.47 | I59.4 I16.4 | 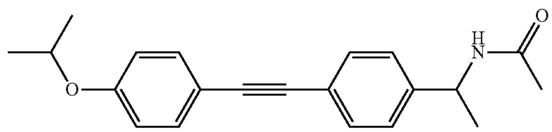 | 322 [M + H]+ | 2.12 (AA) |
| 2.48 | I59.4 I16.1 | 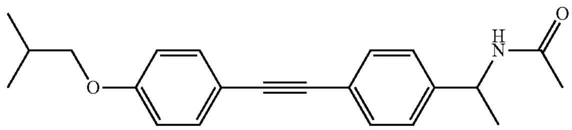 | 336 [M + H]+ | 2.22 (AA) |
| 2.49 | I59.4 I16.6 | 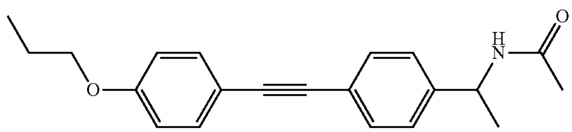 [SMILES: CCCOc1ccc(C#Cc2ccc(C(C)NC(C)=O)cc2)cc1] | 322 [M + H]+ | 2.16 (AA) |
| 2.50 | I59.4 | 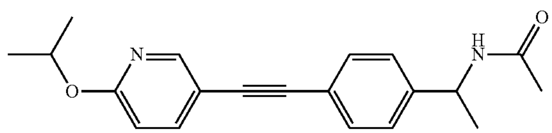 | 323 [M + H]+ | 2.12 (AA) |
| 2.51 | I59.4 I20 | 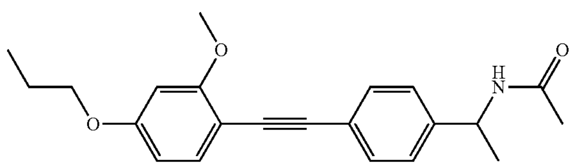 [SMILES: CCCOc1ccc(C#Cc2ccc(C(C)NC(C)=O)cc2)c(OC)c1] | 352 [M + H]+ | 2.12 (AA) |
| 2.52 | I59.4 I16.8 | 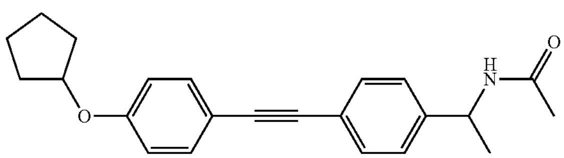 [SMILES: CC(=O)NC(C)c1ccc(C#Cc2ccc(OC3CCCC3)cc2)cc1] | 348 [M + H]+ | 2.23 (AA) |
| 2.53 | I59.4 I16.2 | 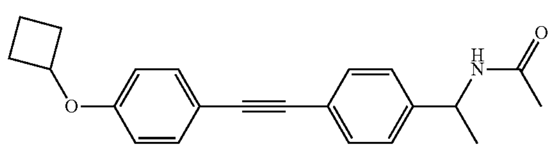 [SMILES: CC(=O)NC(C)c1ccc(C#Cc2ccc(OC3CCC3)cc2)cc1] | 334 [M + H]+ | 2.19 (AA) |
| 2.54 | I59.4 I15.3 | 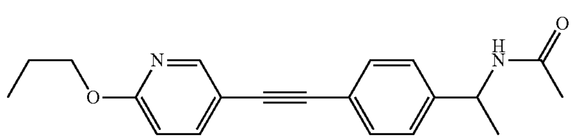 [SMILES: CCCOc1ccc(C#Cc2ccc(C(C)NC(C)=O)cc2)cn1] | 323 [M + H]+ | 2.13 (AA) |
| 2.55 | I59.4** | 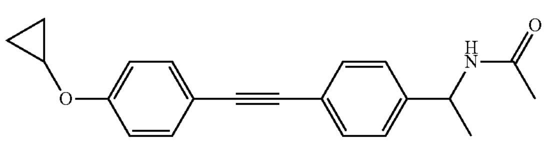 [SMILES: CC(=O)NC(C)c1ccc(C#Cc2ccc(OC3CC3)cc2)cc1] | 320 [M + H]+ | 2.11 (AA) |
| 2.56 | I59.1 | 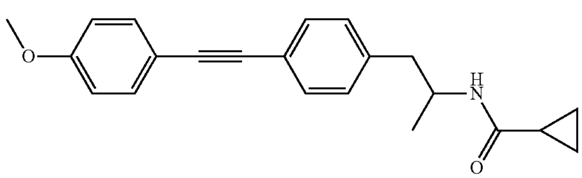 [SMILES: COc1ccc(C#Cc2ccc(CC(C)NC(=O)C3CC3)cc2)cc1] | 334 [M + H]+ | 2.12 (AA) |

-continued

| Ex. | Starting material(s) | Structure | Mass spec result | HPLC retention time (method) |
|---|---|---|---|---|
| 2.57 | I59.1 | 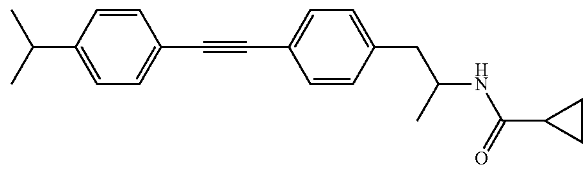 [SMILES: CC(Cc1ccc(C#Cc2ccc(C(C)C)cc2)cc1)NC(=O)C1CC1] | 346 [M + H]+ | 2.27 (AA) |
| 2.58 | I59.1 | 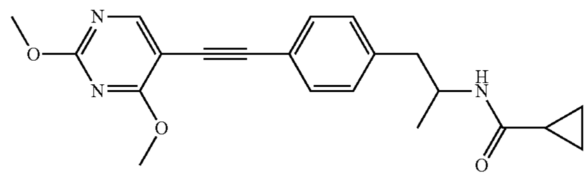 [SMILES: COc1ncc(C#Cc2ccc(CC(C)NC(=O)C3CC3)cc2)c(OC)n1] | 366 [M + H]+ | 1.97 (AA) |
| 2.59 | I59.1 | 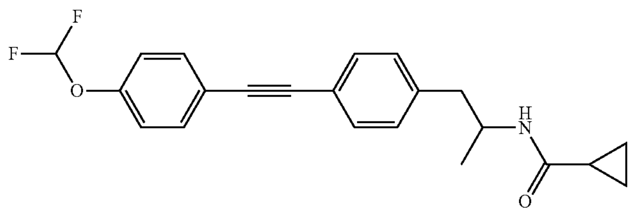 [SMILES: CC(Cc1ccc(C#Cc2ccc(OC(F)F)cc2)cc1)NC(=O)C1CC1] | 370 [M + H]+ | 2.09 (AA) |
| 2.60 | I59.1 I6.1 | 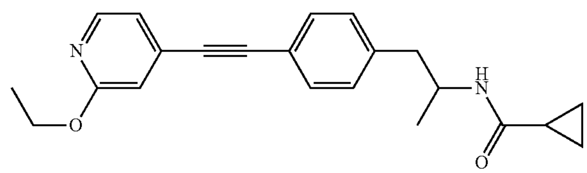 [SMILES: CCOc1cc(C#Cc2ccc(CC(C)NC(=O)C3CC3)cc2)ccn1] | 349 [M + H]+ | 2.13 (AA) |
| 2.61 | I59.1** | 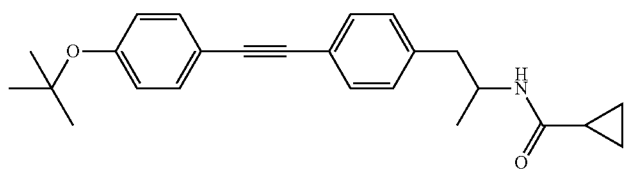 [SMILES: CC(Cc1ccc(C#Cc2ccc(OC(C)(C)C)cc2)cc1)NC(=O)C1CC1] | 376 [M + H]+ | 2.24 (AA) |
| 2.62 | I59.1 | 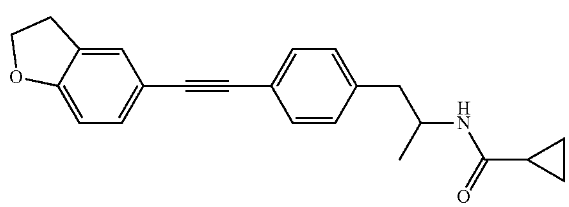 [SMILES: CC(Cc1ccc(C#Cc2ccc3c(c2)CCO3)cc1)NC(=O)C1CC1] | 346 [M + H]+ | 2.12 (AA) |
| 2.63 | I59.1 | 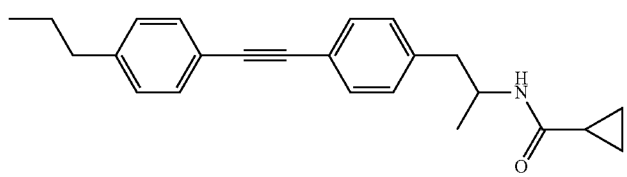 [SMILES: CCCc1ccc(C#Cc2ccc(CC(C)NC(=O)C3CC3)cc2)cc1] | 346 [M + H]+ | 2.29 (AA) |
| 2.64 | I59.1 | 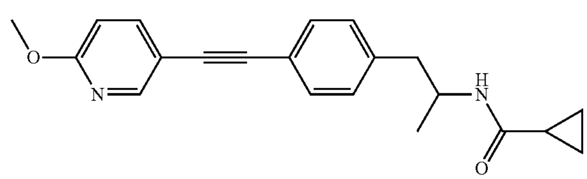 [SMILES: COc1ccc(C#Cc2ccc(CC(C)NC(=O)C3CC3)cc2)cn1] | 335 [M + H]+ | 2.09 (AA) |

-continued

| Ex. | Starting material(s) | Structure | Mass spec result | HPLC retention time (method) |
|---|---|---|---|---|
| 2.65 | I59.1 | 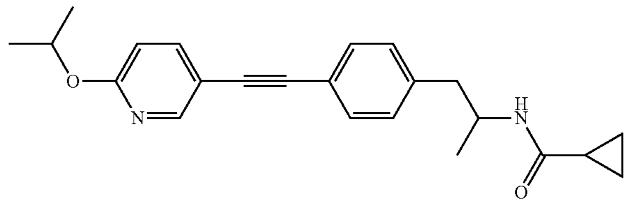 [SMILES: CC(Cc1ccc(C#Cc2ccc(OC(C)C)nc2)cc1)NC(=O)C1CC1] | 363 [M + H]+ | 2.20 (AA) |
| 2.66 | I59.1 | 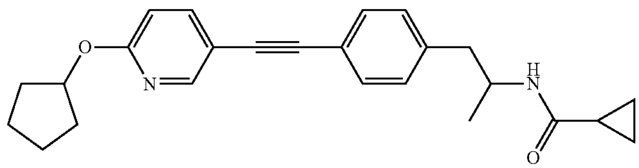 [SMILES: CC(Cc1ccc(C#Cc2ccc(OC3CCCC3)nc2)cc1)NC(=O)C1CC1] | 389 [M + H]+ | 2.28 (AA) |
| 2.67 | I59.1 | 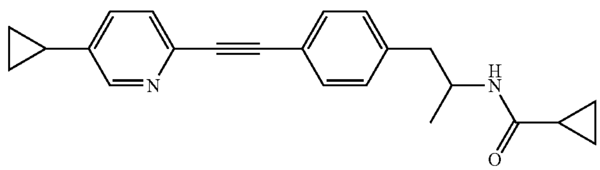 [SMILES: CC(Cc1ccc(C#Cc2ccc(C3CC3)cn2)cc1)NC(=O)C1CC1] | 345 [M + H]+ | 1.80 (AA) |
| 2.68 | I59.1, I20 | 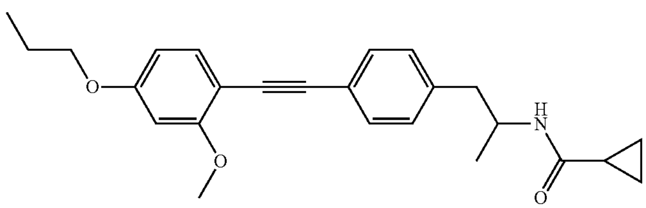 [SMILES: CCCOc1ccc(C#Cc2ccc(CC(C)NC(=O)C3CC3)cc2)c(OC)c1] | 392 [M + H]+ | 2.19 (AA) |
| 2.69 | I59.1, I9.2 | 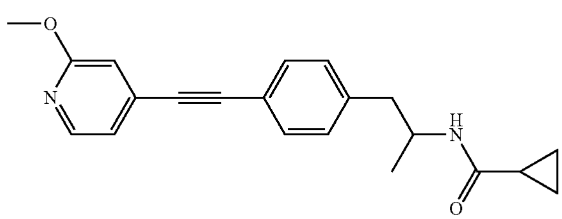 [SMILES: COc1cc(C#Cc2ccc(CC(C)NC(=O)C3CC3)cc2)ccn1] | 335 [M + H]+ | 2.07 (AA) |
| 2.70 | I59.1, I15.3 | 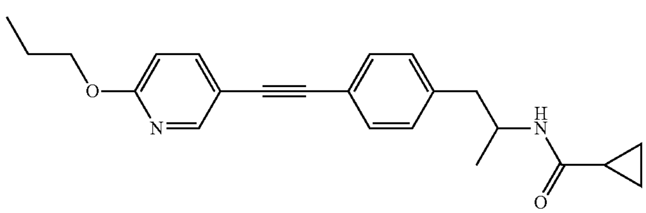 [SMILES: CCCOc1ccc(C#Cc2ccc(CC(C)NC(=O)C3CC3)cc2)cn1] | 363 [M + H]+ | 2.21 (AA) |
| 2.71 | I59.1 | 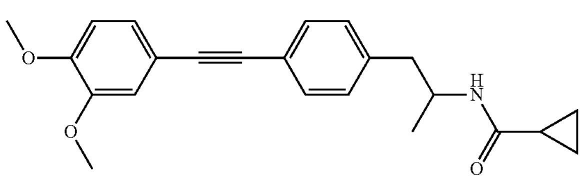 [SMILES: COc1ccc(C#Cc2ccc(CC(C)NC(=O)C3CC3)cc2)cc1OC] | 364 [M + H]+ | 2.01 (AA) |

-continued

| Ex. | Starting material(s) | Structure | Mass spec result | HPLC retention time (method) |
|---|---|---|---|---|
| 2.72 | I58.3** | 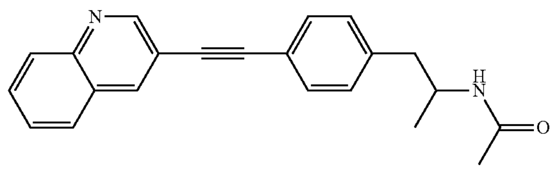 [SMILES: CC(=O)NC(C)Cc1ccc(C#Cc2cnc3ccccc3c2)cc1] | 329 [M + H]⁺ | 1.97 (AA) |
| 2.73 | I58.3 | 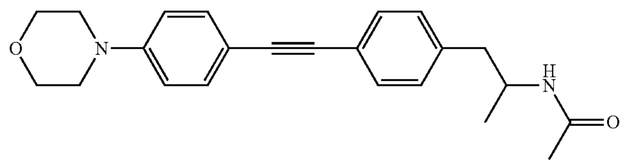 [SMILES: CC(=O)NC(C)Cc1ccc(C#Cc2ccc(N3CCOCC3)cc2)cc1] | 363 [M + H]⁺ | 2.08 (AA) |
| 2.74 | I58.3** | 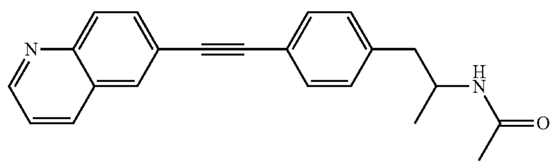 [SMILES: CC(=O)NC(C)Cc1ccc(C#Cc2ccc3ncccc3c2)cc1] | 329 [M + H]⁺ | 1.60 (AA) |
| 2.75 | I58.3** | 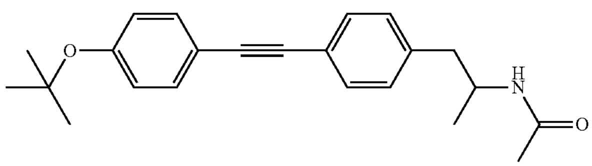 [SMILES: CC(=O)NC(C)Cc1ccc(C#Cc2ccc(OC(C)(C)C)cc2)cc1] | 350 [M + H]⁺ | 2.18 (AA) |
| 2.76 | I58.3 | 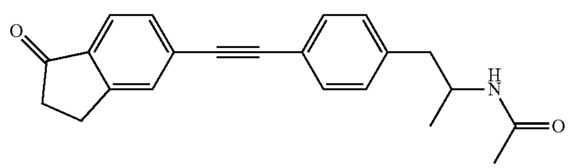 [SMILES: CC(=O)NC(C)Cc1ccc(C#Cc2ccc3c(c2)CCC3=O)cc1] | 332 [M + H]⁺ | 1.96 (AA) |
| 2.77 | I58.3 I14.6 | 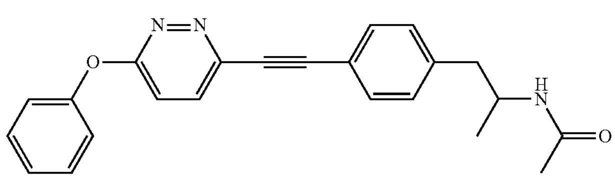 [SMILES: CC(=O)NC(C)Cc1ccc(C#Cc2ccc(Oc3ccccc3)nn2)cc1] | 372 [M + H]⁺ | 1.87 (AA) |
| 2.78 | I58.3 I14.8 | 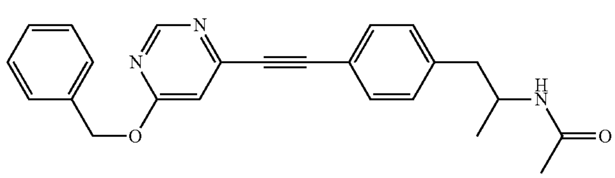 [SMILES: CC(=O)NC(C)Cc1ccc(C#Cc2cc(OCc3ccccc3)ncn2)cc1] | 386 [M + H]⁺ | 2.11 (AA) |
| 2.79 | I58.3 | 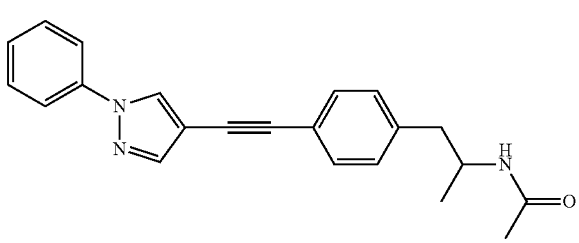 [SMILES: CC(=O)NC(C)Cc1ccc(C#Cc2cnn(-c3ccccc3)c2)cc1] | 344 [M + H]⁺ | 2.04 (AA) |

-continued

| Ex. | Starting material(s) | Structure | Mass spec result | HPLC retention time (method) |
|---|---|---|---|---|
| 2.80 | I58.3 | 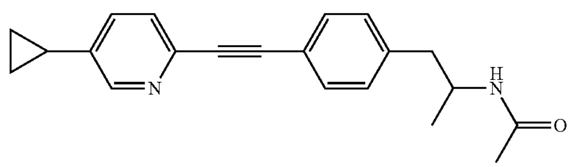 [SMILES: CC(=O)NC(C)Cc1ccc(C#Cc2ccc(C3CC3)cn2)cc1] | 319 [M + H]⁺ | 1.71 (AA) |
| 2.81 | I58.3 I15.6 | 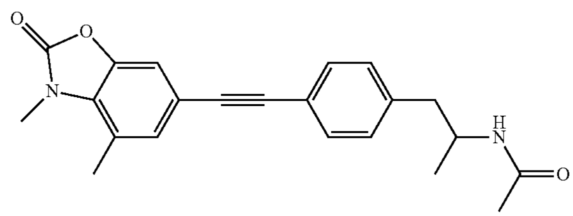 [SMILES: CC(=O)NC(C)Cc1ccc(C#Cc2cc(C)c3c(c2)oc(=O)n3C)cc1] | 363 [M + H]⁺ | 1.97 (AA) |
| 2.82 | I58.3 I2.2 | 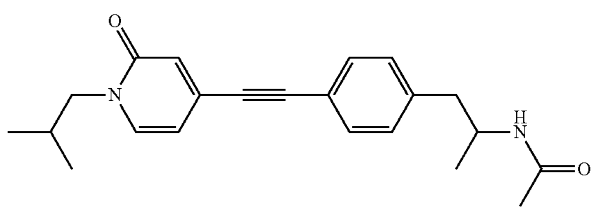 [SMILES: CC(=O)NC(C)Cc1ccc(C#Cc2ccn(CC(C)C)c(=O)c2)cc1] | 351 [M + H]⁺ | 1.87 (AA) |
| 2.83 | I58.3 I2.5 | 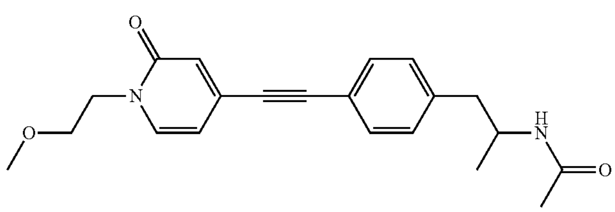 [SMILES: COCCn1ccc(C#Cc2ccc(CC(C)NC(C)=O)cc2)cc1=O] | 353 [M + H]⁺ | 1.68 (AA) |
| 2.84 | I58.3 I2.6 | 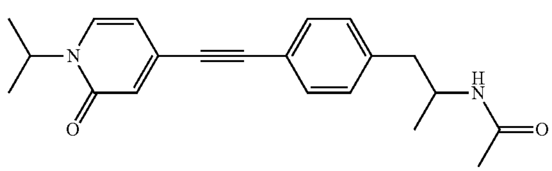 [SMILES: CC(=O)NC(C)Cc1ccc(C#Cc2ccn(C(C)C)c(=O)c2)cc1] | 337 [M + H]⁺ | 1.77 (AA) |
| 2.85 | I58.3 I2.4 | 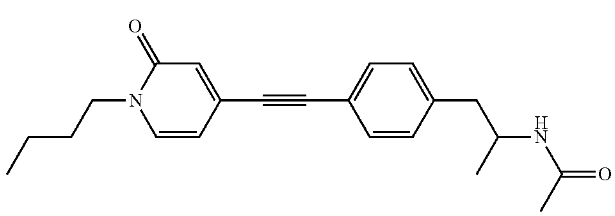 | 351 [M + H]⁺ | 1.88 (AA) |
| 2.86 | I58.3 I14.5 | 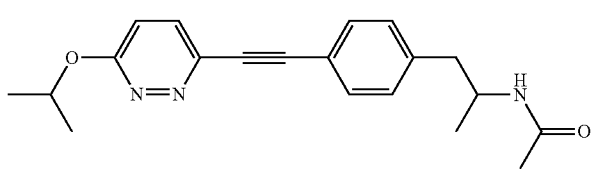 [SMILES: CC(=O)NC(C)Cc1ccc(C#Cc2ccc(OC(C)C)nn2)cc1] | 338 [M + H]⁺ | 1.91 (AA) |

-continued

| Ex. | Starting material(s) | Structure | Mass spec result | HPLC retention time (method) |
|---|---|---|---|---|
| 2.87 | I58.3 I2.3 | 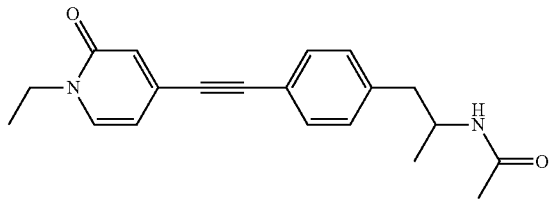 [SMILES: CCn1ccc(C#Cc2ccc(CC(C)NC(C)=O)cc2)cc1=O] | 323 [M + H]⁺ | 1.68 (AA) |
| 2.88 | I58.3 I14.4 | 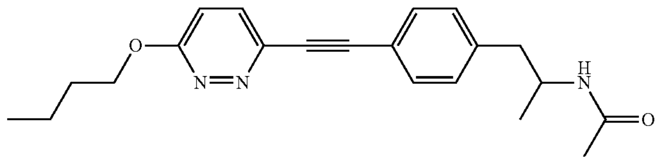 | 352 [M + H]⁺ | 2.02 (AA) |
| 2.89 | I58.3 I4.7 | 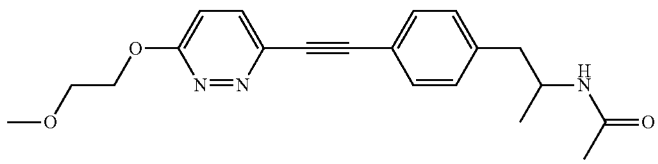 [SMILES: COCCOc1ccc(C#Cc2ccc(CC(C)NC(C)=O)cc2)nn1] | 354 [M + H]⁺ | 1.66 (AA) |
| 2.90 | I58.3 I21 | 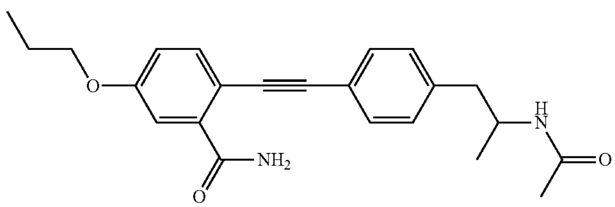 [SMILES: CCCOc1ccc(C#Cc2ccc(CC(C)NC(C)=O)cc2)c(C(N)=O)c1] | 379 [M + H]⁺ | 1.93 (AA) |
| 2.91 | I58.3 I9.5 | 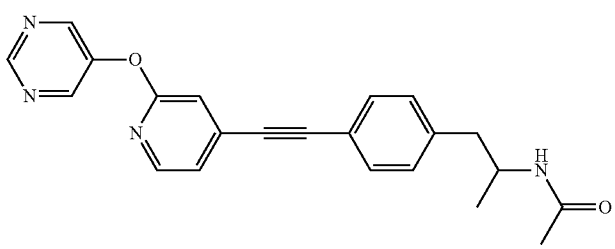 [SMILES: CC(=O)NC(C)Cc1ccc(C#Cc2ccnc(Oc3cncnc3)c2)cc1] | 373 [M + H]⁺ | 1.91 (AA) |
| 2.92 | I58.3 I22 | 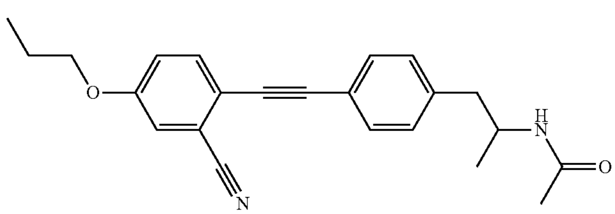 [SMILES: CCCOc1ccc(C#Cc2ccc(CC(C)NC(C)=O)cc2)c(C#N)c1] | 361 [M + H]⁺ | 2.12 (AA) |
| 2.93 | I58.3 I19.2 | 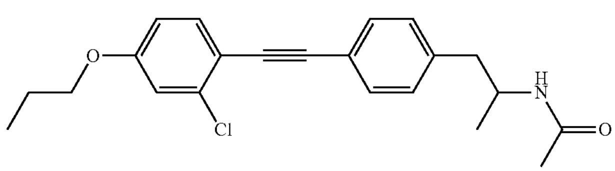 | 370 [M + H]⁺ | 2.26 (AA) |

-continued
| Ex. | Starting material(s) | Structure | Mass spec result | HPLC retention time (method) |
|---|---|---|---|---|
| 2.94 | I58.3 I9.2 | 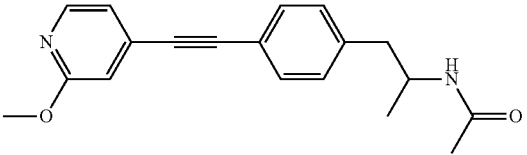 | 309 [M + H]⁺ | 2.01 (AA) |
| 2.95 | I58.3 I19.1 | 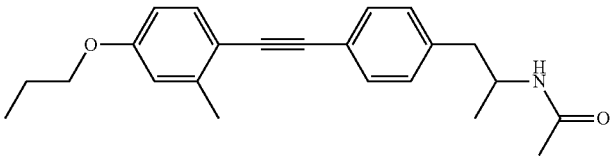 | 350 [M + H]⁺ | 2.25 (AA) |
| 2.96 | I58.3 I9.3 | 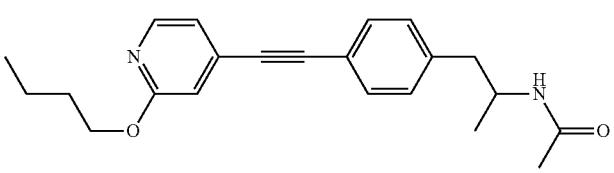 [SMILES: CCCCOc1cc(C#Cc2ccc(CC(C)NC(C)=O)cc2)ccn1] | 351 [M + H]⁺ | 2.23 (AA) |
| 2.97 | I58.3 I10 | 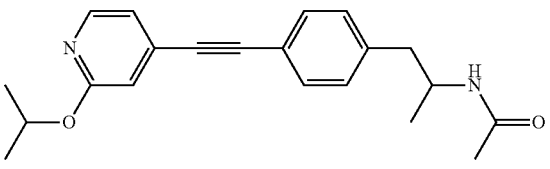 [SMILES: CC(=O)NC(C)Cc1ccc(C#Cc2ccnc(OC(C)C)c2)cc1] | 337 [M + H]⁺ | 2.13 (AA) |
| 2.98 | I58.3 I9.4 | 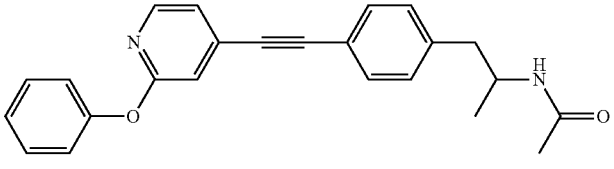 [SMILES: CC(=O)NC(C)Cc1ccc(C#Cc2ccnc(Oc3ccccc3)c2)cc1] | 371 [M + H]⁺ | 2.10 (AA) |
| 2.99 | I58.3 | 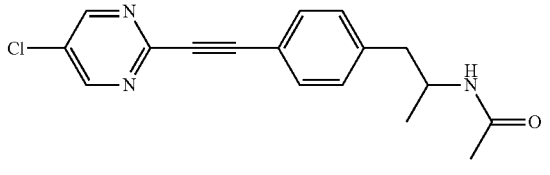 [SMILES: CC(=O)NC(C)Cc1ccc(C#Cc2ncc(Cl)cn2)cc1] | 314 [M + H]⁺ | 1.81 (AA) |
| 2.100 | I58.3** | 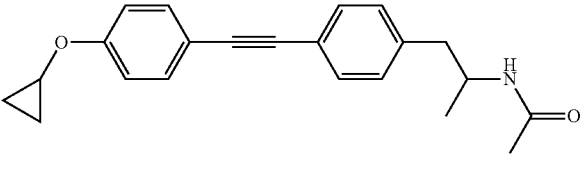 [SMILES: CC(=O)NC(C)Cc1ccc(C#Cc2ccc(OC3CC3)cc2)cc1] | 334 [M + H]⁺ | 2.20 (AA) |
| 2.101 | I59.4 | 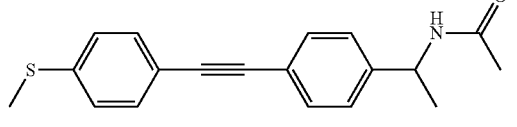 | 310 [M + H]⁺ | 2.11 (AA) |
| 2.102 | I59.4 I9.1 | 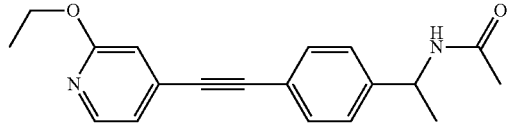 [SMILES: CCOc1cc(C#Cc2ccc(C(C)NC(C)=O)cc2)ccn1] | 309 [M + H]⁺ | 2.03 (AA) |

-continued

| Ex. | Starting material(s) | Structure | Mass spec result | HPLC retention time (method) |
|---|---|---|---|---|
| 2.103 | I59.4 | 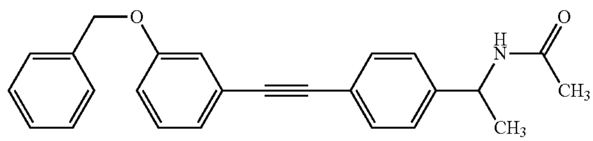 | 370 [M + H]+ | 2.19 (AA) |
| 2.104 | I59.4 | 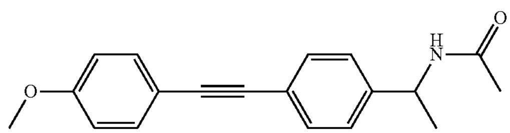 [SMILES: COc1ccc(C#Cc2ccc(C(C)NC(C)=O)cc2)cc1] | 294 [M + H]+ | 2.00 (AA) |
| 2.105 | I59.4 | 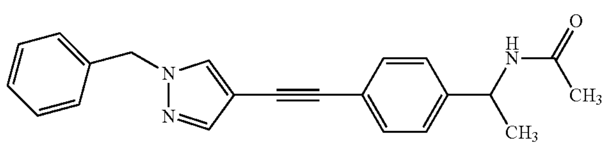 [SMILES: CC(=O)NC(C)c1ccc(C#Cc2cnn(Cc3ccccc3)c2)cc1] | 344 [M + H]+ | 1.89 (AA) |
| 2.106 | I58.3 | 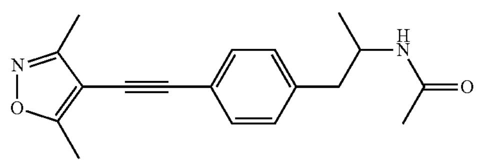 [SMILES: CC(=O)NC(C)Cc1ccc(C#Cc2c(C)noc2C)cc1] | 297 [M + H]+ | 1.04 (P) |
| 2.107 | I58.3 | 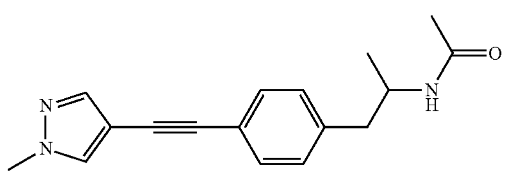 [SMILES: CC(=O)NC(C)Cc1ccc(C#Cc2cnn(C)c2)cc1] | 282 [M + H]+ | 0.83 (P) |
| 2.108 | I58.3 | 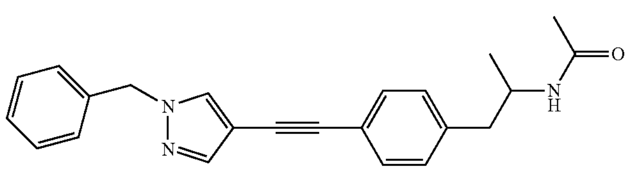 [SMILES: CC(=O)NC(C)Cc1ccc(C#Cc2cnn(Cc3ccccc3)c2)cc1] | 358 [M + H]+ | 1.14 (P) |
| 2.109 | I58.3** | 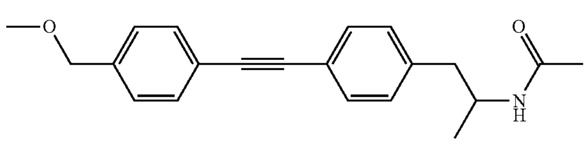 [SMILES: COCc1ccc(C#Cc2ccc(CC(C)NC(C)=O)cc2)cc1] | 322 [M + H]+ | 2.03 (AA) |

*the used aryl-iodide can be synthesized accordingly to WO2005/103032
**for these examples the appropriate aryl-bromide is used

Example 3

Example 3.1

General Route

N-(1-(4-((2,4-Dimethoxyphenyl)ethynyl)phenyl)propan-2-yl)acetamide

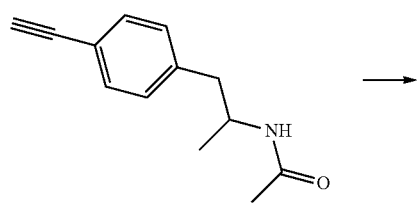

→

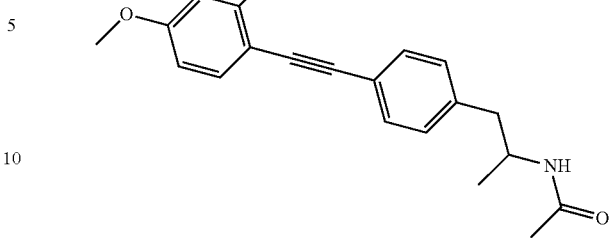

A mixture of 36.2 mg (0.18 mmol) N-(1-(4-ethynylphenyl)propan-2-yl)acetamide (I58.3) and 300 μl acetone is added to 50.6 mg (0.15 mmol) 1-bromo-2,4-dimethoxybenzene followed by a suspension of 14.3 (0.02 mmol) bis(triphenylphosphine)dichloropalladium in 300 μl acetone and 600 μl water. After addition of 22.4 mg (0.20 mmol) piperidine the mixture is stirred in a sealed tube for 1.5 h at 60° C. The solvent is removed in vacuo and the residue is purified by HPLC (ACN/H$_2$O/TFA).

$C_{21}H_{23}NO_3$ (M=337.4 g/mol)
ESI-MS: 338 [M+H]$^+$
R$_t$ (HPLC): 2.56 min (Method D)

The following compounds are prepared analogously to example 3.1

| Ex. | Starting material(s) | Structure | Mass spec result | HPLC retention time (method) |
|---|---|---|---|---|
| 3.1 | I58.3 | 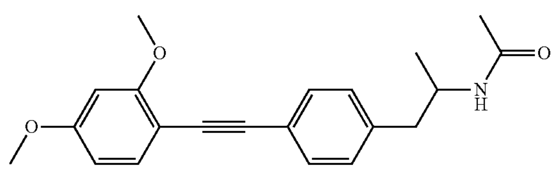 [SMILES: COc1ccc(C#Cc2ccc(CC(C)NC(C)=O)cc2)c(OC)c1] | 338 [M + H]$^+$ | 2.56 (D) |
| 3.2 | I58.3 | 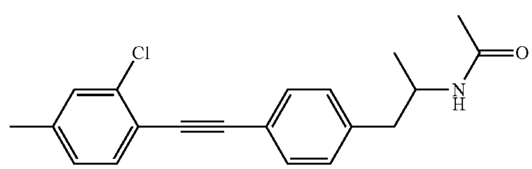 [SMILES: CC(=O)NC(C)Cc1ccc(C#Cc2ccc(C)cc2Cl)cc1] | 326 [M + H]$^+$ | 2.77 (D) |
| 3.3 | I58.3 | 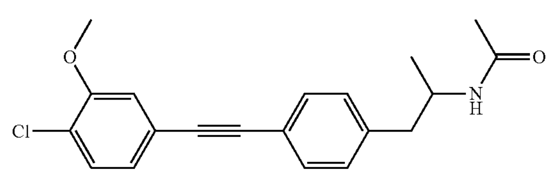 [SMILES: COc1cc(C#Cc2ccc(CC(C)NC(C)=O)cc2)ccc1Cl] | 342 [M + H]$^+$ | 2.71 (D) |
| 3.4 | I58.3 | 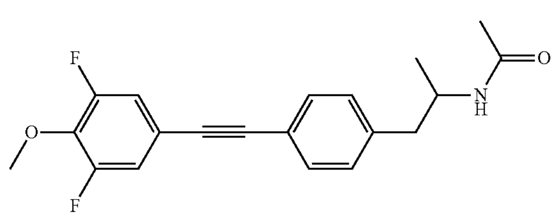 [SMILES: COc1c(F)cc(C#Cc2ccc(CC(C)NC(C)=O)cc2)cc1F] | 344 [M + H]$^+$ | 2.69 (D) |

-continued

| Ex. | Starting material(s) | Structure | Mass spec result | HPLC retention time (method) |
|---|---|---|---|---|
| 3.5 | I58.3 | 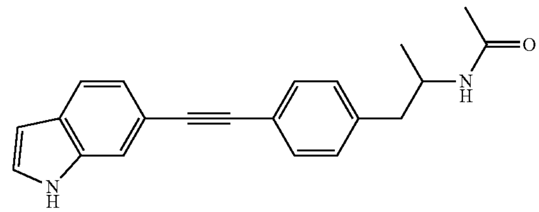 [SMILES: CC(=O)NC(C)Cc1ccc(C#Cc2ccc3cc[nH]c3c2)cc1] | 317 [M + H]⁺ | 2.54 (D) |
| 3.6 | I58.3 | 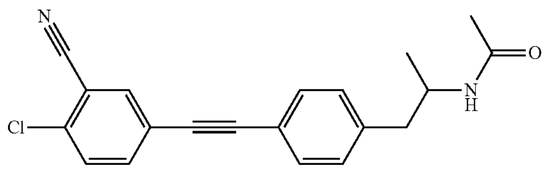 [SMILES: CC(=O)NC(C)Cc1ccc(C#Cc2ccc(Cl)c(C#N)c2)cc1] | 337 [M + H]⁺ | 2.60 (D) |
| 3.7 | I58.3 | 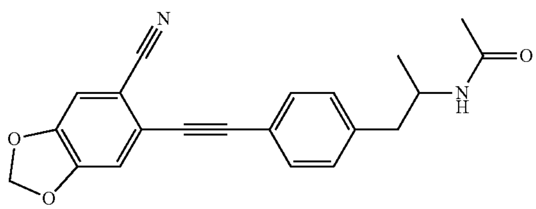 [SMILES: CC(=O)NC(C)Cc1ccc(C#Cc2cc3c(cc2C#N)OCO3)cc1] | 347 [M + H]⁺ | 2.49 (D) |
| 3.8 | I58.3 | 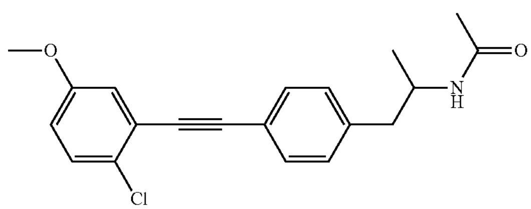 [SMILES: COc1ccc(Cl)c(C#Cc2ccc(CC(C)NC(C)=O)cc2)c1] | 342 [M + H]⁺ | 2.70 (D) |
| 3.9 | I58.3 I6.4 | 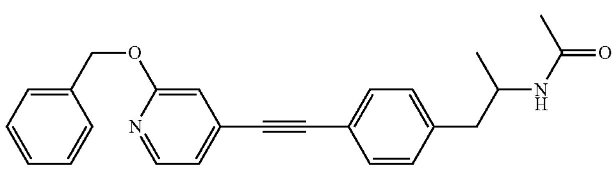 [SMILES: CC(=O)NC(C)Cc1ccc(C#Cc2ccnc(OCc3ccccc3)c2)cc1] | 385 [M + H]⁺ | 2.46 (D) |
| 3.10 | I58.3 | 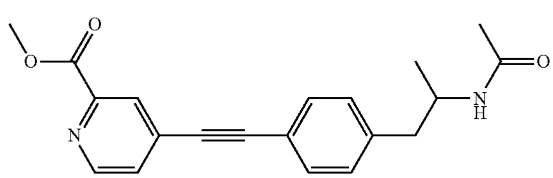 [SMILES: COC(=O)c1cc(C#Cc2ccc(CC(C)NC(C)=O)cc2)ccn1] | 337 [M + H]⁺ | 2.40 (D) |
| 3.11 | I58.3 | 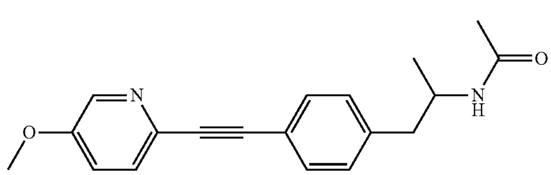 [SMILES: COc1ccc(C#Cc2ccc(CC(C)NC(C)=O)cc2)nc1] | 309 [M + H]⁺ | 2.39 (D) |
| 3.12 | I58.3 | 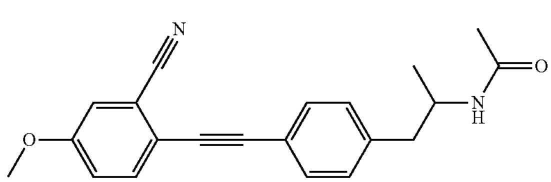 [SMILES: COc1ccc(C#Cc2ccc(CC(C)NC(C)=O)cc2)c(C#N)c1] | 333 [M + H]⁺ | 2.52 (D) |

-continued

| Ex. | Starting material(s) | Structure | Mass spec result | HPLC retention time (method) |
|---|---|---|---|---|
| 3.13 | I58.3 | 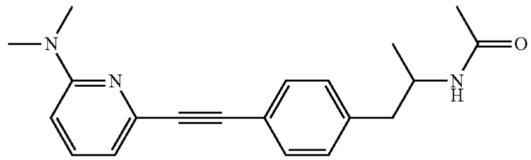 [SMILES: CC(=O)NC(C)Cc1ccc(C#Cc2cccc(N(C)C)n2)cc1] | 322 [M + H]⁺ | 2.55 (D) |
| 3.14 | I58.3 | 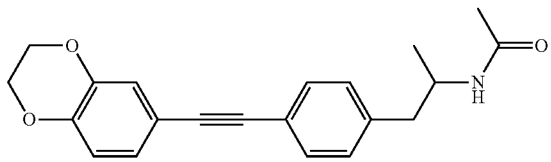 [SMILES: CC(=O)NC(C)Cc1ccc(C#Cc2ccc3c(c2)OCCO3)cc1] | 336 [M + H]⁺ | 2.60 (D) |
| 3.15 | I58.3 | 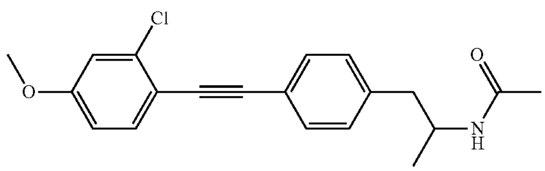 [SMILES: COc1ccc(C#Cc2ccc(CC(C)NC(C)=O)cc2)c(Cl)c1] | 342 [M + H]⁺ | 3.58 (B) |
| 3.16 | I58.3 | 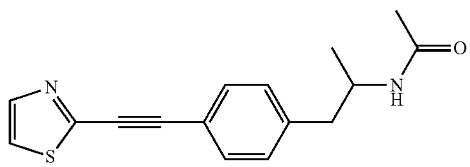 [SMILES: CC(=O)NC(C)Cc1ccc(C#Cc2nccs2)cc1] | 285 [M + H]⁺ | 2.34 (P) |
| 3.17 | I58.3 | 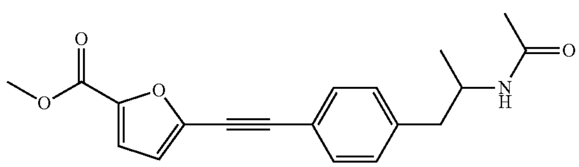 [SMILES: COC(=O)c1ccc(C#Cc2ccc(CC(C)NC(C)=O)cc2)o1] | 326 [M + H]⁺ | 2.47 (P) |

Example 4

Example 4.1

General Route

N-(1-(4-((4-ethoxyphenyl)ethynyl)phenyl)propan-2-yl)butyramide

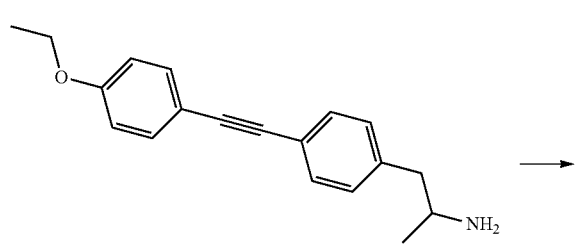

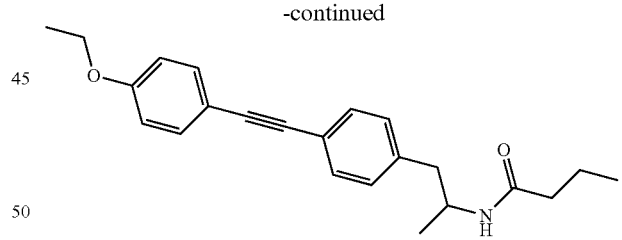

8.41 mg (0.10 mmol) butanoic acid are dissolved in 300 μL DMF together with 32.1 mg (0.10 mmol) TBTU and 50.0 μL (0.30 mmol) DIPEA and the mixture is stirred at r.t. for 5 min. 27.9 mg (0.10 mmol) 1-(4-((4-ethoxyphenyl)ethynyl)phenyl) propan-2-amine (I64) are added and the reaction mixture is stirred at 40° C. over night. The mixture is filtered through a plug of alox, eluted with DMF/MeOH (9/1) and the solvent is removed in vacuo. The residue is purified by HPLC.

$C_{23}H_{27}NO_2$ (M=349.5 g/mol)

ESI-MS: 350 [M+H]⁺

$R_t$ (HPLC): 1.43 min (Method C)

The following compounds are prepared analogously to example 4.1

For examples 4.27, 4.29, 4.34 and 4.74 the BOC protected amino acid is used for the coupling and the PG is removed afterwards by stirring the compound either in 0.5 mL HCl (1.25 M in MeOH) at r.t. for 30 min (4.27, 4.29 and 4.34) or in a 1/1 mixture of TFA/DCM at r.t. for 2 h (4.74).

For examples 4.76-80, the reaction mixture is stirred at r.t.

| Ex. | Starting material(s) | Structure | Mass spec result | HPLC retention time (method) |
|---|---|---|---|---|
| 4.1 | I64 | 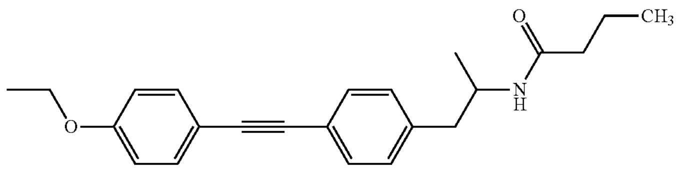 [SMILES: CCCC(=O)NC(C)Cc1ccc(C#Cc2ccc(OCC)cc2)cc1] | 350 [M + H]$^+$ | 1.43 (C) |
| 4.2 | I64 | 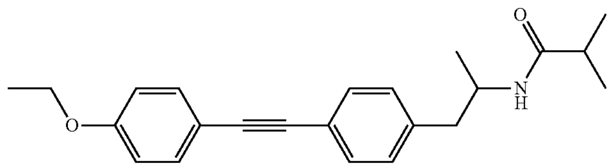 [SMILES: CCOc1ccc(C#Cc2ccc(CC(C)NC(=O)C(C)C)cc2)cc1] | 350 [M + H]$^+$ | 1.43 (C) |
| 4.3 | I64 | 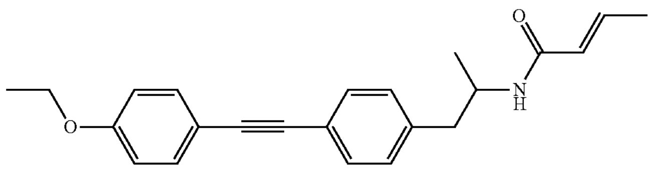 [SMILES: C/C=C/C(=O)NC(C)Cc1ccc(C#Cc2ccc(OCC)cc2)cc1] | 348 [M + H]$^+$ | 1.40 (C) |
| 4.4 | I64 | 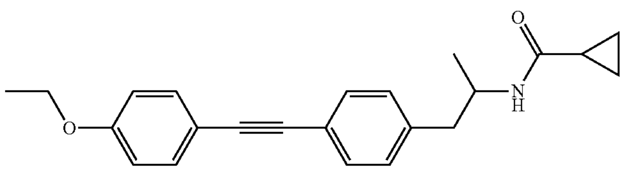 [SMILES: CCOc1ccc(C#Cc2ccc(CC(C)NC(=O)C3CC3)cc2)cc1] | 348 [M + H]$^+$ | 1.40 (C) |
| 4.5 | I64 | 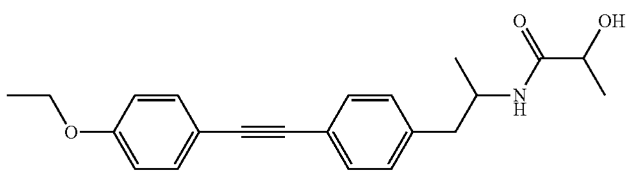 [SMILES: CCOc1ccc(C#Cc2ccc(CC(C)NC(=O)C(C)O)cc2)cc1] | 352 [M + H]$^+$ | 1.28 (C) |
| 4.6 | I64 | 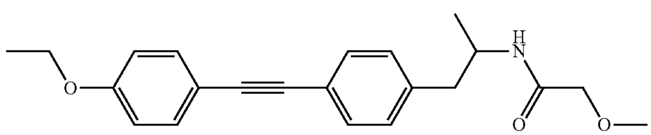 [SMILES: CCOc1ccc(C#Cc2ccc(CC(C)NC(=O)COC)cc2)cc1] | 352 [M + H]$^+$ | 1.37 (C) |
| 4.7 | I64 | 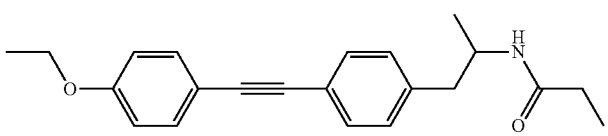 | 336 [M + H]$^+$ | 1.37 (C) |
| 4.8 | I64 | 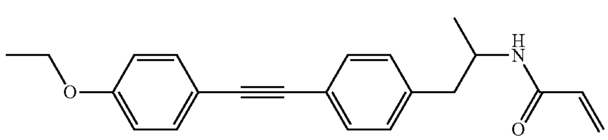 [SMILES: C=CC(=O)NC(C)Cc1ccc(C#Cc2ccc(OCC)cc2)cc1] | 334 [M + H]$^+$ | 1.25 (C) |
| 4.9 | I64 | 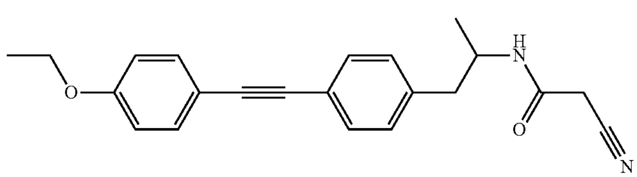 [SMILES: CCOc1ccc(C#Cc2ccc(CC(C)NC(=O)CC#N)cc2)cc1] | 347 [M + H]$^+$ | 1.32 (C) |

-continued

| Ex. | Starting material(s) | Structure | Mass spec result | HPLC retention time (method) |
|---|---|---|---|---|
| 4.10 | I64 | 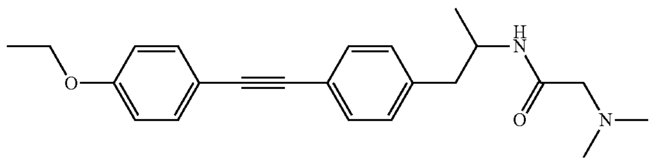 [SMILES: CCOc1ccc(C#Cc2ccc(CC(C)NC(=O)CN(C)C)cc2)cc1] | 365 [M + H]⁺ | 1.43 (C) |
| 4.11 | I64 | 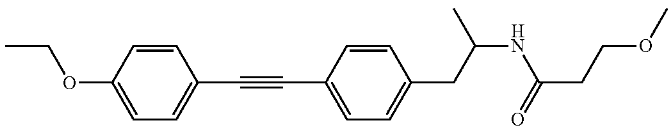 [SMILES: CCOc1ccc(C#Cc2ccc(CC(C)NC(=O)CCOC)cc2)cc1] | 366 [M + H]⁺ | 1.34 (C) |
| 4.12 | I64 | 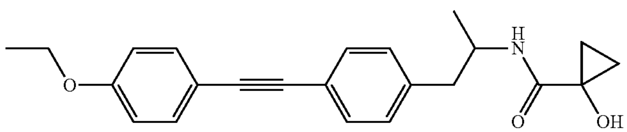 [SMILES: CCOc1ccc(C#Cc2ccc(CC(C)NC(=O)C3(O)CC3)cc2)cc1] | 364 [M + H]⁺ | 1.31 (C) |
| 4.13 | I64 | 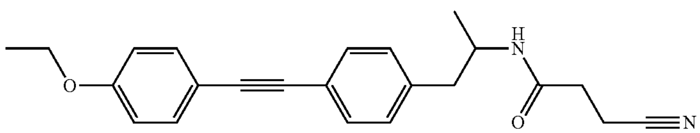 [SMILES: CCOc1ccc(C#Cc2ccc(CC(C)NC(=O)CCC#N)cc2)cc1] | 361 [M + H]⁺ | 1.32 (C) |
| 4.14 | I64 | 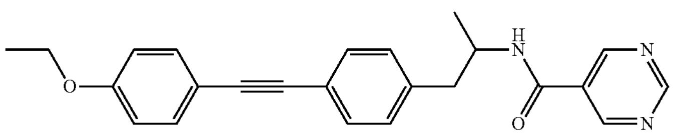 [SMILES: CCOc1ccc(C#Cc2ccc(CC(C)NC(=O)c3cncnc3)cc2)cc1] | 386 [M + H]⁺ | 1.31 (C) |
| 4.15 | I64 | 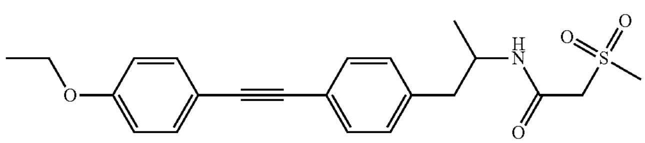 [SMILES: CCOc1ccc(C#Cc2ccc(CC(C)NC(=O)CS(C)(=O)=O)cc2)cc1] | 400 [M + H]⁺ | 1.28 (C) |
| 4.16 | I64 | 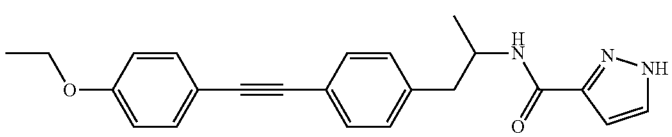 [SMILES: CCOc1ccc(C#Cc2ccc(CC(C)NC(=O)c3cc[nH]n3)cc2)cc1] | 374 [M + H]⁺ | 1.30 (C) |
| 4.17 | I64 | 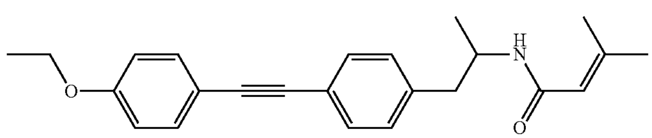 [SMILES: CCOc1ccc(C#Cc2ccc(CC(C)NC(=O)C=C(C)C)cc2)cc1] | 362 [M + H]⁺ | 1.49 (C) |
| 4.18 | I64 | 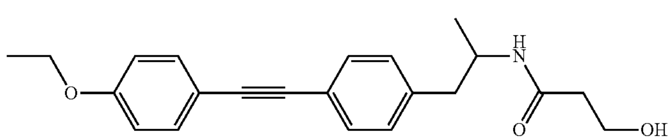 [SMILES: CCOc1ccc(C#Cc2ccc(CC(C)NC(=O)CCO)cc2)cc1] | 352 [M + H]⁺ | 1.22 (C) |
| 4.19 | I64 | 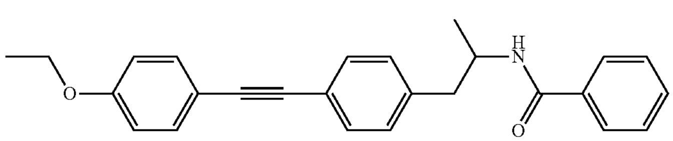 [SMILES: CCOc1ccc(C#Cc2ccc(CC(C)NC(=O)c3ccccc3)cc2)cc1] | 384 [M + H]⁺ | 1.50 (C) |

| Ex. | Starting material(s) | Structure | Mass spec result | HPLC retention time (method) |
|---|---|---|---|---|
| 4.20 | I64 | 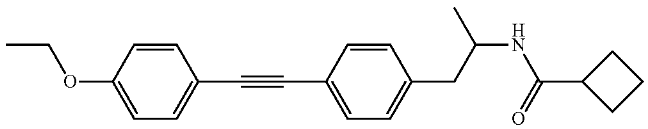 [SMILES: CCOc1ccc(C#Cc2ccc(CC(C)NC(=O)C3CCC3)cc2)cc1] | 362 [M + H]$^+$ | 1.22 (C) |
| 4.21 | I64 | 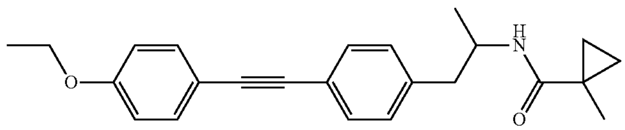 [SMILES: CCOc1ccc(C#Cc2ccc(CC(C)NC(=O)C3(C)CC3)cc2)cc1] | 362 [M + H]$^+$ | 1.48 (C) |
| 4.22 | I64 | 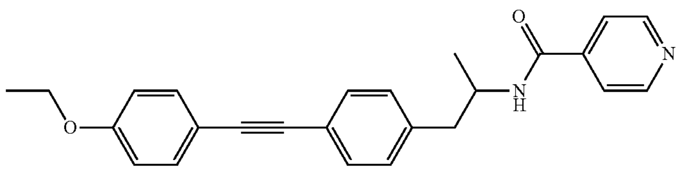 [SMILES: CCOc1ccc(C#Cc2ccc(CC(C)NC(=O)c3ccncc3)cc2)cc1] | 385 [M + H]$^+$ | 1.34 (C) |
| 4.23 | I64 | 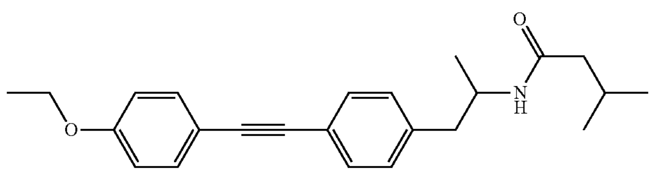 [SMILES: CCOc1ccc(C#Cc2ccc(CC(C)NC(=O)CC(C)C)cc2)cc1] | 364 [M + H]$^+$ | 1.48 (C) |
| 4.24 | I64 | 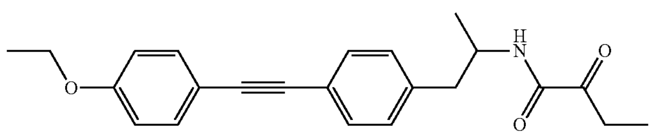 [SMILES: CCOc1ccc(C#Cc2ccc(CC(C)NC(=O)C(=O)CC)cc2)cc1] | 364. [M + H]$^+$ | 1.51 (C) |
| 4.25 | I64 | 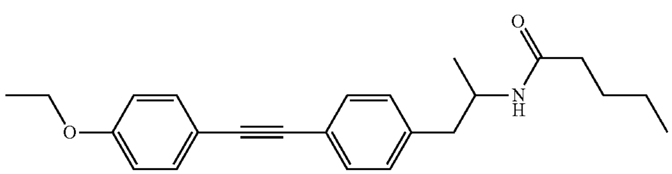 [SMILES: CCCCC(=O)NC(C)Cc1ccc(C#Cc2ccc(OCC)cc2)cc1] | 364 [M + H]$^+$ | 1.49 (C) |
| 4.26 | I64 | 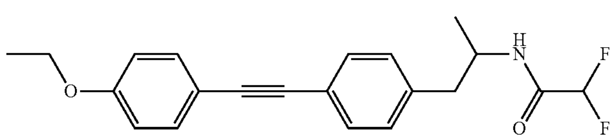 [SMILES: CCOc1ccc(C#Cc2ccc(CC(C)NC(=O)C(F)F)cc2)cc1] | 358 [M + H]$^+$ | 1.41 (C) |
| 4.27 | I64 | 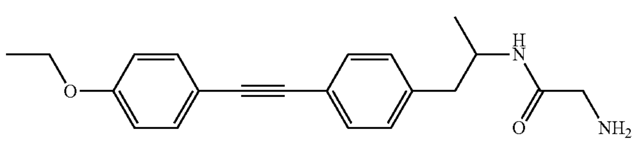 | 377 [M + H]$^+$ | 1.46 (C) |
| 4.28 | I64 | 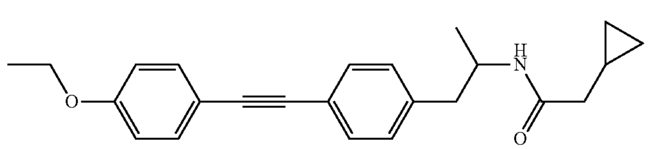 [SMILES: CCOc1ccc(C#Cc2ccc(CC(C)NC(=O)CC3CC3)cc2)cc1] | 361 [M + H]$^+$ | 1.44 (C) |
| 4.29 | I64 | 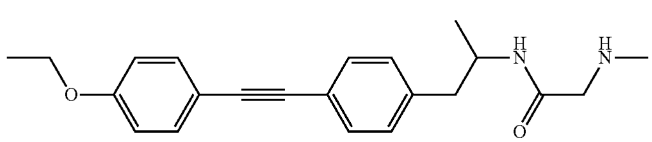 [SMILES: CCOc1ccc(C#Cc2ccc(CC(C)NC(=O)CNC)cc2)cc1] | 351 [M + H]$^+$ | 1.52 (C) |

-continued

| Ex. | Starting material(s) | Structure | Mass spec result | HPLC retention time (method) |
|---|---|---|---|---|
| 4.30 | I64 | 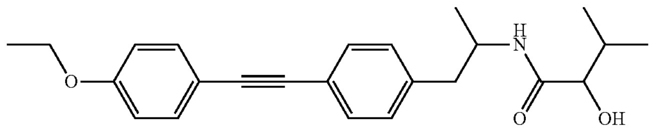 [SMILES: CCOc1ccc(C#Cc2ccc(CC(C)NC(=O)C(O)C(C)C)cc2)cc1] | 380 [M + H]⁺ | 1.41 (C) |
| 4.31 | I64 | 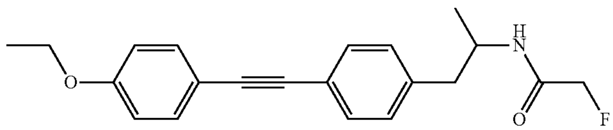 [SMILES: CCOc1ccc(C#Cc2ccc(CC(C)NC(=O)CF)cc2)cc1] | 340 [M + H]⁺ | 1.36 (C) |
| 4.32 | I64 | 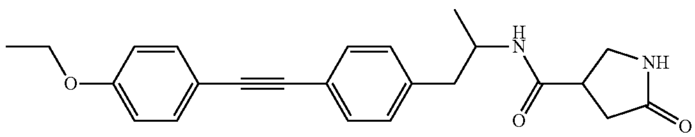 [SMILES: CCOc1ccc(C#Cc2ccc(CC(C)NC(=O)C3CNC(=O)C3)cc2)cc1] | 391 [M + H]⁺ | 1.18 (C) |
| 4.33 | I64 | 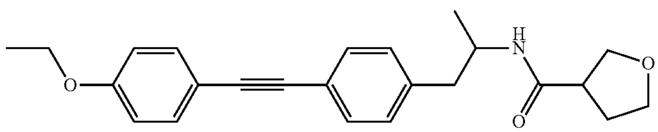 [SMILES: CCOc1ccc(C#Cc2ccc(CC(C)NC(=O)C3CCOC3)cc2)cc1] | 378 [M + H]⁺ | 1.33 (C) |
| 4.34 | I64 | 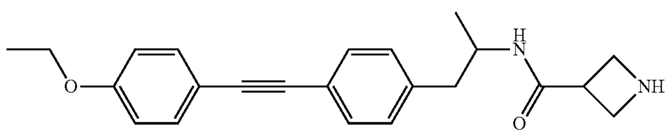 [SMILES: CCOc1ccc(C#Cc2ccc(CC(C)NC(=O)C3CNC3)cc2)cc1] | 363 [M + H]⁺ | 1.49 (C) |
| 4.35 | I64 | 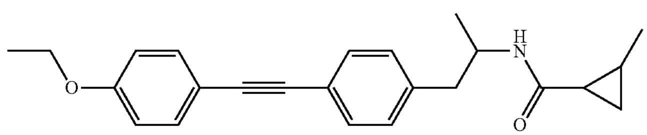 [SMILES: CCOc1ccc(C#Cc2ccc(CC(C)NC(=O)C3CC3C)cc2)cc1] | 362 [M + H]⁺ | 1.47 (C) |
| 4.36 | I64 | 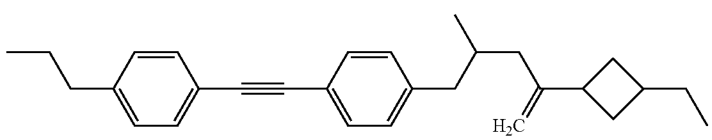 | 392 [M + H]⁺ | 1.38 (C) |
| 4.37 | I64 | 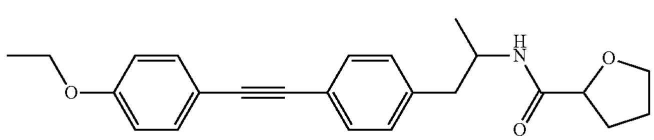 [SMILES: CCOc1ccc(C#Cc2ccc(CC(C)NC(=O)C3CCCO3)cc2)cc1] | 378 [M + H]⁺ | 1.41 (C) |
| 4.38 | I64 | 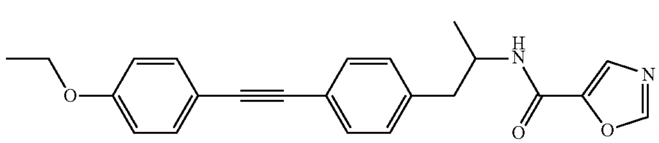 [SMILES: CCOc1ccc(C#Cc2ccc(CC(C)NC(=O)c3cnco3)cc2)cc1] | 375 [M + H]⁺ | 1.18 (C) |
| 4.39 | I63 | 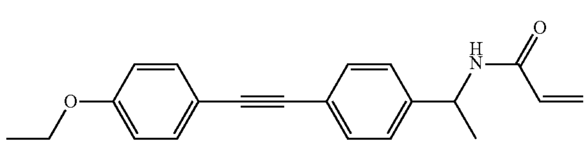 [SMILES: C=CC(=O)NC(C)c1ccc(C#Cc2ccc(OCC)cc2)cc1] | 320 [M + H]⁺ | 2.40 (K) |

-continued

| Ex. | Starting material(s) | Structure | Mass spec result | HPLC retention time (method) |
|---|---|---|---|---|
| 4.40 | I63 | 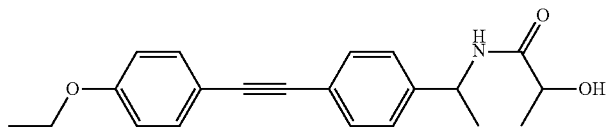 [SMILES: CCOc1ccc(C#Cc2ccc(C(C)NC(=O)C(C)O)cc2)cc1] | 338 [M + H]⁺ | 2.36 (K) |
| 4.41 | I63 | 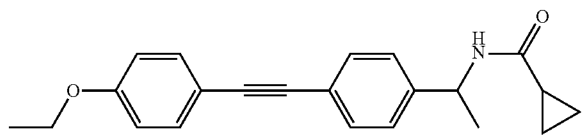 [SMILES: CCOc1ccc(C#Cc2ccc(C(C)NC(=O)C3CC3)cc2)cc1] | 334 [M + H]⁺ | 2.39 (K) |
| 4.42 | I63 | 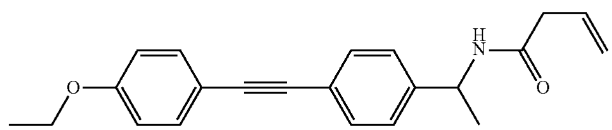 [SMILES: C=CCC(=O)NC(C)c1ccc(C#Cc2ccc(OCC)cc2)cc1] | 334 [M + H]⁺ | 2.37 (K) |
| 4.43 | I63 | 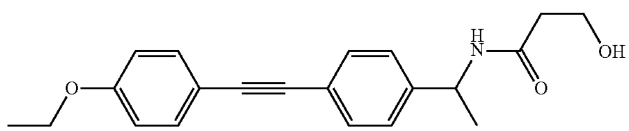 [SMILES: CCOc1ccc(C#Cc2ccc(C(C)NC(=O)CCO)cc2)cc1] | 338 [M + H]⁺ | 2.31 (K) |
| 4.44 | I63 | 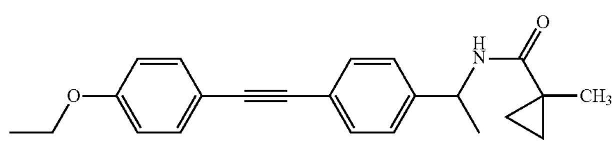 [SMILES: CCOc1ccc(C#Cc2ccc(C(C)NC(=O)C3(C)CC3)cc2)cc1] | 348 [M + H]⁺ | 2.45 (K) |
| 4.45 | I63 | 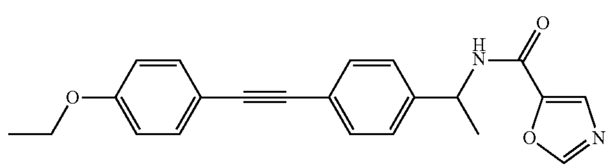 [SMILES: CCOc1ccc(C#Cc2ccc(C(C)NC(=O)c3cnco3)cc2)cc1] | 361 [M + H]⁺ | 1.94 (L) |
| 4.46 | I63 | 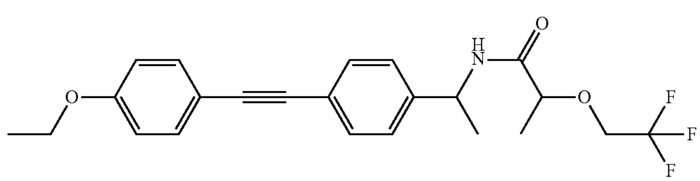 [SMILES: CCOc1ccc(C#Cc2ccc(C(C)NC(=O)C(C)OCC(F)(F)F)cc2)cc1] | 420 [M + H]⁺ | 2.42 (K) |
| 4.47 | I63 | 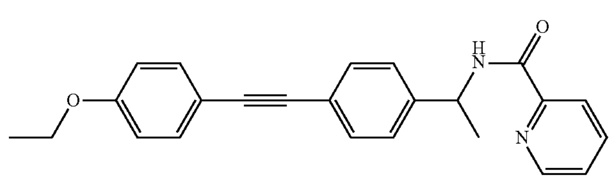 [SMILES: CCOc1ccc(C#Cc2ccc(C(C)NC(=O)c3ccccn3)cc2)cc1] | 371 [M + H]⁺ | 2.48 (K) |
| 4.48 | I63 | 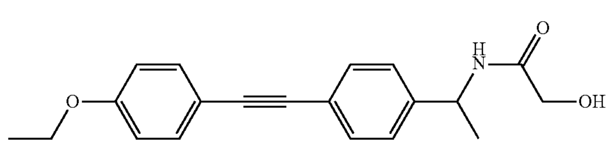 [SMILES: CCOc1ccc(C#Cc2ccc(C(C)NC(=O)CO)cc2)cc1] | 324 [M + H]⁺ | 2.32 (K) |

-continued
| Ex. | Starting material(s) | Structure | Mass spec result | HPLC retention time (method) |
|---|---|---|---|---|
| 4.49 | I64 | 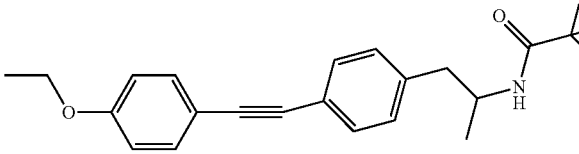 | 368 [M + H]+ | 2.37 (M) |
| 4.50 | I64 | Chiral  | 366 [M + H]+ | 2.37 (M) |
| 4.51 | I64 | 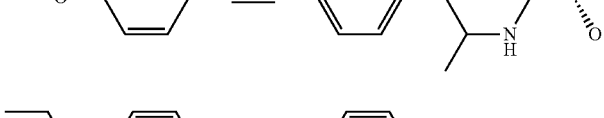 | 378 [M + H]+ | 2.34 (M) |
| 4.52 | I64 | 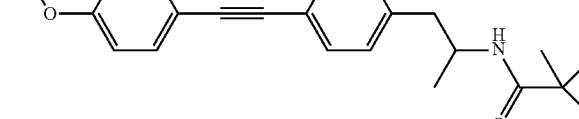 | 404 [M + H]+ | 2.16 (K) |
| 4.53 | I63 | 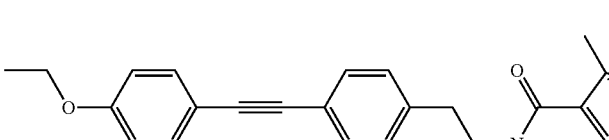 | 377 [M + H]+ | 2.23 (K) |
| 4.54 | I63 | 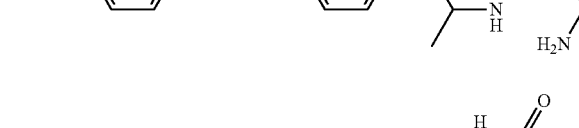 | 361 [M + H]+ | 2.15 (K) |
| 4.55 | I63 | 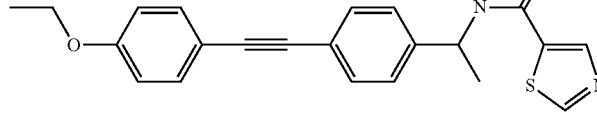 | 360 [M + H]+ | 2.11 (K) |
| 4.56 | I64 | 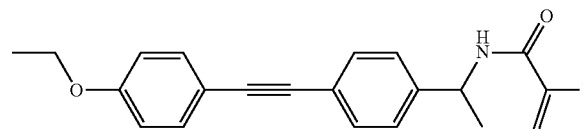 | 375 [M + H]+ | 2.25 (K) |

-continued

| Ex. | Starting material(s) | Structure | Mass spec result | HPLC retention time (method) |
|---|---|---|---|---|
| 4.57 | I64 | 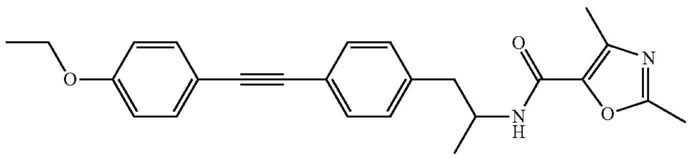 [SMILES: CCOc1ccc(C#Cc2ccc(CC(C)NC(=O)c3oc(C)nc3C)cc2)cc1] | 403 [M + H]⁺ | 2.21 (K) |
| 4.58 | I64 I75 | 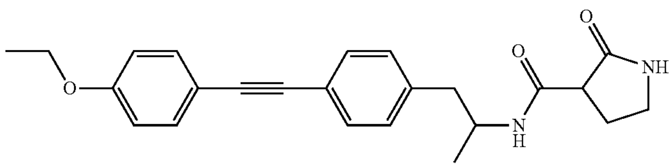 [SMILES: CCOc1ccc(C#Cc2ccc(CC(C)NC(=O)C3CCNC3=O)cc2)cc1] | 391 [M + H]⁺ | 2.13 (K) |
| 4.59 | I64 | 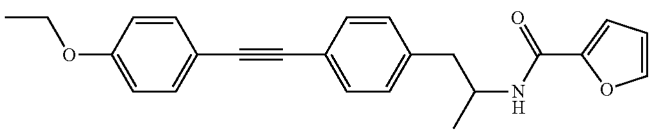 [SMILES: CCOc1ccc(C#Cc2ccc(CC(C)NC(=O)c3ccco3)cc2)cc1] | 374 [M + H]⁺ | 2.26 (K) |
| 4.60 | I64 | 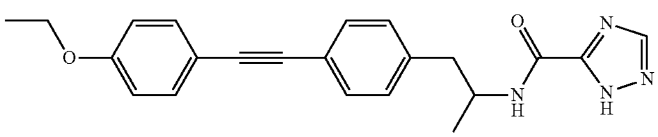 | 375 [M + H]⁺ | 2.14 (K) |
| 4.61 | I64 | 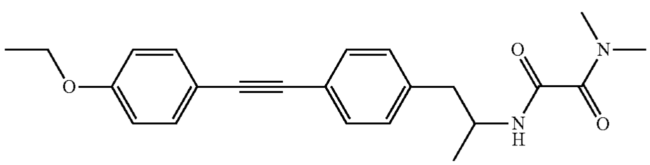 [SMILES: CCOc1ccc(C#Cc2ccc(CC(C)NC(=O)C(=O)N(C)C)cc2)cc1] | 379 [M + H]⁺ | 1.91 (K) |
| 4.62 | I64 | 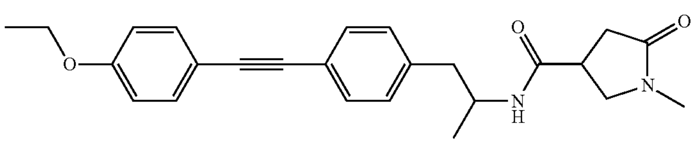 [SMILES: CCOc1ccc(C#Cc2ccc(CC(C)NC(=O)C3CC(=O)N(C)C3)cc2)cc1] | 405 [M + H]⁺ | 2.13 (K) |
| 4.63 | I64 | 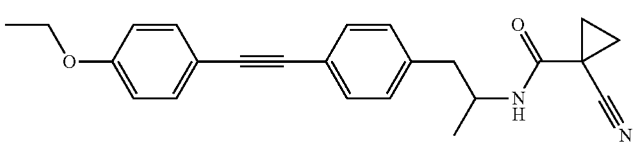 [SMILES: CCOc1ccc(C#Cc2ccc(CC(C)NC(=O)C3(C#N)CC3)cc2)cc1] | 373 [M + H]⁺ | 2.18 (K) |
| 4.64 | I64 | 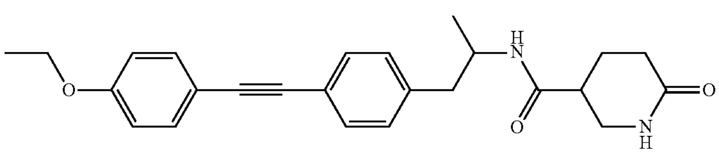 [SMILES: CCOc1ccc(C#Cc2ccc(CC(C)NC(=O)C3CCC(=O)NC3)cc2)cc1] | 405 [M + H]⁺ | 2.2 (K) |
| 4.65 | I64 | 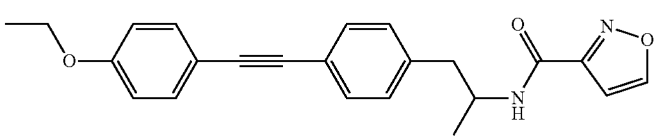 [SMILES: CCOc1ccc(C#Cc2ccc(CC(C)NC(=O)c3ccon3)cc2)cc1] | 375 [M + H]⁺ | 2.18 (K) |
| 4.66 | I64 | 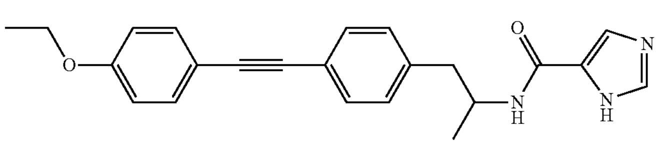 [SMILES: CCOc1ccc(C#Cc2ccc(CC(C)NC(=O)c3cnc[nH]3)cc2)cc1] | 374 [M + H]⁺ | 2.03 (K) |

-continued

| Ex. | Starting material(s) | Structure | Mass spec result | HPLC retention time (method) |
|---|---|---|---|---|
| 4.67 | I64 | 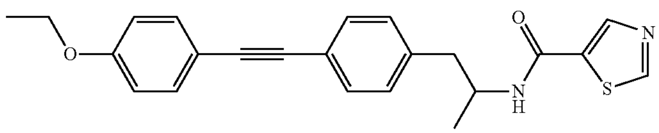 [SMILES: CCOc1ccc(C#Cc2ccc(CC(C)NC(=O)c3cncs3)cc2)cc1] | 391 [M + H]⁺ | 2.17 (K) |
| 4.68 | I64 | 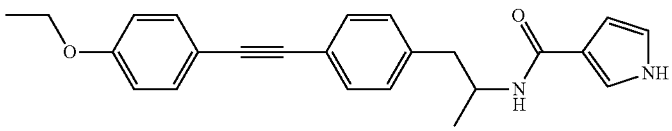 | 373 [M + H]⁺ | 2.14 (K) |
| 4.69 | I64 | 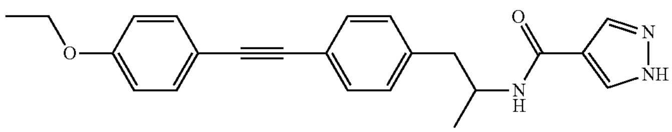 [SMILES: CCOc1ccc(C#Cc2ccc(CC(C)NC(=O)c3cn[nH]c3)cc2)cc1] | 374 [M + H]⁺ | 2.21 (K) |
| 4.70 | I64 | 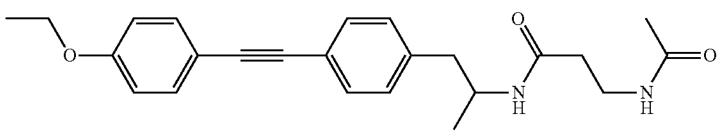 [SMILES: CCOc1ccc(C#Cc2ccc(CC(C)NC(=O)CCNC(C)=O)cc2)cc1] | 393 [M + H]⁺ | 2.13 (K) |
| 4.71 | I64 | 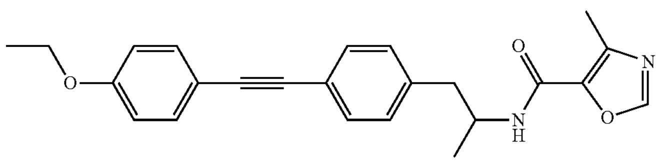 [SMILES: CCOc1ccc(C#Cc2ccc(CC(C)NC(=O)c3ocnc3C)cc2)cc1] | 389 [M + H]⁺ | 2.19 (K) |
| 4.72 | I64 | 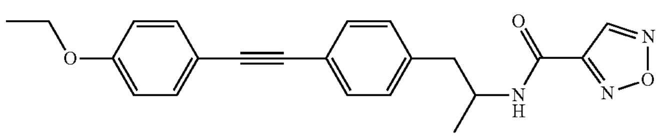 [SMILES: CCOc1ccc(C#Cc2ccc(CC(C)NC(=O)c3cnon3)cc2)cc1] | 376 [M + H]⁺ | 2.21 (K) |
| 4.73 | I64 | 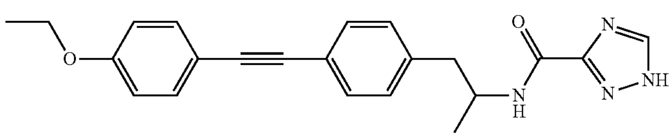 [SMILES: CCOc1ccc(C#Cc2ccc(CC(C)NC(=O)c3nc[nH]n3)cc2)cc1] | 375 [M + H]⁺ | 2.14 (K) |
| 4.74 | I64 | 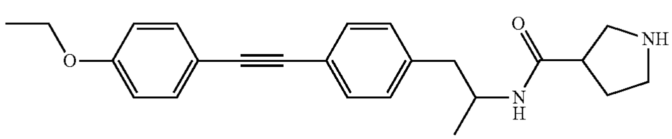 [SMILES: CCOc1ccc(C#Cc2ccc(CC(C)NC(=O)C3CCNC3)cc2)cc1] | 377 [M + H]⁺ | 2.32 (K) |
| 4.75 | I63 | 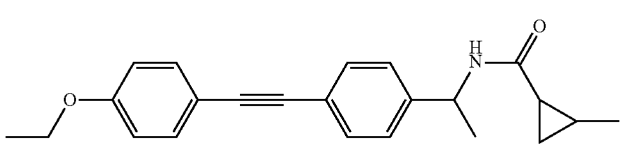 [SMILES: CCOc1ccc(C#Cc2ccc(C(C)NC(=O)C3CC3C)cc2)cc1] | 348 [M + H]⁺ | 2.4 (K) |
| 4.76 | I66 | 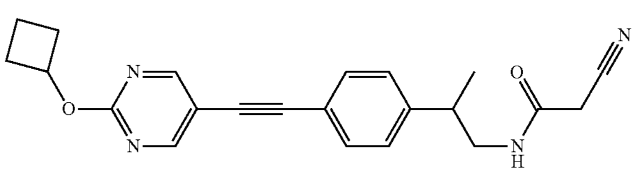 [SMILES: CC(CNC(=O)CC#N)c1ccc(C#Cc2cnc(OC3CCC3)nc2)cc1] | 375 [M + H]⁺ | 2.32 (E) |

-continued

| Ex. | Starting material(s) | Structure | Mass spec result | HPLC retention time (method) |
|---|---|---|---|---|
| 4.77 | I66 | 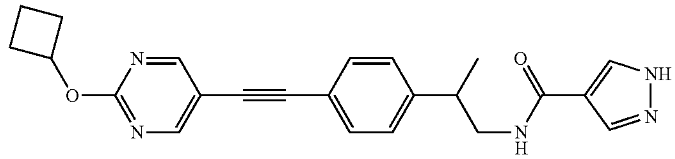 [SMILES: CC(CNC(=O)c1cn[nH]c1)c1ccc(C#Cc2cnc(OC3CCC3)nc2)cc1] | 402 [M + H]+ | 2.40 (E) |
| 4.78 | I66 | 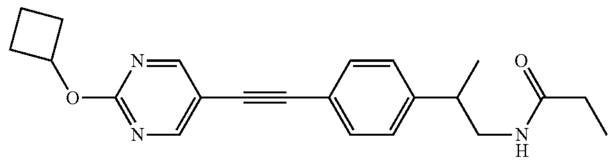 [SMILES: CCC(=O)NCC(C)c1ccc(C#Cc2cnc(OC3CCC3)nc2)cc1] | 364 [M + H]+ | 2.38 (E) |
| 4.79 | I66 | 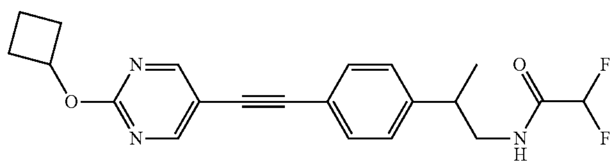 [SMILES: CC(CNC(=O)C(F)F)c1ccc(C#Cc2cnc(OC3CCC3)nc2)cc1] | 386 [M + H]+ | 2.38 (E) |
| 4.80 | I67 | 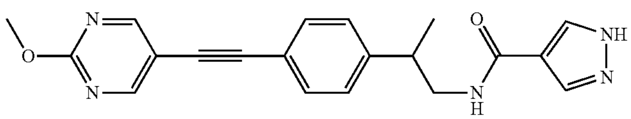 [SMILES: COc1ncc(C#Cc2ccc(C(C)CNC(=O)c3cn[nH]c3)cc2)cn1] | 362 [M + H]+ | 2.05 (E) |

Example 5

Example 5.1

General Route

N-(1-(4-((4-ethoxyphenethynyl)phenyl)propan-2-yl)cyclopropanesulfonamide

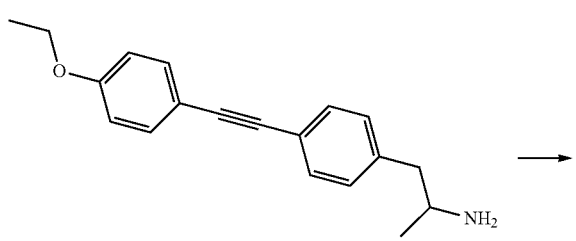

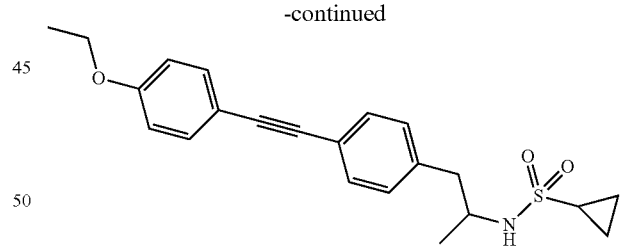

To 27.9 mg (0.10 mmol) 1-(4-(4-ethoxyphenethynyl)phenyl)propan-2-amine (I64) in 2 mL DCM are added 67.0 µL (0.48 mmol) TEA followed by 16.9 mg (0.12 mmol) cyclopropanesulfonyl chloride. The reaction mixture is stirred at r.t. over night. Additional 8.50 mg (0.06 mmol) sulfonyl chloride and 34 µL (0.24 mmol) TEA are added and stirring is continued for 4 h. The solvent is removed in vacuo and the residue is purified by HPLC (MeOH/H$_2$O/TFA).

$C_{22}H_{29}NO_3S$ (M=387.5 g/mol)

ESI-MS: 388 [M+H]+

$R_t$ (HPLC): 2.44 min (Method N)

The following compounds are prepared analogously to example 5.1

| Ex. | Starting material | Structure | Mass spec result | HPLC retention time (method) |
|---|---|---|---|---|
| 5.1 | I64 | (structure) | 384 [M + H]+ | 2.34 (M) |
| 5.2 | I63 | (structure) | 384 [M + H]+ | 1.99 (L) |
| 5.3 | I64 | (structure) | 386 [M + H]+ | 2.35 (M) |
| 5.4 | I64 | (structure) | 358 [M + H]+ | 2.30 (M) |

Example 6

Example 6.1

General Route 1-(4-(Dimethylamino)phenyl)-3-(1-(4-((4-ethoxyphenyl)ethynyl)phenylethyl)urea

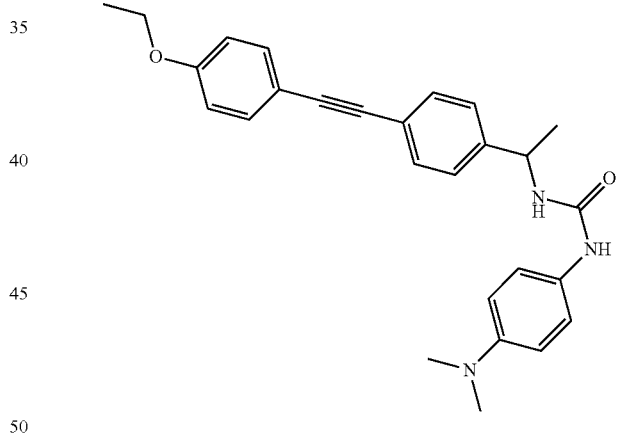

To 26.5 mg (0.10 mmol) 1-(4-((4-ethoxyphenyl)ethynyl)phenyl)ethanamine (I63) in 2 mL DMF are consecutively added 65.0 μL (0.40 mmol) DIPEA and 24.3 mg (0.15 mmol) 4-(dimethylamino)phenyl isocyanate. The reaction mixture is stirred at r.t. over night and purified by HPLC.

$C_{27}H_{29}N_3O_2$ (M=427.5 g/mol)

ESI-MS: 428 [M+H]+

$R_t$ (HPLC): 1.89 min (method N)

The following compounds are prepared analogously to example 6.1

For example 6.4 the ethyl-protected carboxylic acid is used. For the saponification, the compound is dissolved in 1.5 mL ethanol, charged with 1 M NaOH and stirred at r.t. for 3 h. the solvent is removed in vacuo and the residue is washed with DMF.

| Ex. | Starting material | Structure | Mass spec result | HPLC retention time (method) |
|---|---|---|---|---|
| 6.1 | I63 | 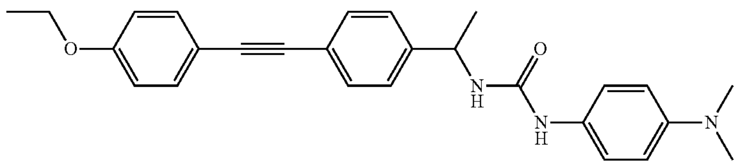 [SMILES: CCOc1ccc(C#Cc2ccc(C(C)NC(=O)Nc3ccc(N(C)C)cc3)cc2)cc1] | 428 [M + H]⁺ | 1.89 (N) |
| 6.2 | I63 | 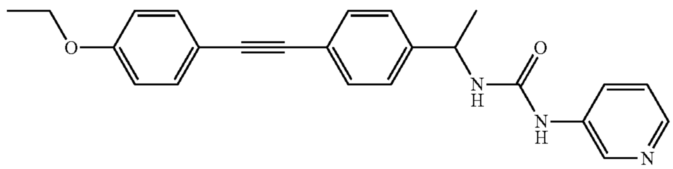 [SMILES: CCOc1ccc(C#Cc2ccc(C(C)NC(=O)Nc3cccnc3)cc2)cc1] | 386 [M + H]⁺ | 1.87 (N) |
| 6.3 | I64 | 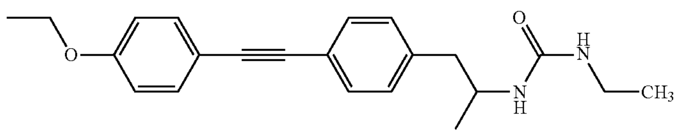 | 351 [M + H]⁺ | 2.34 (M) |
| 6.4 | I63 | 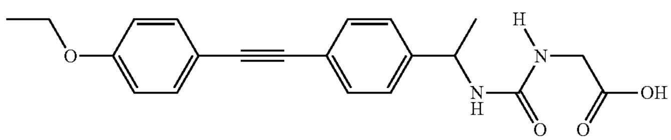 [SMILES: CCOc1ccc(C#Cc2ccc(C(C)NC(=O)NCC(=O)O)cc2)cc1] | 367 [M + H]⁺ | 2.13 (N) |

Example 7

Example 7.1

General Route 3-(1-(4-((4-Ethoxyphenyl)ethynyl)phenyl)ethyl)-1,1-dimethylurea

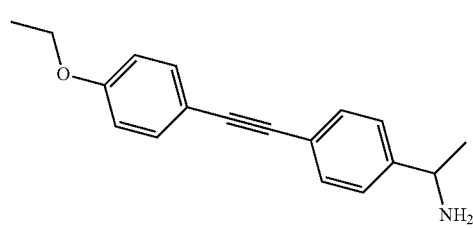

→

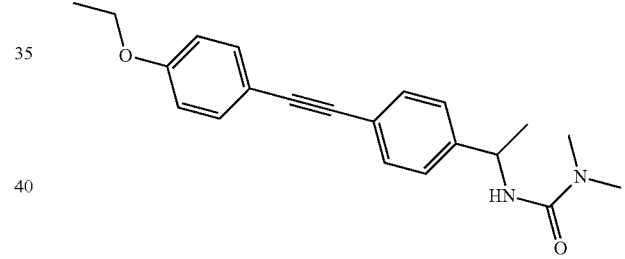

To 26.5 mg (0.10 mmol) 1-(4-((4-ethoxyphenyl)ethynyl)phenyl)ethanamine (I63) and 27.7 µL (0.20 mmol) TEA in 1.5 mL DCM are added 11.0 µl (0.12 mmol) dimethylcarbamyl chloride at 0° C. The reaction mixture is stirred at r.t. over night and directly purified by HPLC (MeOH/H$_2$O/NH$_3$).

$C_{21}H_{24}N_2O_2$ (M=336.4 g/mol)
ESI-MS: 337 [M+H]⁺
R$_t$ (HPLC): 2.37 min (method N)

The following compounds are prepared analogously to example 7.1.

| Ex. | Starting material | Structure | Mass spec result | HPLC retention time (method) |
|---|---|---|---|---|
| 7.1 | I63 | 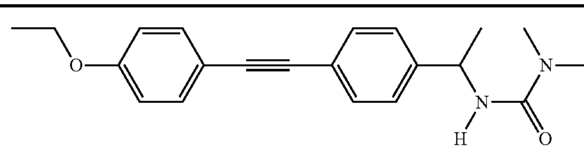 | 337 [M + H]⁺ | 2.37 (N) |

-continued

| Ex. | Starting material | Structure | Mass spec result | HPLC retention time (method) |
|---|---|---|---|---|
| 7.2 | I64 | (structure) | 351 [M + H]⁺ | 2.37 (M) |
| 7.3 | I64 | (structure) | 365 [M + H]⁺ | 2.37 (M) |

Example 8

Example 8.1

General Route

N-(1-(4-((4-(piperidine-1-carbonyl)phenyl)ethynyl)phenyl)propan-2-yl)acetamide

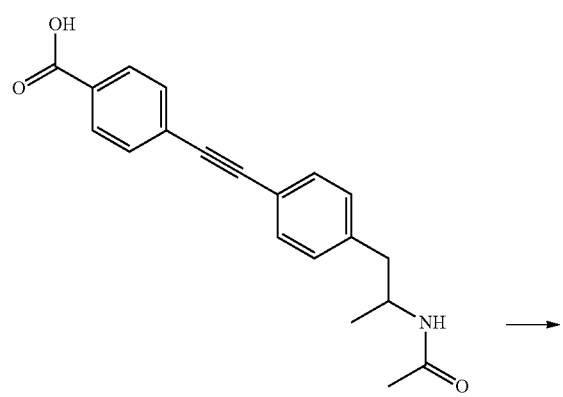

→

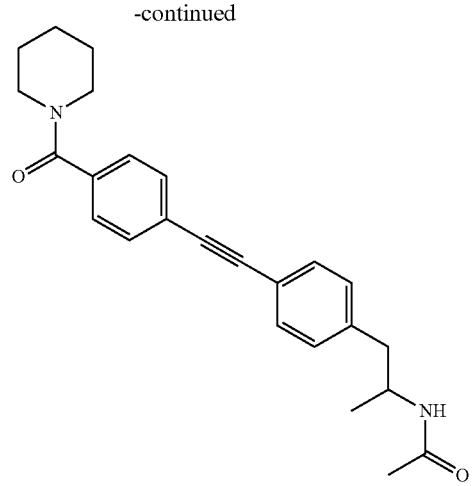

To 30 mg (0.10 mmol) 4-((4-(2-acetamidopropyl)phenyl)ethynyl)benzoic acid (I72.2) in 1 mL DMF are added 20.0 μl (0.10 mmol) TEA and 50 mg (0.15 mmol) TBTU. The mixture is stirred at r.t. for 5 min before it is added to 10 mg (0.12 mmol) piperidine in 500 μl DMF. After stirring at r.t. for 72 h the mixture is purified by HPLC (MeOH/H$_2$O/NH$_3$).

$C_{25}H_{28}N_2O_2$ (M=388.5 g/mol)
ESI-MS: 389 [M+H]⁺
R$_t$ (HPLC): 1.91 min (method L)

The following compounds are prepared analogously to example 8.1

For examples 8.43-8.48 TEA is used as base and the reaction mixture is filtrated through a plug of alox before purification.

| Ex. | Starting material | Structure | Mass spec result | HPLC retention time (method) |
|---|---|---|---|---|
| 8.1 | I72.2 | (structure) | 389 [M + H]⁺ | 1.91 (L) |

-continued

| Ex. | Starting material | Structure | Mass spec result | HPLC retention time (method) |
|---|---|---|---|---|
| 8.2 | I72.2 | 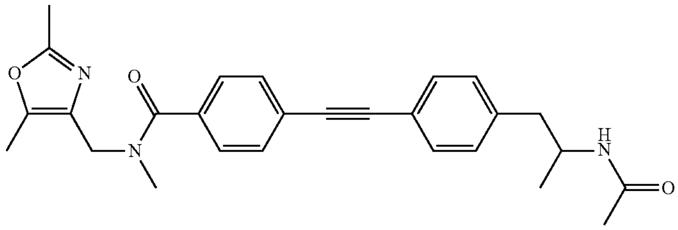 [SMILES: CC(=O)NC(C)Cc1ccc(C#Cc2ccc(C(=O)N(C)Cc3nc(C)oc3C)cc2)cc1] | 444 [M + H]+ | 1.84 (L) |
| 8.3 | I72.2 | 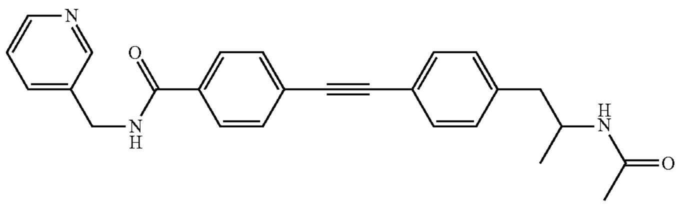 [SMILES: CC(=O)NC(C)Cc1ccc(C#Cc2ccc(C(=O)NCc3cccnc3)cc2)cc1] | 412 [M + H]+ | 1.72 (L) |
| 8.4 | I72.2 | 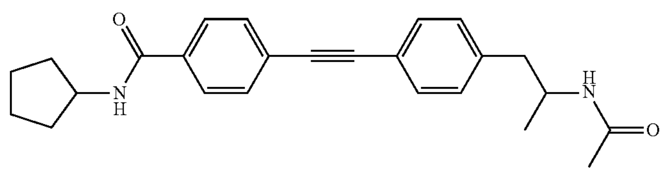 | 389 [M + H]+ | 1.88 (L) |
| 8.5 | I72.2 | 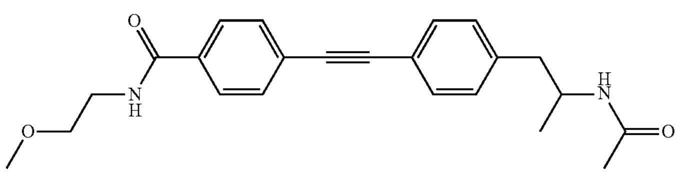 [SMILES: COCCNC(=O)c1ccc(C#Cc2ccc(CC(C)NC(C)=O)cc2)cc1] | 379 [M + H]+ | 1.70 (L) |
| 8.6 | I72.2 | 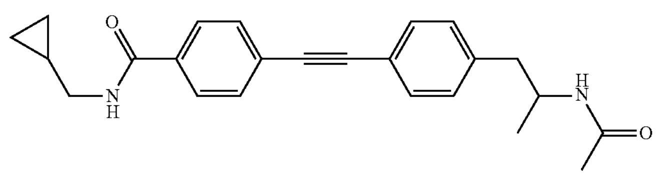 [SMILES: CC(=O)NC(C)Cc1ccc(C#Cc2ccc(C(=O)NCC3CC3)cc2)cc1] | 375 [M + H]+ | 1.81 (L) |
| 8.7 | I72.2 | 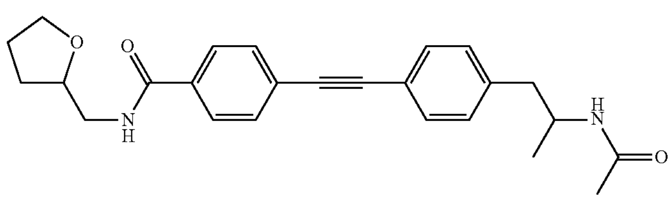 [SMILES: CC(=O)NC(C)Cc1ccc(C#Cc2ccc(C(=O)NCC3CCCO3)cc2)cc1] | 405 [M + H]+ | 1.76 (L) |
| 8.8 | I72.2 | 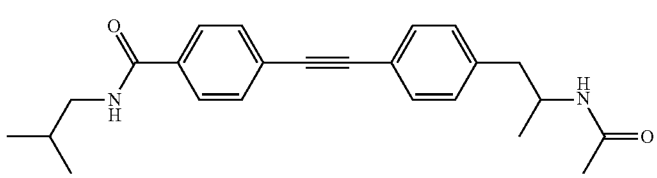 [SMILES: CC(=O)NC(C)Cc1ccc(C#Cc2ccc(C(=O)NCC(C)C)cc2)cc1] | 376 [M + H]+ | 1.86 (L) |

-continued

| Ex. | Starting material | Structure | Mass spec result | HPLC retention time (method) |
|---|---|---|---|---|
| 8.9 | I72.2 | 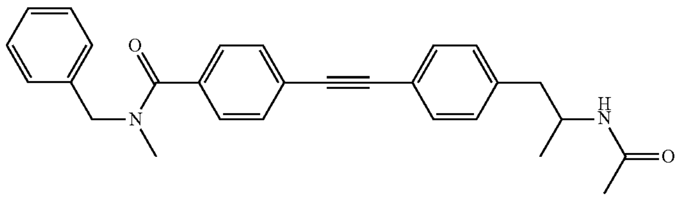 [SMILES: CC(=O)NC(C)Cc1ccc(C#Cc2ccc(C(=O)N(C)Cc3ccccc3)cc2)cc1] | 425 [M + H]⁺ | 1.96 (L) |
| 8.10 | I72.2 | 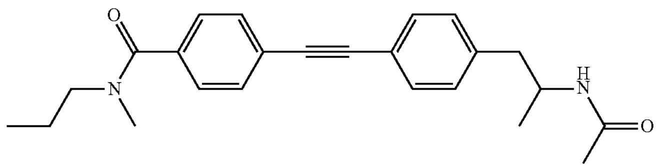 [SMILES: CCCN(C)C(=O)c1ccc(C#Cc2ccc(CC(C)NC(C)=O)cc2)cc1] | 377 [M + H]⁺ | 1.88 (L) |
| 8.11 | I72.2 | 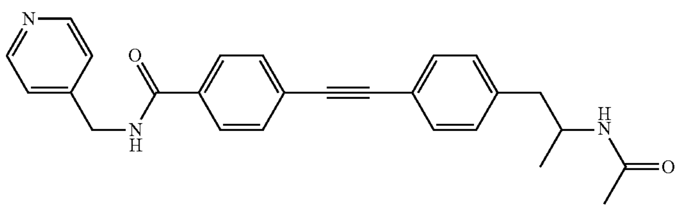 [SMILES: CC(=O)NC(C)Cc1ccc(C#Cc2ccc(C(=O)NCc3ccncc3)cc2)cc1] | 412 [M + H]⁺ | 1.69 (L) |
| 8.12 | I72.2 | 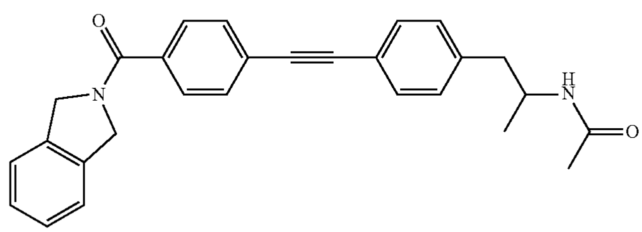 [SMILES: CC(=O)NC(C)Cc1ccc(C#Cc2ccc(C(=O)N3Cc4ccccc4C3)cc2)cc1] | 423 [M + H]⁺ | 1.98 (L) |
| 8.13 | I72.2 | 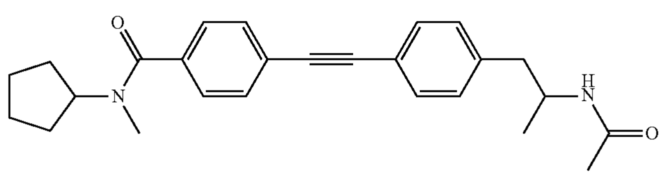 [SMILES: CC(=O)NC(C)Cc1ccc(C#Cc2ccc(C(=O)N(C)C3CCCC3)cc2)cc1] | 403 [M + H]⁺ | 1.97 (L) |
| 8.14 | I72.2 | 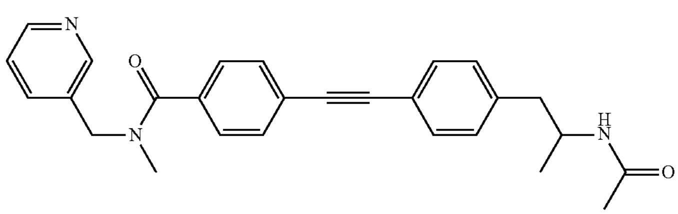 [SMILES: CC(=O)NC(C)Cc1ccc(C#Cc2ccc(C(=O)N(C)Cc3cccnc3)cc2)cc1] | 426 [M + H]⁺ | 1.70 (L) |
| 8.15 | I72.2 | 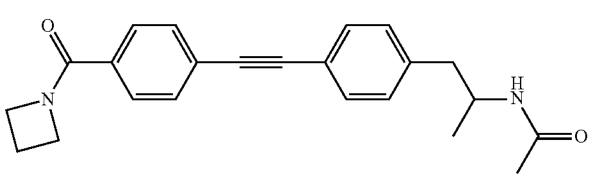 [SMILES: CC(=O)NC(C)Cc1ccc(C#Cc2ccc(C(=O)N3CCC3)cc2)cc1] | 361 [M + H]⁺ | 1.74 (L) |

-continued
| Ex. | Starting material | Structure | Mass spec result | HPLC retention time (method) |
|---|---|---|---|---|
| 8.16 | I72.2 | 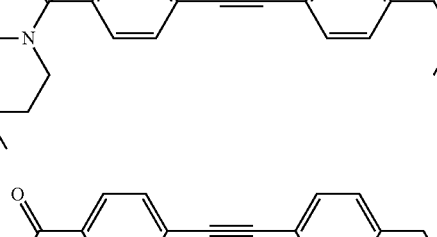 | 417 [M + H]+ | 2.02 (L) |
| 8.17 | I72.2 | 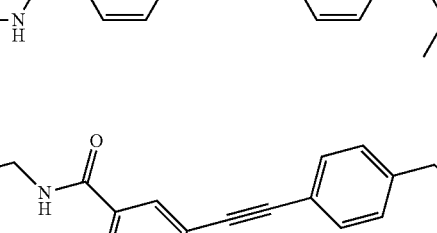 | 349 [M + H]+ | 1.70 (L) |
| 8.18 | I72.1 | 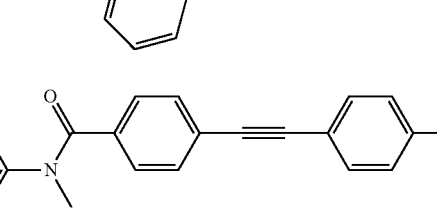 | 403 [M + H]+ | 1.80 (L) |
| 8.19 | I72.2 | 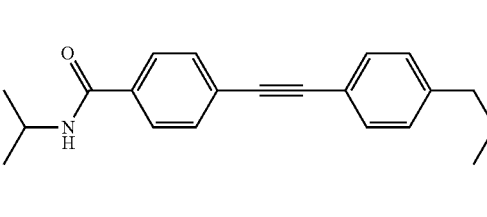 | 411 [M + H]+ | 1.90 (L) |
| 8.20 | I72.2 | 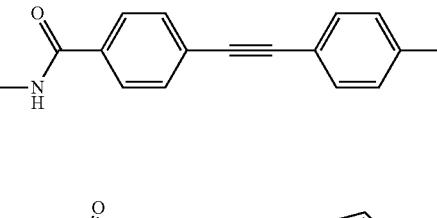 | 363 [M + H]+ | 1.77 (L) |
| 8.21 | I72.2 | 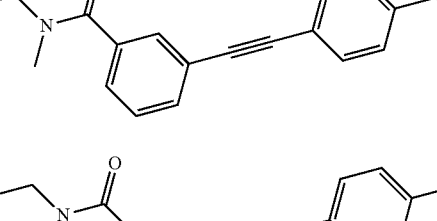 | 375 [M + H]+ | 1.81 (L) |
| 8.22 | I72.1 | 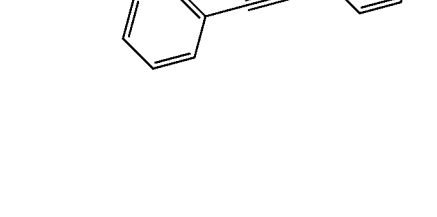 | 379 [M + H]+ | 1.59 (L) |
| 8.23 | I72.1 | 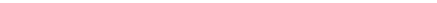 | 412 [M + H]+ | 1.74 (L) |

| Ex. | Starting material | Structure | Mass spec result | HPLC retention time (method) |
|---|---|---|---|---|
| 8.24 | I72.1 | 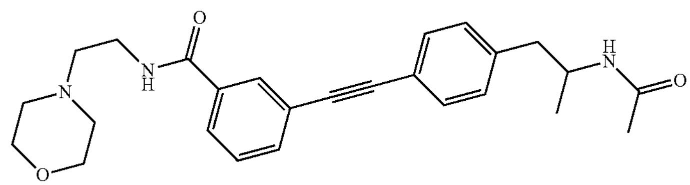 [SMILES: CC(=O)NC(C)Cc1ccc(C#Cc2cccc(C(=O)NCCN3CCOCC3)c2)cc1] | 434 [M + H]+ | 1.71 (L) |
| 8.25 | I72.1 | 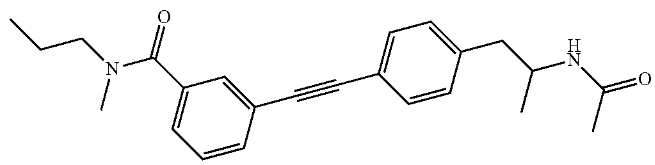 [SMILES: CCCN(C)C(=O)c1cccc(C#Cc2ccc(CC(C)NC(C)=O)cc2)c1] | 377 [M + H]+ | 1.86 (L) |
| 8.26 | I72.1 | 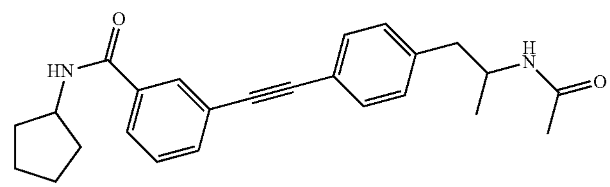 [SMILES: CC(=O)NC(C)Cc1ccc(C#Cc2cccc(C(=O)NC3CCCC3)c2)cc1] | 389 [M + H]+ | 1.86 (L) |
| 8.27 | I72.1 | 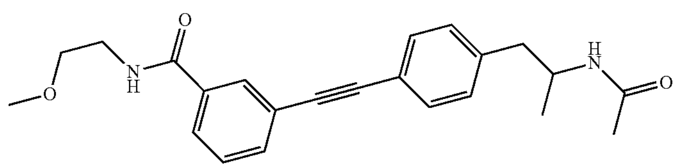 [SMILES: COCCNC(=O)c1cccc(C#Cc2ccc(CC(C)NC(C)=O)cc2)c1] | 379 [M + H]+ | 1.69 (L) |
| 8.28 | I72.1 | 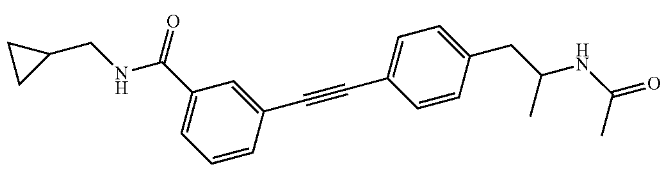 [SMILES: CC(=O)NC(C)Cc1ccc(C#Cc2cccc(C(=O)NCC3CC3)c2)cc1] | 375 [M + H]+ | 1.80 (L) |
| 8.29 | I72.1 | 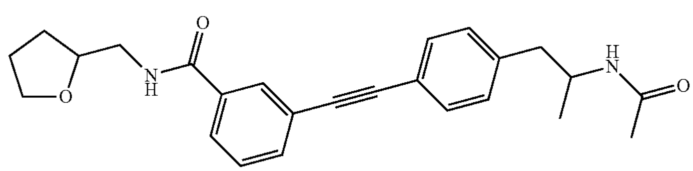 [SMILES: CC(=O)NC(C)Cc1ccc(C#Cc2cccc(C(=O)NCC3CCCO3)c2)cc1] | 405 [M + H]+ | 1.75 (L) |
| 8.30 | I72.1 | 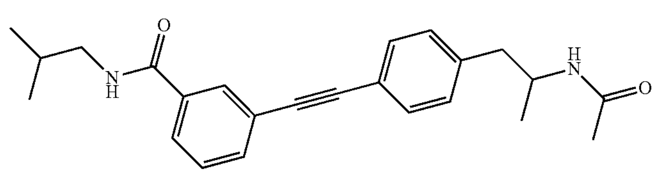 [SMILES: CC(=O)NC(C)Cc1ccc(C#Cc2cccc(C(=O)NCC(C)C)c2)cc1] | 377 [M + H]+ | 1.85 (L) |
| 8.31 | I72.1 | 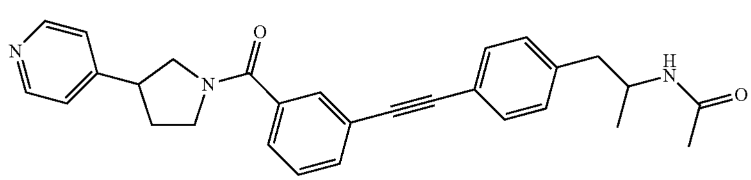 [SMILES: CC(=O)NC(C)Cc1ccc(C#Cc2cccc(C(=O)N3CCC(c4ccncc4)C3)c2)cc1] | 452 [M + H]+ | 1.82 (L) |

-continued
| Ex. | Starting material | Structure | Mass spec result | HPLC retention time (method) |
|---|---|---|---|---|
| 8.32 | I72.1 | 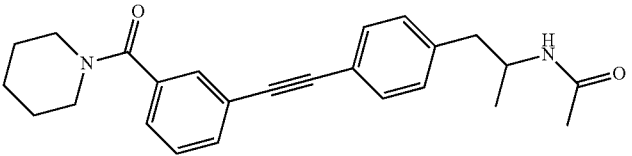 [SMILES: CC(=O)NC(C)Cc1ccc(C#Cc2cccc(C(=O)N3CCCCC3)c2)cc1] | 389 [M + H]+ | 1.88 (L) |
| 8.33 | I72.1 | 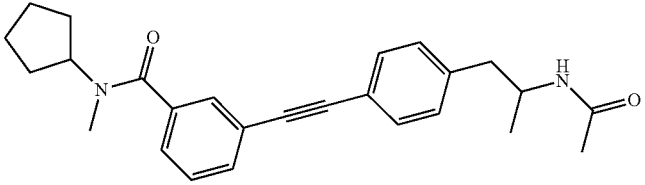 [SMILES: CC(=O)NC(C)Cc1ccc(C#Cc2cccc(C(=O)N(C)C3CCCC3)c2)cc1] | 403 [M + H]+ | 1.95 (L) |
| 8.34 | I72.1 | 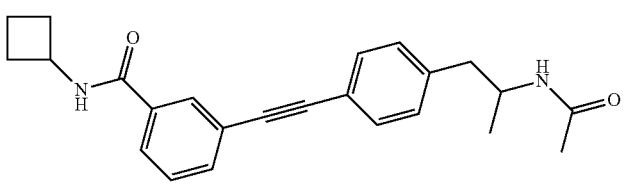 [SMILES: CC(=O)NC(C)Cc1ccc(C#Cc2cccc(C(=O)NC3CCC3)c2)cc1] | 375 [M + H]+ | 1.82 (L) |
| 8.35 | I72.1 | 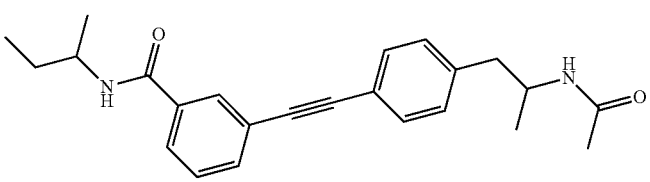 [SMILES: CCC(C)NC(=O)c1cccc(C#Cc2ccc(CC(C)NC(C)=O)cc2)c1] | 377 [M + H]+ | 1.84 (L) |
| 8.36 | I72.1 | 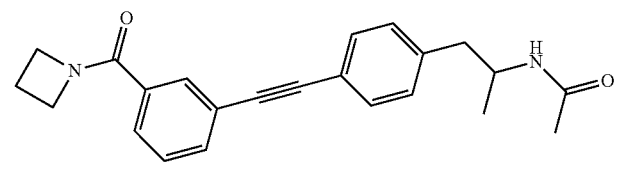 [SMILES: CC(=O)NC(C)Cc1ccc(C#Cc2cccc(C(=O)N3CCC3)c2)cc1] | 360 [M + H]+ | 1.74 (L) |
| 8.37 | I72.1 | 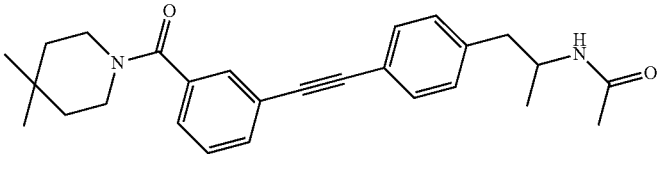 [SMILES: CC(=O)NC(C)Cc1ccc(C#Cc2cccc(C(=O)N3CCC(C)(C)CC3)c2)cc1] | 417 [M + H]+ | 2.01 (L) |
| 8.38 | I72.1 | 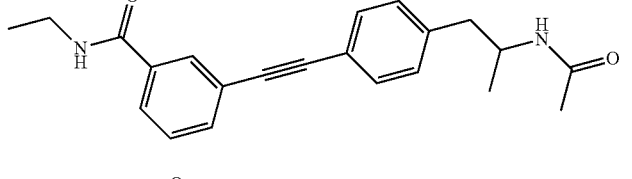 | 349 [M + H]+ | 1.72 (L) |
| 8.39 | I72.1 | 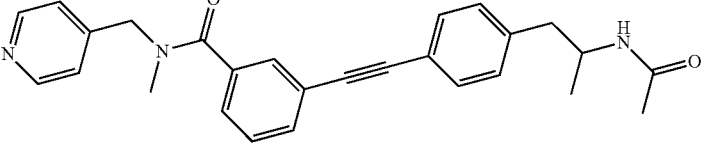 | 426 [M + H]+ | 1.70 (L) |

-continued

| Ex. | Starting material | Structure | Mass spec result | HPLC retention time (method) |
|---|---|---|---|---|
| 8.40 | I72.1 | 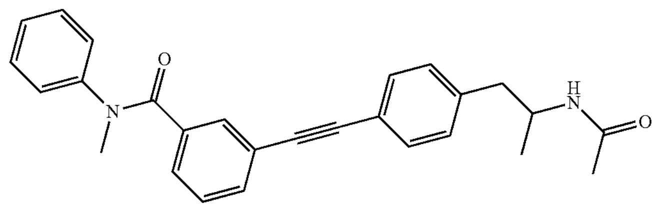 [SMILES: CC(=O)NC(C)Cc1ccc(C#Cc2cccc(C(=O)N(C)c3ccccc3)c2)cc1] | 411 [M + H]+ | 1.88 (L) |
| 8.41 | I72.1 | 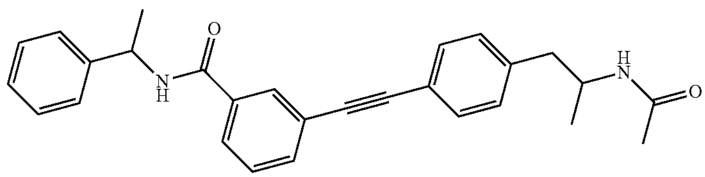 [SMILES: CC(=O)NC(C)Cc1ccc(C#Cc2cccc(C(=O)NC(C)c3ccccc3)c2)cc1] | 425 [M + H]+ | 1.89 (L) |
| 8.42 | I72.1 | 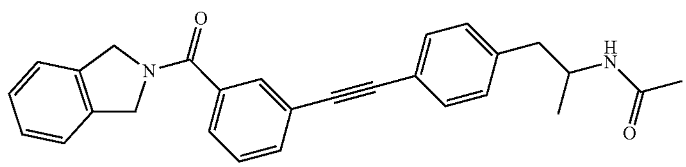 [SMILES: CC(=O)NC(C)Cc1ccc(C#Cc2cccc(C(=O)N3Cc4ccccc4C3)c2)cc1] | 423 [M + H]+ | 2.22 (N) |
| 8.43 | I72.2 | 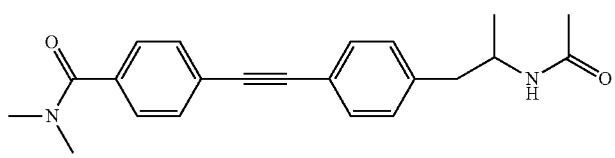 [SMILES: CC(=O)NC(C)Cc1ccc(C#Cc2ccc(C(=O)N(C)C)cc2)cc1] | 349 [M + H]+ | 1.90 (N) |
| 8.44 | I72.2 | 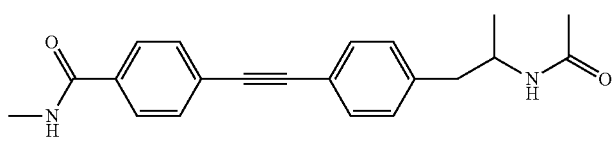 [SMILES: CNC(=O)c1ccc(C#Cc2ccc(CC(C)NC(C)=O)cc2)cc1] | 335 [M + H]+ | 1.84 (N) |
| 8.45 | I72.2 | 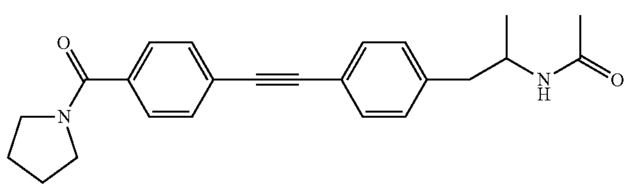 [SMILES: CC(=O)NC(C)Cc1ccc(C#Cc2ccc(C(=O)N3CCCC3)cc2)cc1] | 375 [M + H]+ | 2.15 (M) |
| 8.46 | I72.2 | 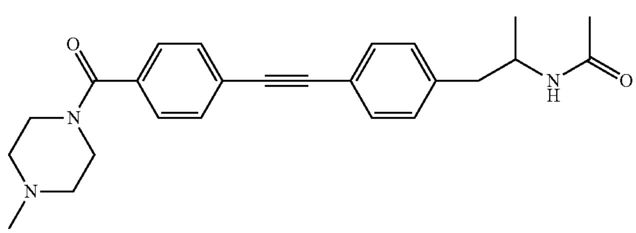 [SMILES: CC(=O)NC(C)Cc1ccc(C#Cc2ccc(C(=O)N3CCN(C)CC3)cc2)cc1] | 404 [M + H]+ | 1.50 (N) |
| 8.47 | I72.1 | 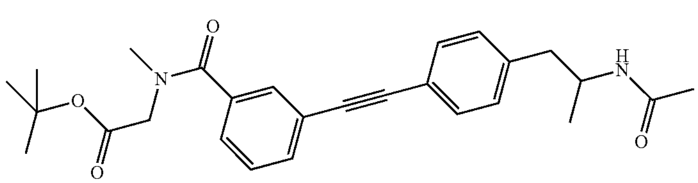 [SMILES: CC(=O)NC(C)Cc1ccc(C#Cc2cccc(C(=O)N(C)CC(=O)OC(C)(C)C)c2)cc1] | 449 [M + H]+ | 2.15 (N) |

-continued

| Ex. | Starting material | Structure | Mass spec result | HPLC retention time (method) |
|---|---|---|---|---|
| 8.48 | I72.1 | 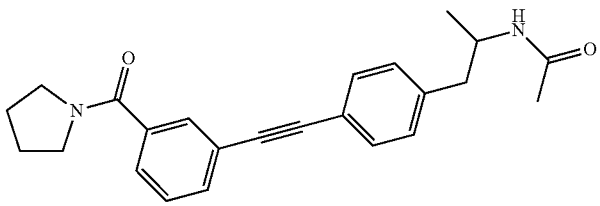 [SMILES: CC(=O)NC(C)Cc1ccc(C#Cc2cccc(C(=O)N3CCCC3)c2)cc1] | 375 [M + H]+ | 2.00 (N) |
| 8.49 | I72.1 | 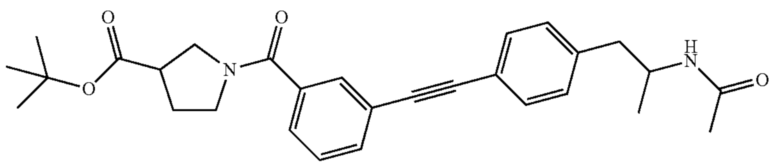 [SMILES: CC(=O)NC(C)Cc1ccc(C#Cc2cccc(C(=O)N3CCC(C(=O)OC(C)(C)C)C3)c2)cc1] | 475 [M + H]+ | 2.23 (N) |
| 8.50 | I72.1 | 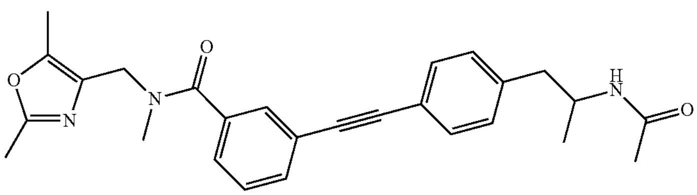 [SMILES: CC(=O)NC(C)Cc1ccc(C#Cc2cccc(C(=O)N(C)Cc3nc(C)oc3C)c2)cc1] | 444 [M + H]+ | 2.01 (N) |
| 8.51 | I72.1 | 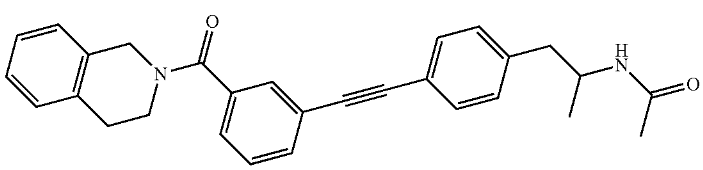 [SMILES: CC(=O)NC(C)Cc1ccc(C#Cc2cccc(C(=O)N3CCc4ccccc4C3)c2)cc1] | 437 [M + H]+ | 2.26 (N) |
| 8.52 | I72.1 | 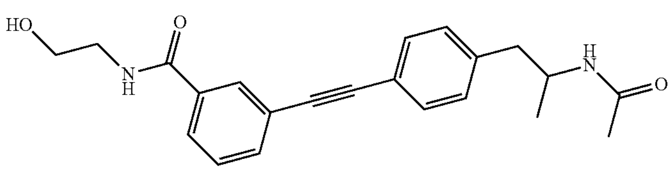 [SMILES: CC(=O)NC(C)Cc1ccc(C#Cc2cccc(C(=O)NCCO)c2)cc1] | 365 [M + H]+ | 1.77 (N) |
| 8.53 | I72.1 | 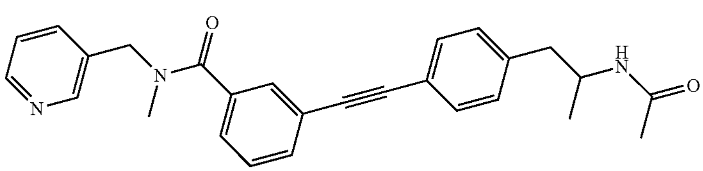 [SMILES: CC(=O)NC(C)Cc1ccc(C#Cc2cccc(C(=O)N(C)Cc3cccnc3)c2)cc1] | 426 [M + H]+ | 1.60 (N) |
| 8.54 | I72.1 | 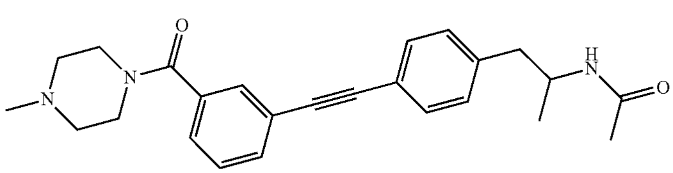 [SMILES: CC(=O)NC(C)Cc1ccc(C#Cc2cccc(C(=O)N3CCN(C)CC3)c2)cc1] | 404 [M + H]+ | 1.51 (N) |

Example 9

Example 9.1

General Route

N-(1-(4-((4-(pentan-3yloxy)phenyl)ethynyl)phenyl)propan-2-yl)acetamide

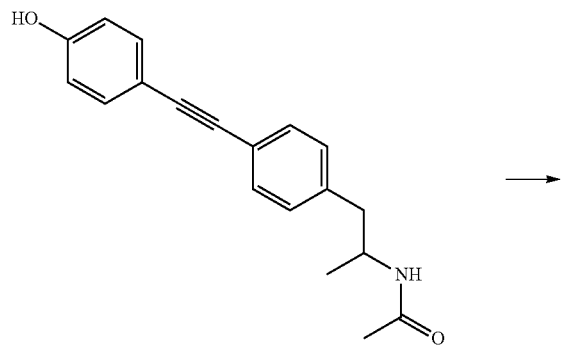

→

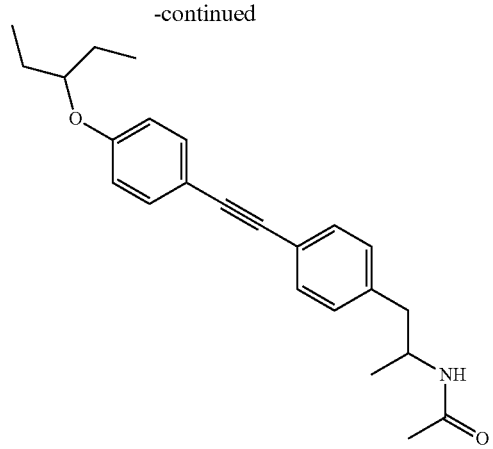

14.7 µl (0.14 mmol) 3-pentanol, 40 mg (0.14 mmol) N-(1-(4-((4-hydroxyphenyl)-ethynyl)phenyl)propan-2-yl)acetamide (I74.1) and 69.8 mg (0.21 mmol) polymer bound triphenylphosphine (~3 mmol/g) are added to 1 mL THF followed by 31.4 mg (0.14 mmol) DBAD. After stirring the mixture for 2 h at r.t. further 7.5 µl (0.07 mmol) 3-pentanol and 16 mg (0.07 mmol) DBAD are added and stirring is continued for 72 h. The reaction mixture is filtered and the filtrate is purified by HPLC (MeOH/H$_2$O/TFA).

$C_{24}H_{29}NO_2$ (M=363.5 g/mol)
ESI-MS: 364 [M+H]$^+$
R$_t$ (HPLC): 2.46 min (method M)

The following compounds are prepared analogously to example 9.1

For example 9.10 the boc-protected azetidine is used in the mitsonobu reaction.

For deprotection, the compound is dissolved in a 2/1 mixture of MeOH and HCl (1.25 mol/l in MeOH) and stirred at 70° C. for 2 h. Purification by HPLC.

For examples 9.13-42 1.5 eq. alcohol, tpp and DBAD are used and after 16 h one more equivalent DBAD is added and stirring is continued for another 24 h.

| Ex. | Starting material | Structure | Mass spec result | HPLC retention time method |
|---|---|---|---|---|
| 9.1 | I74.1 | 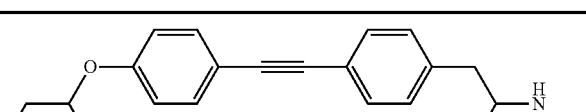 | 364 [M + H]$^+$ | 2.46 (M) |
| 9.2 | I74.1 | 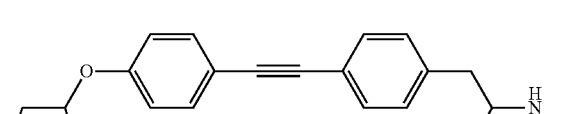 | 362 [M + H]$^+$ | 2.46 (M) |
| 9.3 | I74.1 | 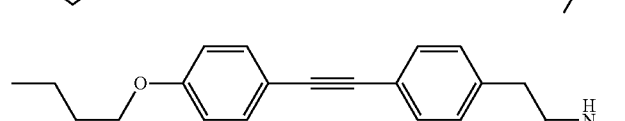 | 350 [M + H]$^+$ | 2.45 (M) |

-continued

| Ex. | Starting material | Structure | Mass spec result | HPLC retention time method |
|---|---|---|---|---|
| 9.4 | I74.1 | 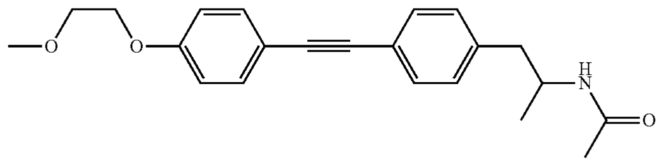 [SMILES: COCCOc1ccc(C#Cc2ccc(CC(C)NC(C)=O)cc2)cc1] | 352 [M + H]⁺ | 2.22 (M) |
| 9.5 | I74.1 | 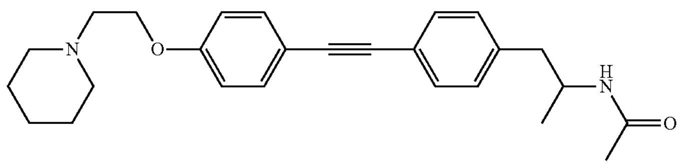 [SMILES: CC(=O)NC(C)Cc1ccc(C#Cc2ccc(OCCN3CCCCC3)cc2)cc1] | 405 [M + H]⁺ | 1.72 (T) |
| 9.6 | I74.1 | 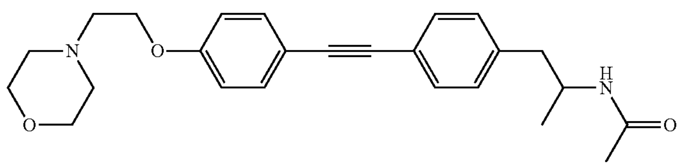 [SMILES: CC(=O)NC(C)Cc1ccc(C#Cc2ccc(OCCN3CCOCC3)cc2)cc1] | 407 [M + H]⁺ | 1.76 (M) |
| 9.7 | I74.1 | 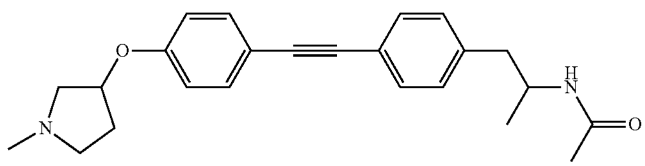 [SMILES: CC(=O)NC(C)Cc1ccc(C#Cc2ccc(OC3CCN(C)C3)cc2)cc1] | 377 [M + H]⁺ | 1.83 (M) |
| 9.8 | I74.2 | 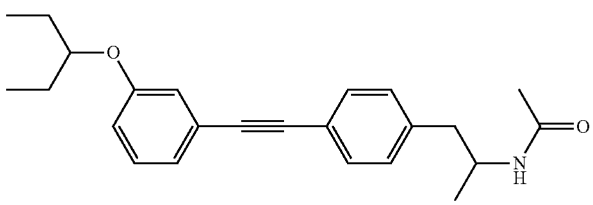 [SMILES: CCC(CC)Oc1cccc(C#Cc2ccc(CC(C)NC(C)=O)cc2)c1] | 364 [M + H]⁺ | 2.51 (M) |
| 9.9 | I74.2 | 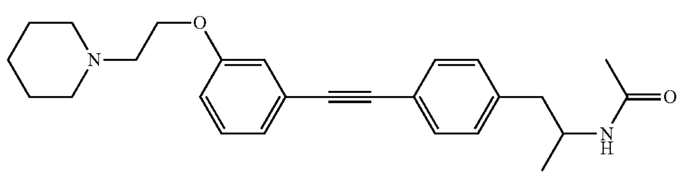 [SMILES: CC(=O)NC(C)Cc1ccc(C#Cc2cccc(OCCN3CCCCC3)c2)cc1] | 405 [M + H]⁺ | 1.85 (M) |
| 9.10 | I74.1 | 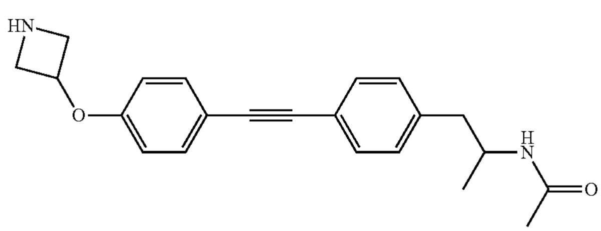 [SMILES: CC(=O)NC(C)Cc1ccc(C#Cc2ccc(OC3CNC3)cc2)cc1] | 349 [M + H]⁺ | 2.47 (D) |
| 9.11 | I74.1 | 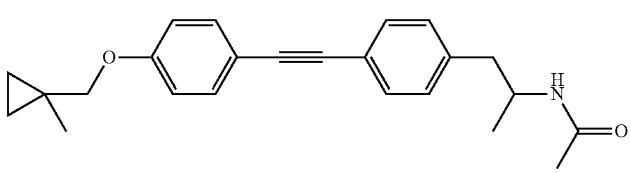 [SMILES: CC(=O)NC(C)Cc1ccc(C#Cc2ccc(OCC3(C)CC3)cc2)cc1] | 362 [M + H]⁺ | 2.44 (AA) |

-continued

| Ex. | Starting material | Structure | Mass spec result | HPLC retention time method |
|---|---|---|---|---|
| 9.12 | I74.1 | 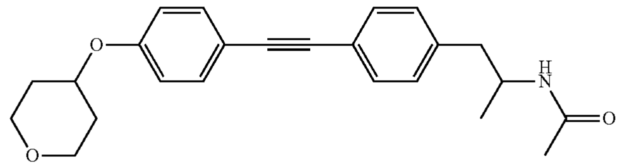 [SMILES: CC(=O)NC(C)Cc1ccc(C#Cc2ccc(OC3CCOCC3)cc2)cc1] | 378 [M + H]+ | 2.27 (AA) |
| 9.13 | I74.2 | 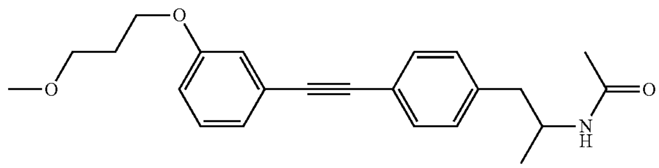 [SMILES: COCCCOc1cccc(C#Cc2ccc(CC(C)NC(C)=O)cc2)c1] | 366 [M + H]+ | 2.06 (AA) |
| 9.14 | I74.2 | 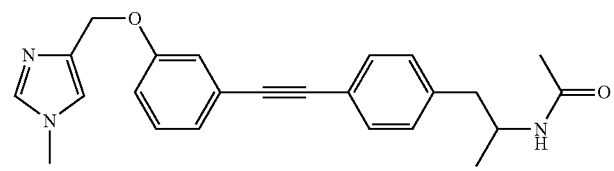 [SMILES: CC(=O)NC(C)Cc1ccc(C#Cc2cccc(OCc3cn(C)cn3)c2)cc1] | 388 [M + H]+ | 1.43 (AA) |
| 9.15 | I74.2 | 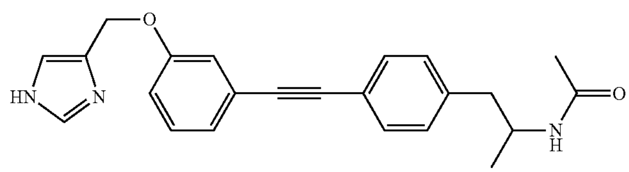 [SMILES: CC(=O)NC(C)Cc1ccc(C#Cc2cccc(OCc3c[nH]cn3)c2)cc1] | 374 [M + H]+ | 1.45 (AA) |
| 9.16 | I74.1 | 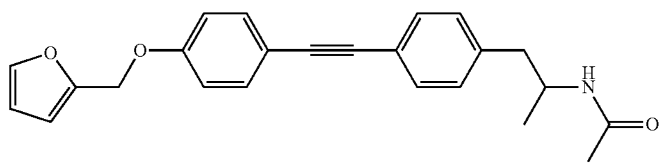 [SMILES: CC(=O)NC(C)Cc1ccc(C#Cc2ccc(OCc3ccco3)cc2)cc1] | 374 [M + H]+ | 2.04 (AA) |
| 9.17 | I74.1 | 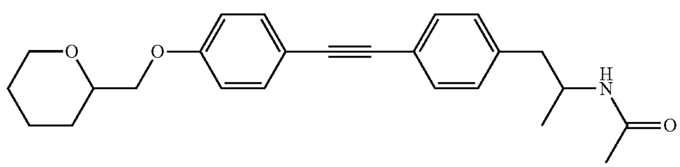 | 392 [M + H]+ | 2.00 (AA) |
| 9.18 | I74.1 | 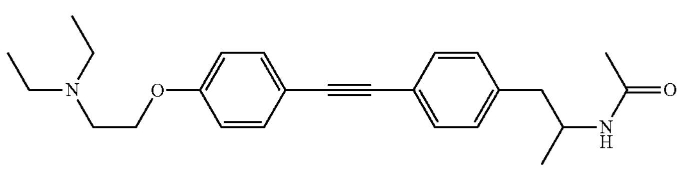 [SMILES: CCN(CC)CCOc1ccc(C#Cc2ccc(CC(C)NC(C)=O)cc2)cc1] | 393 [M + H]+ | 1.40 (AA) |
| 9.19 | I74.1 | 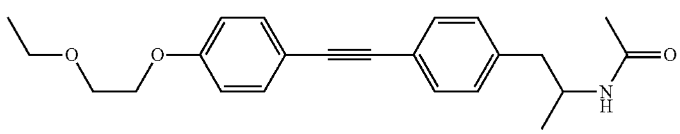 [SMILES: CCOCCOc1ccc(C#Cc2ccc(CC(C)NC(C)=O)cc2)cc1] | 366 [M + H]+ | 2.00 (AA) |
| 9.20 | I74.1 | 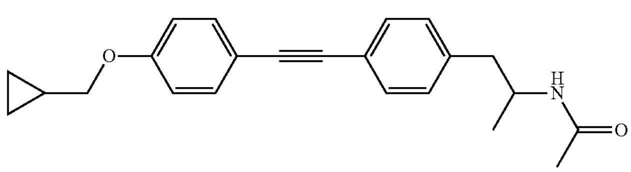 [SMILES: CC(=O)NC(C)Cc1ccc(C#Cc2ccc(OCC3CC3)cc2)cc1] | 348 [M + H]+ | 2.12 (AA) |

-continued

| Ex. | Starting material | Structure | Mass spec result | HPLC retention time method |
|---|---|---|---|---|
| 9.21 | I74.1 | 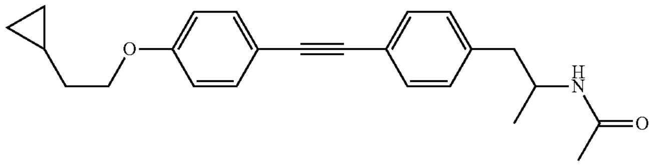 [SMILES: CC(=O)NC(C)Cc1ccc(C#Cc2ccc(OCCC3CC3)cc2)cc1] | 362 [M + H]+ | 2.20 (AA) |
| 9.22 | I74.1 | 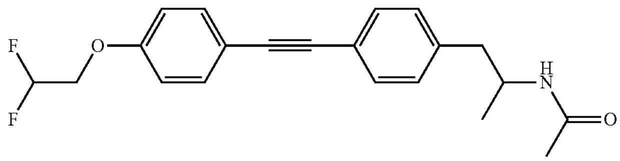 [SMILES: CC(=O)NC(C)Cc1ccc(C#Cc2ccc(OCC(F)F)cc2)cc1] | 358 [M + H]+ | 1.98 (AA) |
| 9.23 | I74.1 | 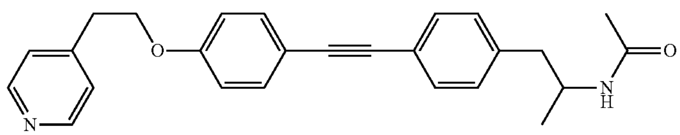 [SMILES: CC(=O)NC(C)Cc1ccc(C#Cc2ccc(OCCc3ccncc3)cc2)cc1] | 399 [M + H]+ | 1.46 (AA) |
| 9.24 | I74.1 | 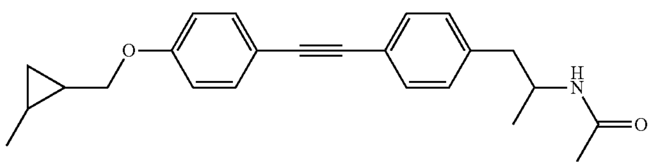 [SMILES: CC(=O)NC(C)Cc1ccc(C#Cc2ccc(OCC3CC3C)cc2)cc1] | 362 [M + H]+ | 2.17 (AA) |
| 9.25 | I74.1 | 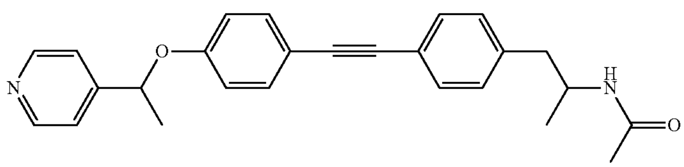 [SMILES: CC(=O)NC(C)Cc1ccc(C#Cc2ccc(OC(C)c3ccncc3)cc2)cc1] | 399 [M + H]+ | 1.53 (AA) |
| 9.26 | I74.1 | 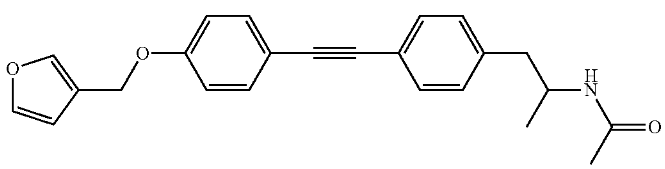 [SMILES: CC(=O)NC(C)Cc1ccc(C#Cc2ccc(OCc3ccoc3)cc2)cc1] | 374 [M + H]+ | 2.05 (AA) |
| 9.27 | I74.1 | 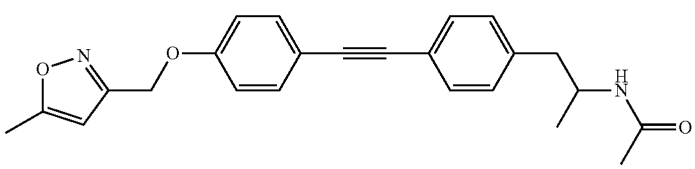 [SMILES: CC(=O)NC(C)Cc1ccc(C#Cc2ccc(OCc3cc(C)on3)cc2)cc1] | 389 [M + H]+ | 1.96 (AA) |
| 9.28 | I74.1 | 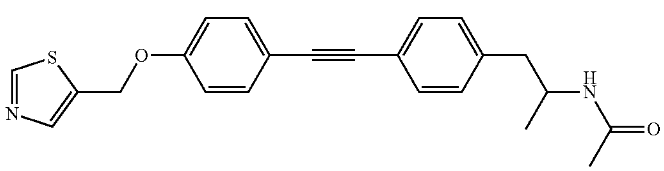 [SMILES: CC(=O)NC(C)Cc1ccc(C#Cc2ccc(OCc3cncs3)cc2)cc1] | 391 [M + H]+ | 1.91 (AA) |
| 9.29 | I74.1 | 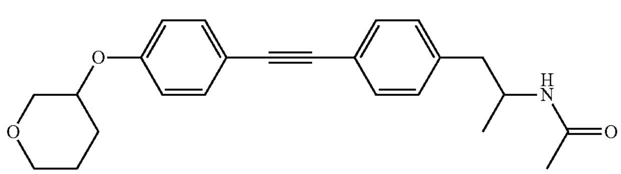 [SMILES: CC(=O)NC(C)Cc1ccc(C#Cc2ccc(OC3CCCOC3)cc2)cc1] | 378 [M + H]+ | 2.01 (AA) |

-continued

| Ex. | Starting material | Structure | Mass spec result | HPLC retention time method |
|---|---|---|---|---|
| 9.30 | I74.1 | 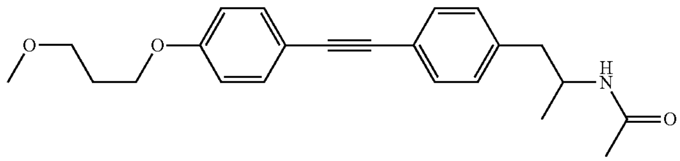 [SMILES: COCCCOc1ccc(C#Cc2ccc(CC(C)NC(C)=O)cc2)cc1] | 366 [M + H]+ | 2.03 (AA) |
| 9.31 | I74.1 | 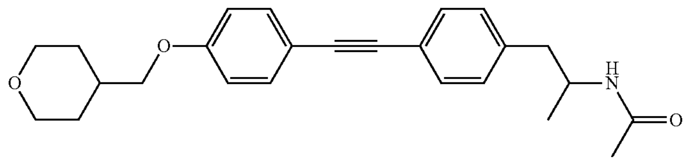 [SMILES: CC(=O)NC(C)Cc1ccc(C#Cc2ccc(OCC3CCOCC3)cc2)cc1] | 392 [M + H]+ | 2.04 (AA) |
| 9.32 | I74.1 | 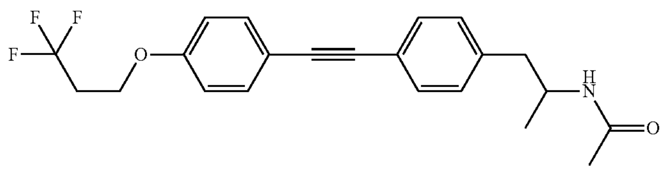 | 390 [M + H]+ | 2.05 (AA) |
| 9.33 | I74.1 | 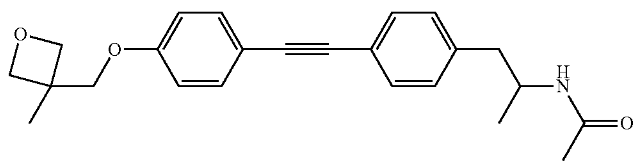 [SMILES: CC(=O)NC(C)Cc1ccc(C#Cc2ccc(OCC3(C)COC3)cc2)cc1] | 378 [M + H]+ | 1.97 (AA) |
| 9.34 | I74.1 | 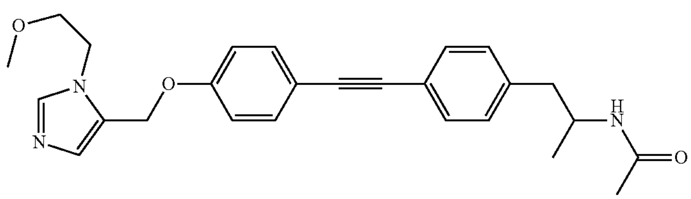 [SMILES: COCCn1cncc1COc1ccc(C#Cc2ccc(CC(C)NC(C)=O)cc2)cc1] | 432 [M + H]+ | 1.45 (AA) |
| 9.35 | I74.1 | 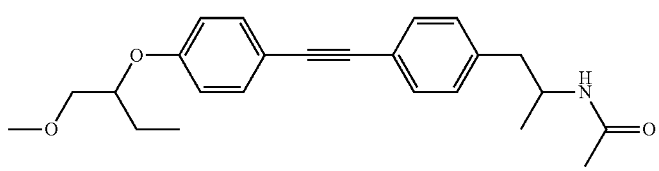 [SMILES: CCC(COC)Oc1ccc(C#Cc2ccc(CC(C)NC(C)=O)cc2)cc1] | 380 [M + H]+ | 2.07 (AA) |
| 9.36 | I74.1 | 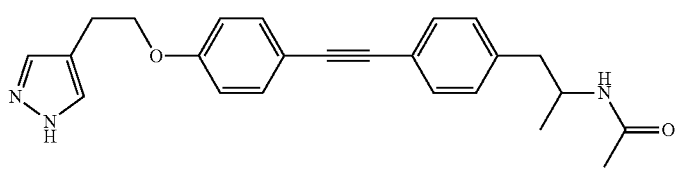 [SMILES: CC(=O)NC(C)Cc1ccc(C#Cc2ccc(OCCc3cn[nH]c3)cc2)cc1] | 388 [M + H]+ | 1.77 (AA) |
| 9.37 | I74.1 | 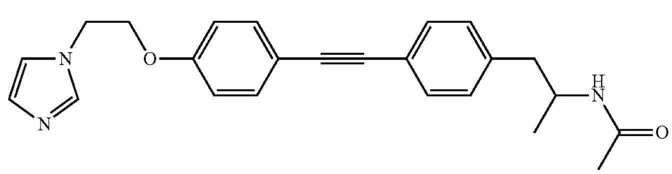 [SMILES: CC(=O)NC(C)Cc1ccc(C#Cc2ccc(OCCn3ccnc3)cc2)cc1] | 388 [M + H]+ | 1.38 (AA) |

-continued
| Ex. | Starting material | Structure | Mass spec result | HPLC retention time method |
|---|---|---|---|---|
| 9.38 | I74.1 | 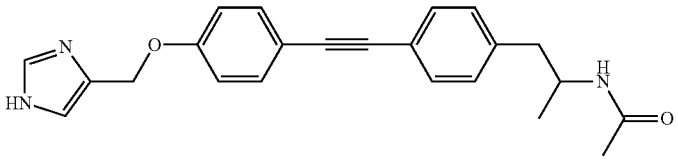 [SMILES: CC(=O)NC(C)Cc1ccc(C#Cc2ccc(OCc3c[nH]cn3)cc2)cc1] | 374 [M + H]+ | 1.41 (AA) |
| 9.39 | I74.1 | 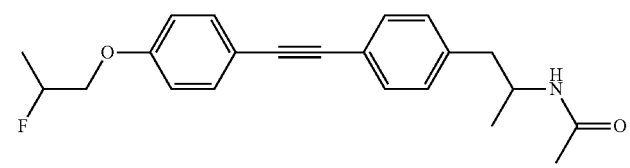 [SMILES: CC(=O)NC(C)Cc1ccc(C#Cc2ccc(OCC(C)F)cc2)cc1] | 354 [M + H]+ | 2.00 (AA) |
| 9.40 | I74.1 | 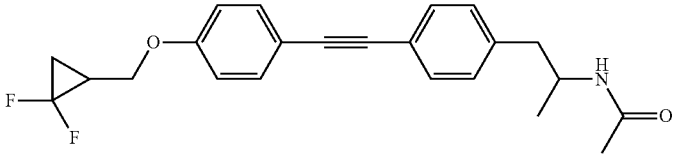 | 384 [M + H]+ | 2.04 (AA) |
| 9.41 | I74.1 | 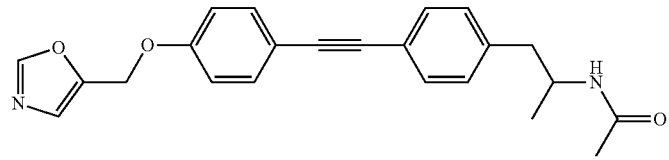 | 375 [M + H]+ | 1.76 (AA) |
| 9.42 | I74.1 | 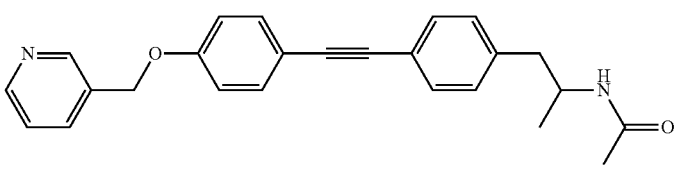 [SMILES: CC(=O)NC(C)Cc1ccc(C#Cc2ccc(OCc3cccnc3)cc2)cc1] | 385 [M + H]+ | 1.53 (AA) |

Example 10

Example 10.1

General Route

N-(1-(4-((4-(Pyrimidin-5-yloxy)phenyl)ethynyl)phenyl)propan-2-yl)acetamide

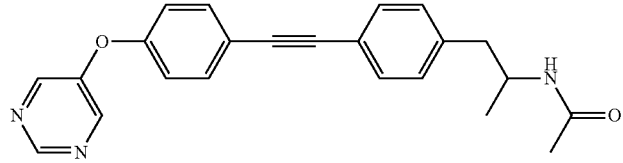 [SMILES: CC(=O)NC(C)Cc1ccc(C#Cc2ccc(Oc3cncnc3)cc2)cc1]

28.1 mg (0.14 mmol) 5-iodopyrimidine, 40.0 mg (0.14 mmol) N-(1-(4-((4-hydroxy-phenyl)ethynyl)phenyl)propan-2-yl)acetamide (I76.1), 1.30 mg (0.07 mmol) CuI, 1.9 mg (0.14 mmol) N,N-dimethylglycine hydrochloride and 58.7 mg (0.18 mmol) $Cs_2CO_3$ are added to 1 mL dioxane. The reaction mixture is stirred at 90° C. for 2 h then filtered through a plug of silica gel and washed with DMF. The filtrate is purified by HPLC (MeOH/$H_2$O/TFA).

$C_{23}H_{21}N_3O_2$ (M=371.4 g/mol)
ESI-MS: 372 [M+H]$^+$
$R_t$ (HPLC): 2.22 min (method M)

The following compounds are prepared analogously to example 10.1

In case of 10.3 the reaction mixture is stirred at 120° C. overnight.

| Ex. | Starting material | Structure | Mass spec result | HPLC retention time (method) |
|---|---|---|---|---|
| 10.1 | I76.1 | 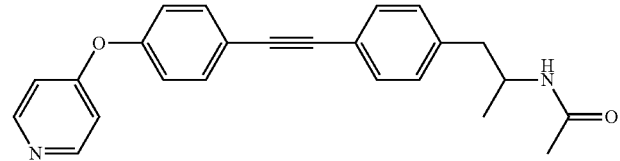 [SMILES: CC(=O)NC(C)Cc1ccc(C#Cc2ccc(Oc3ccncc3)cc2)cc1] | 372 [M + H]$^+$ | 2.22 (M) |
| 10.2 | I76.1 | 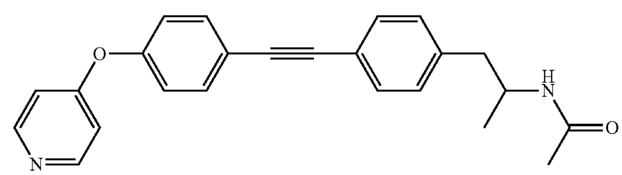 | 371 [M + H]$^+$ | 1.75 (T) |
| 10.3 | I76.2 | 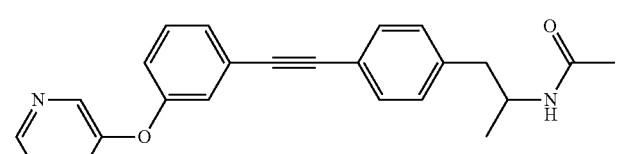 | 372 [M + H]+ | 2.24 (M) |

Example 11

Example 11.1

General Route

N-(1-(4-((2-((2-Methoxyethyl)(methyl)amino)pyrimidin-4-yl)ethynyl)phenyl)propan-2-yl)acetamide

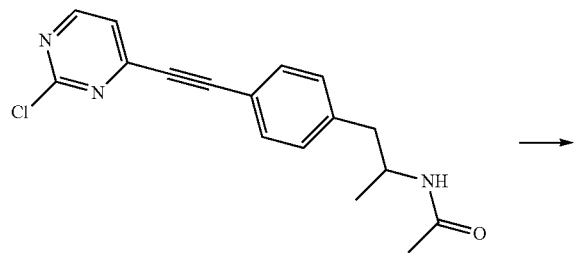

→

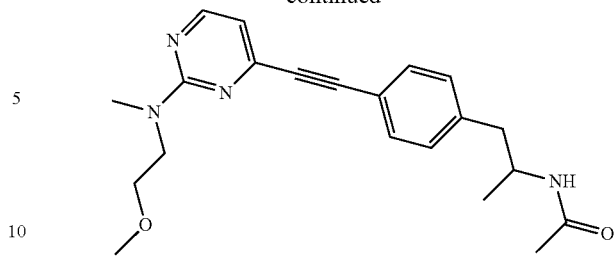

To 31.4 mg (0.10 mmol) N-(1-(4-((2-chloropyrimidin-4-yl)ethynyl)phenyl)propan-2-yl)-acetamide (170) and 25.8 μl (0.15 mmol) DIPEA in 1 mL NMP are added 26.7 mg (0.30 mmol) N-(2-methoxyethyl)methylamine. The reaction mixture is stirred in a sealed tube at 120° C. over night and purified by HPLC (MeOH/H$_2$O/TFA).

$C_{21}H_{26}N_4O_2$ (M=366.5 g/mol)
ESI-MS: 367 [M+H]$^+$
R$_t$ (HPLC): 2.19 min (method K)

The following compounds are prepared analogously to example 11.1

For example 11.49 4 eq. of the amine are used and the reaction conditions are 3 h at 100° C.

| Ex. | Start. material | Structure | Mass spec result | HPLC ret. time method |
|---|---|---|---|---|
| 11.1 | I70 | 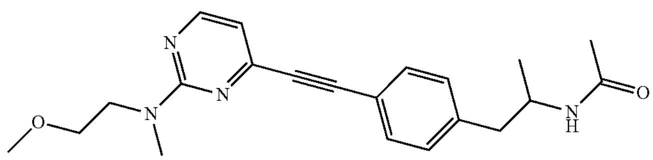 [SMILES: COCCN(C)c1nccc(C#Cc2ccc(CC(C)NC(C)=O)cc2)n1] | 367 [M + H]$^+$ | 2.19 (K) |
| 11.2 | I70 | 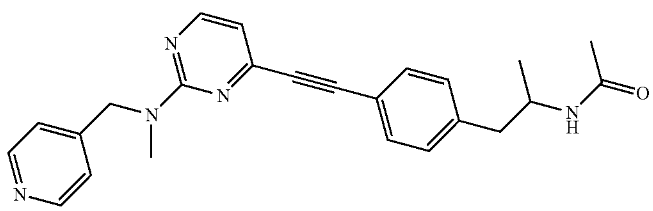 [SMILES: CC(=O)NC(C)Cc1ccc(C#Cc2ccnc(N(C)Cc3ccncc3)n2)cc1] | 400 [M + H]$^+$ | 1.82 (K) |
| 11.3 | I70 | 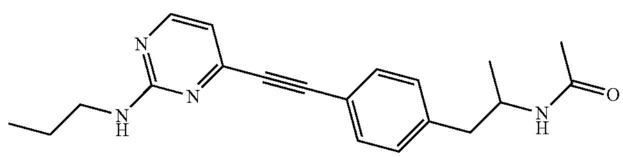 [SMILES: CCCNc1nccc(C#Cc2ccc(CC(C)NC(C)=O)cc2)n1] | 337 [M + H]$^+$ | 2.14 (K) |
| 11.4 | I70 | 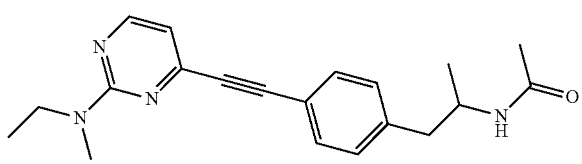 [SMILES: CCN(C)c1nccc(C#Cc2ccc(CC(C)NC(C)=O)cc2)n1] | 337 [M + H]$^+$ | 2.20 (K) |
| 11.5 | I70 | 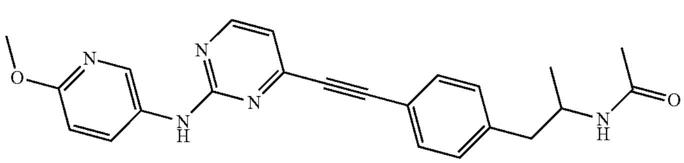 [SMILES: COc1ccc(Nc2nccc(C#Cc3ccc(CC(C)NC(C)=O)cc3)n2)cn1] | 402 [M + H]$^+$ | 2.18 (K) |

-continued

| Ex. | Start. material | Structure | Mass spec result | HPLC ret. time method |
|---|---|---|---|---|
| 11.6 | I70 | 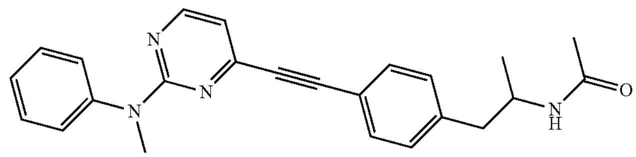 [SMILES: CC(=O)NC(C)Cc1ccc(C#Cc2ccnc(N(C)c3ccccc3)n2)cc1] | 385 [M + H]+ | 2.24 (K) |
| 11.7 | I70 | 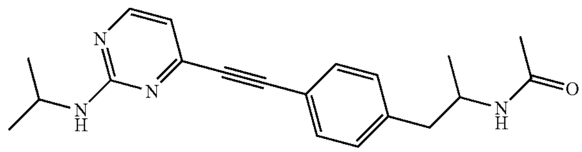 [SMILES: CC(=O)NC(C)Cc1ccc(C#Cc2ccnc(NC(C)C)n2)cc1] | 337 [M + H]+ | 2.10 (K) |
| 11.8 | I70 | 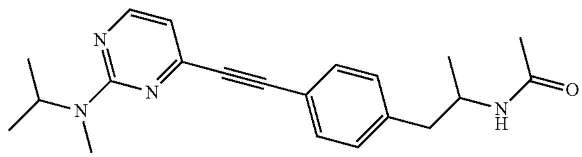 [SMILES: CC(=O)NC(C)Cc1ccc(C#Cc2ccnc(N(C)C(C)C)n2)cc1] | 351 [M + H]+ | 2.23 (K) |
| 11.9 | I70 | 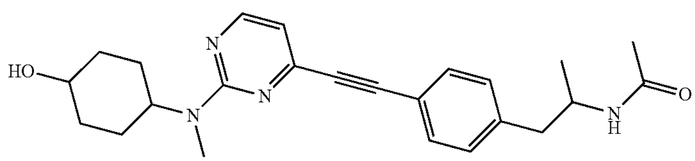 [SMILES: CC(=O)NC(C)Cc1ccc(C#Cc2ccnc(N(C)C3CCC(O)CC3)n2)cc1] | 407 [M + H]+ | 2.16 (K) |
| 11.10 | I70 | 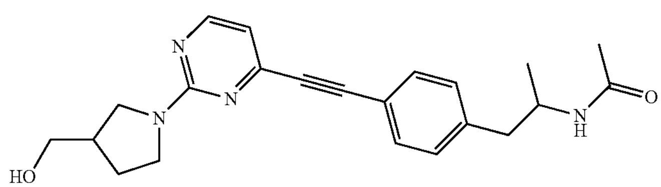 [SMILES: CC(=O)NC(C)Cc1ccc(C#Cc2ccnc(N3CCC(CO)C3)n2)cc1] | 379 [M + H]+ | 1.98 (K) |
| 11.11 | I70 | 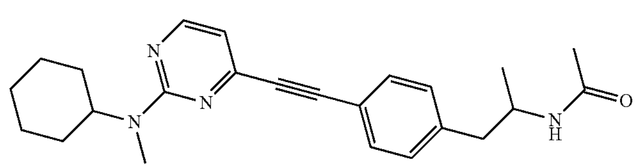 [SMILES: CC(=O)NC(C)Cc1ccc(C#Cc2ccnc(N(C)C3CCCCC3)n2)cc1] | 391 [M + H]+ | 2.34 (K) |
| 11.12 | I70 | 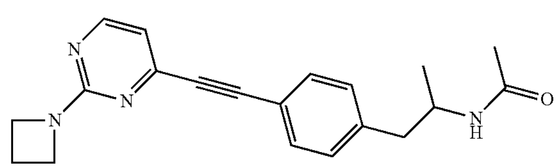 [SMILES: CC(=O)NC(C)Cc1ccc(C#Cc2ccnc(N3CCC3)n2)cc1] | 335 [M + H]+ | 2.09 (K) |
| 11.13 | I70 | 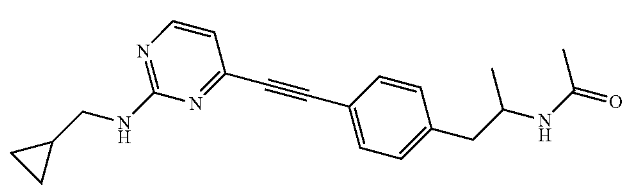 [SMILES: CC(=O)NC(C)Cc1ccc(C#Cc2ccnc(NCC3CC3)n2)cc1] | 349 [M + H]+ | 2.17 (K) |
| 11.14 | I70 | 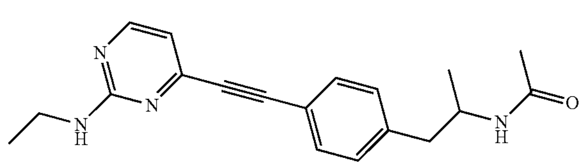 [SMILES: CCNc1nccc(C#Cc2ccc(CC(C)NC(C)=O)cc2)n1] | 323 [M + H]+ | 2.04 (K) |

-continued
| Ex. | Start. material | Structure | Mass spec result | HPLC ret. time method |
|---|---|---|---|---|
| 11.15 | I70 | 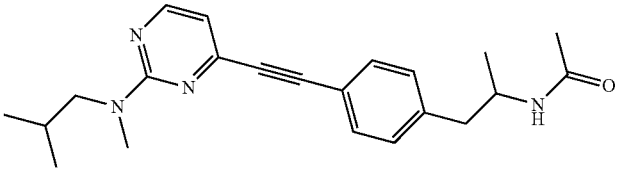 | 365 [M + H]+ | 2.30 (K) |
| 11.16 | I70 | 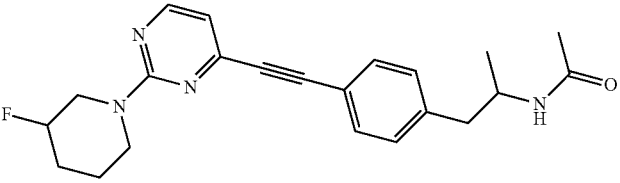 [SMILES: CC(=O)NC(C)Cc1ccc(C#Cc2ccnc(N3CCCC(F)C3)n2)cc1] | 381 [M + H]+ | 2.22 (K) |
| 11.17 | I70 | 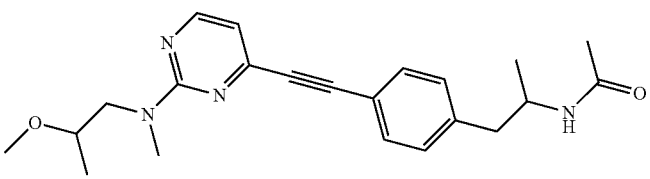 [SMILES: COC(C)CN(C)c1nccc(C#Cc2ccc(CC(C)NC(C)=O)cc2)n1] | 381 [M + H]+ | 2.20 (K) |
| 11.18 | I70 | 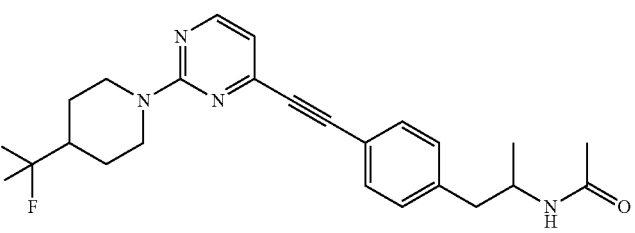 | 431 [M + H]+ | 2.31 (K) |
| 11.19 | I70 | 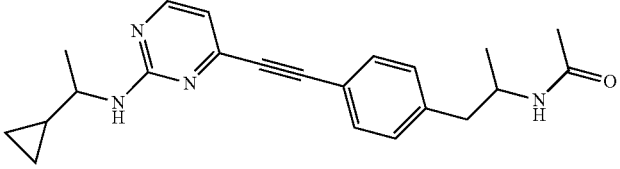 [SMILES: CC(=O)NC(C)Cc1ccc(C#Cc2ccnc(NC(C)C3CC3)n2)cc1] | 363 [M + H]+ | 2.16 (K) |
| 11.20 | I70 | 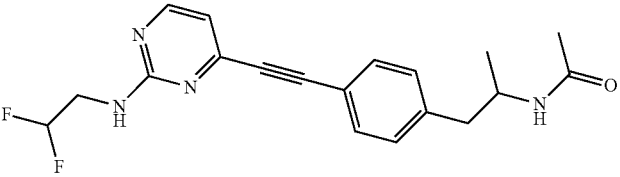 [SMILES: CC(=O)NC(C)Cc1ccc(C#Cc2ccnc(NCC(F)F)n2)cc1] | 358 [M + H]+ | 2.15 (K) |
| 11.21 | I70 | 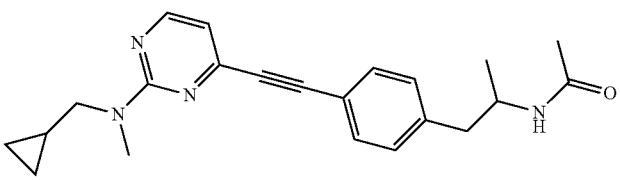 [SMILES: CC(=O)NC(C)Cc1ccc(C#Cc2ccnc(N(C)CC3CC3)n2)cc1] | 363 [M + H]+ | 2.24 (K) |
| 11.22 | I70 | 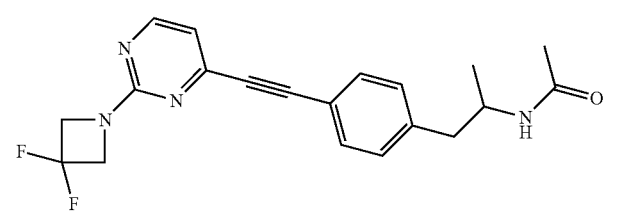 [SMILES: CC(=O)NC(C)Cc1ccc(C#Cc2ccnc(N3CC(F)(F)C3)n2)cc1] | 371 [M + H]+ | 2.20 (K) |

-continued

| Ex. | Start. material | Structure | Mass spec result | HPLC ret. time method |
|---|---|---|---|---|
| 11.23 | I70 | 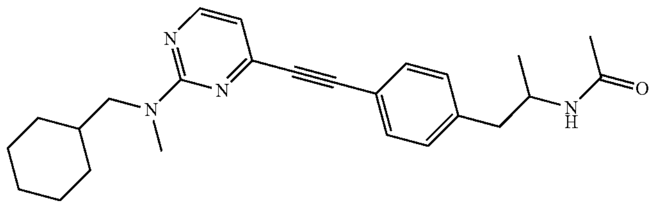 [SMILES: CC(=O)NC(C)Cc1ccc(C#Cc2ccnc(N(C)CC3CCCCC3)n2)cc1] | 405 [M + H]+ | 2.38 (K) |
| 11.24 | I70 | 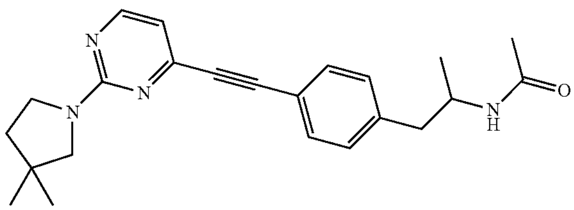 [SMILES: CC(=O)NC(C)Cc1ccc(C#Cc2ccnc(N3CCC(C)(C)C3)n2)cc1] | 377 [M + H]+ | 2.23 (K) |
| 11.25 | I70 | 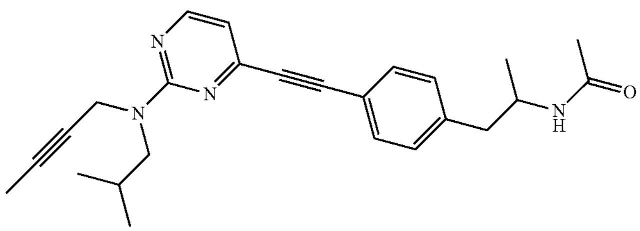 [SMILES: CC#CCN(CC(C)C)c1nccc(C#Cc2ccc(CC(C)NC(C)=O)cc2)n1] | 403 [M + H]+ | 2.34 (K) |
| 11.26 | I70 | 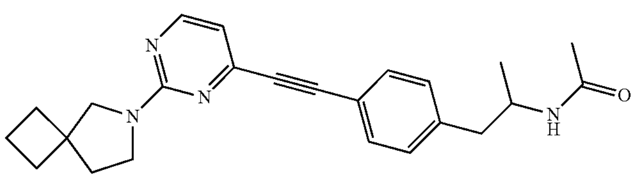 [SMILES: CC(=O)NC(C)Cc1ccc(C#Cc2ccnc(N3CCC4(CCC4)C3)n2)cc1] | 389 [M + H]+ | 2.25 (K) |
| 11.27 | I70 | 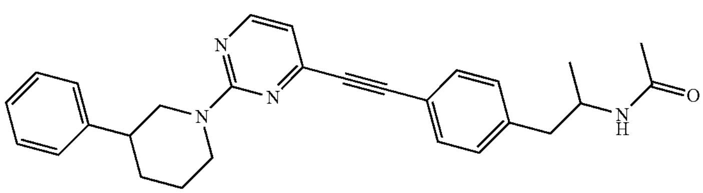 [SMILES: CC(=O)NC(C)Cc1ccc(C#Cc2ccnc(N3CCCC(c4ccccc4)C3)n2)cc1] | 439 [M + H]+ | 2.39 (K) |
| 11.28 | I70 | 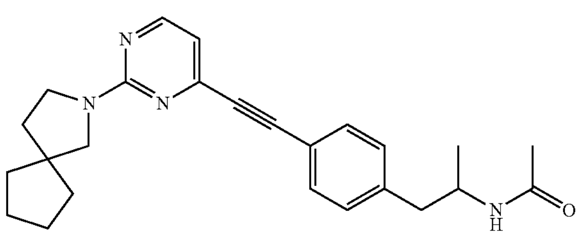 [SMILES: CC(=O)NC(C)Cc1ccc(C#Cc2ccnc(N3CCC4(CCCC4)C3)n2)cc1] | 403 [M + H]+ | 2.29 (K) |
| 11.29 | I70 | 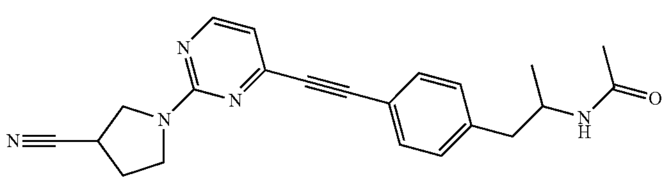 [SMILES: CC(=O)NC(C)Cc1ccc(C#Cc2ccnc(N3CCC(C#N)C3)n2)cc1] | 374 [M + H]+ | 2.12 (K) |

-continued

| Ex. | Start. material | Structure | Mass spec result | HPLC ret. time method |
|---|---|---|---|---|
| 11.30 | I70 | 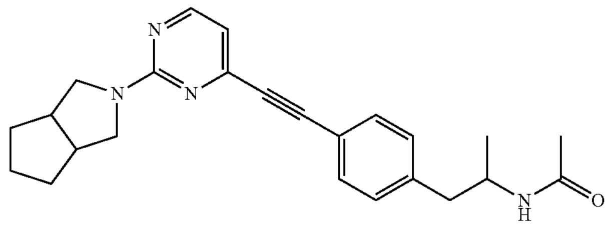 [SMILES: CC(=O)NC(C)Cc1ccc(C#Cc2ccnc(N3CC4CCCC4C3)n2)cc1] | 388 [M + H]+ | 2.28 (K) |
| 11.31 | I70 | 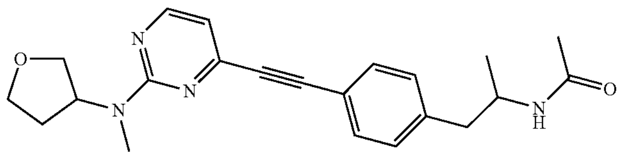 [SMILES: CC(=O)NC(C)Cc1ccc(C#Cc2ccnc(N(C)C3CCOC3)n2)cc1] | 379 [M + H]+ | 2.17 (K) |
| 11.32 | I70 | 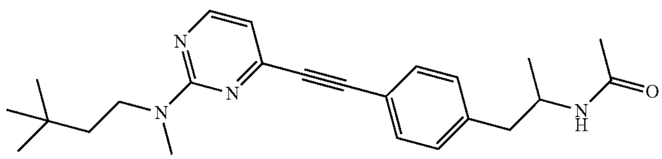 [SMILES: CC(=O)NC(C)Cc1ccc(C#Cc2ccnc(N(C)CCC(C)(C)C)n2)cc1] | 393 [M + H]+ | 2.37 (K) |
| 11.33 | I70 | 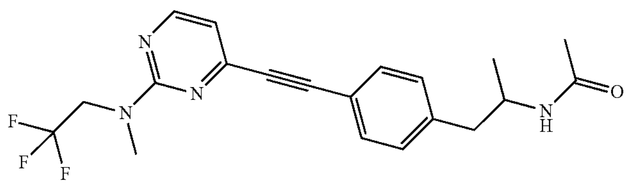 [SMILES: CC(=O)NC(C)Cc1ccc(C#Cc2ccnc(N(C)CC(F)(F)F)n2)cc1] | 391 [M + H]+ | 2.25 (K) |
| 11.34 | I70 | 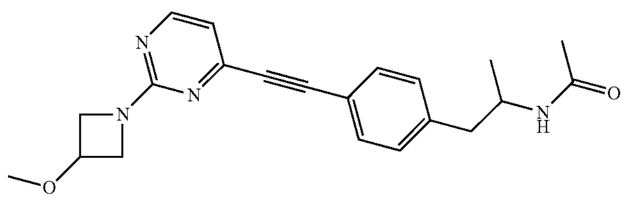 [SMILES: COC1CN(c2nccc(C#Cc3ccc(CC(C)NC(C)=O)cc3)n2)C1] | 365 [M + H]+ | 2.12 (K) |
| 11.35 | I70 | 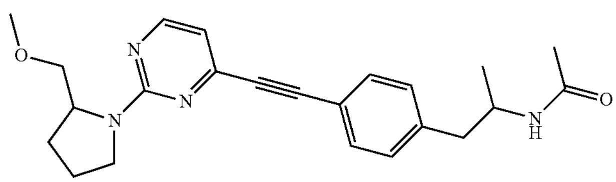 [SMILES: COCC1CCCN1c1nccc(C#Cc2ccc(CC(C)NC(C)=O)cc2)n1] | 393 [M + H]+ | 2.22 (K) |
| 11.36 | I70 | 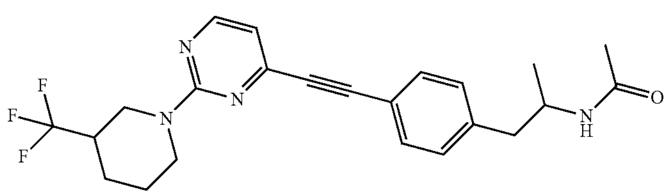 [SMILES: CC(=O)NC(C)Cc1ccc(C#Cc2ccnc(N3CCCC(C(F)(F)F)C3)n2)cc1] | 431 [M + H]+ | 2.33 (K) |
| 11.37 | I70 | 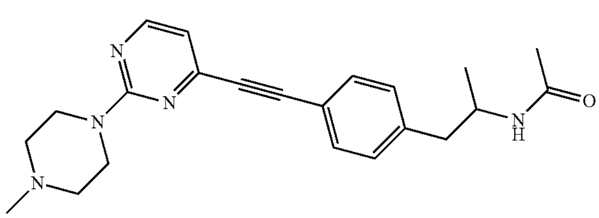 [SMILES: CC(=O)NC(C)Cc1ccc(C#Cc2ccnc(N3CCN(C)CC3)n2)cc1] | 378 [M + H]+ | 1.80 (K) |

-continued
| Ex. | Start. material | Structure | Mass spec result | HPLC ret. time method |
|---|---|---|---|---|
| 11.38 | I70 | 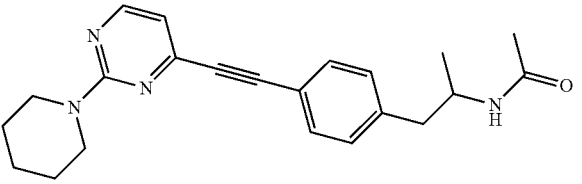 | 363 [M + H]+ | 2.33 (K) |
| 11.39 | I70 | 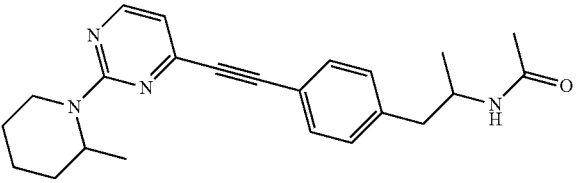 [SMILES: CC(=O)NC(C)Cc1ccc(C#Cc2ccnc(N3CCCCC3C)n2)cc1] | 377 [M + H]+ | 2.34 (K) |
| 11.40 | I70 | 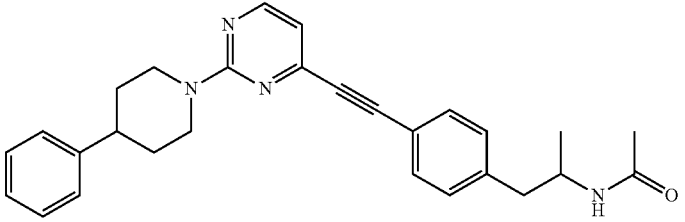 [SMILES: CC(=O)NC(C)Cc1ccc(C#Cc2ccnc(N3CCC(c4ccccc4)CC3)n2)cc1] | 439 [M + H]+ | 2.42 (K) |
| 11.41 | I70 | 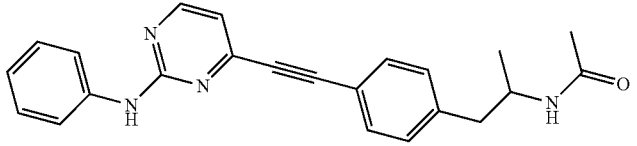 [SMILES: CC(=O)NC(C)Cc1ccc(C#Cc2ccnc(Nc3ccccc3)n2)cc1] | 371 [M + H]+ | 2.25 (K) |
| 11.42 | I70 | 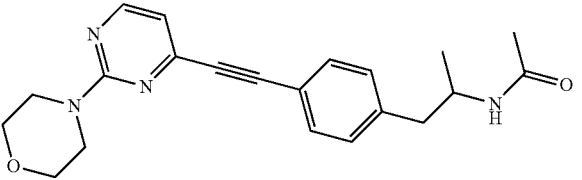 [SMILES: CC(=O)NC(C)Cc1ccc(C#Cc2ccnc(N3CCOCC3)n2)cc1] | 365 [M + H]+ | 2.22 (K) |
| 11.43 | I70 | 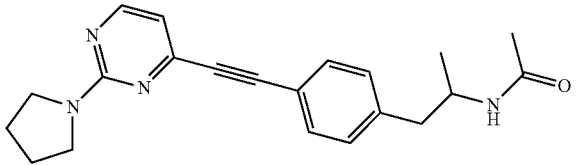 [SMILES: CC(=O)NC(C)Cc1ccc(C#Cc2ccnc(N3CCCC3)n2)cc1] | 349 [M + H]+ | 2.14 (K) |
| 11.44 | I70 | 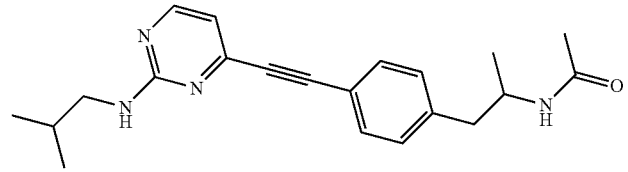 [SMILES: CC(=O)NC(C)Cc1ccc(C#Cc2ccnc(NCC(C)C)n2)cc1] | 351 [M + H]+ | 2.19 (K) |
| 11.45 | I70 | 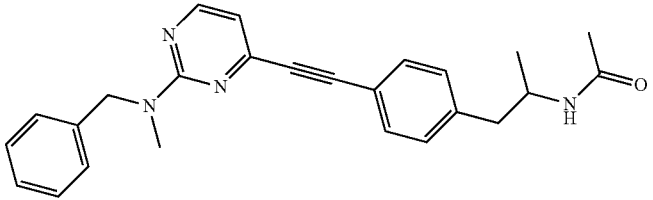 [SMILES: CC(=O)NC(C)Cc1ccc(C#Cc2ccnc(N(C)Cc3ccccc3)n2)cc1] | 399 [M + H]+ | 2.32 (K) |

-continued

| Ex. | Start. material | Structure | Mass spec result | HPLC ret. time method |
|---|---|---|---|---|
| 11.46 | I70 | 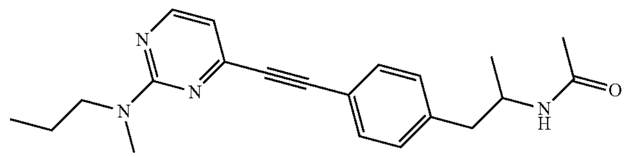 [SMILES: CCCN(C)c1nccc(C#Cc2ccc(CC(C)NC(C)=O)cc2)n1] | 351 [M + H]+ | 2.27 (K) |
| 11.47 | I70 | 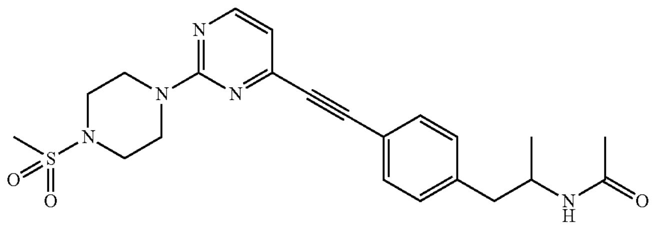 [SMILES: CC(=O)NC(C)Cc1ccc(C#Cc2ccnc(N3CCN(S(C)(=O)=O)CC3)n2)cc1] | 464 [M + Na]+ | 2.13 (K) |
| 11.48 | I70 | 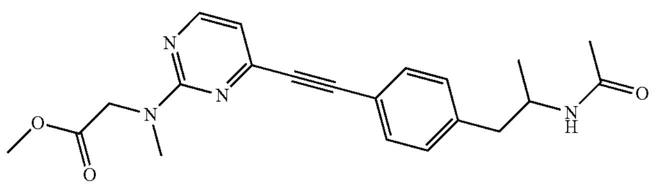 [SMILES: COC(=O)CN(C)c1nccc(C#Cc2ccc(CC(C)NC(C)=O)cc2)n1] | 381 [M + H]+ | 2.18 (K) |
| 11.49 | I70 | 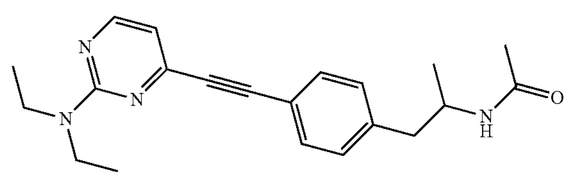 [SMILES: CCN(CC)c1nccc(C#Cc2ccc(CC(C)NC(C)=O)cc2)n1] | 351 [M + H]+ | 2.23 (M) |

Example 12

Example 12.1

General Route

N-(1-(4-((2-ethoxypyrimidin-4-yl)ethynyl)phenyl)propan-2-yl)acetamide

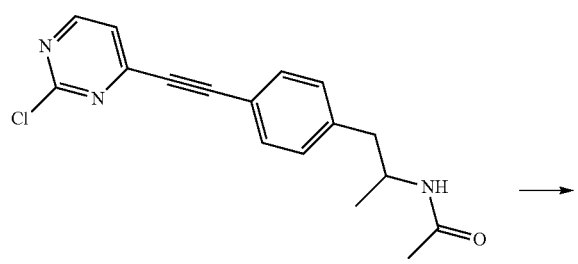

→

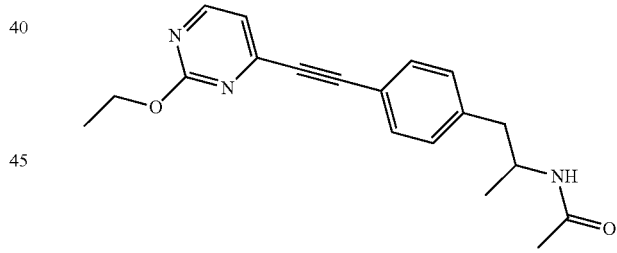

25 mg (0.08 mmol) N-(1-(4-((2-chloropyrimidin-4-yl)ethynyl)phenyl)propan-2-yl)acetamide (I70) in 1.0 mL dioxane are added to 9.3 µl (0.16 mmol) ethanol in 0.5 ml dioxane and cooled down to 0° C. 10 mg (0.24 mmol) NaH are added and the mixture is stirred at r.t. over night. The reaction is quenched with water and the solvent is evaporated in vacuo. The residue is purified by HPLC (MeOH/H$_2$O/TFA).

$C_{19}H_{21}N_3O_2$ (M=351.5 g/mol)
ESI-MS: 353 [M+H]+
R$_t$ (HPLC): 1.99 min (method K)

The following compounds are prepared analogously to example 12.1

For example 12.19 the reaction mixture is stirred at 80° C. for 5 h.

For examples 12.58-68 the reaction mixture is stirred at r.t. for 3 h.

For example 12.66 the commercially available sodium alkoxide is used.

| Ex. | Start. material | Structure | Mass spec result | HPLC ret. time (method) |
|---|---|---|---|---|
| 12.1 | I70 | 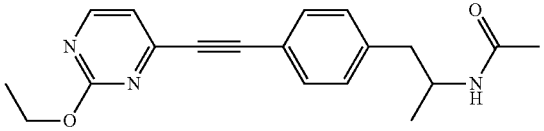 | 352 [M + H]+ | 1.99 (K) |
| 12.2 | I70 | 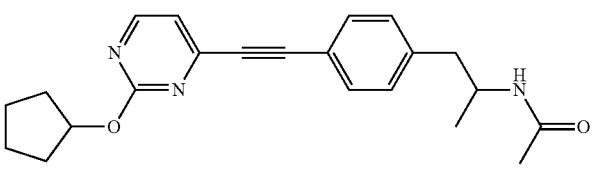 [SMILES: CC(=O)NC(C)Cc1ccc(C#Cc2ccnc(OC3CCCC3)n2)cc1] | 364 [M + H]+ | 2.09 (K) |
| 12.3 | I70 | 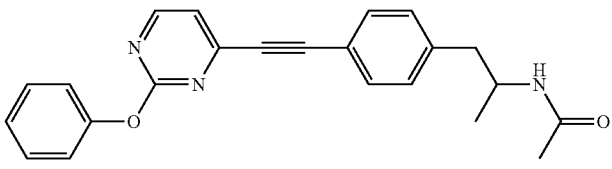 [SMILES: CC(=O)NC(C)Cc1ccc(C#Cc2ccnc(Oc3ccccc3)n2)cc1] | 372 [M + H]+ | 2.00 (K) |
| 12.4 | I70 | 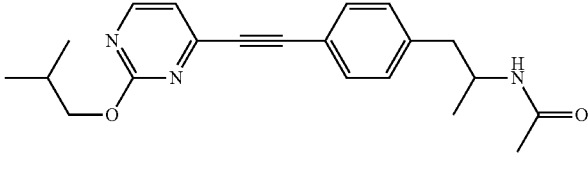 [SMILES: CC(=O)NC(C)Cc1ccc(C#Cc2ccnc(OCC(C)C)n2)cc1] | 352 [M + H]+ | 2.08 (K) |
| 12.5 | I70 | 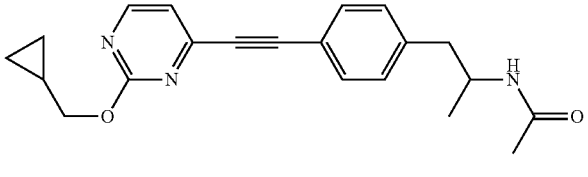 | 350 [M + H]+ | 2.03 (K) |
| 12.6 | I70 | 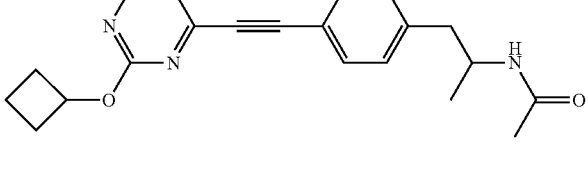 | 350 [M + H]+ | 2.05 (K) |
| 12.7 | I70 | 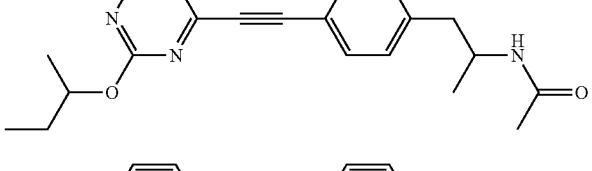 | 352 [M + H]+ | 2.06 (K) |
| 12.8 | I70 | 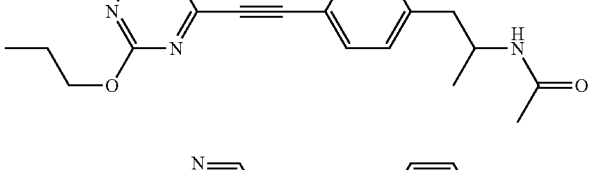 | 338 [M + H]+ | 2.03 (K) |
| 12.9 | I69.1 | 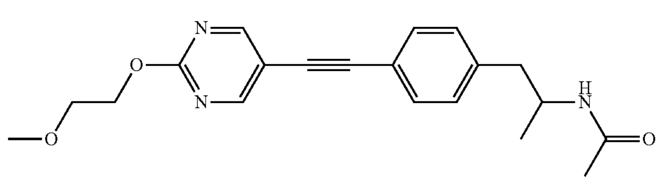 [SMILES: COCCOc1ncc(C#Cc2ccc(CC(C)NC(C)=O)cc2)cn1] | 354 [M + H]+ | 1.97 (K) |

-continued

| Ex. | Start. material | Structure | Mass spec result | HPLC ret. time (method) |
|---|---|---|---|---|
| 12.10 | I69.1 | 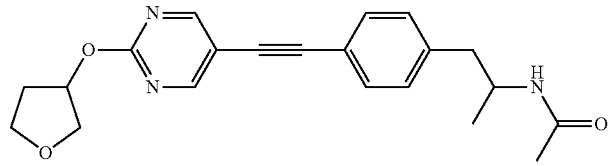 | 366 [M + H]⁺ | 1.97 (K) |
| 12.11 | I69.1 | 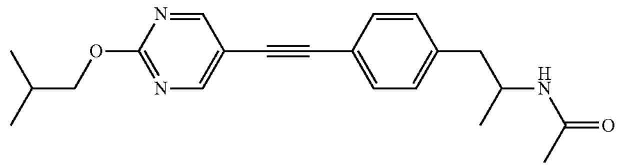 | 352 [M + H]⁺ | 2.12 (K) |
| 12.12 | I69.1 | 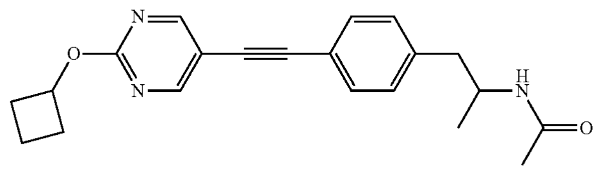 | 350 [M + H]⁺ | 2.10 (K) |
| 12.13 | I69.1 | 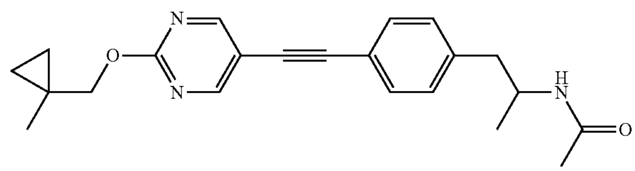 [SMILES: CC(=O)NC(C)Cc1ccc(C#Cc2cnc(OCC3(C)CC3)nc2)cc1] | 364 [M + H]⁺ | 2.12 (K) |
| 12.14 | I69.1 | 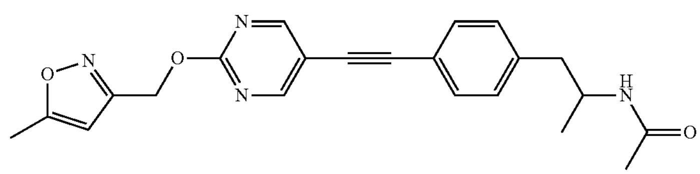 [SMILES: CC(=O)NC(C)Cc1ccc(C#Cc2cnc(OCc3cc(C)on3)nc2)cc1] | 391 [M + H]⁺ | 1.97 (K) |
| 12.15 | I69.1 | 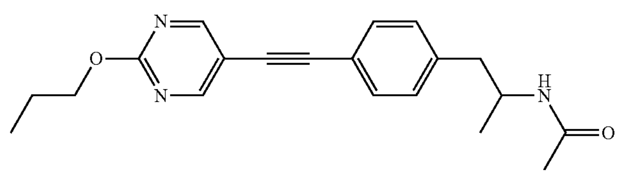 [SMILES: CCCOc1ncc(C#Cc2ccc(CC(C)NC(C)=O)cc2)cn1] | 338 [M + H]⁺ | 2.08 (K) |
| 12.16 | I69.1 | 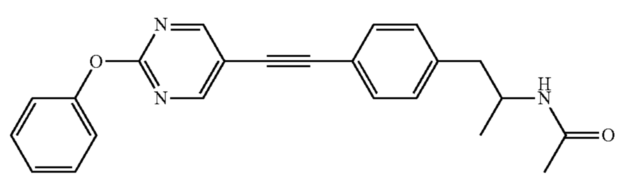 [SMILES: CC(=O)NC(C)Cc1ccc(C#Cc2cnc(Oc3ccccc3)nc2)cc1] | 372 [M + H]⁺ | 2.05 (K) |
| 12.17 | I69.1 | 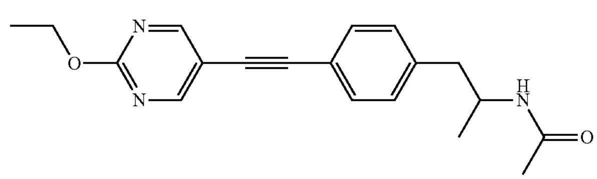 [SMILES: CCOc1ncc(C#Cc2ccc(CC(C)NC(C)=O)cc2)cn1] | 324 [M + H]⁺ | 2.03 (K) |

-continued

| Ex. | Start. material | Structure | Mass spec result | HPLC ret. time (method) |
|---|---|---|---|---|
| 12.18 | I70 | 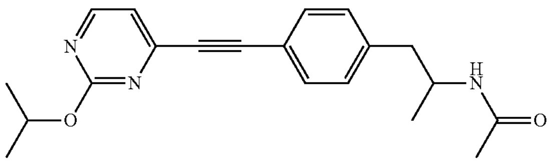 [SMILES: CC(=O)NC(C)Cc1ccc(C#Cc2ccnc(OC(C)C)n2)cc1] | 338 [M + H]⁺ | 2.27 (M) |
| 12.19 | I69.1 | 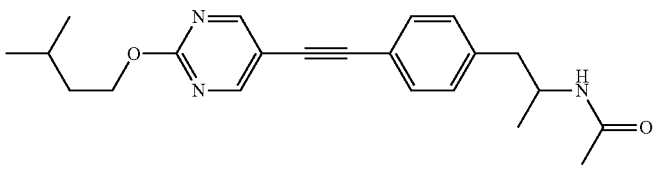 [SMILES: CC(=O)NC(C)Cc1ccc(C#Cc2cnc(OCCC(C)C)nc2)cc1] | 366 [M + H]⁺ | 2.29 (T) |
| 12.20 | I69.1 | 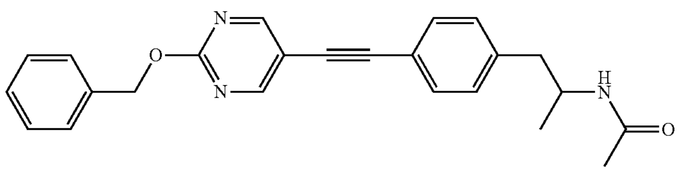 | 386 [M + H]⁺ | 2.30 (M) |
| 12.21 | I69.1 | 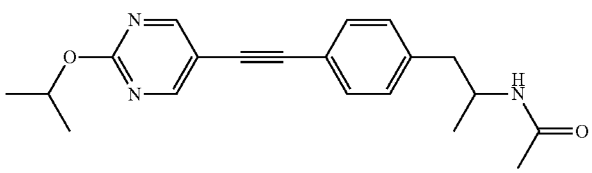 | 338 [M + H]⁺ | 2.27 (M) |
| 12.22 | I69.3 | 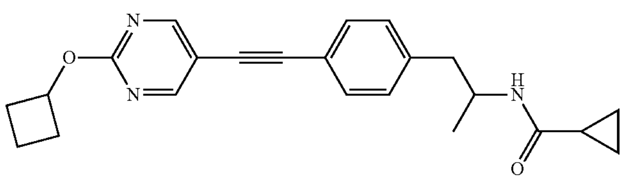 | 376 [M + H]⁺ | 2.17 (K) |
| 12.23 | I69.3 | 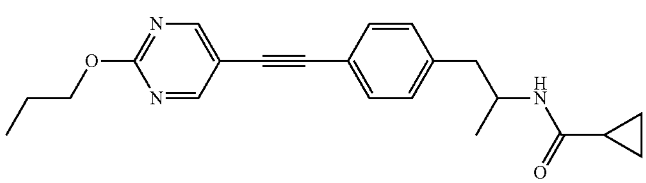 [SMILES: CCCOc1ncc(C#Cc2ccc(CC(C)NC(=O)C3CC3)cc2)cn1] | 364 [M + H]⁺ | 2.14 (K) |
| 12.24 | I69.3 | 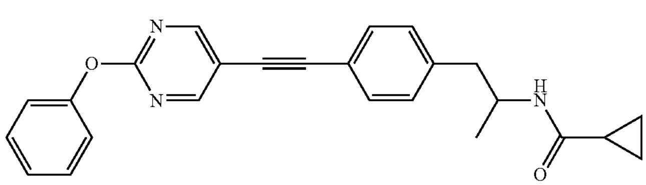 [SMILES: CC(Cc1ccc(C#Cc2cnc(Oc3ccccc3)nc2)cc1)NC(=O)C1CC1] | 398 [M + H]⁺ | 2.11 (K) |
| 12.25 | I69.3 | 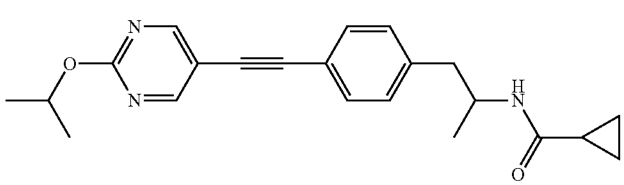 [SMILES: CC(Cc1ccc(C#Cc2cnc(OC(C)C)nc2)cc1)NC(=O)C1CC1] | 364 [M + H]⁺ | 2.12 (K) |

-continued
| Ex. | Start. material | Structure | Mass spec result | HPLC ret. time (method) |
|---|---|---|---|---|
| 12.26 | I69.4 | 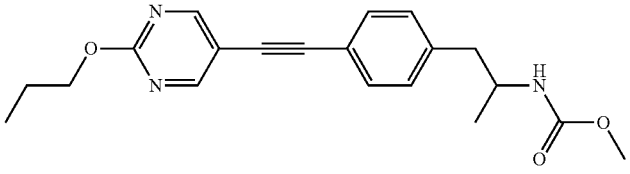 [SMILES: CCCOc1ncc(C#Cc2ccc(CC(C)NC(=O)OC)cc2)cn1] | 354 [M + H]+ | 2.14 (K) |
| 12.27 | I69.4 | 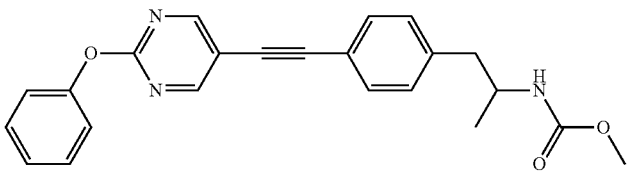 [SMILES: COC(=O)NC(C)Cc1ccc(C#Cc2cnc(Oc3ccccc3)nc2)cc1] | 388 [M + H]+ | 2.1 (K) |
| 12.28 | I69.4 | 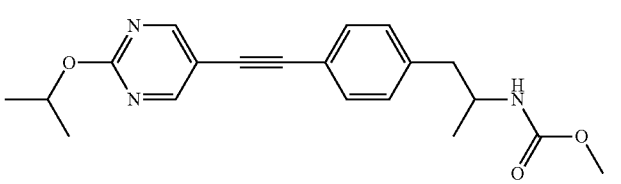 [SMILES: COC(=O)NC(C)Cc1ccc(C#Cc2cnc(OC(C)C)nc2)cc1] | 354 [M + H]+ | 2.13 (K) |
| 12.29 | I69.2 | 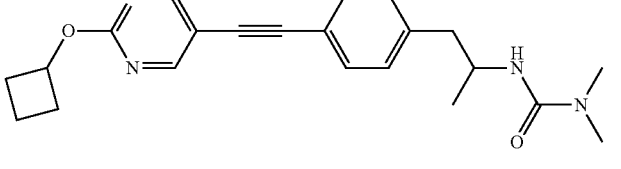 | 379 [M + H]+ | 2.30 (AA) |
| 12.30 | I69.2 | 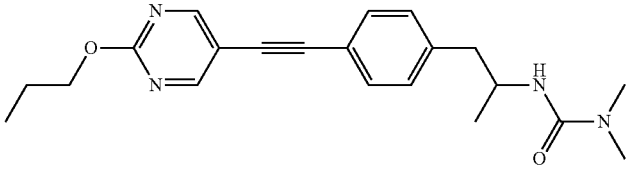 | 367 [M + H]+ | 2.25 (AA) |
| 12.31 | I69.1 | 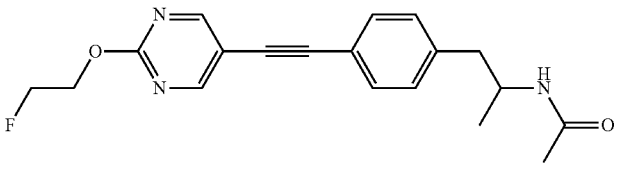 | 342 [M + H]+ | 2.00 (K) |
| 12.32 | I69.1 | 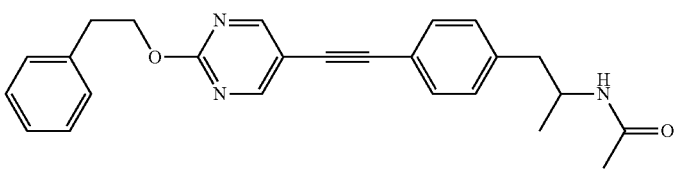 [SMILES: CC(=O)NC(C)Cc1ccc(C#Cc2cnc(OCCc3ccccc3)nc2)cc1] | 400 [M + H]+ | 2.18 (K) |
| 12.33 | I69.1 | 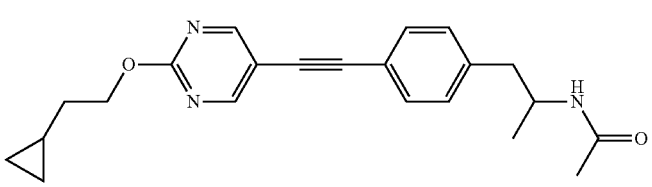 [SMILES: CC(=O)NC(C)Cc1ccc(C#Cc2cnc(OCCC3CC3)nc2)cc1] | 364 [M + H]+ | 2.18 (K) |

-continued
| Ex. | Start. material | Structure | Mass spec result | HPLC ret. time (method) |
|---|---|---|---|---|
| 12.34 | I69.1 | 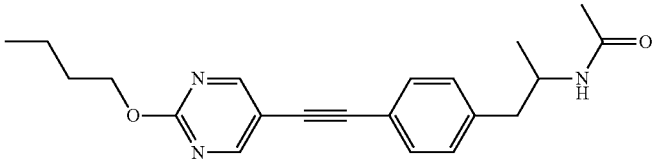 | 352 [M + H]+ | 2.07 (K) |
| 12.35 | I69.1 | 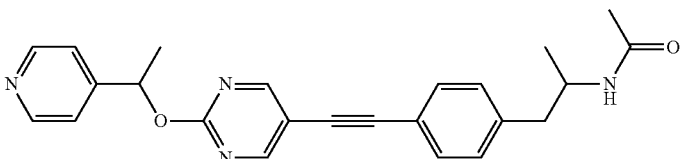 | 401 [M + H]+ | 1.71 (K) |
| 12.36 | I69.1 | 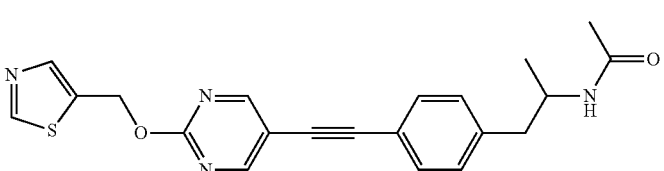 | 393 [M + H]+ | 1.99 (K) |
| 12.37 | I69.1 | 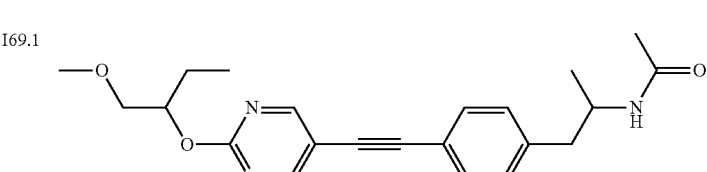 | 382 [M + H]+ | 2.02 (K) |
| 12.38 | I69.1 | 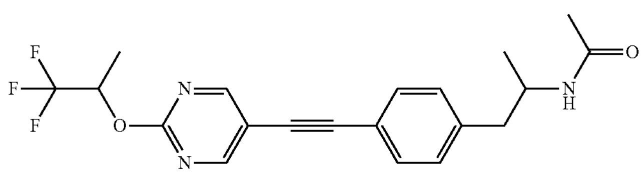 | 392 [M + H]+ | 2.11 (K) |
| 12.39 | I69.1 | 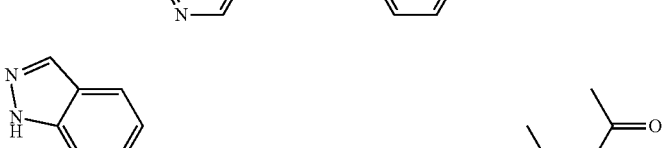 | 412 [M + H]+ | 2.01 (K) |
| 12.40 | I69.1 | 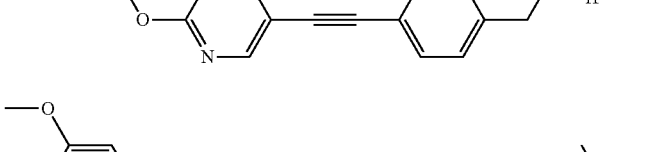 | 403 [M + H]+ | 2.07 (K) |
| 12.41 | I69.1 | 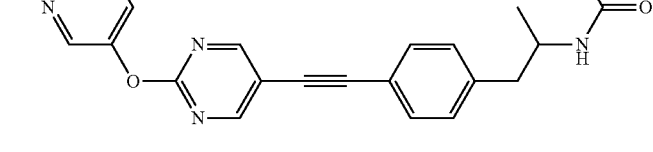 | 356 [M + H]+ | 2.04 (K) |

-continued

| Ex. | Start. material | Structure | Mass spec result | HPLC ret. time (method) |
|---|---|---|---|---|
| 12.42 | I69.1 | 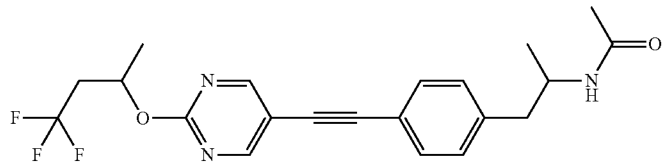 [SMILES: CC(=O)NC(C)Cc1ccc(C#Cc2cnc(OC(C)CC(F)(F)F)nc2)cc1] | 406 [M + H]+ | 2.09 (K) |
| 12.43 | I69.1 | 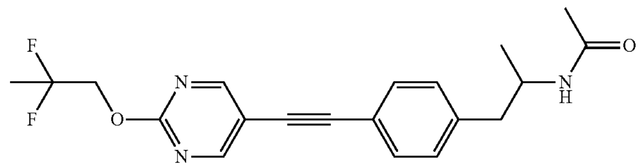 [SMILES: CC(=O)NC(C)Cc1ccc(C#Cc2cnc(OCC(C)(F)F)nc2)cc1] | 374 [M + H]+ | 2.07 (K) |
| 12.44 | I69.1 | 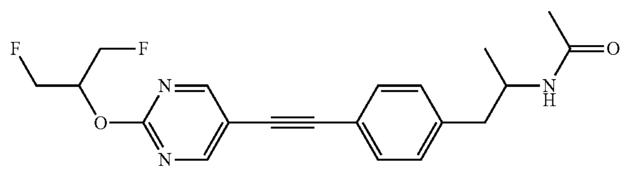 [SMILES: CC(=O)NC(C)Cc1ccc(C#Cc2cnc(OC(CF)CF)nc2)cc1] | 374 [M + H]+ | 2.06 (K) |
| 12.45 | I69.1 | 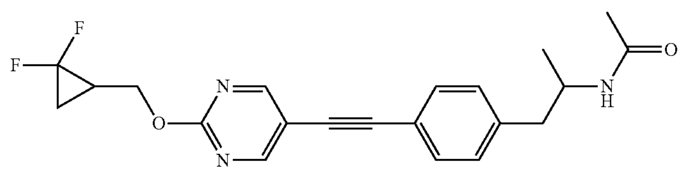 [SMILES: CC(=O)NC(C)Cc1ccc(C#Cc2cnc(OCC3CC3(F)F)nc2)cc1] | 386 [M + H]+ | 2.07 (K) |
| 12.46 | I69.1 | 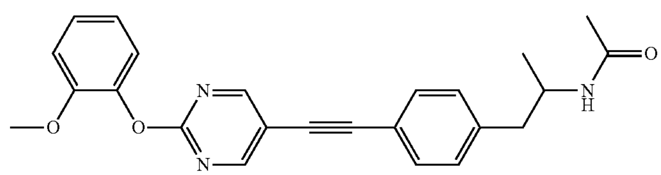 [SMILES: COc1ccccc1Oc1ncc(C#Cc2ccc(CC(C)NC(C)=O)cc2)cn1] | 402 [M + H]+ | 2.06 (K) |
| 12.47 | I69.1 | 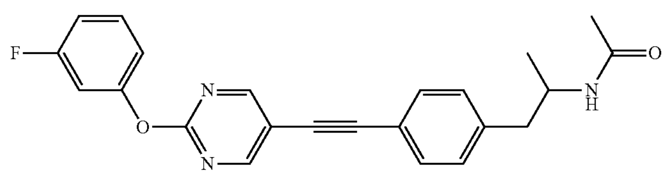 [SMILES: CC(=O)NC(C)Cc1ccc(C#Cc2cnc(Oc3cccc(F)c3)nc2)cc1] | 390 [M + H]+ | 2.11 (K) |
| 12.48 | I69.1 | 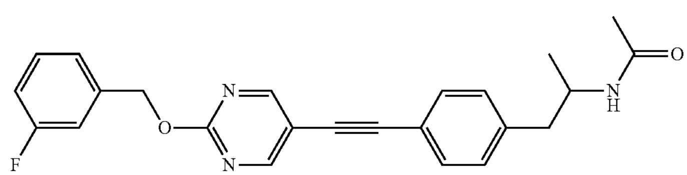 [SMILES: CC(=O)NC(C)Cc1ccc(C#Cc2cnc(OCc3cccc(F)c3)nc2)cc1] | 402 [M + H]+ | 2.10 (K) |
| 12.49 | I69.1 | 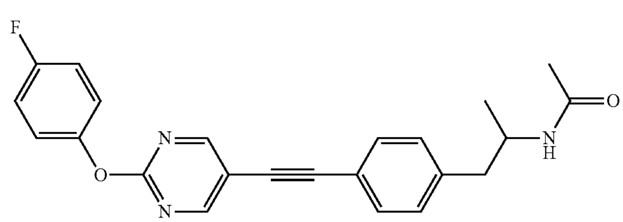 [SMILES: CC(=O)NC(C)Cc1ccc(C#Cc2cnc(Oc3ccc(F)cc3)nc2)cc1] | 390 [M + H]+ | 2.09 (K) |

-continued

| Ex. | Start. material | Structure | Mass spec result | HPLC ret. time (method) |
|---|---|---|---|---|
| 12.50 | I69.1 | 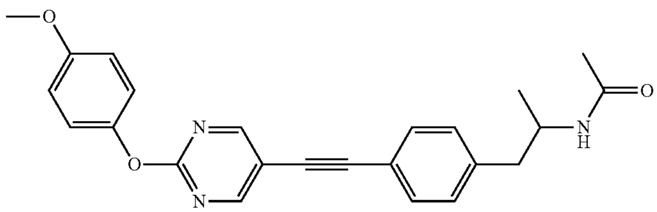 [SMILES: COc1ccc(Oc2ncc(C#Cc3ccc(CC(C)NC(C)=O)cc3)cn2)cc1] | 402 [M + H]+ | 2.09 (K) |
| 12.51 | I69.1 | 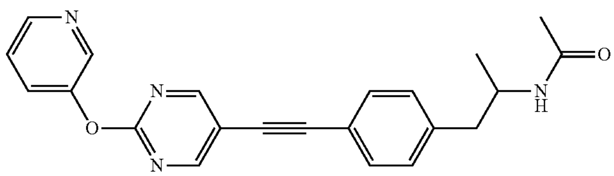 [SMILES: CC(=O)NC(C)Cc1ccc(C#Cc2cnc(Oc3cccnc3)nc2)cc1] | 373 [M + H]+ | 1.90 (K) |
| 12.52 | I69.1 | 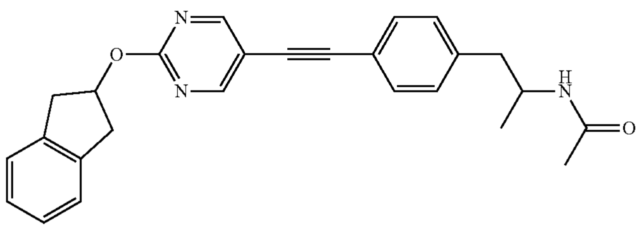 [SMILES: CC(=O)NC(C)Cc1ccc(C#Cc2cnc(OC3Cc4ccccc4C3)nc2)cc1] | 412 [M + H]+ | 2.22 (K) |
| 12.53 | I69.1 | 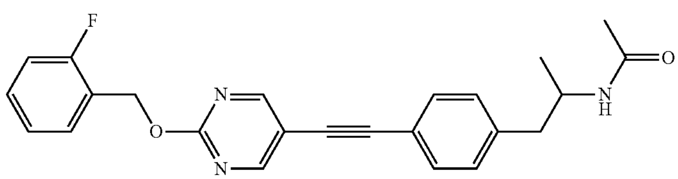 [SMILES: CC(=O)NC(C)Cc1ccc(C#Cc2cnc(OCc3ccccc3F)nc2)cc1] | 404 [M + H]+ | 2.15 (K) |
| 12.54 | I69.1 | 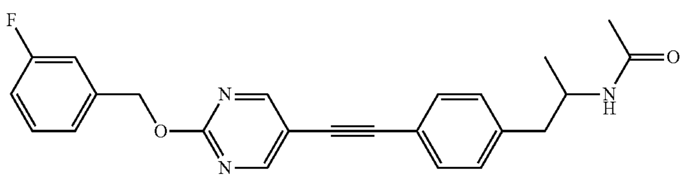 [SMILES: CC(=O)NC(C)Cc1ccc(C#Cc2cnc(OCc3cccc(F)c3)nc2)cc1] | 404 [M + H]+ | 2.16 (K) |
| 12.55 | I69.1 | 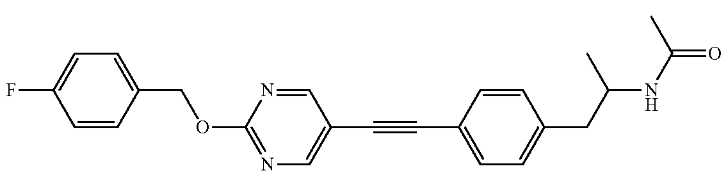 [SMILES: CC(=O)NC(C)Cc1ccc(C#Cc2cnc(OCc3ccc(F)cc3)nc2)cc1] | 404 [M + H]+ | 2.14 (K) |
| 12.56 | I69.1 | 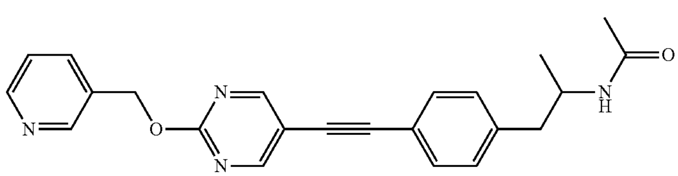 [SMILES: CC(=O)NC(C)Cc1ccc(C#Cc2cnc(OCc3cccnc3)nc2)cc1] | 387 [M + H]+ | 1.72 (K) |
| 12.57 | I69.1 | 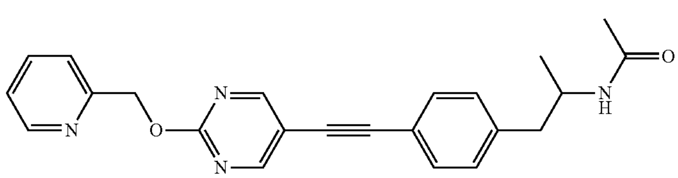 [SMILES: CC(=O)NC(C)Cc1ccc(C#Cc2cnc(OCc3ccccn3)nc2)cc1] | 387 [M + H]+ | 1.86 (K) |

-continued
| Ex. | Start. material | Structure | Mass spec result | HPLC ret. time (method) |
|---|---|---|---|---|
| 12.58 | I69.5 | 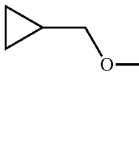 Chiral | 362 [M + H]+ | 2.06 (E) |
| 12.59 | I69.6 | 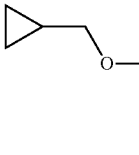 Chiral | 336 [M + H]+ | 2.00 (E) |
| 12.60 | I69.6 | 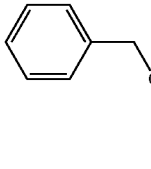 Chiral | 372 [M + H]+ | 2.04 (E) |
| 12.61 | I69.6 | 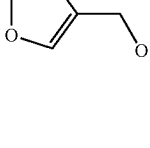 Chiral | 362 [M + H]+ | 1.93 (E) |
| 12.62 | I69.6 | 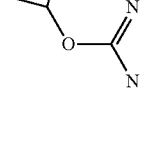 Chiral | 336 [M + H]+ | 2.00 (E) |
| 12.63 | I69.5 | 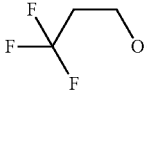 Chiral | 404 [M + H]+ | 2.02 (E) |
| 12.64 | I69.6 | 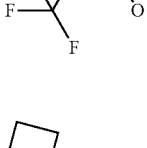 Chiral | 378 [M + H]+ | 1.95 (E) |
| 12.65 | I69.5 | 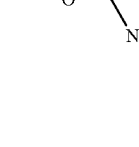 Chiral | 362 [M + H]+ | 2.11 (E) |

| Ex. | Start. material | Structure | Mass spec result | HPLC ret. time (method) |
|---|---|---|---|---|
| 12.66 | I69.5 | Chiral | 336 [M + H]⁺ | 1.95 (E) |
| 12.67 | I69.5 | Chiral | 384 [M + H]⁺ | 1.99 (E) |
| 12.68 | I69.6 | Chiral | 358 [M + H]⁺ | 1.90 (E) |
| 12.69 | I69.6 | Chiral | 310 [M + H]⁺ | 1.87 (E) |

Example 13

Example 13.1

General Route

N-(1-(4-((2-((2-Methoxyethyl)(methyl)amino)pyrimidin-5-yl)ethynyl)phenyl)propan-2-yl)acetamide

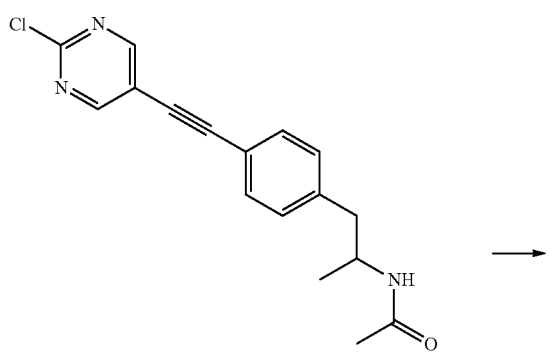

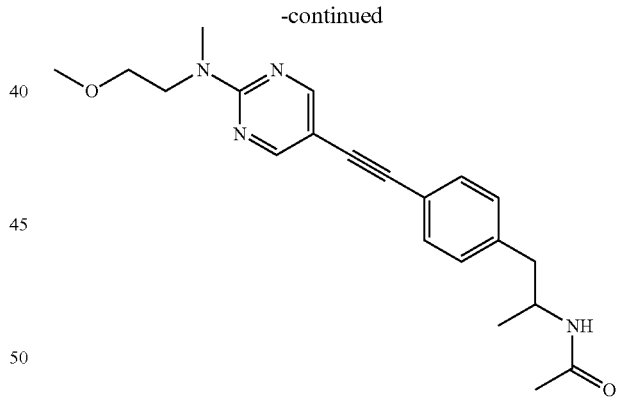

28.2 mg (0.09 mmol) N-(1-(4-((2-chloropyrimidin-5-yl)ethynyl)phenyl)propan-2-yl)-acetamide (I69.1) in 1.5 mL DMSO are added to 12.0 mg (0.14 mmol) N-(2-methoxyethyl)-methylamine followed by 21.8 µl (0.14 mmol) DIPEA. The reaction mixture is stirred at r.t. over night and is directly purified by HPLC (MeOH/H₂O/TFA).

$C_{21}H_{26}N_4O_2$ (M=366.5 g/mol)

ESI-MS: 367 [M+H]⁺

R$_t$ (HPLC): 2.06 min (method K)

The following compounds are prepared analogously to example 13.1

For examples 13.88-91 DMF is used as solvent and the reaction time is 3 h at r.t.

| Ex. | Start. material | Structure | Mass spec result | HPLC retention time (method) |
|---|---|---|---|---|
| 13.1 | I69.1 | (structure) | 367 [M + H]⁺ | 2.06 (K) |
| 13.2 | I69.1 | (structure) | 337 [M + H]⁺ | 2.03 (K) |
| 13.3 | I69.1 | (structure) | 337 [M + H]⁺ | 2.11 (K) |
| 13.4 | I69.1 | (structure) | 337 [M + H]⁺ | 2.03 (K) |
| 13.5 | I69.1 | (structure) | 367 [M + H]⁺ | 1.93 (K) |
| 13.6 | I69.1 | (structure) | 385 [M + H]⁺ | 2.07 (K) |
| 13.7 | I69.1 | (structure) | 363 [M + H]⁺ | 2.22 (K) |
| 13.8 | I69.1 | (structure) | 363 [M + H]⁺ | 2.10 (K) |
| 13.9 | I69.1 | (structure) | 352 [M + H]⁺ | 1.97 (K) |
| 13.10 | I69.1 | (structure) | 349 [M + H]⁺ | 2.05 (K) |

-continued
| Ex. | Start. material | Structure | Mass spec result | HPLC retention time (method) |
|---|---|---|---|---|
| 13.11 | I69.1 | 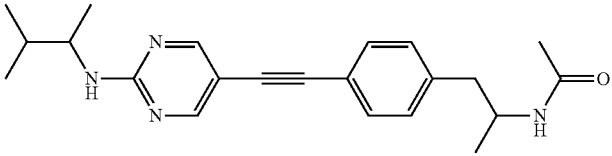 [SMILES: CC(=O)NC(C)Cc1ccc(C#Cc2cnc(NC(C)C(C)C)nc2)cc1] | 365 [M + H]⁺ | 2.11 (K) |
| 13.12 | I69.1 | 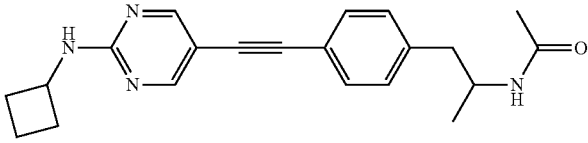 [SMILES: CC(=O)NC(C)Cc1ccc(C#Cc2cnc(NC3CCC3)nc2)cc1] | 349 [M + H]⁺ | 2.06 (K) |
| 13.13 | I69.1 | 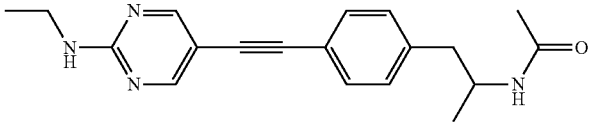 | 323 [M + H]⁺ | 1.99 (K) |
| 13.14 | I69.1 | 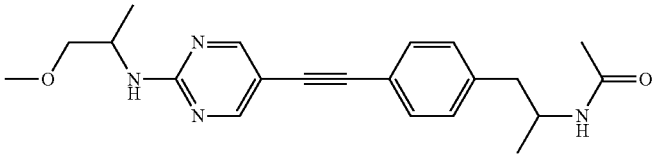 [SMILES: COCC(C)Nc1ncc(C#Cc2ccc(CC(C)NC(C)=O)cc2)cn1] | 367 [M + H]⁺ | 2.01 (K) |
| 13.15 | I69.1 | 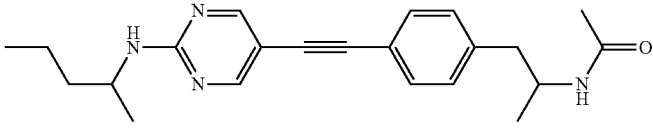 | 365 [M + H]⁺ | 2.12 (K) |
| 13.16 | I69.1 | 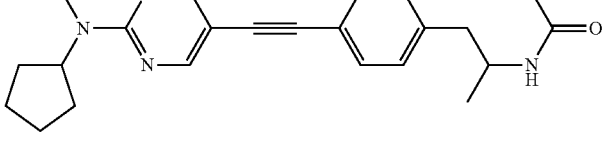 | 377 [M + H]⁺ | 2.25 (K) |
| 13.17 | I69.1 | 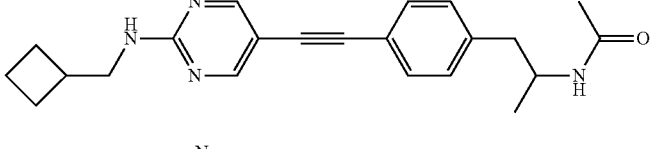 | 363 [M + H]⁺ | 2.10 (K) |
| 13.18 | I69.1 | 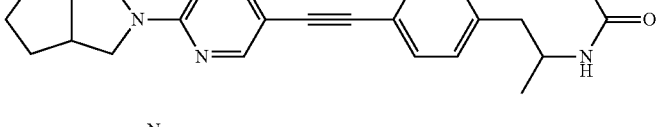 | 389 [M + H]⁺ | 2.23 (K) |
| 13.19 | I69.1 | 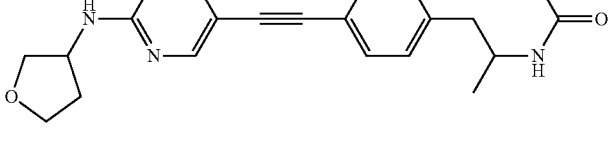 | 365 [M + H]⁺ | 1.96 (K) |
| 13.20 | I69.1 | 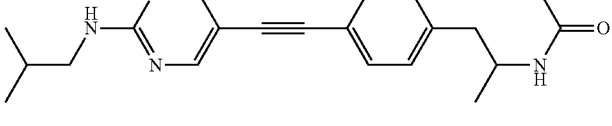 | 351 [M + H]⁺ | 2.08 (K) |

-continued

| Ex. | Start. material | Structure | Mass spec result | HPLC retention time (method) |
|---|---|---|---|---|
| 13.21 | I69.1 | 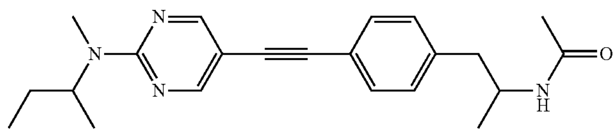 [SMILES: CCC(C)N(C)c1ncc(C#Cc2ccc(CC(C)NC(C)=O)cc2)cn1] | 365 [M + H]+ | 2.2 (K) |
| 13.22 | I69.1 | 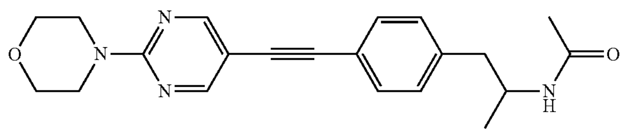 [SMILES: CC(=O)NC(C)Cc1ccc(C#Cc2cnc(N3CCOCC3)nc2)cc1] | 365 [M + H]+ | 2.22 (T) |
| 13.23 | I69.1 | 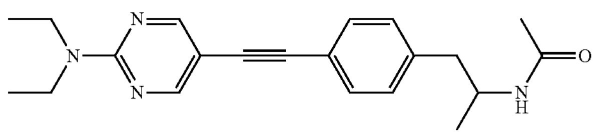 | 351 [M + H]+ | 2.17 (K) |
| 13.24 | I69.2 | 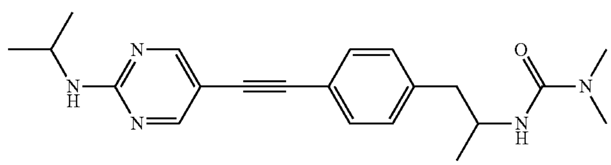 [SMILES: CC(C)Nc1ncc(C#Cc2ccc(CC(C)NC(=O)N(C)C)cc2)cn1] | 366 [M + H]+ | 2.16 (AA) |
| 13.25 | I69.2 | 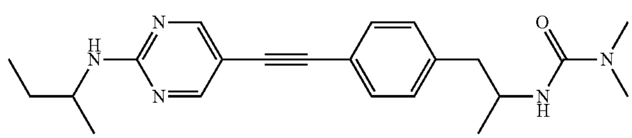 [SMILES: CCC(C)Nc1ncc(C#Cc2ccc(CC(C)NC(=O)N(C)C)cc2)cn1] | 380 [M + H]+ | 2.26 (AA) |
| 13.26 | I69.2 | 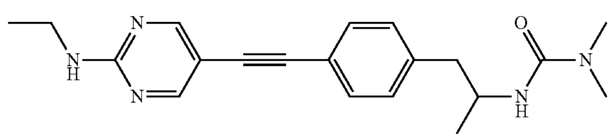 [SMILES: CCNc1ncc(C#Cc2ccc(CC(C)NC(=O)N(C)C)cc2)cn1] | 352 [M + H]+ | 2.10 (AA) |
| 13.27 | I69.2 | 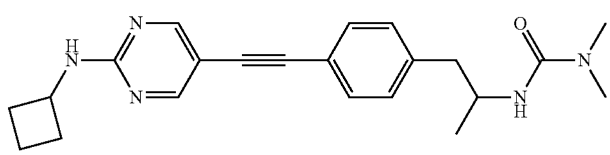 [SMILES: CC(Cc1ccc(C#Cc2cnc(NC3CCC3)nc2)cc1)NC(=O)N(C)C] | 378 [M + H]+ | 2.24 (AA) |
| 13.28 | I69.4 | 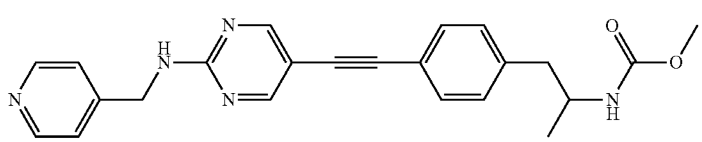 [SMILES: COC(=O)NC(C)Cc1ccc(C#Cc2cnc(NCc3ccncc3)nc2)cc1] | 402 [M + H]+ | 1.72 (K) |
| 13.29 | I69.4 | 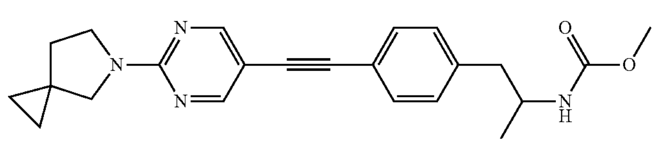 [SMILES: COC(=O)NC(C)Cc1ccc(C#Cc2cnc(N3CCC4(CC4)C3)nc2)cc1] | 391 [M + H]+ | 2.24 (K) |
| 13.30 | I69.4 | 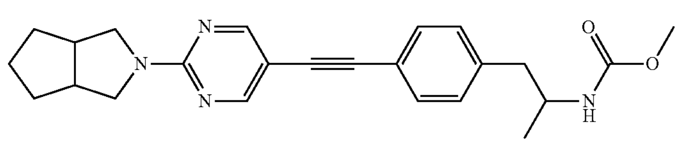 | 405 [M + H]+ | 2.31 (K) |

-continued
| Ex. | Start. material | Structure | Mass spec result | HPLC retention time (method) |
|---|---|---|---|---|
| 13.31 | I69.4 | 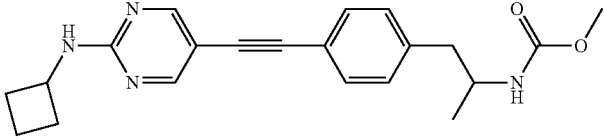 [SMILES: COC(=O)NC(C)Cc1ccc(C#Cc2cnc(NC3CCC3)nc2)cc1] | 365 [M + H]⁺ | 2.13 (K) |
| 13.32 | I69.4 | 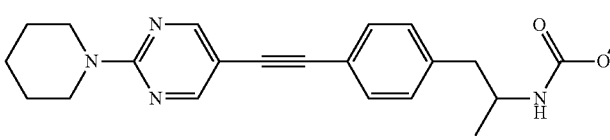 | 379 [M + H]⁺ | 2.29 (K) |
| 13.33 | I69.4 | 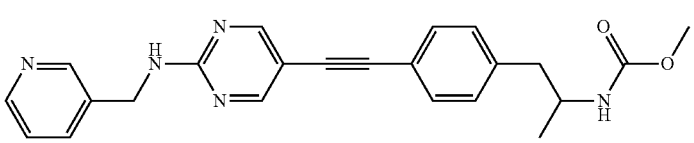 | 402 [M + H]⁺ | 1.73 (K) |
| 13.34 | I69.4 | 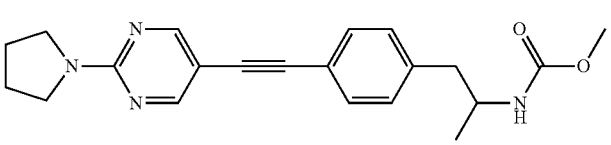 [SMILES: COC(=O)NC(C)Cc1ccc(C#Cc2cnc(N3CCCC3)nc2)cc1] | 365 [M + H]⁺ | 2.16 (K) |
| 13.35 | I69.4 | 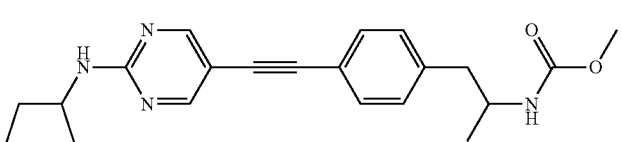 | 379 [M + H]⁺ | 2.17 (K) |
| 13.36 | I69.4 | 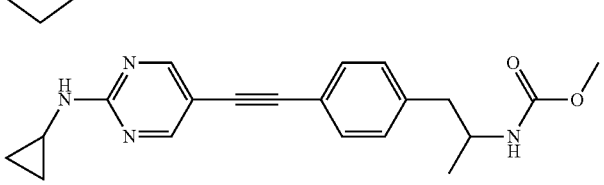 | 351 [M + H]⁺ | 2.03 (K) |
| 13.37 | I69.3 | 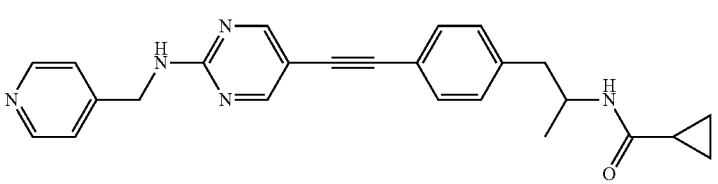 [SMILES: CC(Cc1ccc(C#Cc2cnc(NCc3ccncc3)nc2)cc1)NC(=O)C1CC1] | 412 [M + H]⁺ | 1.71 (K) |
| 13.38 | I69.4 | 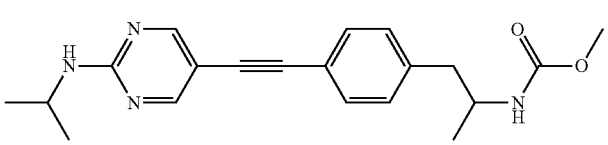 | 353 [M + H]⁺ | 2.1 (K) |
| 13.39 | I69.4 | 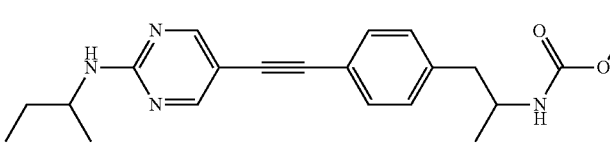 | 367 [M + H]⁺ | 2.15 (K) |
| 13.40 | I69.4 | 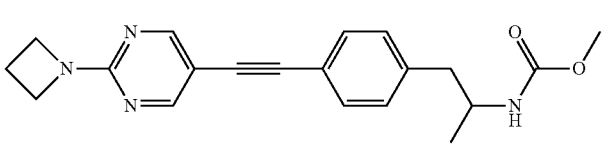 [SMILES: COC(=O)NC(C)Cc1ccc(C#Cc2cnc(N3CCC3)nc2)cc1] | 351 [M + H]⁺ | 2.08 (K) |

-continued
| Ex. | Start. material | Structure | Mass spec result | HPLC retention time (method) |
|---|---|---|---|---|
| 13.41 | I69.4 | 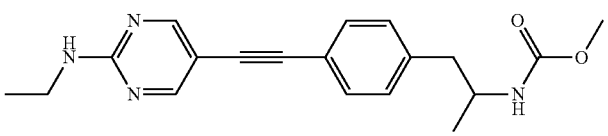 [SMILES: CCNc1ncc(C#Cc2ccc(CC(C)NC(=O)OC)cc2)cn1] | 339 [M + H]+ | 2.09 (K) |
| 13.42 | I69.4 | 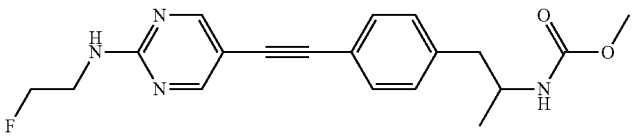 [SMILES: COC(=O)NC(C)Cc1ccc(C#Cc2cnc(NCCF)nc2)cc1] | 357 [M + H]+ | 2.02 (K) |
| 13.43 | I69.3 | 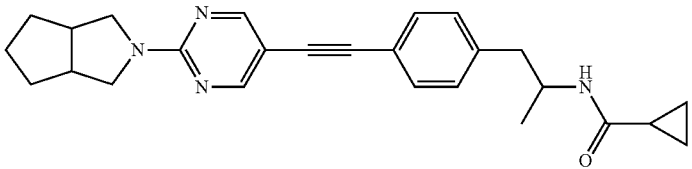 [SMILES: CC(Cc1ccc(C#Cc2cnc(N3CC4CCCC4C3)nc2)cc1)NC(=O)C1CC1] | 415 [M + H]+ | 2.3 (K) |
| 13.44 | I69.3 | 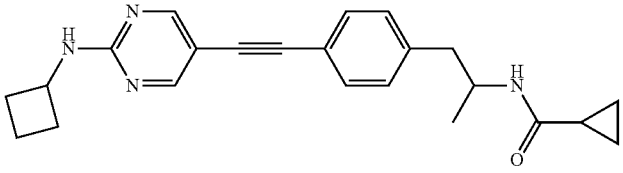 [SMILES: CC(Cc1ccc(C#Cc2cnc(NC3CCC3)nc2)cc1)NC(=O)C1CC1] | 375 [M + H]+ | 2.13 (K) |
| 13.45 | I69.3 | 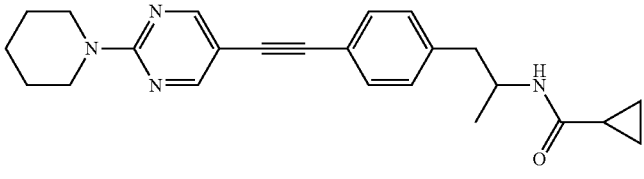 | 389 [M + H]+ | 2.3 (K) |
| 13.46 | I69.3 | 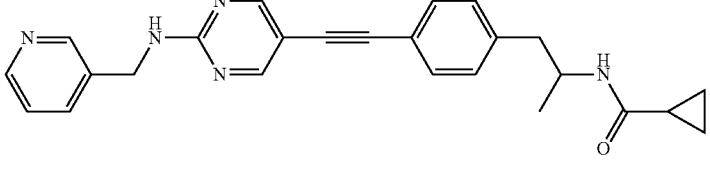 | 412 [M + H]+ | 1.73 (K) |
| 13.47 | I69.3 | 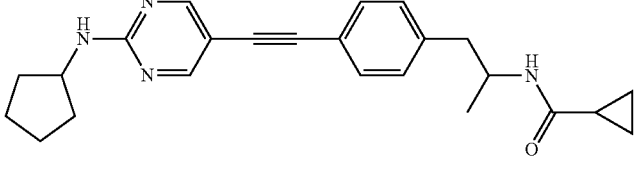 | 389 [M + H]+ | 2.17 (K) |
| 13.48 | I69.3 | 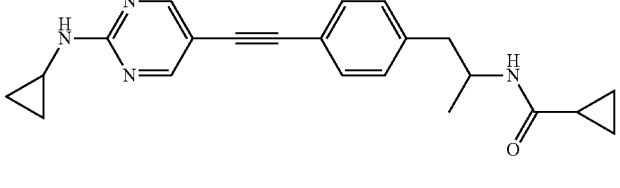 | 361 [M + H]+ | 2.03 (K) |

-continued
| Ex. | Start. material | Structure | Mass spec result | HPLC retention time (method) |
|---|---|---|---|---|
| 13.49 | I69.3 | 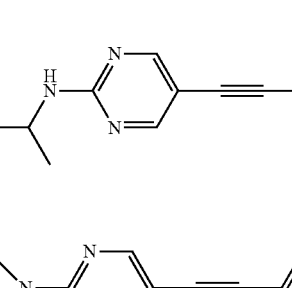 | 363 [M + H]+ | 2.1 (K) |
| 13.50 | I69.3 | 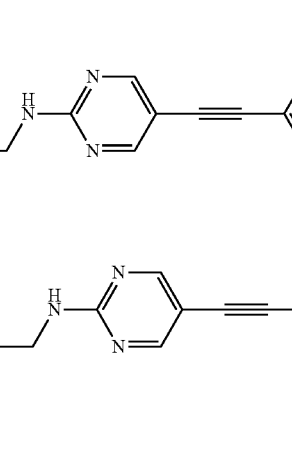 | 377 [M + H]+ | 2.14 (K) |
| 13.51 | I69.3 | 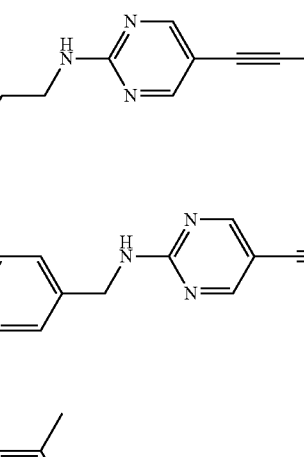 | 361 [M + H]+ | 2.07 (K) |
| 13.52 | I69.3 | 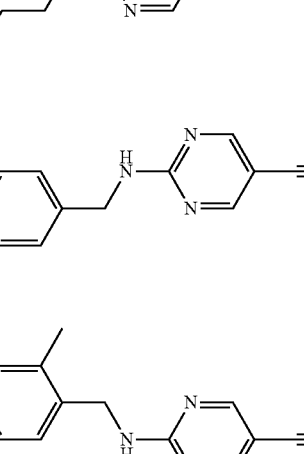 | 349 [M + H]+ | 2.06 (K) |
| 13.53 | I69.3 | 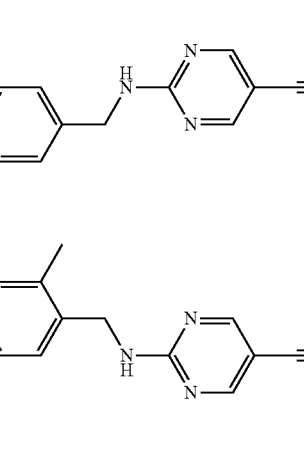 | 367 [M + H]+ | 2.02 (K) |
| 13.54 | I69.3 | 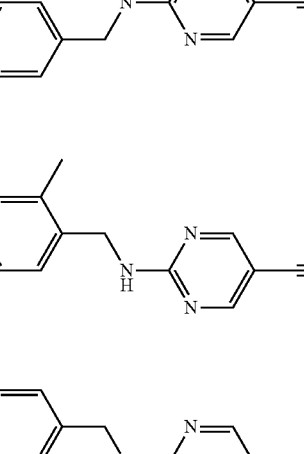 | 411 [M + H]+ | 2.14 (K) |
| 13.55 | I69.1 | 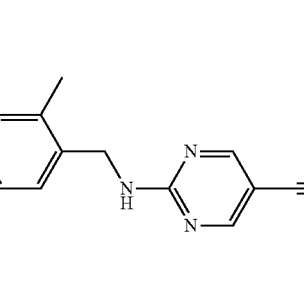 | 399 [M + H]+ | 2.17 (K) |
| 13.56 | I69.1 | 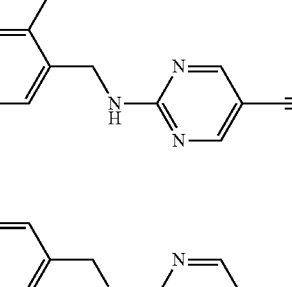 | 399 [M + H]+ | 2.18 (K) |

-continued
| Ex. | Start. material | Structure | Mass spec result | HPLC retention time (method) |
|---|---|---|---|---|
| 13.57 | I69.1 | 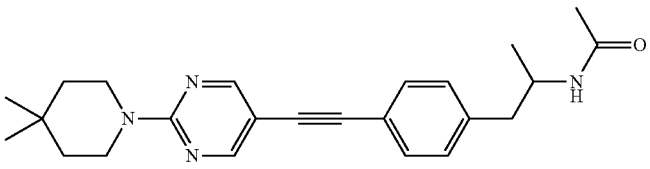 [SMILES: CC(=O)NC(C)Cc1ccc(C#Cc2cnc(N3CCC(C)(C)CC3)nc2)cc1] | 391 [M + H]+ | 2.39 (K) |
| 13.58 | I69.1 | 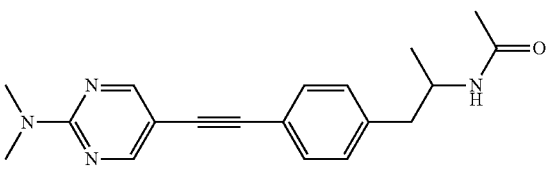 [SMILES: CC(=O)NC(C)Cc1ccc(C#Cc2cnc(N(C)C)nc2)cc1] | 323 [M + H]+ | 2.11 (K) |
| 13.59 | I69.1 | 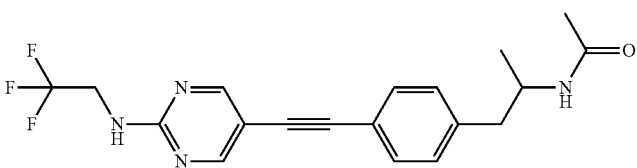 [SMILES: CC(=O)NC(C)Cc1ccc(C#Cc2cnc(NCC(F)(F)F)nc2)cc1] | 377 [M + H]+ | 2.07 (K) |
| 13.60 | I69.1 | 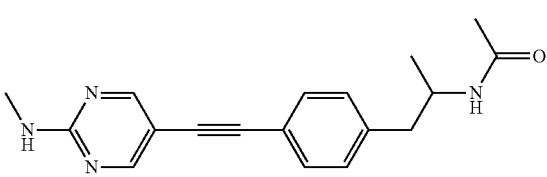 [SMILES: CNc1ncc(C#Cc2ccc(CC(C)NC(C)=O)cc2)cn1] | 309 [M + H]+ | 1.98 (K) |
| 13.61 | I69.1 | 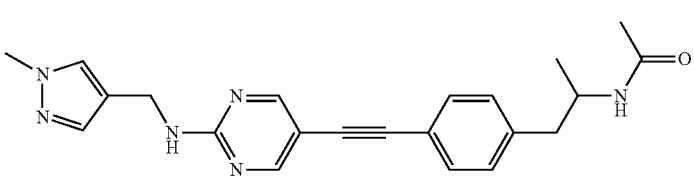 [SMILES: CC(=O)NC(C)Cc1ccc(C#Cc2cnc(NCc3cnn(C)c3)nc2)cc1] | 389 [M + H]+ | 1.96 (K) |
| 13.62 | I69.1 | Chiral 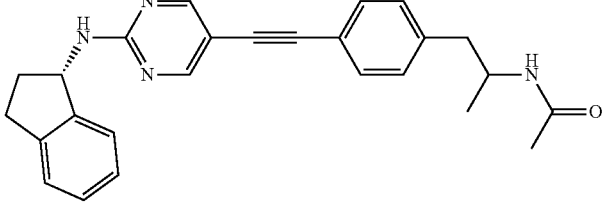 | 411 [M + H]+ | 2.22 (K) |
| 13.63 | I69.1 | Chiral 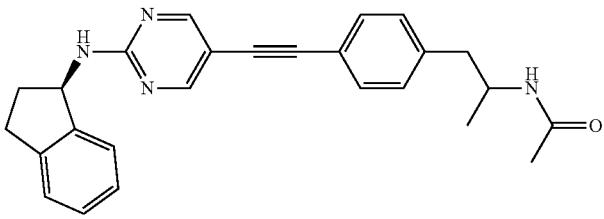 | 411 [M + H]+ | 2.21 (K) |

US 8,835,472 B2
-continued
| Ex. | Start. material | Structure | Mass spec result | HPLC retention time (method) |
|---|---|---|---|---|
| 13.64 | I69.1 | 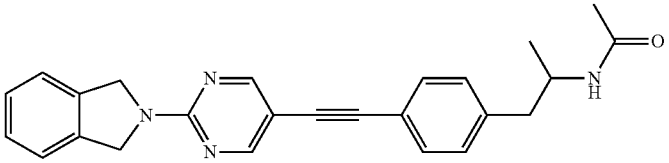 [SMILES: CC(=O)NC(C)Cc1ccc(C#Cc2cnc(N3Cc4ccccc4C3)nc2)cc1] | 397 [M + H]+ | 2.35 (K) |
| 13.65 | I69.1 | 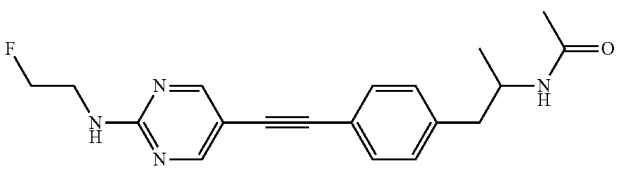 | 341 [M + H]+ | 1.99 (K) |
| 13.66 | I69.1 | 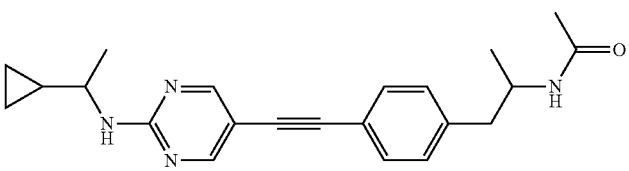 [SMILES: CC(=O)NC(C)Cc1ccc(C#Cc2cnc(NC(C)C3CC3)nc2)cc1] | 363 [M + H]+ | 2.08 (K) |
| 13.67 | I69.1 | 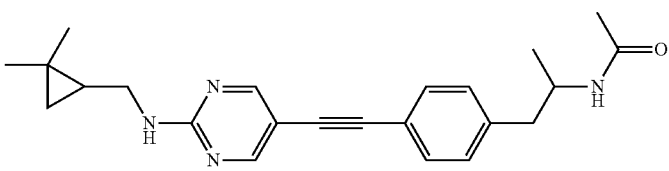 [SMILES: CC(=O)NC(C)Cc1ccc(C#Cc2cnc(NCC3CC3(C)C)nc2)cc1] | 377 [M + H]+ | 2.19 (K) |
| 13.68 | I69.1 | 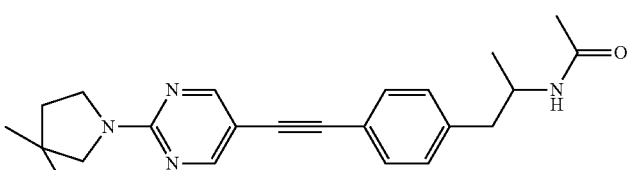 | 377 [M + H]+ | 2.22 (K) |
| 13.69 | I69.1 | 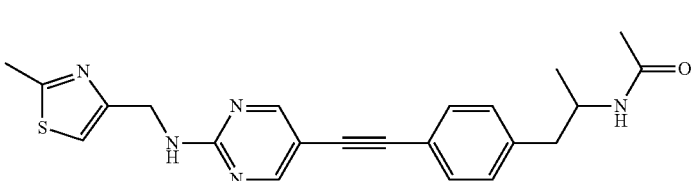 | 406 [M + H]+ | 2.02 (K) |
| 13.70 | I69.1 | 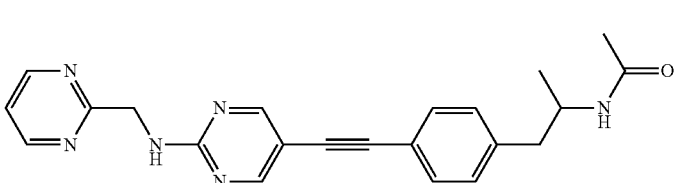 | 387 [M + H]+ | 1.94 (K) |
| 13.71 | I69.1 | 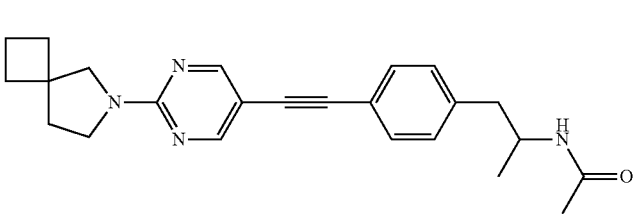 [SMILES: CC(=O)NC(C)Cc1ccc(C#Cc2cnc(N3CCC4(CCC4)C3)nc2)cc1] | 389 [M + H]+ | 2.27 (K) |

-continued
| Ex. | Start. material | Structure | Mass spec result | HPLC retention time (method) |
|---|---|---|---|---|
| 13.72 | I69.1 | 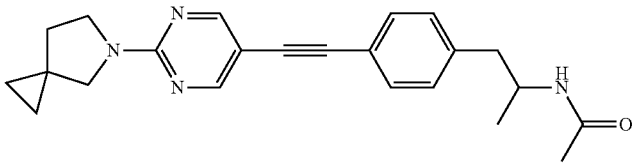 | 375 [M + H]+ | 2.22 (K) |
| 13.73 | I69.1 | 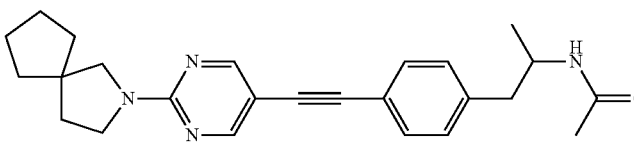 | 403 [M + H]+ | 2.32 (K) |
| 13.74 | I69.1 | 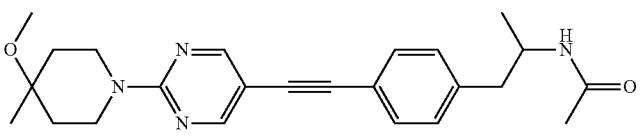 | 407 [M + H]+ | 2.21 (K) |
| 13.75 | I69.1 | 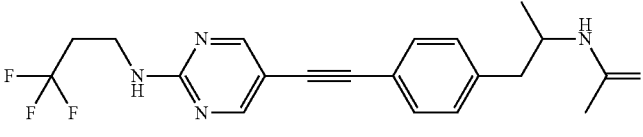 | 391 [M + H]+ | 2.08 (K) |
| 13.76 | I69.1 | 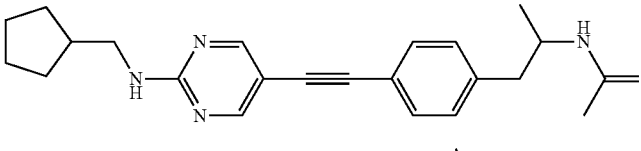 | 377 [M + H]+ | 2.19 (K) |
| 13.77 | I69.1 | 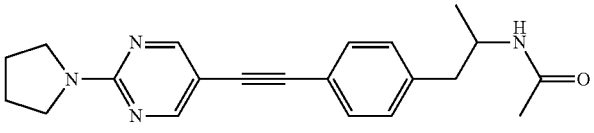 [SMILES: CC(=O)NC(C)Cc1ccc(C#Cc2cnc(N3CCCC3)nc2)cc1] | 349 [M + H]+ | 2.13 (K) |
| 13.78 | I69.1 | 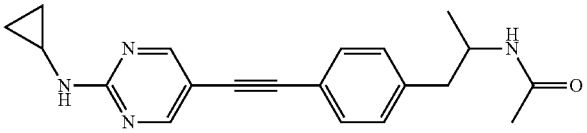 | 335 [M + H]+ | 2.00 (K) |
| 13.79 | I69.1 | 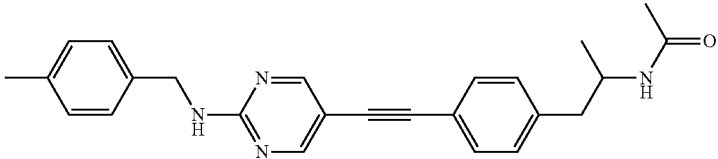 | 399 [M + H]+ | 2.16 (K) |
| 13.80 | I69.1 | 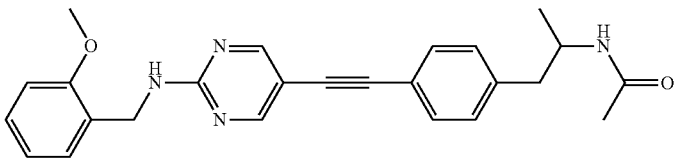 [SMILES: COc1ccccc1CNc1ncc(C#Cc2ccc(CC(C)NC(C)=O)cc2)cn1] | 415 [M + H]+ | 2.12 (K) |
| 13.81 | I69.1 | 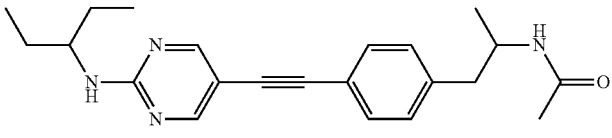 [SMILES: CCC(CC)Nc1ncc(C#Cc2ccc(CC(C)NC(C)=O)cc2)cn1] | 365 [M + H]+ | 2.16 (K) |

-continued
| Ex. | Start. material | Structure | Mass spec result | HPLC retention time (method) |
|---|---|---|---|---|
| 13.82 | I69.1 | 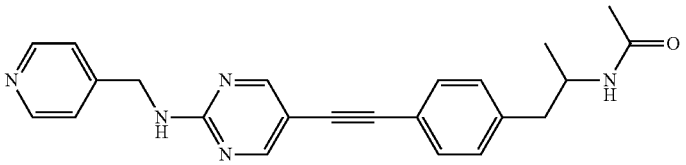 | 386 [M + H]+ | 1.66 (K) |
| 13.83 | I69.1 | 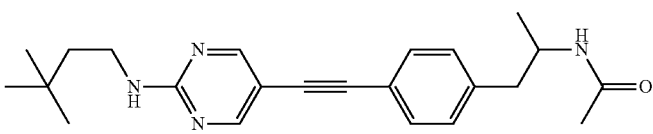 [SMILES: CC(=O)NC(C)Cc1ccc(C#Cc2cnc(NCCC(C)(C)C)nc2)cc1] | 379 [M + H]+ | 2.21 (K) |
| 13.84 | I69.1 | 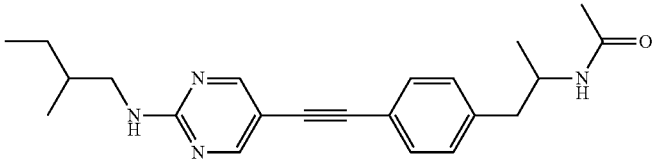 | 365 [M + H]+ | 2.17 (K) |
| 13.85 | I69.1 | 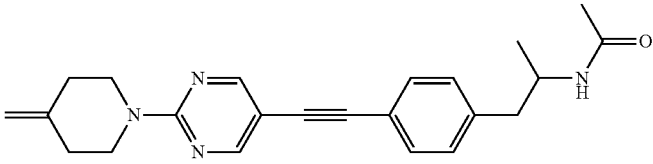 [SMILES: C=C1CCN(c2ncc(C#Cc3ccc(CC(C)NC(C)=O)cc3)cn2)CC1] | 375 [M + H]+ | 2.30 (K) |
| 13.86 | I69.1 | 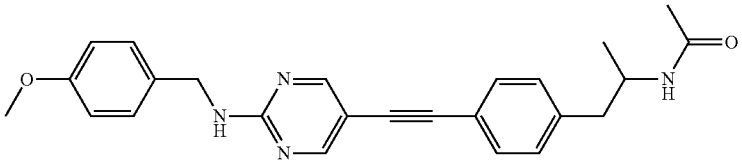 [SMILES: COc1ccc(CNc2ncc(C#Cc3ccc(CC(C)NC(C)=O)cc3)cn2)cc1] | 415 [M + H]+ | 2.11 (K) |
| 13.87 | I69.1 | 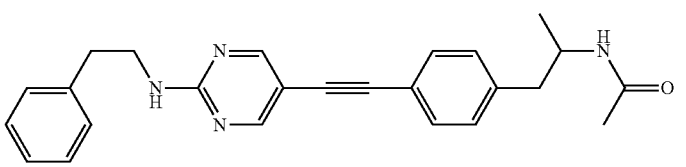 [SMILES: CC(=O)NC(C)Cc1ccc(C#Cc2cnc(NCCc3ccccc3)nc2)cc1] | 399 [M + H]+ | 2.15 (K) |
| 13.88 | I69.5 | Chiral 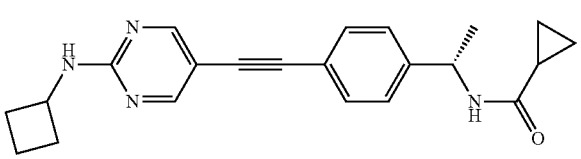 | 361 [M + H]+ | 2.02 (E) |
| 13.89 | I69.6 | Chiral 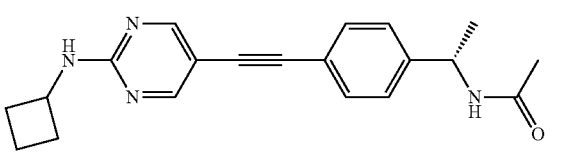 | 335 [M + H]+ | 1.95 (E) |

-continued

| Ex. | Start. material | Structure | Mass spec result | HPLC retention time (method) |
|---|---|---|---|---|
| 13.90 | I69.6 | Chiral | 321 [M + H]+ | 1.74 (E) |
| 13.91 | I69.5 | Chiral | 347 [M + H]+ | 1.83 (E) |
| 13.92 | I69.6 | Chiral | 371 [M + H]+ | 2.00 (E) |
| 13.93 | I69.6 | Chiral | 375 [M + H]+ | 2.19 (E) |
| 13.94 | I69.6 | Chiral | 377 [M + H]+ | 1.95 (E) |
| 13.95 | I69.6 | Chiral | 309 [M + H]+ | 1.72 (E) |

Example 14

Example 14.1

General Route

N-{1-Methyl-2-[4-(2-methylsulfanyl-pyrimidin-4-ylethynyl)-phenyl]-ethyl}acetamide

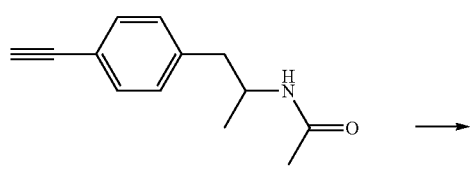

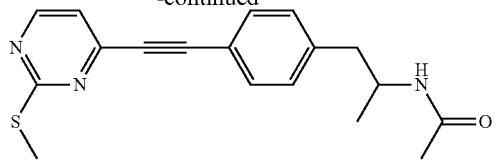

To 0.52 g (2.58 mmol) N-[2-(4-ethynyl-phenyl)-1-methyl-ethyl]-acetamide (I58.3) and 0.50 g (1.98 mmol) 4-iodo-2-(methylthio)pyrimidine in 3 mL sec-butylamine and 3 mL water are added 0.14 g (0.20 mmol) bis(triphenylphosphine)dichloro-palladium and the mixture is stirred at r.t. over night. The reaction mixture is diluted with water and extracted with DCM. The organic layer is dried with $Na_2SO_4$ and the solvent is removed in vacuo. The residue is purified by column chromatography (silica gel, DCM/MeOH 96/4). The resulting product is triturated with diethylether.

$C_{18}H_{19}N_3OS$ (M=325.4 g/mol)
ESI-MS: 651 $[2M+H]^+$
$R_t$ (HPLC): 2.80 min (method B)

The following compounds are prepared analogously to example 14.1

| Ex. | Starting material(s) | Structure | Mass spec result | HPLC retention time (method) |
|---|---|---|---|---|
| 14.1 | I58.3 | 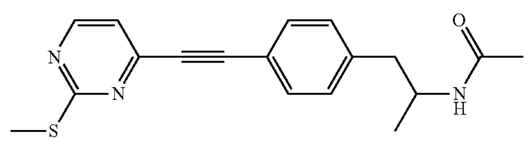 | 651 $[2M + H]^+$ | 2.80 (B) |
| 14.2 | I59.4 | 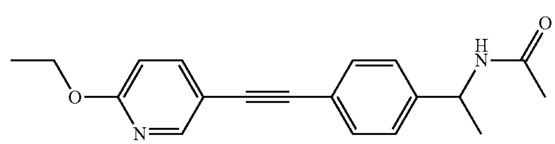 [SMILES: CCOc1ccc(C#Cc2ccc(C(C)NC(C)=O)cc2)cn1] | 309 $[M + H]^+$ | 2.95 (B) |
| 14.3 | I59.4 I7 | 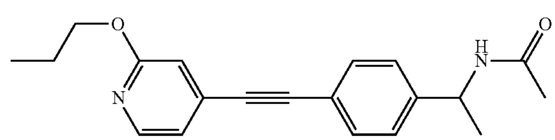 [SMILES: CCCOc1cc(C#Cc2ccc(C(C)NC(C)=O)cc2)ccn1] | 323 $[M + H]^+$ | 3.10 (B) |
| 14.4 | I59.4 I6.3 | 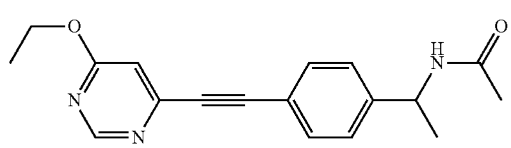 [SMILES: CCOc1cc(C#Cc2ccc(C(C)NC(C)=O)cc2)ncn1] | 310 $[M + H]^+$ | 2.70 (B) |
| 14.5 | I58.3 I2.1 | 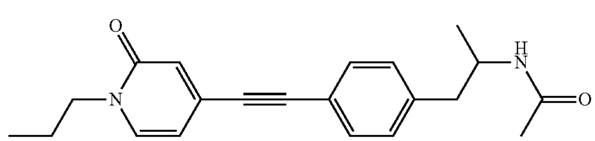 [SMILES: CCCn1ccc(C#Cc2ccc(CC(C)NC(C)=O)cc2)cc1=O] | 337 $[M + H]^+$ | 1.81 (E) |
| 14.6 | I58.3 I16.2 | 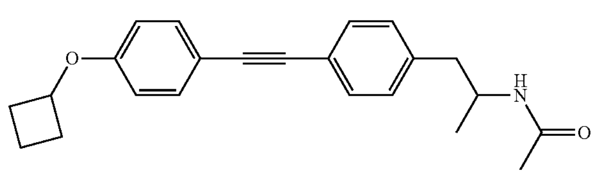 [SMILES: CC(=O)NC(C)Cc1ccc(C#Cc2ccc(OC3CCC3)cc2)cc1] | 348 $[M + H]^+$ | 2.27 (E) |

-continued

| Ex. | Starting material(s) | Structure | Mass spec result | HPLC retention time (method) |
|---|---|---|---|---|
| 14.7 | I58.10 I16.2 | Chiral | 334 [M + H]+ | 2.22 (E) |
| 14.8 | I59.3 | 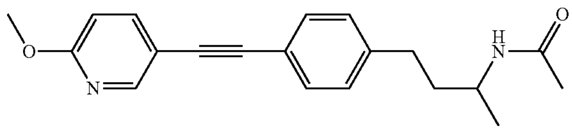 [SMILES: COc1ccc(C#Cc2ccc(CCC(C)NC(C)=O)cc2)cn1] | 323 [M + H]+ | 2.09 (E) |
| 14.9 | I59.3 I16.4 | 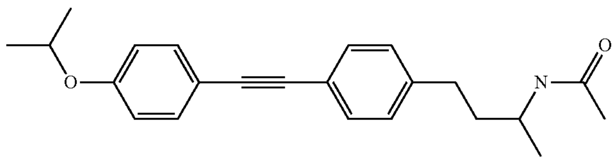 [SMILES: CC(=O)NC(C)CCc1ccc(C#Cc2ccc(OC(C)C)cc2)cc1] | 350 [M + H]+ | 2.26 (E) |
| 14.10 | I59.3 | 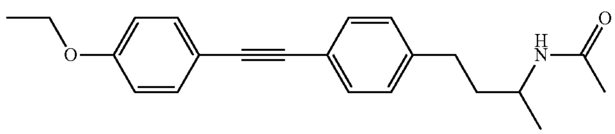 [SMILES: CCOc1ccc(C#Cc2ccc(CCC(C)NC(C)=O)cc2)cc1] | 336 [M + H]+ | 2.20 (E) |
| 14.11 | I59.3 I16.6 | 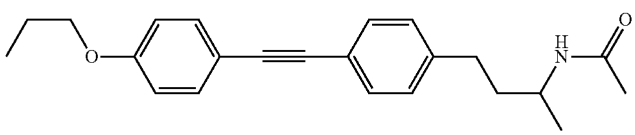 [SMILES: CCCOc1ccc(C#Cc2ccc(CCC(C)NC(C)=O)cc2)cc1] | 350 [M + H]+ | 2.28 (E) |
| 14.12 | I59.3 I16.7 | 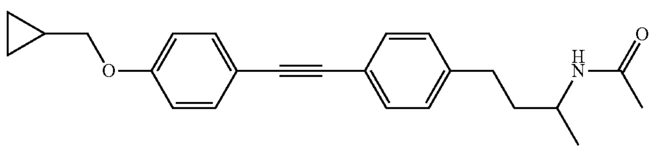 [SMILES: CC(=O)NC(C)CCc1ccc(C#Cc2ccc(OCC3CC3)cc2)cc1] | 362 [M + H]+ | 2.27 (E) |
| 14.13 | I59.3 I16.1 | 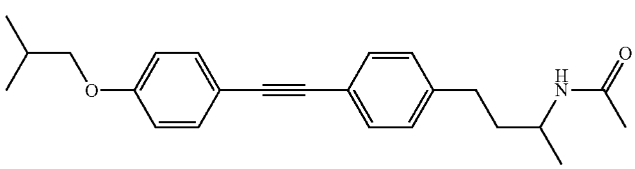 [SMILES: CC(=O)NC(C)CCc1ccc(C#Cc2ccc(OCC(C)C)cc2)cc1] | 364 [M + H]+ | 2.36 (E) |
| 14.14 | I59.3 I16.8 | 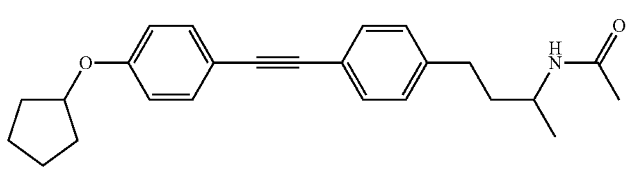 [SMILES: CC(=O)NC(C)CCc1ccc(C#Cc2ccc(OC3CCCC3)cc2)cc1] | 376 [M + H]+ | 2.38 (E) |
| 14.15 | I59.3 I16.3 | 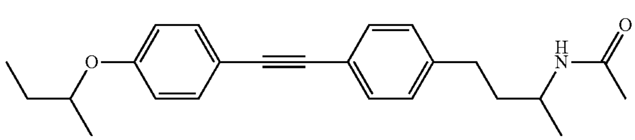 | 364 [M + H]+ | 2.33 (E) |

-continued
| Ex. | Starting material(s) | Structure | Mass spec result | HPLC retention time (method) |
|---|---|---|---|---|
| 14.16 | I59.3 I7 | 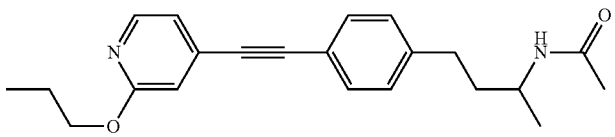 [SMILES: CCCOc1cc(C#Cc2ccc(CCC(C)NC(C)=O)cc2)ccn1] | 351 [M + H]+ | 2.26 (E) |
| 14.17 | I59.1 I16.1 | 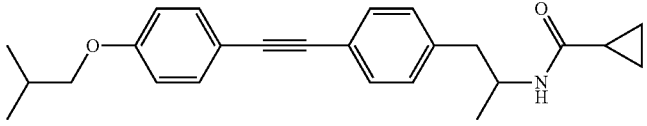 | 376 [M + H]+ | 2.35 (E) |
| 14.18 | I59.1 I16.7 | 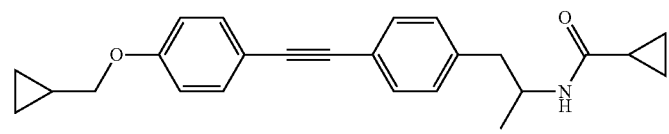 | 374 [M + H]+ | n.d. |
| 14.19 | I58.10 | Chiral 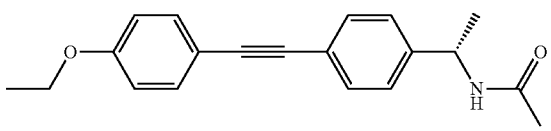 | 308 [M + H]+ | 2.10 (E) |
| 14.20 | I58.10 I16.4 | Chiral 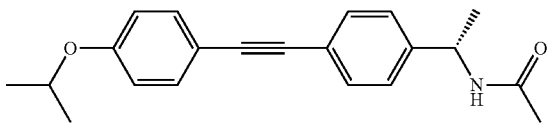 | 322 [M + H]+ | 2.15 (E) |
| 14.21 | I58.3 I14.3 | 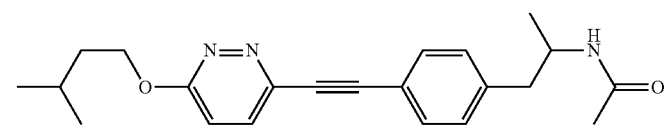 [SMILES: CC(=O)NC(C)Cc1ccc(C#Cc2ccc(OCCC(C)C)nn2)cc1] | 366 [M + H]+ | 2.14 (E) |
| 14.22 | I58.11 I7 | Chiral 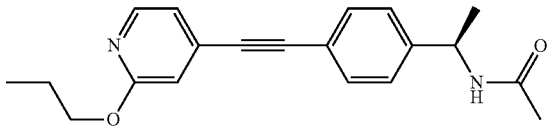 | 323 [M + H]+ | 3.18 (B) |
| 14.23 | I58.10 I16.6 | Chiral 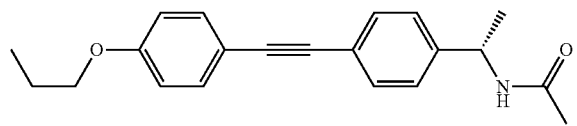 | 322 [M + H]+ | 3.32 (B) |
| 14.24 | I58.10 I7 | Chiral 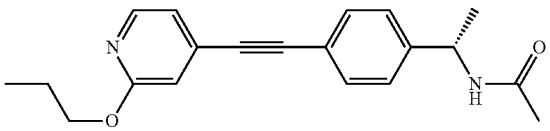 | 323 [M + H]+ | 3.18 (B) |

-continued

| Ex. | Starting material(s) | Structure | | Mass spec result | HPLC retention time (method) |
|---|---|---|---|---|---|
| 14.25 | I58.10 | 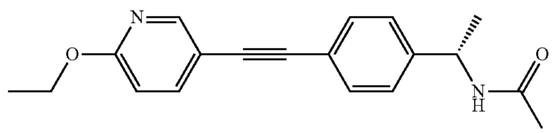 | Chiral | 309 [M + H]⁺ | 3.05 (B) |
| 14.26 | I58.10 I16.1 | 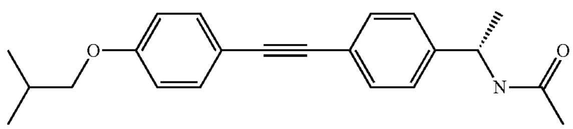 | Chiral | 336 [M + H]⁺ | 2.28 (E) |
| 14.27 | I59.1 I9.5 | 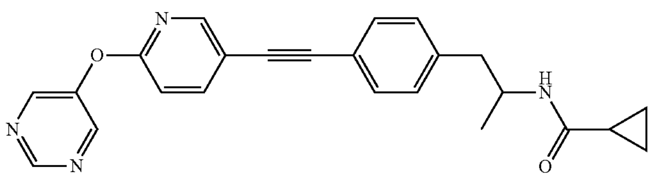 [SMILES: CC(Cc1ccc(C#Cc2ccc(Oc3cncnc3)nc2)cc1)NC(=O)C1CC1] | | 399 [M + H]⁺ | 1.95 (E) |
| 14.28 | I59.2 I16.4 | 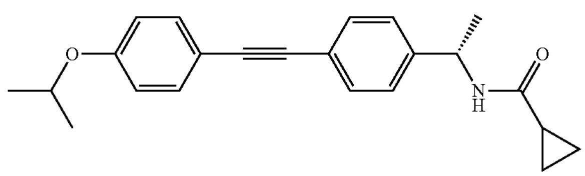 | Chiral | 348 [M + H]⁺ | 2.20 (E) |
| 14.29 | I59.1 I16.2 | 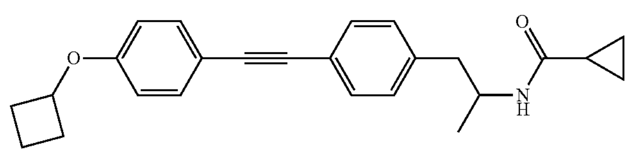 [SMILES: CC(Cc1ccc(C#Cc2ccc(OC3CCC3)cc2)cc1)NC(=O)C1CC1] | | 374 [M + H]⁺ | 2.33 (E) |
| 14.30 | I59.1* | 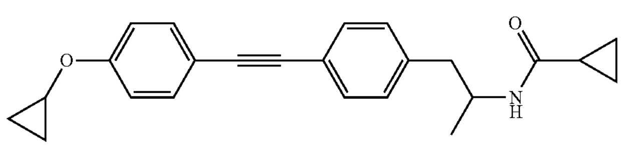 [SMILES: CC(Cc1ccc(C#Cc2ccc(OC3CC3)cc2)cc1)NC(=O)C1CC1] | | 360 [M + H]⁺ | 2.25 (E) |
| 14.31 | I59.1 I16.9 | 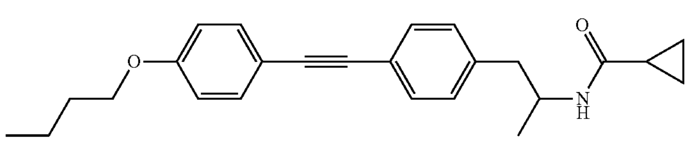 [SMILES: CCCCOc1ccc(C#Cc2ccc(CC(C)NC(=O)C3CC3)cc2)cc1] | | 376 [M + H]⁺ | 2.37 (E) |
| 14.32 | I59.1 I16.10 | 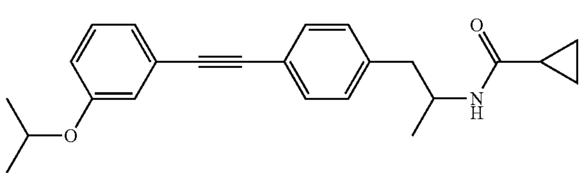 [SMILES: CC(Cc1ccc(C#Cc2cccc(OC(C)C)c2)cc1)NC(=O)C1CC1] | | 362 [M + H]⁺ | 2.23 (E) |
| 14.33 | I59.1 I16.5 | 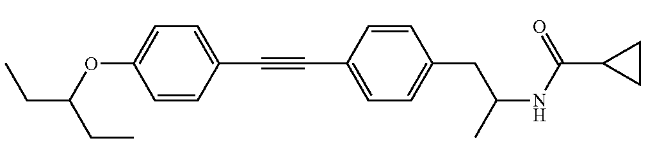 [SMILES: CCC(CC)Oc1ccc(C#Cc2ccc(CC(C)NC(=O)C3CC3)cc2)cc1] | | 390 [M + H]⁺ | 2.36 (E) |

-continued

| Ex. | Starting material(s) | Structure | Mass spec result | HPLC retention time (method) |
|---|---|---|---|---|
| 14.34 | I58.1 I16.1 | 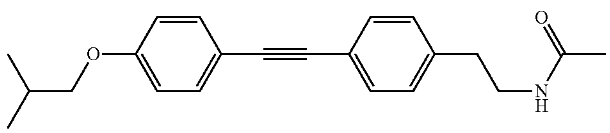 | 336 [M + H]+ | 2.29 (E) |
| 14.35 | I58.1 I16.4 | 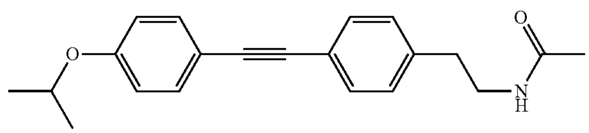 [SMILES: CC(=O)NCCc1ccc(C#Cc2ccc(OC(C)C)cc2)cc1] | 322 [M + H]+ | 2.16 (E) |
| 14.36 | I58.1 | 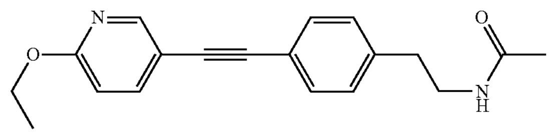 | 309 [M + H]+ | 2.05 (E) |
| 14.37 | I58.1 I16.6 | 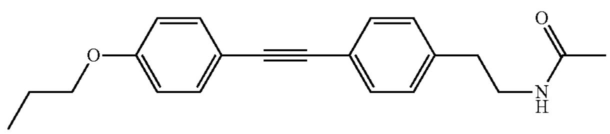 [SMILES: CCCOc1ccc(C#Cc2ccc(CCNC(C)=O)cc2)cc1] | 322 [M + H]+ | 2.21 (E) |
| 14.38 | I58.1 | 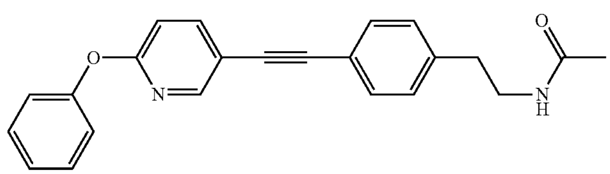 [SMILES: CC(=O)NCCc1ccc(C#Cc2ccc(Oc3ccccc3)nc2)cc1] | 357 [M + H]+ | 2.08 (E) |
| 14.39 | I58.1 I7 | 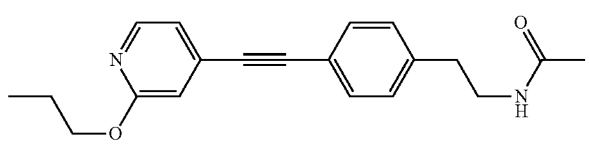 [SMILES: CCCOc1cc(C#Cc2ccc(CCNC(C)=O)cc2)ccn1] | 323 [M + H]+ | 2.14 (E) |
| 14.40 | I59.1 I16.6 | 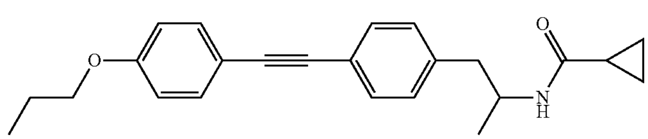 [SMILES: CCCOc1ccc(C#Cc2ccc(CC(C)NC(=O)C3CC3)cc2)cc1] | 362 [M + H]+ | 2.28 (E) |
| 14.41 | I59.1 I16.4 | 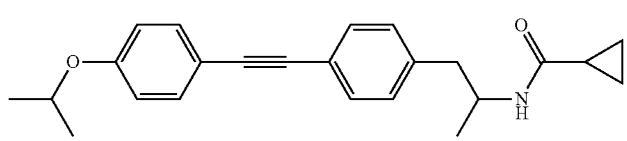 [SMILES: CC(Cc1ccc(C#Cc2ccc(OC(C)C)cc2)cc1)NC(=O)C1CC1] | 362 [M + H]+ | 2.24 (E) |
| 14.42 | I59.1 | 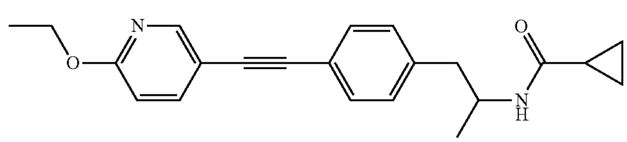 [SMILES: CCOc1ccc(C#Cc2ccc(CC(C)NC(=O)C3CC3)cc2)cn1] | 350 [M + H]+ | 1.90 (E) |
| 14.43 | I59.1 | 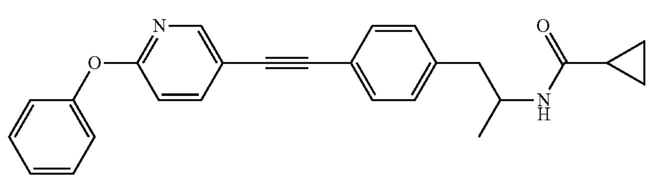 | 397 [M + H]+ | 2.18 (E) |

-continued

| Ex. | Starting material(s) | Structure | Mass spec result | HPLC retention time (method) |
|---|---|---|---|---|
| 14.44 | I59.1 I7 | 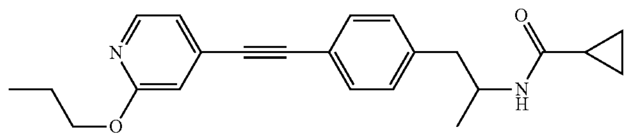 [SMILES: CCCOc1cc(C#Cc2ccc(CC(C)NC(=O)C3CC3)cc2)ccn1] | 363 [M + H]⁺ | 2.24 (E) |
| 14.45 | I59.1 | 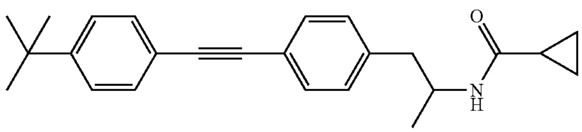 [SMILES: CC(Cc1ccc(C#Cc2ccc(C(C)(C)C)cc2)cc1)NC(=O)C1CC1] | 360 [M + H]⁺ | 2.38 (E) |
| 14.46 | I59.1 I16.3 | 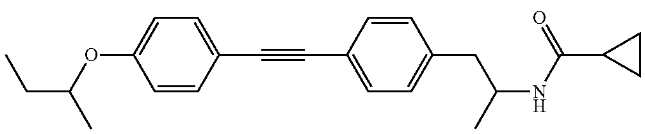 | 376 [M + H]⁺ | 2.81 (E) |
| 14.47 | I59.1 I16.8 | 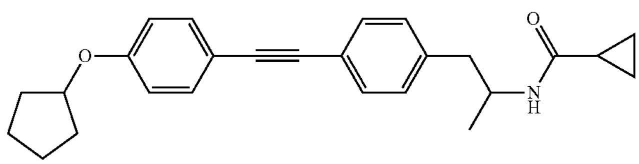 [SMILES: CC(Cc1ccc(C#Cc2ccc(OC3CCCC3)cc2)cc1)NC(=O)C1CC1] | 388 [M + H]⁺ | 2.36 (E) |
| 14.48 | I59.2 I16.1 | Chiral | 362 [M + H]⁺ | 2.32 (E) |
| 14.49 | I59.2 | Chiral | 334 [M + H]⁺ | 2.15 (E) |
| 14.50 | I58.3 | 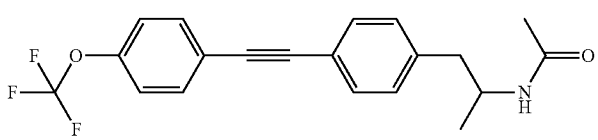 [SMILES: CC(=O)NC(C)Cc1ccc(C#Cc2ccc(OC(F)(F)F)cc2)cc1] | 362 [M + H]⁺ | TLC: R$_f$=: 0.4 (silica gel, PE/EtOAc 2/8) |
| 14.51 | I59.4 | 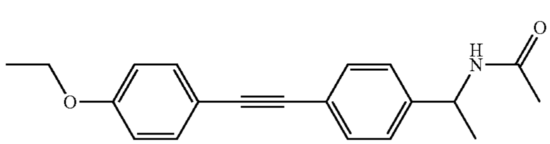 [SMILES: CCOc1ccc(C#Cc2ccc(C(C)NC(C)=O)cc2)cc1] | 308 [M + H]⁺ | 3.06 (B) |
| 14.52 | I59.1 | 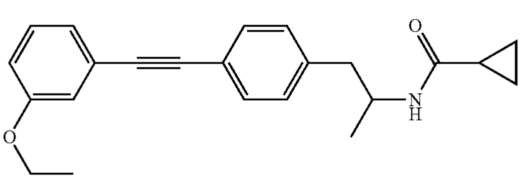 [SMILES: CCOc1cccc(C#Cc2ccc(CC(C)NC(=O)C3CC3)cc2)c1] | 348 [M + H]⁺ | 2.20 (E) |

-continued

| Ex. | Starting material(s) | Structure | Mass spec result | HPLC retention time (method) |
|---|---|---|---|---|
| 14.53 | I59.3 | 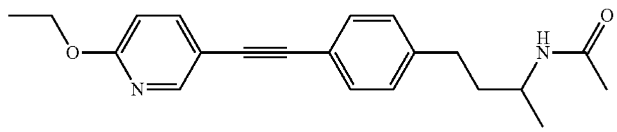 | 337 [M + H]⁺ | 2.18 (E) |
| 14.54 | I59.3 I15.4 | 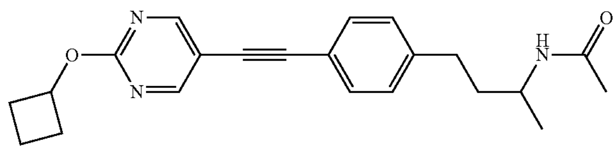 [SMILES: CC(=O)NC(C)CCc1ccc(C#Cc2cnc(OC3CCC3)nc2)cc1] | 364 [M + H]⁺ | 2.17 (E) |
| 14.55 | I58.3 I15.5 | 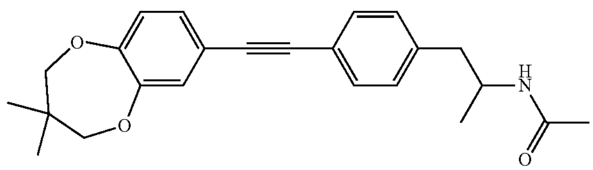 [SMILES: CC(=O)NC(C)Cc1ccc(C#Cc2ccc3c(c2)OCC(C)(C)CO3)cc1] | 378 [M + H]⁺ | 2.14 (AD) |

*The appropriate aryl-bromide is used

Example 15

N-(1-(4-((2-(sec-Butylamino)pyrimidin-5-yl)ethynyl)phenyl)propan-2-yl)acetamide 2.50 g (12.4 mmol) N-(1-(4-ethynylphenyl)propan-2-yl)acetamide (I58.3), 3.0 g (12.42 mmol) 2-chloro-5-iodopyrimidine and 872 mg (1.24 mmol) bis(triphenylphosphine)dichloropalladium in 10 mL water and 10 mL sec-butylamine are stirred at r.t. over night. The reaction mixture is diluted with water and extracted with DCM. The organic layer is dried with $Na_2SO_4$ and the solvent is removed in vacuo. The residue is purified by column chromatography (silica gel, DCM/MeOH 98/2).

$C_{21}H_{26}N_4O$ (M=350.5 g/mol)

ESI-MS: 351 [M+H]⁺

$R_t$ (HPLC): 2.07 (method E)

Example 16

Example 16.1

General Route

N-(4-((4-Ethoxyphenyl)ethynyl)phenethyl)propionamide

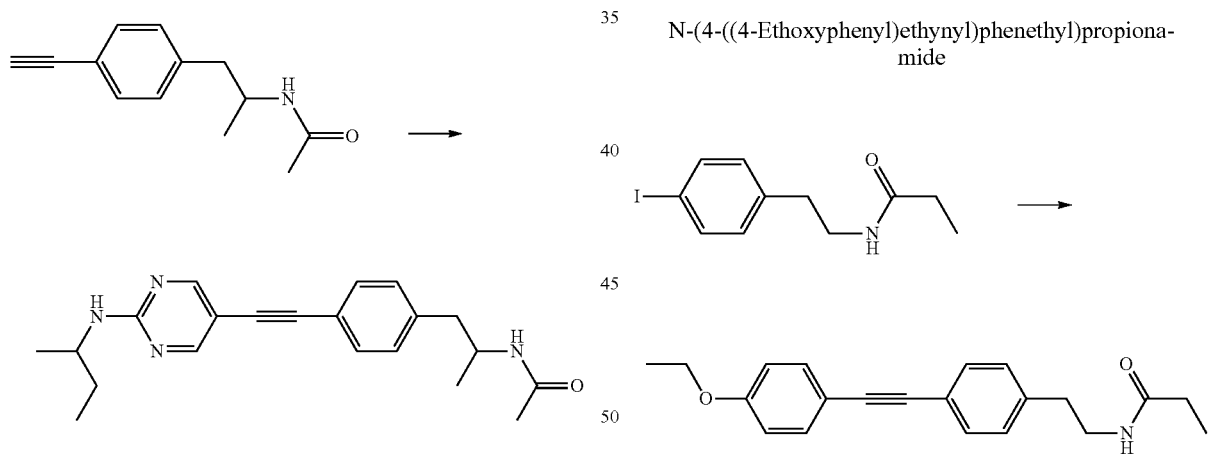

150 mg (1.03 mmol) 1-ethoxy-4-ethynylbenzene, 327 mg (1.08 mmol) N-(4-iodophen-ethyl)propionamide (I47.2) and 36 mg (0.05 mmol) bis(triphenylphosphine)dichloro-palladium in 2.0 mL water and 1.5 mL sec-butylamine are stirred at r.t. over night and for additional 4 h at 30° C. The reaction mixture is partitioned between DCM and water. The solvent of the organic layer is evaporated in vacuo and the residue is purified by HPLC (MeOH/$H_2O$/$NH_3$).

$C_{21}H_{23}NO_2$ (M=321.4 g/mol)

ESI-MS: 322 [M+H]⁺

$R_t$ (HPLC): 2.16 min (method E)

The following compounds are prepared analogously to example 16.1

| Ex. | Starting material | Structure | Mass spec result | HPLC retention time (method) |
|---|---|---|---|---|
| 16.1 | I47.2 | 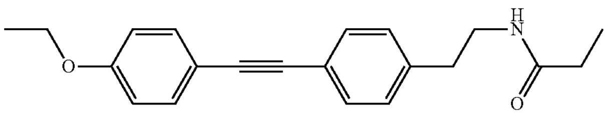 [SMILES: CCOc1ccc(C#Cc2ccc(CCNC(=O)CC)cc2)cc1] | 322 [M + H]+ | 2.16 (E) |
| 16.2 | I43 | 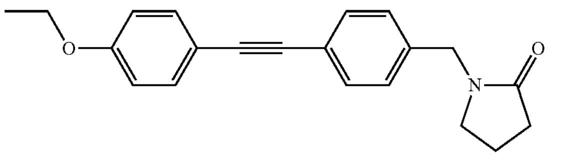 [SMILES: CCOc1ccc(C#Cc2ccc(CN3CCCC3=O)cc2)cc1] | 320 [M + H]+ | 2.16 (E) |
| 16.3 | I47.1 | 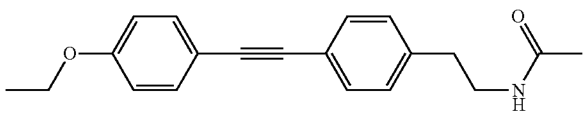 | 308 [M + H]+ | TLC: R_f = 0.5 (silica gel, DCM/MeOH 9/1) |

Example 17

N-(1-(4-((6-Ethoxypyrimidin-4-yl)ethynyl)phenyl)propan-2-yl)acetamide

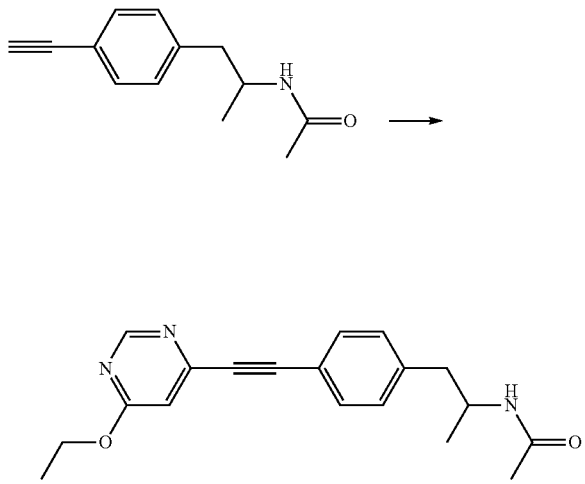

To 290 mg (1.44 mmol) (N-{2-[4-(6-ethoxy-pyrimidin-4-ylethynyl)-phenyl]-1-methyl-ethyl}-acetamide (I58.3), 370 mg (1.46 mmol) 4-ethoxy-6-iodo-pyrimidine (I6.3) and 0.60 ml triethylamin in 8 mL THF are added 0.05 g (0.07 mmol) bis-(triphenyl-phosphin)-palladium(II)-chloride and 0.03 g (0.16 mmol) CuI. The reaction mixture is stirred at r.t. for 1 h. The reaction is poured onto icewater and EtOAC and afterwards neutralized with citric acid (10% in water). The organic layer is separated, dried with $Na_2SO_4$ and the solvent is evaporated in vacuo. The residue is purified by column chromatography (silica gel, DCM/MeOH 91/9). The resulting product is triturated with diethylether and dried at 80° C. in vacuo.

$C_{19}H_{21}N_3O_2$ (M=323.4 g/mol)
ESI-MS: 324 [M+H]+
$R_t$ (HPLC): 3.00 min (method B)

Example 18

Example 18.1

General Route

N-{2-[4-(4-Ethoxy-phenylethynyl)-phenyl]-1-methyl-ethyl}-N-methyl-acetamide

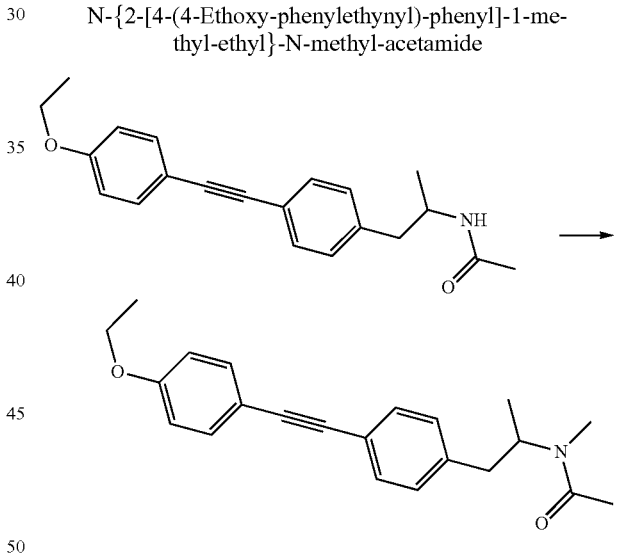

32.1 mg (100 μmol) N-{2-[4-(4-ethoxy-phenylethynyl)-phenyl]-1-methyl-ethyl}-acetamide are added to an ice cooled mixture of 40.0 mg (1.00 mmol) sodium NaH and 2.50 mL THF. The reaction mixture is stirred at 0° C. for 10 min. Then 25.0 μL (0.40 mmol) methyliodide are added dropwise and the mixture is stirred at r.t. for 2 h. The reaction is quenched by the addition of water and sat. $NH_4Cl$ solution, and is extracted with DCM. The organic layer is separated and the solvent is removed in vacuo. The residue is lyophilised from ACN/water.

$C_{22}H_{25}NO_2$ (M=335.4 g/mol)
ESI-MS: 336 [M+H]+
$R_t$ (HPLC): 2.34 min (method M)

The following compounds are prepared analogously to example 18.1

For example 18.2 the crude product was purified by HPLC

| Ex. | Starting material | Structure | Mass spec result | HPLC retention time (method) |
|---|---|---|---|---|
| 18.1 | I.28 | 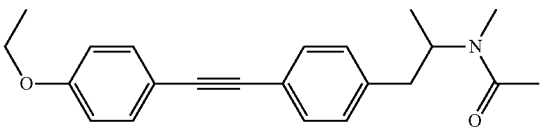 [SMILES: CCOc1ccc(C#Cc2ccc(CC(C)N(C)C(C)=O)cc2)cc1] | 336 [M + H]+ | 2.34 (M) |
| 18.2 | 4.7 | 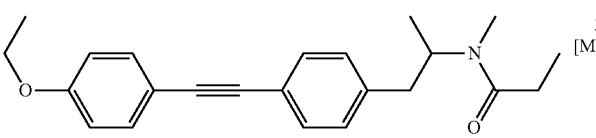 | 350 [M + H]+ | 2.39 (M) |

Example 19

1-{2-[4-(4-Ethoxy-phenylethynyl)-phenyl]-1-methyl-ethyl}-3,3-dimethyl-azetidin-2-one

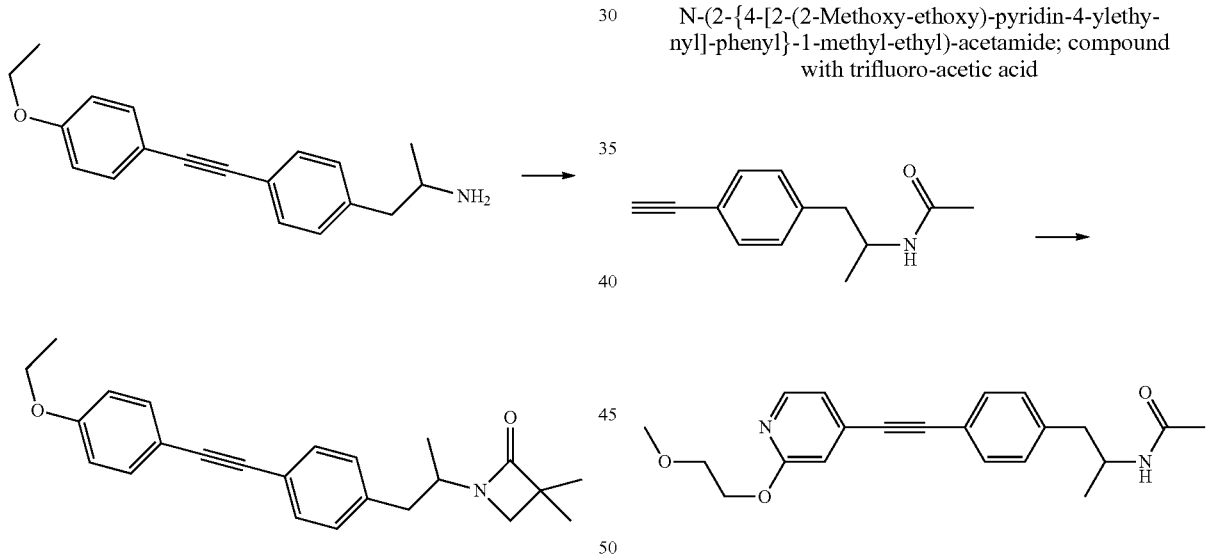

To 33.5 mg (120 µmol) 2-[4-(4-ethoxy-phenylethynyl)-phenyl]-1-methyl-ethylamine (I64) in 2.0 mL ACN are added 166 mg (1.20 mmol) K$_2$CO$_3$, a few crystals DMAP and finally 23.5 µL (0.18 mmol) 3-chloropivaloyl chloride (in 1.0 mL ACN). The reaction mixture is stirred at reflux for 6 h. The solvent is removed in vacuo and the residue is resolved EtOAc and washed with water (1×), sat. aq. NaHCO$_3$ solution (2×) and again with water. The organic layer is dried with Na$_2$SO$_4$ and the solvent is evaporated in vacuo. The residue is purified by HPLC (MeOH/H$_2$O/TFA).

C$_{24}$H$_{27}$NO$_2$ (M=361.5 g/mol)
ESI-MS: 362 [M+H]+
R$_t$ (HPLC): 2.41 min (method M)

Example 20

Example 20.1

General Route

N-(2-{4-[2-(2-Methoxy-ethoxy)-pyridin-4-ylethynyl]-phenyl}-1-methyl-ethyl)-acetamide; compound with trifluoro-acetic acid To 435 mg (1.56 mmol) 2-(2-methoxy-ethoxy)-pyridine (I8) and 0.45 g (1.56 mmol) N-[2-(4-ethynyl-phenyl)-1-methyl-ethyl]-acetamide (I58.3) in 5.0 mL DMF and 0.66 mL (4.68 mmol) TEA are added 6.87 mg (0.01 mmol) [1,1'-bis(diphenyl-phosphino)ferrocene]-dichloropalladium(II), complex with dichlormethane (1:1) and 14.8 mg (0.08 mmol) CuI. The mixture is stirred at r.t. for 3 h. The reaction is quenched by the addition of water and extracted with DCM. The organic layer is dried with MgSO$_4$, filtrated and the solvent is removed in vacuo. The residue is purified by HPLC (ACN/MeOH/TFA).

C$_{21}$H$_{24}$N$_2$O$_3$×C$_2$HF$_3$O$_2$ (M=466.5 g/mol)
ESI-MS: 353 [M+H]+
R$_t$ (HPLC): 2.80 min (method B)

The following compounds are prepared analogously to example 20.1

| Ex. | Starting materials | Structure | Mass spec result | HPLC retention time (method) |
|---|---|---|---|---|
| 20.1 | I58.3 I8 | 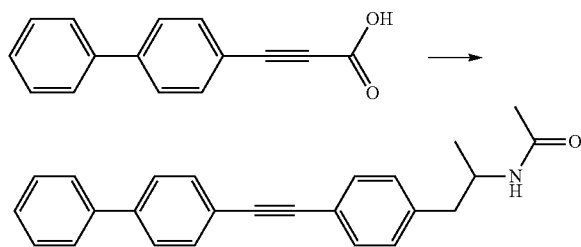 | 353 [M + H]$^+$ | 2.80 (B) |
| 20.2 | I58.6 I6.1 | 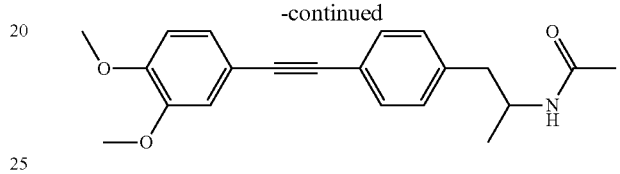 | 352 [M + H]$^+$ | 3.08 (B) |

Example 21

N-[2-(4-Biphenyl-4-ylethynyl-phenyl)-1-methyl-ethyl]acetamide

To 0.22 g (1.00 mmol) biphenyl-4-yl-propynoic acid (I28) and 0.26 g (1.00 mmol) N-[2-(4-bromo-phenyl)-1-methyl-ethyl]-acetamide (I44.1) in 3.00 mL NMP are added 0.06 g (0.10 mmol) 1,1'-bis(diphenylphosphonino)ferrocene, 1.68 g (6.00 mmol) TBAF*H$_2$O and 0.05 g (0.05 mmol) tris(dibenzylidenacetone)dipalladium(0). The reaction mixture is stirred at 90° C. for 3 h. The mixture is allowed to cool to r.t. and poured onto saturated aq NH$_4$Cl solution. The precipitate is filtered, washed with water and purified by column chromatographie (silica gel; DCM/MeOH 9/1). The resulting product is triturated with isopropanol and dried at 60° C. in vacuo.

C$_{25}$H$_{23}$NO (M=353.5 g/mol)
ESI-MS: 354 [M+H]$^+$
R$_t$ (HPLC): 3.57 min (method B)

Example 22

N-{2-[4-(3,4-Dimethoxy-phenylethynyl)-phenyl]-1-methyl-ethyl}-acetamide

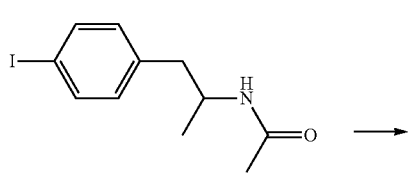

-continued

To 0.40 g (1.32 mmol) N-[2-(4-iodo-phenyl)-1-methyl-ethyl]-acetamide (I52.1) and 0.21 g (1.32 mmol) 3,4-dimethoxyphenyl acetylene in 5 mL THF are added 0.10 g (0.13 mmol) bis-(triphenylphosphin)-palladium(II)-chlorid, 26.0 mg (0.14 mmol) CuI and 0.56 g (1.72 mmol) Cs$_2$CO$_3$. The mixture is stirred in a sealed tube at r.t. over night. The reaction mixture is poured onto sat. aq. NaHCO$_3$ solution and extracted with EtOAc (2×). The organic layer is dried with Na$_2$SO$_4$ and the solvent is removed in vacuo. The residue is purified by HPLC (ACN/MeOH/TFA).

C$_{21}$H$_{23}$NO$_3$ (M=337.4 g/mol)
ESI-MS: 338 [M+H]$^+$
R$_t$ (HPLC): 2.85 min (method B)

Example 23

Example 23.1

General Route

N-{2-[4-(2-Ethoxy-pyridin-4-ylethynyl)-phenyl]-1-methyl-ethyl}-acetamide

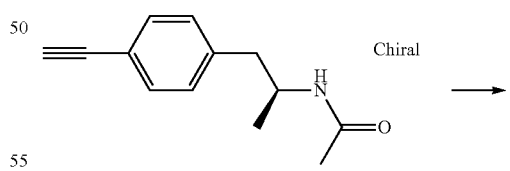

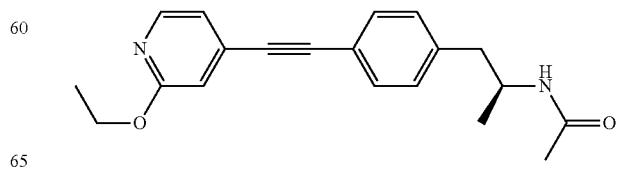

To 100 mg (0.50 mmol) N-[2-(4-ethynyl-phenyl)-1-methyl-ethyl]-acetamide (I58.2) and 124 mg (0.50 mmol) 2-ethoxy-4-iodo-pyridine (I6.1) in 5.00 mL ACN are added 20.3 mg (0.03 mmol) 1,1'-bis[diphenylphosphino]ferrocene-palladium dichloride dichloromethane complex (1:1), 4.83 mg (0.03 mmol) CuI and 0.16 mL (1.16 mmol) TEA. The mixture is stirred at r.t. over night, then poured onto water and extracted with DCM. The organic layer is dried with MgSO$_4$ and the solvent is removed in vacuo. The residue is purified by column chromatographie (silica gel; PE/EtOAc 1/1→EtOAc 100%).

$C_{20}H_{22}N_2O_2$ (M=332.4 g/mol)

ESI-MS: 323 [M+H]$^+$

R$_t$ (HPLC): 2.10 min (method E)

The following compounds are prepared analogously to example 23.1

For examples 23.11, 23.14 and 23.15 TEA and ACN are replaced by diisopropylamine and THF.

| Ex. | Starting material(s) | Structure | | Mass spec result | HPLC retention time (method) |
|---|---|---|---|---|---|
| 23.1 | I58.2 I6.1 | 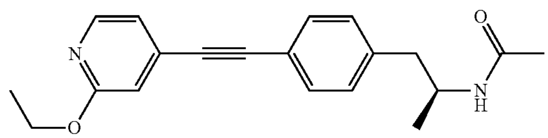 | Chiral | 323 [M + H]$^+$ | 2.1 (E) |
| 23.2 | I58.2 I16.4 | 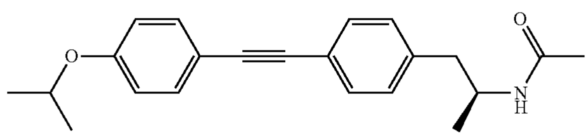 | Chiral | 336 [M + H]$^+$ | 2.21 (E) |
| 23.3 | I58.2 I16.1 | 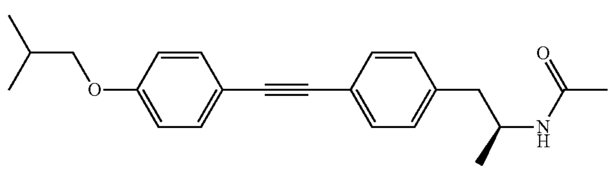 | Chiral | 350 [M + H]$^+$ | 2.33 (E) |
| 23.4 | I58.2 | 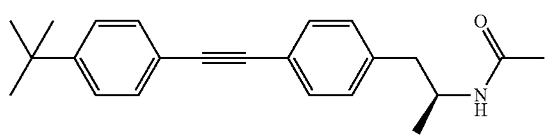 | Chiral | 334 [M + H]$^+$ | 2.36 (E) |
| 23.5 | I58.2 | 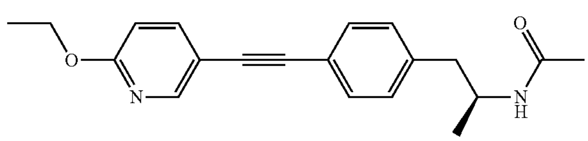 | Chiral | 323 [M + H]$^+$ | 2.13 (E) |
| 23.6 | I58.2 I16.6 | 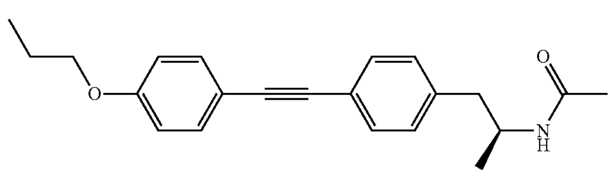 | Chiral | 336 [M + H]$^+$ | 2.28 (E) |
| 23.7 | I58.3 I15.4 | 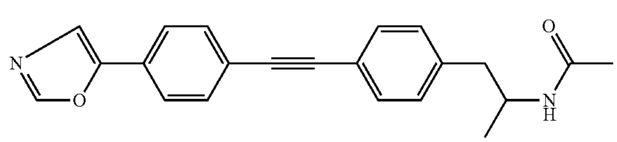 | | 345 [M + H]$^+$ | 2.05 (AB) |

-continued

| Ex. | Starting material(s) | Structure | Mass spec result | HPLC retention time (method) |
|---|---|---|---|---|
| 23.8 | I58.3 I11.2 | 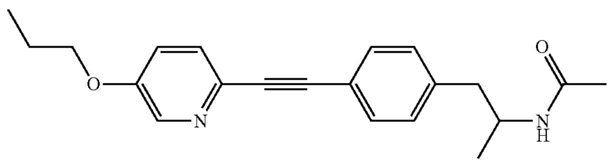 [SMILES: CCCOc1ccc(C#Cc2ccc(CC(C)NC(C)=O)cc2)nc1] | 337 [M + H]+ | 2.10 (AB) |
| 23.9 | I58.3 I16.3 | 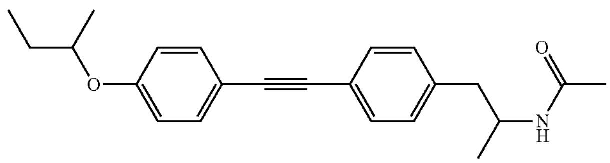 [SMILES: CCC(C)Oc1ccc(C#Cc2ccc(CC(C)NC(C)=O)cc2)cc1] | 350 [M + H]+ | 2.33 (AB) |
| 23.10 | I58.3 | 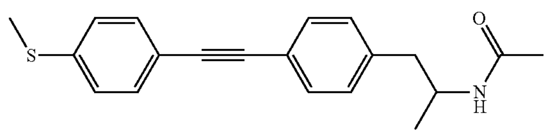 [SMILES: CSc1ccc(C#Cc2ccc(CC(C)NC(C)=O)cc2)cc1] | 324 [M + H]+ | 2.20 (AB) |
| 23.11 | I59.1 I17 | 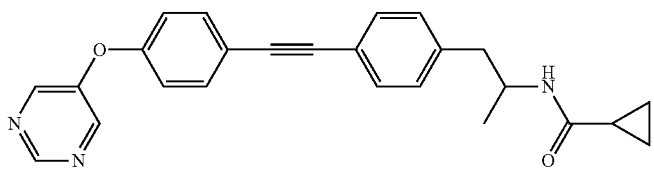 [SMILES: CC(Cc1ccc(C#Cc2ccc(Oc3cncnc3)cc2)cc1)NC(=O)C1CC1] | 398 [M + H]+ | 2.10 (E) |
| 23.12 | I58.3 I11.3 | 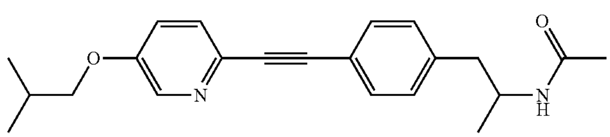 [SMILES: CC(=O)NC(C)Cc1ccc(C#Cc2ccc(OCC(C)C)cn2)cc1] | 351 [M + H]+ | 2.10 (E) |
| 23.13 | I58.3 I11.1 | 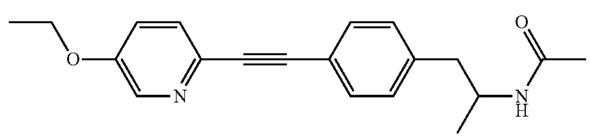 [SMILES: CCOc1ccc(C#Cc2ccc(CC(C)NC(C)=O)cc2)nc1] | 323 [M + H]+ | 1.91 (E) |
| 23.14 | I58.4 I11.2 | 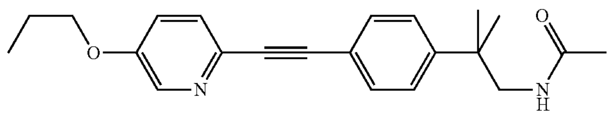 [SMILES: CCCOc1ccc(C#Cc2ccc(C(C)(C)CNC(C)=O)cc2)nc1] | 351 [M + H]+ | 2.34 (E) |
| 23.15 | I58.5 I15.4 | 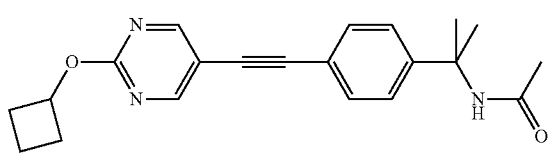 [SMILES: CC(=O)NC(C)(C)c1ccc(C#Cc2cnc(OC3CCC3)nc2)cc1] | 350 [M + H]+ | 2.34 (E) |

Example 24

Example 24.1

General Route

N-{1-Methyl-2-[4-(4-propoxy-phenylethynyl)-phenyl]-ethyl}-acetamide

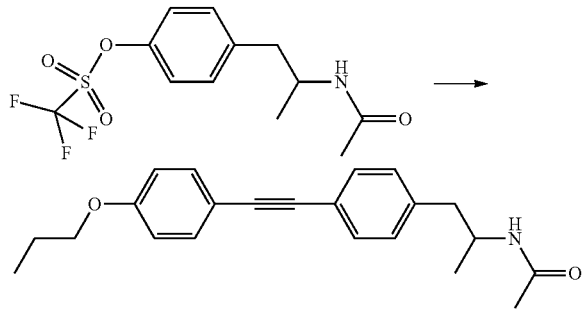

To 0.33 g (1.00 mmol) trifluoromethanesulfonic acid 4-(2-acetylamino-propyl)-phenyl ester (I53.2) and 0.18 g (1.10 mmol) 1-ethynyl-4-propoxybenzene in 3 mL DMF and 0.60 mL (4.50 mmol) TEA are added 0.04 g (0.06 mmol) bis-(triphenylphosphin)-palladiumdichlorid. The mixture is stirred in a sealed tube at 80° C. for 24 h. The reaction mixture is partitioned between EtOAc and water, the organic layer is dried with $Na_2SO_4$ and the solvent is removed in vacuo. The residue is purified by column chromatographie (silica gel, DCM/EtOAc 1/1). The resulting product is triturated with diethylether and dried at 80° C. in vacuo.

$C_{22}H_{25}NO_2$ (M=335.4 g/mol)

ESI-MS: 336 [M+H]$^+$ $R_t$ (HPLC): 3.32 min (method B)

The following compounds are prepared analogously to example 24.1

For examples 24.2 and 24.3 the reaction is stirred at 90° C. for 3 h.

| Ex. | Starting material(s) | Structure | | Mass spec result | HPLC ret. time method |
|---|---|---|---|---|---|
| 24.1 | I53.2 | 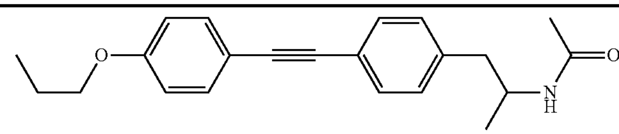 | | 336 [M + H]$^+$ | 3.32 (B) |
| 24.2 | I53.1 | 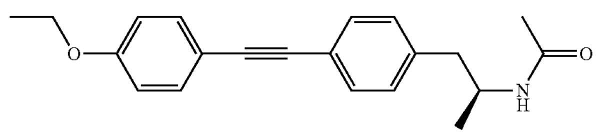 | Chiral | 322 [M + H]+ | 3.15 (B) |
| 24.3 | I53.1 I4.2 | 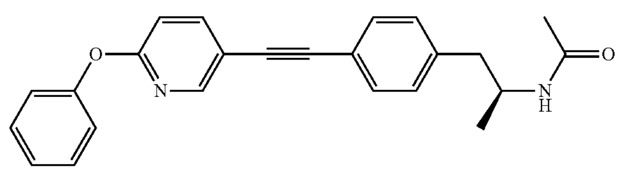 | Chiral | 371 [M + H]+ | 2.15 (E) |

Example 25

N-{2-[4-(4-tert-Butylphenylethynyl)-phenyl]-1-methyl-ethyl}-acetamide

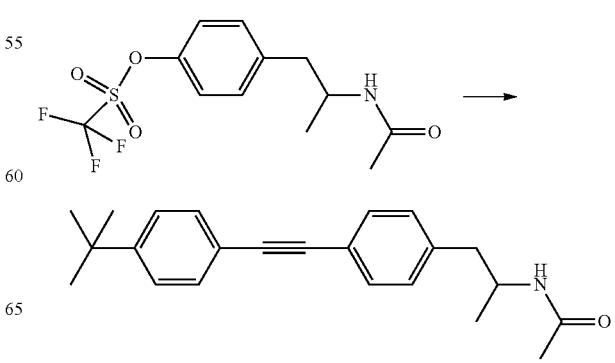

To 0.50 g (1.54 mmol) trifluoro-methanesulfonic acid 4-(2-acetylamino-propyl)-phenyl ester (I53.2) and 0.32 g (2.00 mmol) 4-tert.butylphenylacetylen in 3.0 mL water and 3.0 mL sec-butylamine are added 0.10 g (0.14 mmol) bis(triphenyphosphine)dichloropalladium and the mixture is stirred at r.t. for 4 h and at 80° C. for 1 h. The reaction mixture is allowed to cool to r.t. and is then partitioned between EtOAc and citric acid (10% in water). The organic layer is dried with $Na_2SO_4$ and the solvent is removed in vacuo. The residue is purified twice by column chromatography (silica gel; DCM/MeOH 9/1 and aluminium oxide DCM/EtOAc 4/1). The resulting product is triturated with MeOH.

$C_{23}H_{27}NO$ (M=333.5 g/mol)
ESI-MS: 334 $[M+H]^+$
$R_t$ (HPLC): 3.53 min (method B)

Example 26

N-{2-[5-(4-Ethoxy-phenylethynyl)-pyridin-2-yl]-ethyl}-acetamide

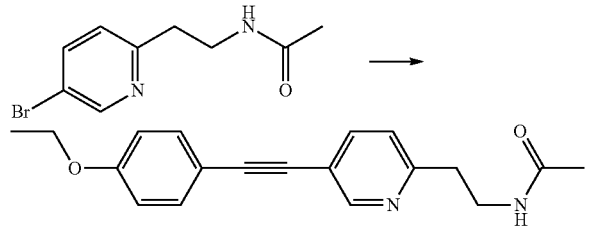

0.55 mL (3.91 mmol) DIPEA is added to 190 mg (0.78 mmol) N-[2-(5-bromo-pyridin-2-yl)-ethyl]-acetamide (I48.1), 3.72 mg (0.02 mmol) CuI and 13.7 mg (0.02 mmol) bis(triphenylphosphin)palladium-(II)-chloride. 171 mg (1.17 mmol) 4-ethoxyphenylacetylene are added and the reaction mixture is heated for 10 min at 80° C. in a microwave oven. The mixture is diluted with EtOAc and washed with water (1×) and diluted aq. ammonia solution. The organic layer is dried with $MgSO_4$ and the solvent is removed in vacuo. The residue is purified by HPLC (MeOH/$H_2O$/$NH_3$).

$C_{19}H_{20}N_2O_2$ (M=308.4 g/mol)
ESI-MS: 309 $[M+H]^+$
$R_t$ (HPLC): 1.97 (E)

Example 27

Example 27.1

General Route

N-{2-[4-(2-Cyclopentyloxy-pyrimidin-5-ylethynyl)-phenyl]-1-methyl-ethyl}-acetamide

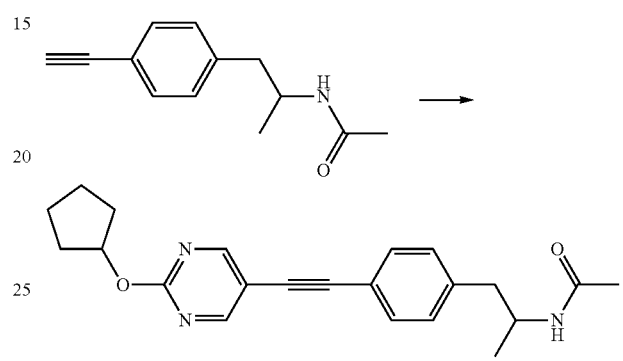

To 33.1 mg (0.17 mmol) N-[2-(4-ethynyl-phenyl)-1-methyl-ethyl]-acetamide (I58.3) and 40.0 mg (0.17 mmol) 5-bromo-2-cyclopentyloxypyrimidine (I14.1) in 2.0 mL THF are added 11.6 mg (0.02 mmol) bis(triphenylphosphin)palladiumdichlorid, 1.57 mg (8.00 µmol) CuI and 56.0 µL (0.33 mmol) DIPEA. The reaction mixture is stirred at r.t. over night. The solvent is removed in vacuo and the residue is purified by HPLC (MeOH/$H_2O$/TFA).

$C_{22}H_{25}N_3O_2$ (M=363.5 g/mol)
ESI-MS: 364 $[M+H]^+$
$R_t$ (HPLC): 2.27 min (method T)

The following compounds are prepared analogously to example 27.1

For examples 27.2 and 27.3. Pd(dppf)$Cl_2$ is used as catalyst.

| Ex. | Starting material(s) | Structure | Mass spec result | HPLC retention time (method) |
|---|---|---|---|---|
| 27.1 | I58.3 I14.1 | 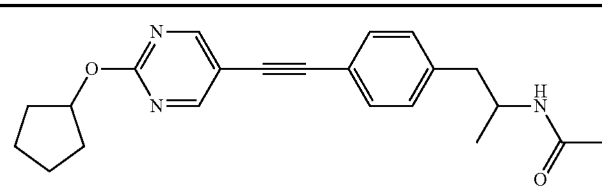 | 364 $[M+H]^+$ | 2.27 (T) |
| 27.2 | I44.13 | 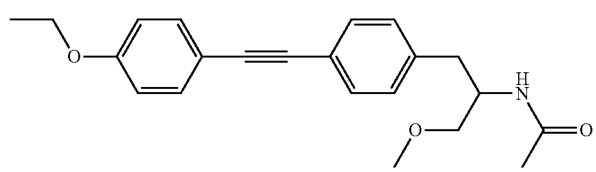 | 352 $[M+H]^+$ | 2.14 (E) |

| Ex. | Starting material(s) | Structure | Mass spec result | HPLC retention time (method) |
|---|---|---|---|---|
| 27.3 | I44.12 | 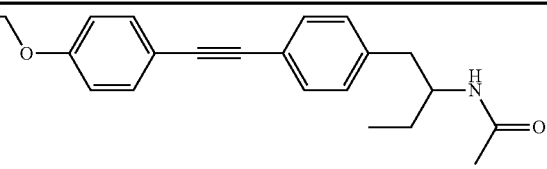 | 336 [M + H]+ | 2.20 (E) |

Example 28

(S)—N-(1-(4-((1-Methyl-1H-pyrazol-4-yl) ethynyl) phenyl]ethyl}cyclopropanecarboxamide

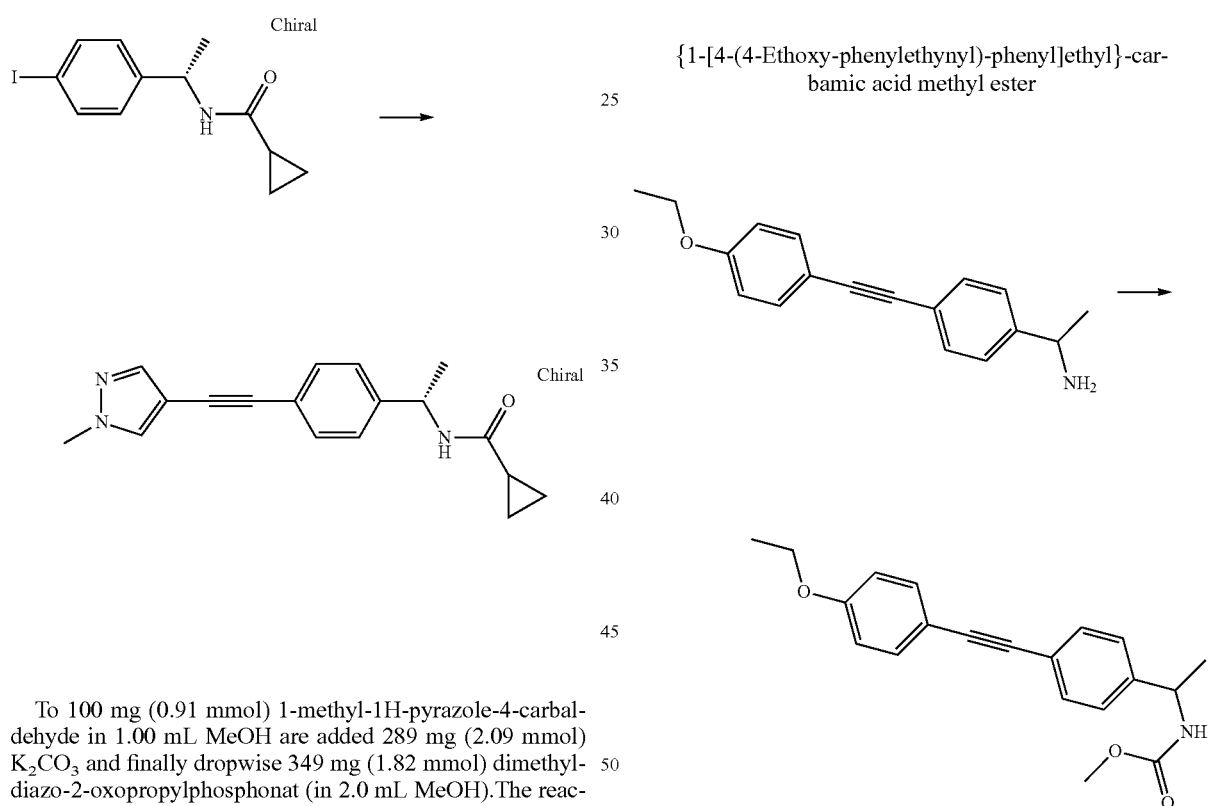

To 100 mg (0.91 mmol) 1-methyl-1H-pyrazole-4-carbaldehyde in 1.00 mL MeOH are added 289 mg (2.09 mmol) $K_2CO_3$ and finally dropwise 349 mg (1.82 mmol) dimethyldiazo-2-oxopropylphosphonat (in 2.0 mL MeOH). The reaction mixture is stirred at r.t. over night. The reaction is quenched by the addition of water and EtOAc. The organic layer is separated, dried with $Na_2SO_4$ and the solvent is removed in vacuo. To the residue is added 286 mg (0.91 mmol) cyclopropanecarboxylic acid [1-(4-iodo-phenyl)-ethyl]amide (I52.2), 63.7 mg (0.09 mmol) bis-(triphenylphosphin)-palladiumdichlorid, 2.00 mL 2-butylamine and 2.00 mL water. The reaction mixture is stirred at r.t. over night. The mixture is diluted with water and extracted with DCM. The organic layer is dried with $Na_2SO_4$ and the solvent is evaporated in vacuo. The residue is purified consecutively by column chromatography (silica gel, DCM/MeOH 98:2) and HPLC (MeOH/$H_2O$/$NH_3$).

$C_{18}H_{19}N_3O$ (M=293.4 g/mol)

ESI-MS: 294 [M+H]+

$R_t$ (HPLC): 1.65 (method E)

Example 29

Example 29.1

General Route

{1-[4-(4-Ethoxy-phenylethynyl)-phenyl]ethyl}-carbamic acid methyl ester

To 26.5 mg (0.10 mmol) 1-[4-(4-ethoxy-phenylethynyl)-phenyl]-ethylamine (I63) in 2.00 mL acetone are added 47.7 mg (0.45 mmol) $Na_2CO_3$ and 10.2 µL methyl chloroformate. The reaction mixture is stirred at 40° C. for 3 h. After cooling down to r.t. the reaction mixture is filtered and the solvent is removed in vacuo. The residue is purified by HPLC (MeOH/$H_2O$/TFA).

$C_{20}H_{21}NO_3$ (M=323.4 g/mol)

ESI-MS: 324 [M+H]+

$R_t$ (HPLC): 2.33 min (method T)

The following compounds are prepared analogously to example 29.1

| Ex. | Starting material | Structure | Mass spec result | HPLC retention time (method) |
|---|---|---|---|---|
| 29.1 | I63 | 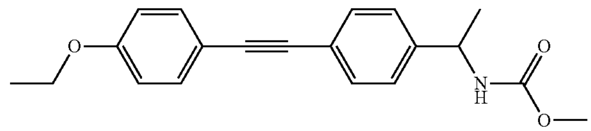 [SMILES: CCOc1ccc(C#Cc2ccc(C(C)NC(=O)OC)cc2)cc1] | 324 [M + H]⁺ | 2.33 (T) |
| 29.2 | I65 | 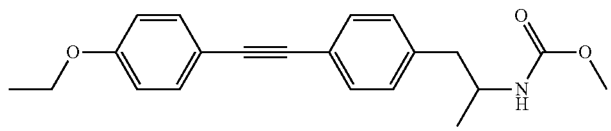 [SMILES: CCOc1ccc(C#Cc2ccc(CC(C)NC(=O)OC)cc2)cc1] | 338 [M + H]⁺ | 2.36 (M) |

Example 30

N-(2-{4-[2-(Cyclopentyl-methyl-amino)-pyrimidin-4-ylethynyl]-phenyl}-1-methyl-ethyl)-acetamide

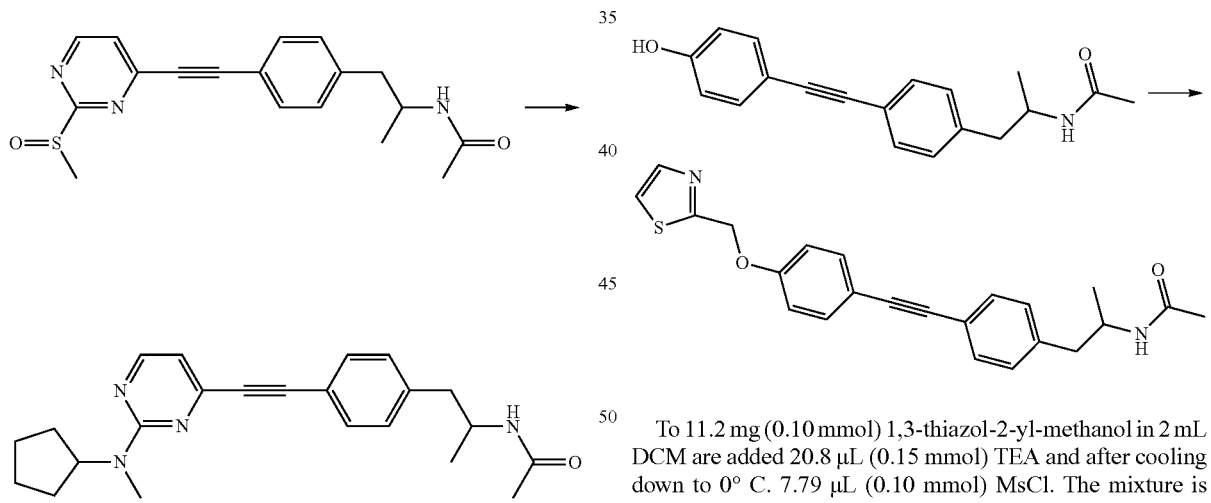

The mixture from intermediate 73 is further diluted with 11 mL DCM. 0.50 mL (4.44 mmol) N-methylcyclopentylamine are added and the reaction mixture is stirred at r.t. for 2 days, and at 50° C. for 1 day. The mixture is washed with water, the organic layer is separated, dried with $Na_2SO_4$ and the solvent is removed in vacuo. The residue is consecutively purified by column chromatography (silica gel, DCM/MeOH 92/8) and HPLC (MeOH/$H_2O$/TEA).

$C_{23}H_{28}N_4O$ (M=376.5 g/mol)

ESI-MS: 377 [M+H]⁺

$R_t$ (HPLC): 3.26 min (method B)

Example 31

Example 31.1

General Route

N-(1-Methyl-2-(4-(4-(thiazol-2-ylmethoxy)-phenylethynyl)-phenyl)-ethyl)-acetamide To 11.2 mg (0.10 mmol) 1,3-thiazol-2-yl-methanol in 2 mL DCM are added 20.8 µL (0.15 mmol) TEA and after cooling down to 0° C. 7.79 µL (0.10 mmol) MsCl. The mixture is stirred at r.t. for 1.5 h. The solvent is removed in vacuo and the residue added to 2 mL DMF. Then 29.3 mg (0.10 mmol) phenol I74.1 and 65.1 mg (0.20 mmol) $Cs_2CO_3$ are added and the reaction mixture is stirred at 75° C. for 4 h. The reaction mixture is filtered through a plug of alox, the solvent is removed in vacuo and the residue is purified by HPLC (MeOH/$H_2O$/TFA).

$C_{23}H_{22}N_2O_2S$ (M=390.5 g/mol)

ESI-MS: 391 [M+H]⁺

$R_t$ (HPLC): 2.23 min (method AA)

The following compounds are prepared analogously to example 31.1

For example 31.2 the second part of the reaction is proceded at 100° C. over night.

| Ex. | Starting material | Structure | Mass spec result | HPLC retention time (method) |
|---|---|---|---|---|
| 31.1 | I74.1 | 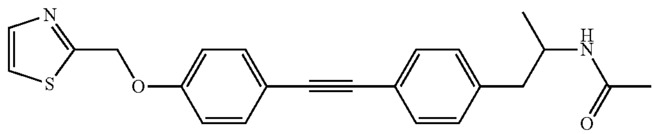 [SMILES: CC(=O)NC(C)Cc1ccc(C#Cc2ccc(OCc3nccs3)cc2)cc1] | 391 [M + H]⁺ | 2.23 (AA) |
| 31.2 | I74.1 | 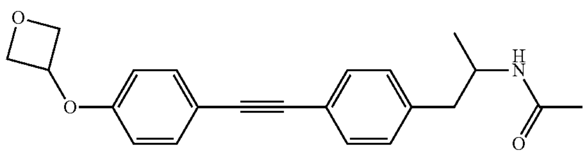 [SMILES: CC(=O)NC(C)Cc1ccc(C#Cc2ccc(OC3COC3)cc2)cc1] | 350 [M + H]⁺ | 2.18 (AA) |

Example 32

Example 32.1

General Route

N-{2-[4-(4-Propoxy-phenylethynyl)-phenyl]-propyl}-acetamide

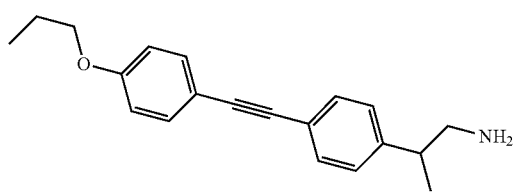

→

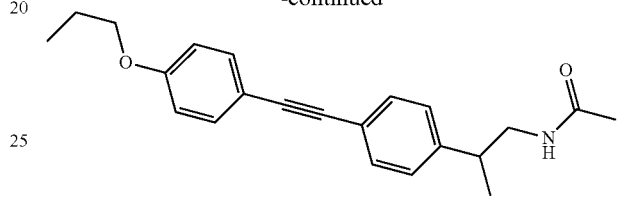

To 0.12 g (0.41 mmol) 2-[4-(4-propoxy-phenylethynyl)-phenyl]-propylamine (I65) in 5.0 mL DCM are consecutively added 0.14 mL (1.02 mmol) TEA and 34.9 µL (0.49 mmol) acetyl chloride. The reaction mixture is stirred at r.t. for 3 h. The solvent is removed in vacuo and the residue is purified by HPLC (MeOH/H₂O/NH₃).

$C_{22}H_{25}NO_2$ (M=335.4 g/mol)
ESI-MS: 336 [M+H]⁺
$R_t$ (HPLC): 2.23 min (method E)

The following compounds are prepared analogously to example 32.1

| Ex. | Starting material | Structure | Mass spec result | HPLC retention time (method) |
|---|---|---|---|---|
| 32.1 | I65 | 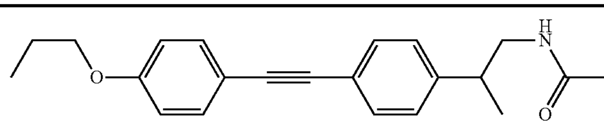 | 336 [M + H]⁺ | 2.23 (E) |
| 32.2 | I65 | 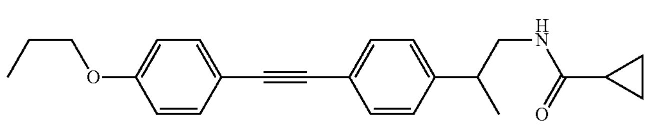 [SMILES: CCCOc1ccc(C#Cc2ccc(C(C)CNC(=O)C3CC3)cc2)cc1] | 362 [M + H]⁺ | 2.28 (E) |
| 32.3 | I66 | 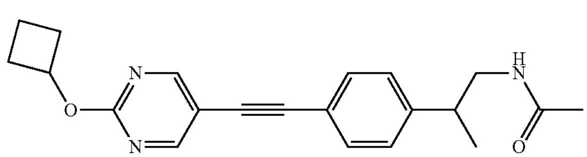 [SMILES: CC(=O)NCC(C)c1ccc(C#Cc2cnc(OC3CCC3)nc2)cc1] | 350 [M + H]⁺ | 2.34 (E) |
| 32.4 | I66 | 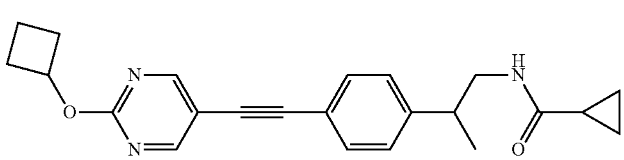 [SMILES: CC(CNC(=O)C1CC1)c1ccc(C#Cc2cnc(OC3CCC3)nc2)cc1] | 376 [M + H]⁺ | 2.40 (E) |

Example 33

Example 33.1

General Route 1,1-Dimethyl-3-{2-[4-(4-propoxy-phenylethynyl)-phenyl]-propyl}-urea

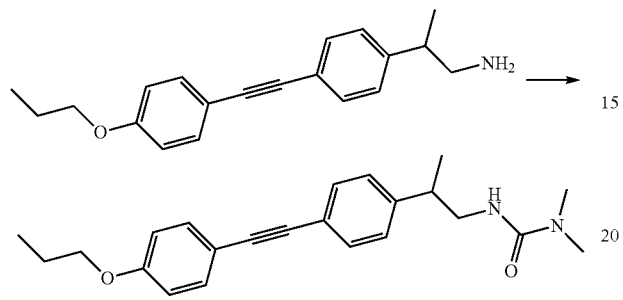

0.14 g (0.48 mmol) 2-[4-(4-propoxy-phenylethynyl)-phenyl]-propylamine (I65) and 0.10 mL (0.72 mmol) TEA in 5.0 mL DCM are cooled down to 0° C. and charged with 82.2 mg (0.50 mmol) CDT. The mixture is stirred at 0-5° C. for 15 min. Additional 20.0 mg (0.12 mmol) CDT are added and stirring is continued for 15 min. Then 0.06 g (1.43 mmol) dimethylamine are added and the mixture is stirred at r.t. for 3 h. The solvent is removed in vacuo and the residue is purified by HPLC (MeOH/H$_2$O/FA).

$C_{23}H_{28}N_2O_2$ (M=364.5 g/mol)

ESI-MS: 365 [M+H]$^+$

R$_t$ (HPLC): 2.28 min (method E)

The following compounds are prepared analogously to example 33.1

For example 33.4 NaOMe dissolved in MeOH is added instead of an amine and the mixture is stirred at r.t. over night.

| Ex. | Starting material | Structure | Mass spec result | HPLC retention time (method) |
|---|---|---|---|---|
| 33.1 | I65 | 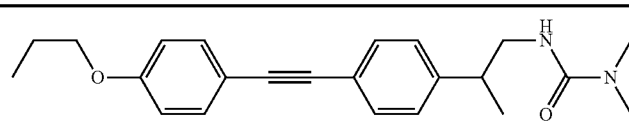 | 365 [M + H]$^+$ | 2.28 (E) |
| 33.2 | I66 | 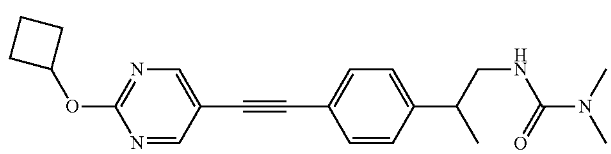 [SMILES: CC(CNC(=O)N(C)C)c1ccc(C#Cc2cnc(OC3CCC3)nc2)cc1] | 379 [M + H]$^+$ | 2.36 (E) |
| 33.3 | I66 | 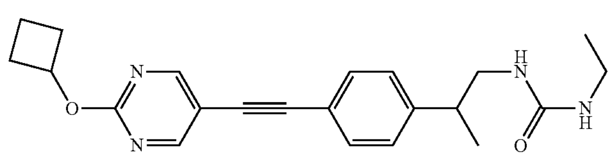 [SMILES: CCNC(=O)NCC(C)c1ccc(C#Cc2cnc(OC3CCC3)nc2)cc1] | 379 [M + H]$^+$ | 2.40 (E) |
| 33.4 | I66 | 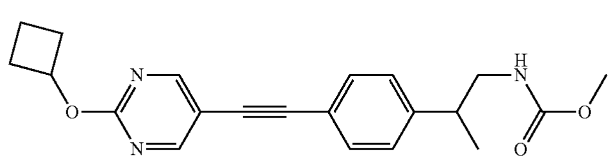 [SMILES: COC(=O)NCC(C)c1ccc(C#Cc2cnc(OC3CCC3)nc2)cc1] | 366 [M + H]$^+$ | 2.42 (E) |

Example 34

Thiazole-5-carboxylic acid (2-(4-(2-cyclobutoxy-pyrimidin-5-ylethynyl)-phenyl)-1-methyl-ethyl)-amide

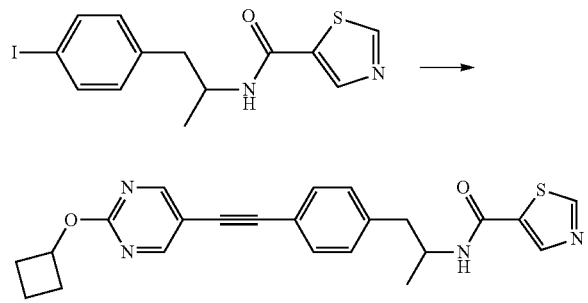

100 mg (0.27 mmol) thiazole-5-carboxylic acid (2-(4-iodophenyl)-1-methylethyl)-amide (I76) are added to 2.0 mL THF and cooled down to 0° C. 2.87 mg (4.00 μmol) bis(triphenylphosphine)palladium dichloride, 1.02 mg (5.00 μmol) CuI, 90.6 μL (0.65 mmol) diisopropylamine and finally 51.5 mg 2-cyclobutoxy-5-ethynyl-pyrimidine (I25.7) are added and the reaction mixture is stirred at r.t. over night. The solvent is removed in vacuo and the residue is dissolved in EtOAc and washed with diluted ammonia solution (1×) and water (2×). The organic layer is dried with MgSO$_4$ and the solvent is removed in vacuo. The crude product is purified by HPLC (MeOH/H$_2$O/TFA).

$C_{23}H_{22}N_4O_2S$ (M=418.5 g/mol)
ESI-MS: 419 [M+H]$^+$
R$_t$ (HPLC): 2.30 min (method AA)

Example 35

Example 35.1

General Route

N-(1,1-Dimethyl-2-(4-(4-propoxyphenylethynyl)-phenyl)-ethyl)-acetamide

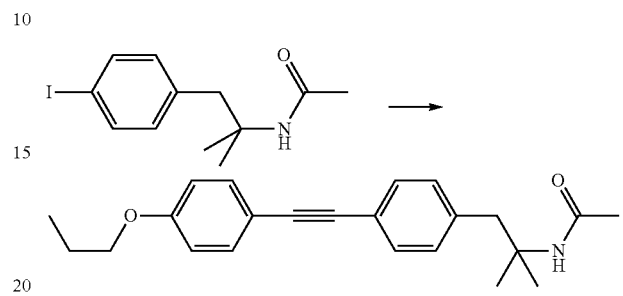

To 350 mg (1.10 mmol) of intermediate I44.9 and 180 mg (1.10 mmol) 1-ethynyl-4-propoxy-benzene in 4 mL THF are added 18.0 mg (20.2 μmol) [1,1'bis(diphenyl-phosphino)ferrocene]dichloropalladium(II), complex with dichloromethane, 4.20 mg (20.2 μmol) CuI and 0.31 mL (2.21 mmol) diisopropylamine. The reaction mixture is stirred at r.t. for 3 h. EtOAc is added and the resulting mixture is washed with diluted aq. ammonia solution (1×) and water (1×), dried with MgSO$_4$ and the solvent is removed in vacuo. The crude product is purified by HPLC (MeOH/H$_2$O/NH$_3$).

$C_{23}H_{22}N_4O_2S$ (M=349.5 g/mol)
ESI-MS: 350 [M+H]$^+$
R$_t$ (HPLC): 2.33 min (method E)

The following compounds are prepared analogously to example 35.1

For example 35.3 ACN and TEA are used instead of THF and diisopropylamine and the reaction conditions are 10 h at 100° C.

| Ex. | Starting material | Structure | Mass spec result | HPLC retention time (method) |
|---|---|---|---|---|
| 35.1 | I44.9 | ![structure] | 350 [M + H]$^+$ | 2.33 (E) |
| 35.2 | I44.6 | ![structure] | 376 [M + H]$^+$ | 2.36 (E) |
| 35.3 | I48.2 | ![structure] | 309 [M + H]$^+$ | 1.20 (U) |

Examples of Formulations

The following examples of formulations, which may be obtained analogously to methods known in the art, serve to illustrate the present invention more fully without restricting it to the contents of these examples. The term "active substance" denotes one or more compounds according to the invention, including the salts thereof.

Example 1

Tablet Containing 50 mg of Active Substance

Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

Example 2

Tablet Containing 350 mg of Active Substance

Preparation:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

Example 3

Capsules Containing 50 mg of Active Substance

Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing. This powder mixture is packed into size 3 hard gelatin capsules in a capsule filling machine.

Example 4

Capsules Containing 350 mg of Active Substance

Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing. This powder mixture is packed into size 0 hard gelatin capsules in a capsule filling machine.

Example 5

Dry Ampoule Containing 35 mg of Active Substance Per 2 ml

Composition:

| | |
|---|---|
| Active substance | 35.0 mg |
| Mannitol | 100.0 mg |
| water for injections | ad 2.0 ml |

Preparation:

The active substance and mannitol are dissolved in water. After packaging, the solution is freeze-dried. To produce the solution ready for use, the product is dissolved in water for injections.

The invention claimed is:

1. A compound of formula I

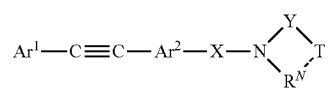

wherein $Ar^1$ is selected from the group consisting of

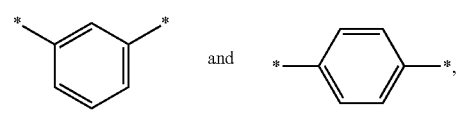

and wherein the asterisk to the right side of the cyclic group indicates the bond which is connected to the —C≡C— group of the core structure of the formula (I), and the asterisk to the left side of the cyclic group indicates the bond which is connected to a substituent $R^A$, and in addition the phenyl group is optionally substituted with one or more substituents L; and $R^A$ is selected from the group consisting of F, Br, I, CN, $C_{1-5}$-alkyl, $C_{3-6}$-cycloalkyl, $C_{1-5}$-alkyl-O—, $C_{3-6}$-cycloalkyl-O—, $C_{3-6}$-cycloalkyl-$C_{1-3}$-alkyl-O—, $R^{N1}R^{N2}N$—, phenyl, phenyl-O—, phenyl-$CH_2$—O—, heteroaryl, heteroaryl-O— and heteroaryl-$CH_2$—O—;

wherein each cycloalkyl is optionally substituted with one or more $C_{1-3}$-alkyl, which may be substituted as defined hereinafter; and wherein each alkyl and cycloalkyl are optionally substituted with one or more substituents selected from F; and wherein in each cycloalkyl group, a $CH_2$-group is optionally replaced by —O—; and wherein each alkyl and cycloalkyl are optionally substituted with one or two substituents $R^C$; and wherein heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, benzofuranyl, indolyl and quinolinyl; and wherein each phenyl and heteroaryl group are optionally substituted with one or more substituents L;

$R^C$ is selected from the group consisting of F, Cl, Br, CN, OH, $C_{1-4}$-alkyl-O—, $C_{3-7}$-cycloalkyl-O—, $C_{3-7}$-cycloalkyl-$C_{1-3}$-alkyl-O—, $H_2N$—, $(C_{1-4}$-alkyl)NH—, $(C_{1-4}$-alkyl)$_2$N—, $C_{1-4}$-alkyl-C(=O)—, $C_{1-4}$-alkyl-S(=O)$_2$—, HO—C(=O)— and $C_{1-4}$-alkyl-O—C(=O)—, wherein each alkyl or cycloalkyl may be optionally substituted with one or more substituents selected from F and OH; and $R^{N1}$ is selected from the group consisting of H, $C_{1-6}$-alkyl, $C_{3-10}$-carbocyclyl, $C_{3-10}$-carbocyclyl-$C_{1-3}$-alkyl, $C_{3-6}$alkenyl, $C_{3-6}$-alkynyl, heterocyclyl, heterocyclyl-$C_{1-3}$-alkyl, aryl, aryl-$C_{1-3}$-alkyl, heteroaryl and heteroaryl-$C_{1-3}$-alkyl, wherein each carbocyclyl and heterocyclyl may be optionally substituted with one or more $C_{1-4}$-alkyl, and wherein in each carbocyclyl and heterocyclyl a —$CH_2$- group may optionally be replaced by —C(=O)—, and wherein each alkyl, carbocyclyl and heterocyclyl may be optionally substituted with one or more substituents $R^C$, and wherein each aryl and heteroaryl group may be optionally substituted with one or more substituents L, $R^{N2}$ is selected from the group consisting of H and $C_{1-6}$-alkyl; and $R^{Alk}$ is selected from the group consisting of H and $C_{1-6}$-alkyl which may be substituted with one or more F atoms; and $Ar^2$ is

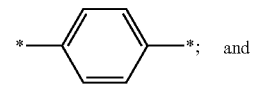; and

L is selected from the group consisting of F, Cl, Br, CN, OH, $C_{1-4}$-alkyl-, $C_{1-4}$-alkyl-O—, $C_{1-4}$-alkyl-S—, $C_{1-4}$-alkyl-S(=O)$_2$—, $H_2N$—, $(C_{1-4}$-alkyl)NH—, $(C_{1-4}$-alkyl)$_2$N— and heterocyclyl, wherein each alkyl may be optionally substituted with one or more F-atoms and/or with a substituent selected from OH, $C_{1-3}$-alkyl-O— and CN; and wherein two substituents L attached to an aryl or heteroaryl group may be linked to each other and form a $C_{2-5}$-alkylene bridging group in which 1 or 2-$CH_2$- groups may be replaced by a group independently of each other selected from O, S, NH and N($C_{1-4}$-alkyl)-, wherein the $C_{2-5}$-alkylene bridging group is optionally be substituted by 1 or 2 $C_{1-3}$-alkyl groups; and X is selected from the group consisting of

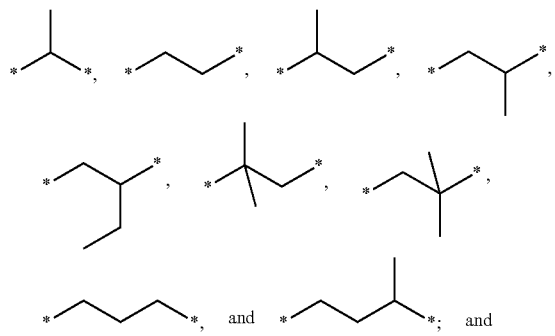

Y is —C(=O)—;

$R^N$ is H, and

T is selected from the group consisting of $C_{1-4}$-alkyl, $C_{3-6}$-cycloalkyl, $C_{1-4}$-alkyl-O—, $R^{T1}R^{T2}$—N—, heterocyclyl, phenyl and heteroaryl, wherein in each cycloalkyl and heterocyclyl, a $CH_2$-group is optionally replaced by —C(=O)—; and wherein each cycloalkyl and heterocyclyl are optionally substituted with one or more $C_{1-4}$-alkyl, which is optionally substituted with one or more substituents $R^C$; and wherein each alkyl, cycloalkyl and heterocyclyl are optionally substituted with one or more substituents $R^C$; and wherein heterocyclyl is selected from the group consisting of

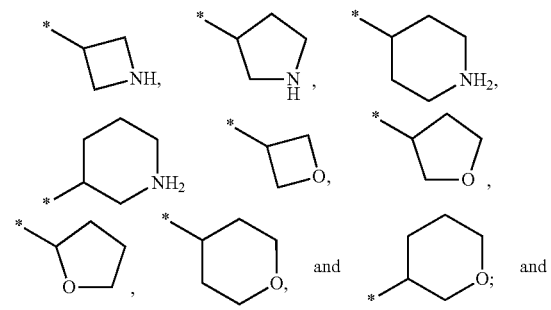

wherein heteroaryl is selected from the group consisting of pyridyl, pyrimidinyl, pyridazinyl, pyrazinyl, furanyl, thienyl, pyrrolyl, imidazolyl, pyrazolyl, triazolyl, oxazolyl, isoxazolyl and thiazolyl; and wherein each heteroaryl group is optionally substituted with one or more substituents L;

or a salt thereof.

2. A compound according to claim 1 wherein $R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, $(C_{1-3}$-alkyl)NH—, $(C_{1-3}$-alkyl)$_2$N—, HO—C(=O)— and $C_{1-3}$-alkyl-O—C(=O)—;

$R^{N1}$ is selected from the group consisting of H, $C_{1-6}$-alkyl, $C_{3-6}$-cycloalkyl, $C_{3-6}$-cycloalkyl-$CH_2$— and phenyl-$CH_2$—, wherein each cycloalkyl is optionally substituted with one or more $C_{1-4}$-alkyl, and wherein each alkyl and cycloalkyl are optionally substituted with one or more F, and wherein each alkyl and cycloalkyl are optionally substituted with a substituent selected from OH, $C_{1-3}$-alkyl-O— and $H_2N$—;

$R^{T1}$ is H, $C_{1-4}$-alkyl, $C_{3-6}$-cycloalkyl or $C_{3-6}$-cycloalkyl-$C_{1-3}$-alkyl; and $R^{T2}$ is H or $C_{1-4}$-alkyl.

3. A compound according to claim 1 wherein T is selected from the group consisting of $C_{1-3}$-alkyl, $C_{3-5}$-cycloalkyl, $C_{1-3}$-alkyl-O— and $R^{T1}R^{T2}$—N—; wherein each cycloalkyl is optionally substituted with one or more $C_{1-3}$-alkyl; and wherein $R^{T1}$ and $R^{T2}$ are independently of each other selected from H and $C_{1-3}$-alkyl.

4. A compound according to claim 1 wherein X is

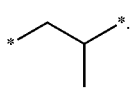

5. A compound according to claim 1 wherein T is selected from the group consisting of $H_3C$—, $H_3C$—O—, $(H_3C)_2N$—,

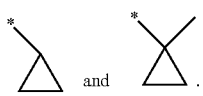

6. A compound selected from the group consisting of:

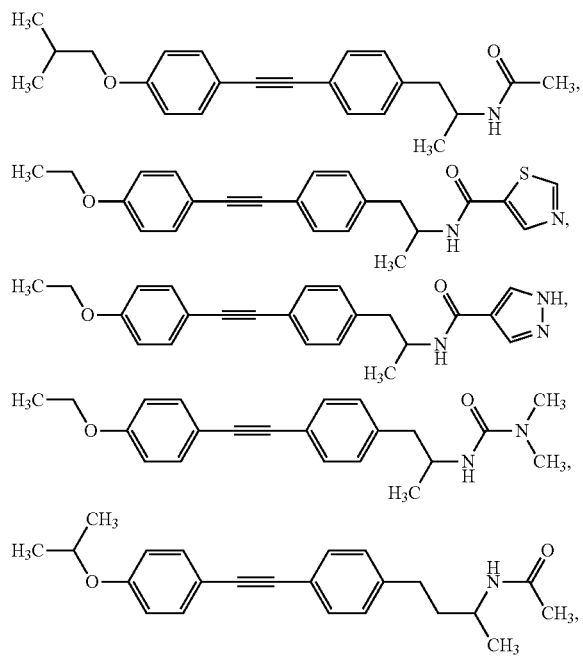

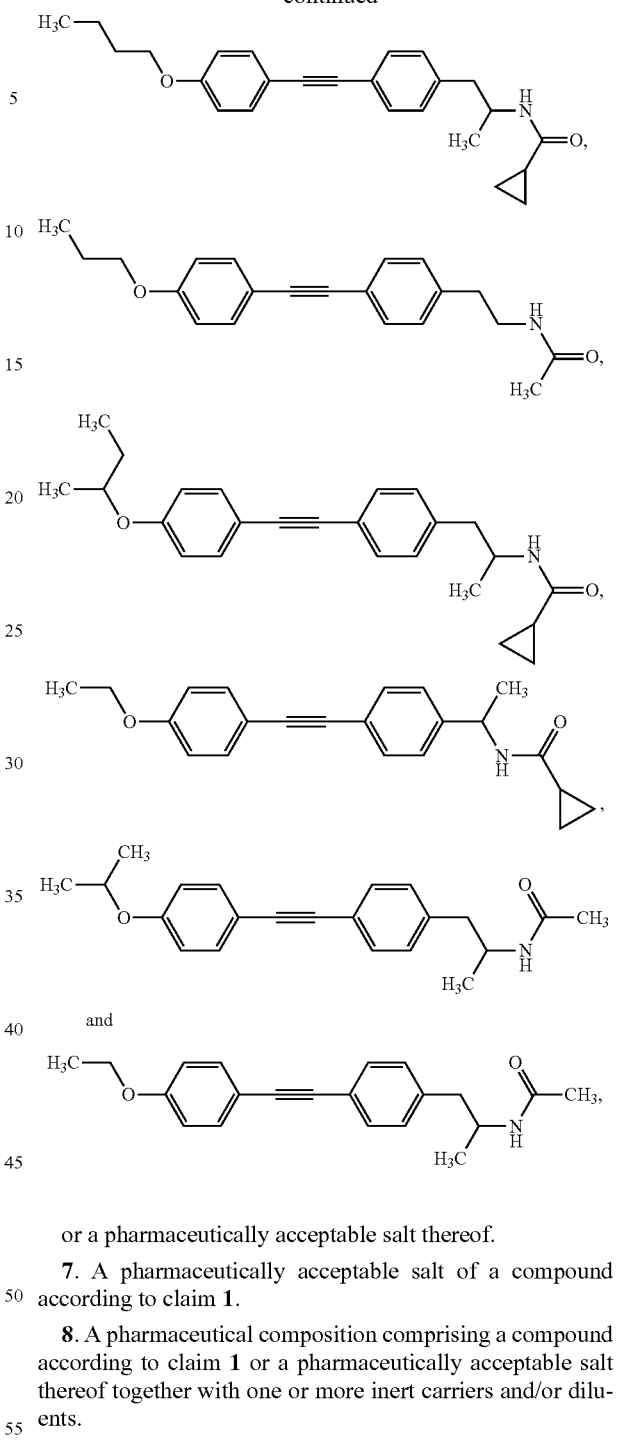

or a pharmaceutically acceptable salt thereof.

7. A pharmaceutically acceptable salt of a compound according to claim 1.

8. A pharmaceutical composition comprising a compound according to claim 1 or a pharmaceutically acceptable salt thereof together with one or more inert carriers and/or diluents.

* * * * *